US009139620B2

(12) United States Patent
Yuen et al.

(10) Patent No.: US 9,139,620 B2
(45) Date of Patent: Sep. 22, 2015

(54) FELINE MORBILLIVIRUS AND USES THEREOF

(71) Applicants: Kwok-Yung Yuen, Hong Kong (CN); Patrick Chiu-Yat Woo, Hong Kong (CN); Susanna Kar-Pui Lau, Hong Kong (CN)

(72) Inventors: Kwok-Yung Yuen, Hong Kong (CN); Patrick Chiu-Yat Woo, Hong Kong (CN); Susanna Kar-Pui Lau, Hong Kong (CN)

(73) Assignees: THE GOVERNMENT OF THE HONG KONG SPECIAL ADMINISTRATIVE REGION OF THE PEOPLE'S REPUBLIC OF CHINA, Hong Kong (CN); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 13/746,947

(22) Filed: Jan. 22, 2013

(65) Prior Publication Data

US 2013/0230529 A1  Sep. 5, 2013

Related U.S. Application Data

(60) Provisional application No. 61/588,778, filed on Jan. 20, 2012.

(51) Int. Cl.
*C12Q 1/70* (2006.01)
*C12Q 1/68* (2006.01)
(Continued)

(52) U.S. Cl.
CPC .............. *C07K 14/115* (2013.01); *A61K 39/12* (2013.01); *C07K 14/005* (2013.01); *C07K 16/1027* (2013.01); *C12N 7/00* (2013.01);
(Continued)

(58) Field of Classification Search
None
See application file for complete search history.

(56) References Cited

U.S. PATENT DOCUMENTS

| 4,444,887 A | 4/1984 | Hoffmann |
| 4,522,811 A | 6/1985 | Eppstein et al. |

(Continued)

FOREIGN PATENT DOCUMENTS

| GB | 2220211 A | 4/1990 |
| WO | WO-91/10741 A1 | 7/1991 |

(Continued)

OTHER PUBLICATIONS

Rozenblatt et al., "Sequence Homology within the Morbilliviruses," Journal of Virology, vol. 52, No. 2: pp. 684-690 (1985).*

(Continued)

*Primary Examiner* — Zachariah Lucas
*Assistant Examiner* — M. Franco Salvoza
(74) *Attorney, Agent, or Firm* — Leason Ellis LLP.

(57) ABSTRACT

Described herein are isolated *paramyxovirus*, a *morbillivirus* (FmoPV), nucleic acid molecules, polypeptides and antibodies related to FmoPV and uses thereof. In certain embodiments, the FmoPV is a feline *morbillivirus*. Also described herein is a recombinant FmoPV comprising a modified FmoPV gene or gene segments and uses thereof. Also described is a recombinant FmoPV for the prevention and/or treatment of diseases related to FmoPV or a delivery vector. Also described herein is a diagnostic assay for FmoPV, natural or artificial variants, analogs, or derivatives thereof. Also described herein is a vaccine and a kit containing the vaccine for the prevention and treatment of FmoPV infection. Also provided is a diagnostic kit comprising nucleic acid molecules for the detection of FmoPV.

9 Claims, 45 Drawing Sheets

Figure 1:
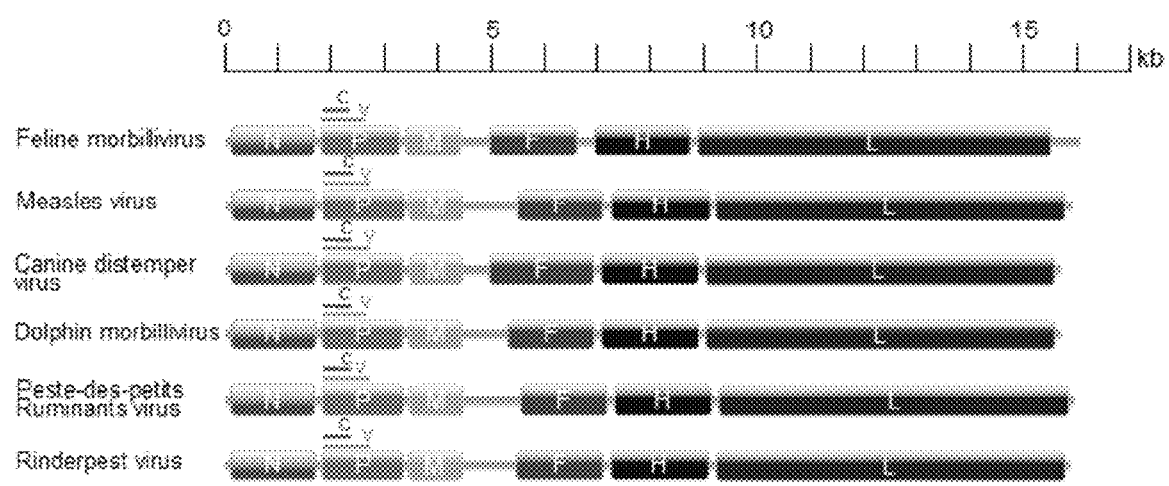

(51) Int. Cl.
    C07K 14/115    (2006.01)
    C07K 16/10     (2006.01)
    G01N 33/68     (2006.01)
    C12N 7/00      (2006.01)
    A61K 39/12     (2006.01)
    C07K 14/005    (2006.01)
    C07H 21/04     (2006.01)
    A61K 39/00     (2006.01)

(52) U.S. Cl.
    CPC ........... *C12Q 1/701* (2013.01); *G01N 33/6893* (2013.01); *A61K 2039/55566* (2013.01); *C07K 2317/76* (2013.01); *C12N 2760/18421* (2013.01); *C12N 2760/18422* (2013.01); *C12N 2760/18434* (2013.01)

(56) References Cited

U.S. PATENT DOCUMENTS

| | | |
|---|---|---|
| 4,716,111 A | 12/1987 | Osband et al. |
| 5,057,540 A | 10/1991 | Kensil et al. |
| 6,309,647 B1 * | 10/2001 | Paoletti et al. ............ 424/199.1 |

FOREIGN PATENT DOCUMENTS

| | | |
|---|---|---|
| WO | WO-96/33735 A1 | 10/1996 |
| WO | WO-96/34096 A1 | 10/1996 |
| WO | WO-98/16654 A1 | 4/1998 |
| WO | WO-98/24893 A2 | 6/1998 |
| WO | WO-98/46645 A2 | 10/1998 |
| WO | WO-98/50433 A2 | 11/1998 |

OTHER PUBLICATIONS

Barrett, "Morbillivirus infections, with special emphasis on morbilliviruses of carnivores", *Vet Microbiol*, 1999, vol. 69, pp. 3-13.
Chua et al., "Nipah virus: a recently emergent deadly paramyxovirus", *Science*, 2000, vol. 288, pp. 1432-1435.
Halpin et al., "Isolation of Hendra virus from pteropid bats: a natural reservoir of Hendra virus", 2000, *J Gen Virol*, vol. 81, pp. 1927-1932.
Moreno-Lopez et al., "Characterization of a paramyxovirus isolated from the brain of a piglet in Mexico", *Arch Virol*, 1986, vol. 91, pp. 221-231.
Osterhaus et al., "Morbillivirus infections of aquatic mammals: newly identified members of the genus", *Vet Microbiol*, 1995, vol. 44, pp. 219-227.
Philbey et al.,"An apparently new virus (family Paramyxoviridae) infectious for pigs, humans, and fruit bats", *Emerg Infect Dis*, 1998, vol. 4(2), pp. 269-271.
Tidona et al.,"Isolation and molecular characterization of a novel cytopathogenic paramyxovirus from tree shrews", *Virology*, 1999, vol. 258, pp. 425-434.
Stone et al., "Fatal cetacean morbillivirus infection in an Australian offshore bottlenose dolphin (*Tursiops truncatus*)", *Aust Vet J*, 2011, vol. 89, pp. 452-457.
Young et al., "Serologic evidence for the presence in *Pteropus* bats of a paramyxovirus related to equine morbillivirus", *Emerg Infect Dis*, 1996, vol. 2, pp. 239-240.
Lau et al., "Human parainfluenza virus 4 outbreak and the role of diagnostic tests", *J Clin Microboil*, 2005, vol. 43, pp. 4515-4521.
Lau et al., "Clinical and molecular epidemiology of human parainfluenza virus 4 infections in hong kong: subtype 4B as common as subtype 4A", *J Clin Microbiol*, 2009, vol. 47, pp. 1549-1552.
Virtue et al., "Paramyxoviruses infecting humans: the old, the new and the unknown", *Future Microbiol*, 2009, vol. 4, pp. 537-554.
Lau et al., "Identification and complete genome analysis of three novel paramyxoviruses, Tuhoko virus 1, 2 and 3, in fruit bats from China", *Virology*, 2010, vol. 404, pp. 106-116.
Woo et al., "Complete genome sequence of a novel paramyxovirus, Tailam virus, discovered in Sikkim rats", *J Virol*, 2011, vol. 85, pp. 13473-13474.
Bart et al., "Feline infectious pneumonia: a short literature review and a retrospective immunohistological study on the involvement of Chlamydia spp. and distemper virus". *Vet J*, 2000, vol. 159, pp. 220-230.
Chatziandreou et al., "Relationships and host range of human, canine, simian and porcine isolates of simian virus 5 (parainfluenza virus 5)", *J Gen Virol*, 2004, vol. 85, pp. 3007-3016.
Herrewegh et al., "Feline coronavirus type II strains 79-1683 and 79-1146 originate from a double recombination between feline coronavirus type I and canine coronavirus", *J Virol*, vol. 72, pp. 4508-4514.
Siegl et al., "Characteristics and taxonomy of Parvoviridae.", *Intervirology*, 1985, vol. 23, pp. 61-73.
Truyen "Evolution of canine parvovirus—a need for new vaccines?", *Vet Microbial*, 2006, vol. 117, pp. 9-13.
King et al., "Virus Taxonomy: Ninth report of the International Committee on Taxonomy of Viruses", 2012, pp. 111-122, pp. 235-248, Elsevier, San Diego, US.
Knipe et al., *"Fields Virology"*, 2007, pp. 1551-1586, Lippincott Williams and Wilkins, Philadelphia, U.S.A.
Lau et al., "Identification of a novel feline picornavirus from the domestic cat", *J Virol*, 2011.
Lau et al., "Severe acute respiratory syndrome coronavirus-like virus in Chinese horseshoe bats", *Prac Natl Acad Sci USA*, 2005, vol. 102, pp. 14040-14045.
Woo et al., "Characterization and complete genome sequence of a novel coronavirus, coronavirus HKU1, from patients with pneumonia", *J Virol*, 2005, vol. 79, pp. 884-895.
Guindon et al., "New algorithms and methods to estimate maximum-likelihood phylogenies: assessing the performance of PhyML 3.0.", *Syst Biol*, 2010, vol. 59, pp. 307-321.
Woo et al.,"Relative rates of non-pneumonic SARS coronavirus infection and SARS coronavirus pneumonia", *Lancet*, 2004, vol. 363, pp. 841-845.
Li et al., "Differential susceptibility of different cell lines to swine-origin influenza A H1N1, seasonal human influenza A H1N1, and avian influenza A H5N1 viruses", *J Clin Virol*, 2009, vol. 46, pp. 325-330.
Peiris et al., "Clinical progression and viral load in a community outbreak of coronavirus-associated SARS pneumonia: a prospective study", *Lancet*, 2003, vol. 361, pp. 1767-1772.
Chan et al., "Wild type and mutant 2009 pandemic influenza A (H1N1) viruses cause more severe disease and higher mortality in pregnant BALB/c mice", 2010, *PLoS One*, vol. 5, pp. e13757.
Susta et al.,"An in situ hybridization and immunohistochemical study of cytauxzoonosis in domestic cats", *Vet Pathol*, 2009, vol. 46, pp. 1197-1204.
Miyazaki et al., "Tubulointerstitial nephritis causes decreased renal expression and urinary excretion of cauxin, a major urinary protein of the domestic cat", *Res Vet Sci*, 2007, vol. 82, pp. 76-79.
Chard et al.,"Full genome sequences of two virulent strains of peste-des-petits ruminants virus, the Cote d'Ivoire 1989 and Nigeria 1976 strains", *Virus Res*, 2008, vol. 136, pp. 192-197.
Visser et al., "Fusion protein gene nucleotide sequence similarities, shared antigenic sites and phylogenetic analysis suggest that phocid distemper virus type 2 and canine distemper virus belong to the same virus entity", *J Gen Virol*, 1993, vol. 74, pp. 1989-1994.
Terai et al.,*"Felis domesticus"* papillomavirus, isolated from a skin lesion, is related to canine oral papillomavirus and contains a 1.3 kb non-coding region between the E2 and L2 open reading frames ", *J Gen Virol*, 2002, vol. 83, pp. 2303-2307.
Whittemore et al., "Antibodies against Crandell Rees feline kidney (CRFK) cell line antigens, alpha-enolase, and annexin A2 in vaccinated and CRFK hyperinoculated cats", *J Vet Intern Med*, 2010, vol. 24, pp. 306-313.
Lappin et al., "Investigation of the induction of antibodies against Crandell-Rees feline kidney cell lysates and feline renal cell lysates after parenteral administration of vaccines against feline viral rhinotracheitis, calicivirus, and panleukopenia in cats", *Am J Vet Res*, 2005, vol. 66, pp. 506-511.
Lappin et al., "Interstitial nephritis in cats inoculated with Crandell Rees feline kidney cell lysates", *J Feline Med Surg*, 2006, vol. 8(5), pp. 353-356.

(56) References Cited

OTHER PUBLICATIONS

Kul et al., "Natural peste des petits ruminants virus infection: novel pathologic findings resembling other morbillivirus infections", *Vet Pathal*, 2007, vol. 44, pp. 479-486.
Liess et al., "Studies on the Pathogenesis of Rinderpest in Experimental Cattle. I. Correlation of Clinical Signs, Viraemia and Virus Excretion by Various Routes", *J Hyg* (Lond), 1964, vol. 62, pp. 81-100.
Saito et al., "Detection of canine distemper virus by reverse transcriptase-polymerase chain reaction in the urine of dogs with clinical signs of distemper encephalitis", *Res Vet Sci*, 2006, vol. 80, pp. 116-119.
Marschall et al., "Avian influenza A H5N1 infections in cats", *J Feline Med Surg*, 2008, vol. 10, pp. 359-365.
Martina et al., "Virology: SARS virus infection of cats and ferrets", *Nature*, 2003, vol. 425, pp. 915.
Van Riel et al., "Highly pathogenic avian influenza virus H7N7 isolated from a fatal human case causes respiratory disease in cats but does not spread systemically". *Am J Pathol*, 2010, vol. 177, pp. 2185-2190.
Chomel et al., "Zoonoses in the bedroom", *Emerg Infect Dis*, 2011, vol. 17, pp. 167-172.
Karlin et al., "Methods for assessing the statistical significance of molecular sequence features by using general scoring schemes", *Proc Natl Acad Sci USA*, 1990, vol. 87(6), pp. 2264-2268.
Karlin et al., "Applications and statistics for multiple high-scoring segments in molecular sequences", *Proc Natl Acad Sci USA*, 1993, vol. 90(12), pp. 5873-5877.
Altschul et al., "Basic local alignment search tool", *J Mol Biol*, 1990, vol. 215(3), pp. 403-410.
Altschul et al., "Gapped BLAST and PSI-BLAST: a new generation of protein database search programs", *Nucleic Acids Res*, 1997, vol. 25(17), pp. 389-402.
Myers et al., "Optimal alignment in linear space", *Comput Appl Biosci*, 1988, vol. 4(1), pp. 11-17.
Quinlivan et al., "Attenuation of Equine Influenza Viruses through Truncations of the NS1 Protein", *Journal of Virology*, 2005, vol. 79, pp. 8431-8439.
Hoffmann et al., "A DNA transfection system for generation of influenza A virus from eight plasmids", *Proc Natl Acad Sci USA,* 2000, vol. 97(11), pp. 6108-6113.
Wang et al., "Cloning of the canine RNA polymerase I promoter and establishment of reverse genetics for influenza A and B in MDCK cells", *Virology,* 2007, vol. 4, pp. 102.
Sambrook et al., "Molecular Cloning: A Laboratory Manual", *Cold Spring Harbor Laboratory Press,* 3rd Edition, Cold Spring Harbor, New York, U.S.A.
Tao et al., "Replacement of the Ectodomains of the Hemagglutinin-Neuraminidase and Fusion Glycoproteins of Recombinant Parainfluenza Virus Type 3 (PIV3) with Their Counterparts from PIV2 Yields Attenuated PIV2 Vaccine Candidates", *Journal of Virology,* 2000, vol. 74(14), pp. 6448-6458.
Durbin et al., "Human parainfluenza virus type 3 (PIV3) expressing the hemagglutinin protein of measles virus provides a potential method for immunization against measles virus and PIC3 in early infancy", *Journal of Virology,* 2000, vol. 74(15), pp. 6821-6831.
Skiadopoulos et al., "Three amino acid substitutions in the L protein of the human parainfluenza virus type 3 cp45 live attenuated vaccine candidate contribute to its temperature-sensitive and attenuation phenotypes", *Journal of Virology,* 1998, vol. 72(3), pp. 1762-1768.
Teng et al., "Recombinant respiratory syncytial virus that does not express the NS1 or M2-2 protein is highly attenuated and immunogenic in chimpanzees", *Journal of Virology,* 2000, vol. 74(19), pp. 9317-9321.
Kensil et al., "Vaccine Design: subunit & Adjuvant Approach", *Powell & Newman,* Plenum Press, 1995, New York, U.S.A.
Stoute et al., "A preliminary evaluation of a recombinant circumsporozoite protein vaccine against *Plasmodium falciparum* malaria. RTS,S Malaria Vaccine Evaluation Group", *N Engl J Med,* 1997, vol. 336(2), pp. 86-91.
Woo et al., "Feline morbillivirus, a previously undescribed paramyxovirus associated with tubulointerstitial nephritis in domestic cats", *Proc Natl Acad Sci USA,* 2012, vol. 109(14), pp. 5435-5440.
Audit Commission, "Control of pet animals(Chapter 4)",*Agriculture, Fisheries and Conservation Department, Housing Department,* Mar. 29, 2010, Hong Kong, China (www.aud.gov.hk/pdf_e/e54ch04.pdf).

* cited by examiner

Figure 2-1

FmoPV 761U Cats/Hong Kong/2009 16050 bp

ACCAGACAAAGATGTTTGTGACCTATTCTAACGACAAGACTATTATTAAATATTTAGGAA
TAACGATTCCATTAGTGAGGTGAGGGGGAGGAATCAGGTATTCCACAATGTCTAGTCTAT
TGAGGTCACTTGCTGCATTTAAGAGACATAGGGAGCAACCAACAGCACCGTCAGGTTCGG
GTGGTGCAATTAAAGGATTGAAAAATACAATTATTGTTCCAGTTCCAGGGGATACAGTAA
TTACTACAAGGTCTAATTTGTTATTTAGATTAGTTTATATAATAGGCAATCCGGATACAC
CTTTAAGCACCTCGACGGGAGCAATAATATCATTGTTGACCTTATTTGTCGAATCTCCAG
GTCAATTAATTCAAAGAATTGCTGATGACCCTGATGCAGTTTTTAAATTGGTAGAGGTCA
TTCCTGAAGCTGGTAATCCTGGAGAATTAACTTTTGCATCTCGAGGGATTAATTTAGACA
AGCAAGCTCAACAATACTTTAAATTGGCTGAGAAAAATGATCAGGGGTATTATGTTAGCT
TAGGATTTGAGAACCCACCAAATGATGACGATATAACATCAGTCCTGAGATATTCAATT
ATATCCTGGCATCTGTACTTGCACAAGTTTGGATTCTTCTGGCAAAAGCTGTGACTGCTC
CAGATACGGCTGCTGAAGCCGAAAATCGTAGATGGATTAAATTAATGCAACAACGTAGGG
TGGATGGTGAACTGAGATTGAGCAAGGGATGGCTAGATTTGGTGAGAAACAAGATTGCGT
CAGATATTACAATAAGGCGATTCATGGTAGCATTAGTTCTTGACATCAAACGTTCTCCTG
GGACAAGACCCAGGATAGCTGAAATGATTTGTGATATTGATAATTATATTGTAGAGGCAG
GGCTTGCAAGTTTCTTGTTAACTATTAAATTTGGCATAGAGACACGTTATCCAGCACTGG
CACTACATGAGTTTTCTGGAGAACTAGCCACTATTGAGGGGCTTATGAAATTGTACCAAT
CTATGGGGGAAATGGCACCATACATGGTAATTCTGGAAAATTCAATCCAAACCAGGTTTA
GTGCAGGGTCTTATCCTCTGCTATGGAGTTATGCCATGGGTGTCGGGGTGGAGCTTGAAA
GATCAATGGGTGGACTCAATTTCACTAGAAGCTTCTTTGACCCTACATATTTCAGACTTG
GTCAAGAGATGGTGAGGAGATCTTCAGGGATGGTTAATAGTTCATTTGCGAGAGAACTTG
GCCTATCTGATCATGAAACACAACTGGTCAGCCAGATTGTCAATTCGGGAGGTGAATCTG
GGATACCTAAATTTGATGGATTCAGAGCAAATCCAACAACTTTTCTAGGAACCAAAGATA
ACATAAATGATAGAGGTGAAGATCAGTCAAATTCGATATCAGGGTTACCTGGTCCACTAT
TACCCAGCCGTGACCTAAATCTTTCAGGTGATTCATATGGAATTAATAGTGGTGTGAAAA

Figure 2-2

ATGTCAGTGACAAACTGAATGAAGGAGTAGGTCCAGACCATGATGTGTCCAGTTCTGCCA
TGGAAGAATTGAGAAGATTGGTTGAGTCCACCAACAGAATAGACACCAAACAGCCAGAAG
CTTCAGGTGTCACCAACCATTATAATGATACTGACCTTCTAAAATAATATGAGCATACCC
TAATTGCTTATTATGCAACTCAAATTAAGAAAAACTTAGGACCTCAAGGTTCACAACTGT
TGGCATATCACTAAAATACAGTCAGCTCTTCACCCACCACATGTCCTCTCACCAAATCCA
GCAAGTCAAACATGGCCTCGAATCTTTACAAGAGATCAAAAACAACCCTCCGTCTTCCCA
AGATGTCAATCTTGCCAGGGAGATTTACGAATCCATTAGACAAACAGGAACATCTTCAGT
GCAAGGAGGAGCCATTGCGGGAGATAATATTACGTCAGGGGGTAACAATGACTCAATGTA
TAGCCAAGGACCAAGTCCTCCTATTTCAAGTGTTAACAAGAATATCGAAGGACCTACTGG
ATTCGATCATTCAGGACTATGGGATCCAGAGGGTAACCTCTGCATGCTATTCGAAAGCGA
TGATGATGAAAACCATTATTCAGAGATTAATGGCCGGTCTTCCGCTATCGAAGGACTGGA
TGAACAGGATAATGAGAACTCAATTATTAAACAACCAGGAAATCAGTGTACTGAGGGAGT
GTCTAAGACTGATTCATCTCTTAGTTCCCAGGAAACTACACTATCTGTTGGGGGATCTGA
TATACCTGGGGCAGGAATATCAACCTGTGCCTCTTTGGATATAACTGTAAATGAACTCGA
AGATGCAACTGTAAGAAATAGCAACAATATGAAAGGGAACTGGCCAATTCCTAAATTACT
TGTTAAGCCGCCACCTAGGGTAAAAACAAGCGTTGATCACAGTAATCCATTAAAAGGGGC
CACAGGAGGGAAATTAGCCTCACCTGGGATGGAGACTACATTATTCGAGAGGAGTGGTGC
AACCCCATCTGTACACCCATATACTCAACCTGCAAGCGACTTCAATGTAGGTGCAAGCAA
TGTCCATCAACCTGCCCTAAATGTGAATAATAATTGCAATGATGGTAGGGTAACAGCGCC
TAACTCACATAAAGATATCGAGGGTGAGTCTGAAATATCTATTCAAGATATATATAACTT
GATTCTTGGATTTAAGGATGATTACAGGAAATTATCAAACAAATTAGATATGGTATTAGA
GATGAAACAAGACATTGACAATCTAAAAAAGAATAGTGCTAAAGTGCAATTGGCTCTATC
AACTATTGAGGGACATCTATCCAGTGTTATGATTGCCATCCCTGGTTCAGGTATTGATTC
CACAGGGGATGAGGAAAAGGATCAGATAAATTCTGACTTAAAACCACTGCTAGGAAGGGA
TCATTGTAGAGCATTTCGAGAAGTTACCAATCCTCTAGATGAGTCTTCACTAGCCAATTC
TCCAACAAAACATGTTGCCAAGGTAAACAAAACTGCACTCTTCAGAAGATCAACAAGAA
CGAAACATCTGCAATCAAATTTGTTCCTAGTGACAGTCATGCAAGCACATCAACCATCAG
ATCAATTATCAGGTCATCTAATCTCGATCAGGATTTGAAAACAAAATTGCTCACAATTCT

Figure 2-3

ATCCCAGATTAGAGGGGCAGACAATATTAGAGAATTCTATGAAAAGGTTATGATATTAAT
AAAGAATAAGAATTAAATATTACAAATCTACATTCATTATAGGTTGTAATTGTCTTCAAT
AAGATTTGGTCAGTTTCATATATATGGTTATTGATTTGTGATAATTATAAAAAACTTAGG
AGCTAAAGGTTACTCAGTCATATACAGCATGACTGAGATATTCAACCTTGATGAGAGCTC
ATGGTCAGTCAAAGGGATACTAGATCCGTTAACACCTGATACCTATCCTGATGGTCGACT
AGTGCCTAAAGTTCGAGTTATCGATCCGGGTCTAGGAGATCGCAAGAGTGGGGGGTATAT
GTACCTACTTCTTCATGGTGTCATAGAAGATAGTGAGACTATAATTAGCCCGAAAGGAAG
AGCATTTGGTGCATTCCCATTAGGAGTGGGTCAATCAACTGAAAACCCGGAAGACTTGTT
TAAGGAAATATTAACTCTCAACATCGTGACTCGTAGGACTGCTGGATTTAATGAGAAATT
GGTTTATTATAATACCACACCTCTACATTTACTGACCCCCTGGAAAAAGTGTTGGCATA
TGGAGGCATTTTTAATGCTAATCAGGTCTGCAGTGATACAAGTTCCATACCAATAGACAT
TCCACAAAAATTTAGGCCAGTATATTTGACTGTTACAAAATTATCTGATGATGGCTATTA
TCAGATCCCAAAGATGATTCAAGATTTCAAATCGTCAAATTCTGTTGCATTCAACATCCT
TGTGCATCTGTCAATGGGCATAAATTTACTTGACCAATCCAAGGACCCTAGATTAAGAAA
TGCTGCAGAAACTGTGATCACATTTATGATTCATATTGGAAACTTTAAACGGAAGAGTAA
TAAGTCTTACTCACCTGAATATTGCAAGAGGAAAATAATGAGGCTGGGTTTAATATTCTC
ATTAGGTGCAATTGGTGGCACAAGCTTGCATATTAGATGTACAGGTAAGATGAGCAAACG
ACTACAGGCTTATTTAGGATTCAAAAGGACTTTATGTTACCCTTTGATGTATGTTAATGA
AGGGCTGAACAAGACCCTGTGGAGAAGTGAATGCAGAATAGAGAAGGTTCAAGCAGTCTT
ACAGCCATCAGTCCCGAATGAATTTAAGATATATGATGATGTTATTATTGATAATACCAA
TGGTCTCTTCAAGATTAAATAGACTATAACAATAATAAACAGCTACTAAATAGTATTATG
TATTTAAGTGTACACTGATAATTGCGAATAAAATACACCAGATTAATAACAGTATAGAGT
TAAGATCTAATTGATATGTGGGTTGGTACTCGATCATTTATTAGCTCTACTGATTATCTA
TATCTTGAATCACCAAATGTAAGAGCATCAACAGGTAATAAGTTTTGGATTGCTAGATTG
ACACTTAATTCTCAGAACTAGAATACCCAGATTGTCAAACCTATAACCTTGTTAGATTCA
TTAAAGTTAGATTCTTGTAATGTTGATCAATTATCACTTGAGCAATTATAAAAAACTAAG
GACCTAATGTAATAGGAACCCAAACTCCATCCAGTGAGCTCTAAATCGCCATGCTTGAAT
ATTAATTTATCTAGGGCCTGTCTAACTCAGAACAAAGATCACAACTAGAGTCTAAAGGAG

Figure 2-4

TGGGTCAAGTCTGAACAATTATCAAGAGCCGAGATTCAAAACTGATTCCTCCTTAAACTC
AGAACCCTAACAATATATCATCCACTCAACATCATGAACAGAATTAAGGTTATGATAATT
AGTTCTTTATTATTATCAGATATTACGATTGCACAAATAGGTTGGGATAATTTGACTTCG
ATTGGAGTTATAAGTACTAAGCAATACGACTATAAAATAACTACTCTGAACACTGACCAG
TTAATGGTTATAAAGATGGTTCCTAATATATCATCAATCATTAATTGCACTAAACTCGAA
TTAACAAAATATAGAGAGTTAGTCTCAGGGATCATTAGACCAATAAATGAGTCATTAGAA
TTAATGAATTCATACATTAACATGAGAGCAGGTTCAGAGAGATTTATAGGGGCTGTAATA
GCTGGTGTAGCCTTAGGAGTGGCAACTGCAGCACAAATAACATCAGGGATTGCCCTACAT
AATTCAATTATGAACAAAAACAAATACAAGAATTGAGGAAGGCTCTTAGTACTACCAAC
AAAGCAATTGATGAAATAAGGATTGCAGGTGAAAGAACATTAATAGCAATTCAAGGTGTA
CAGGATTATATTAATAATATAATTATCCCTATGCAGGACAAACTCCAATGTGATATTTTA
TCATCACAACTTTCTGTTGCTTTACTCAGATATTATACAAATATACTAACAGTTTTTGGG
CCAAGTATACGGGATCCTATTACTAGTACAATTTCAGTACAAGCACTCAGTCAAGCATTC
AATGGTAATCTTCAGGCATTGCTTGATGGACTGGGGTATACTGGGAGAGACTTACGTGAT
CTTCTAGAGAGTAAATCTATCACTGGCCAGATAATTCATGCAGATATGACTGATTTGTTC
CTTGTTTTGAGAATAAATTATCCTTCCATAACTGAGATGCAGGGAGTAACAATATATGGG
CTCAATTCAATTACATATCATATTGGGCCTGAAGAGTGGTATACCATTATGCCTGATTTT
ATTGCTGTTCAGGGTTTTTTAATATCTAATTTTGATGAGAGAAAGTGTTCAGTAACTAAA
TCAAGTATATTGTGCCAACAAAATTCAATTTACCCAATGTCAACAGAGATGCAAAGATGT
ATTAAGGGCGAGATAAGATTCTGTCCAAGATCCAAGGCAATTGGGACATTAGTTAATCGG
TTTATATTGACCAAAGGTAATTTAATGGCTAATTGTTTAGGGATTATATGCAGATGTTAT
ACTTCAGGACAAGTTATAACACAAGACCCAAGTAAATTGATTACGATAATATCGCAAGAG
GAGTGCAAGGAAGTTGGTGTTGATGGTATTCGTATTATGGTAGGACCTAGAAAATTACCA
GATATTACCTTTAATGCTAGGTTGGAAATTGGTGTACCAATATCATTGAGCAAATTGGAT
GTCGGGACTGATTTAGCGATTGCTTCAGCTAAACTTAATAATTCTAAGGCATTGTTAGAG
CAATCAGATAAGATTTTAGATTCAATGTCTAAATTGGATTCTATGAATTCAAGAATAATA
GGATTAATCTTAGCAATTATGATAATCTTTATAATCATTATTACTATTATCTGGATCATA
TATAAAAAATGTAGGAATAAAGATAATAAATTCAGTACTTCAATTGAACCGCTCTACATA

Figure 2-5

CCCCCTTCTTATAACTCACCTCATAGTGTGGTTAAGTCTATTTGAGCACTGACCATATGA

TCCACTGTAATAAGTCCAATGAAAGTATCAATTAATAATATTGGTAGTGCAATGAGTATT

GATTGTATAATATACTCCTTTAAACTAGATAGTGATAAAGGGTTATAGATGATTTCAGTT

ATTTTAATATAATCATATATTGATTTTATTATCTTACATGACTATTATGTAATTGAATTA

TGTGTCATCAATTAATAGCTTAATAATATCGTTTAATGTACTTATATTGATGGATAGATG

TGTTATATTGTAATCAAGGATTTAGTATTTAGAAAAGGAAAGAGTTTAATTTGTTGTTAA

TTAGTTATTGTGTATTCAATTAGAAAAAACTTAGGAATCCATGTTAATAAAAATTTATTA

TCATGGAGTCCAACAATATTAAGTATTACAAAGATTCTAGCCGGTACTTTGGTAAAATAT

TAGATGAACACAAAACAATTAATAGTCAATTGTACAGTTTGAGTATCAAGGTAATTACCA

TTATTGCTATTATTGTAAGCCTGATTGCAACAATAATAACTATTATCAATGCCACTAGTG

GGAGAACTACCCTAAATAGTAATACAGACATACTACTCAGCCAACGAGATGAGATTCATA

ACATCCAAGAAATGATATTTGATCGTATTTATCCTTTGATAAATGCTATGAGTACAGAGC

TAGGACTTCATATTCCTACCTTATTGGATGAACTTACTAAAGCGATTGACCAGAAAATTA

AAATAATGCATCCTCCTGTGGACACTGTGACTTCTGACCTTAATTGGTGCATCAAACCCC

CTAATGGAATTATCATAGACCCAAAAAGTTATTGTGAGAGTATGGAATTGTCTAAAACTT

ATGAACTGTTACTTGACCAGTTAGATGTCTCAAGAAAGAAATCACTTATTATAAATAGAA

AGAATATCAACCAGTGCCAATTAGTTGATAATTCAAAGATCATTTTTGCTACTGTCAACA

TACAATCTACACCGAGGTTTTTAAACTTTGGTCACACGGTCAGCAATCAACGTATAACAT

TTGGTCAAGGAACATATAGTAGTACTTATGTTATAACTATCCAAGAAGATGGAGTAACTG

ATGTTCAATATCGAGTGTTTGAGATCGGATATATTTCTGATCAGTTTGGTGTATTCCCCT

CCTTAATAGTATCGAGAGTGTTGCCGATACGTATGCTATTAGGAATGGAATCCTGTACCT

TGACAAGTGATAGACTAGGCGGGTATTTTTATGTATGAATACACTGACACGATCTATAT

ATGATTATGTTAGCATAAGGGATTTGAAATCACTTTATATAACAATCCCTCATTATGGTA

AAGTTAATTATACTTACTTTAATTTTGGTAAGATCAGGAGCCCACATGAGATTGATAAAA

TTTGGTTAACATCTGATAGAGGCCAAATTATCTCTGGTTATTTTGCAGCATTTGTTACCA

TTACAATTCGGAACTATAATAATTATCCCTACAAATGCTTAAATAACCCATGTTTTGACA

ACTCTGAGAATTACTGTAGAGGATGGTATAAAAACATAACAGGAACTGATGATGTTCCGA

TATTAGCATACTTATTGGTTGAAATGTATGATGAGGAGGGACCTTTAATTACACTTGTGG

Figure 2-6

CAATACCACCTTACAATTATACAGCTCCATCTCATAATTCTCTTTACTATGATGACAAAA

TTAATAAATTAATAATGACTACATCTCACATAGGTTATATTCAAATCAACGAGGTGCATG

AGGTAATTGTTGGCGATAATTTGAAGGCTATCCTCTTAAACAGATTGTCTGATGAACATC

CTAACCTGACTGCCTGTAGACTCAATCAGGGTATTAAGGAGCAATACAAGTCTGACGGAA

CAATAATTTCAAATTCTGCACTTATTGATATACAAGAACGAATGTACATTACAGTTAAAG

CTATTCCACCAGCAGGTAACTATAACTTTACAGTTGAGTTGCATTCTAGATCAAACACAT

CCTATGTATCGTTACCAAAACAGTTTAATGCTAAGTATGACAAATTACATCTTGAGTGCT

TTAGCTGGGACAAATCCTGGTGGTGTGCTCTGATACCCCAGTTTTCATTAAGTTGGAATG

AATCCCTTTCTGTTGATACTGCCATTTTCAATTTAATAAGCTGTAAATGAACACATCAAT

CTATAGTTGATAGTTGTCAAAACATTAGCTAATTTGGGTTTAAGAAATAGGAAAATGAAA

TTACCAATATCTAATTAGATGTATGTTCAAGCTAAATTACAAAAACTTAGGAGTCAGAG

ACTTCGTTGCAATGGAGCAGTCAGACTACCAAGATATTCTATACCCGGAAGTACATCTTA

ACAGTCCTATAGTAATTTCCAAATTAGTAGGTATTTTAGAATACGCCCAAATTGCTCATA

ATCAACAATTATCAGACCGTACAATTATCAAGAATATTCAATTTAGATTAAGGAACGGAT

TTAATAGTTCAAGGGTACAGGTACTATCAGCTATGGGTGAAATTATCAACAAAATTAGAA

ATAAATATCCTAATTATTTACACATACCTTACCCTGAATGCAACCAAAAACTATTTCGAA

TAGTAGATCCAGAACTAACATCAAAATTAGAATCTCTTCTAAACAAAGGTGACACACTGT

ATCTCAAGATTCGATCAGATATCATAAAATGTTTTGATAGATTGAAAATGAAAATGAATA

TAAAGAATGATCTTCTTAATGACAATAGTCAATTGATTCTAGATCTTCCTTTAATTATCA

AAGGATCTCAGTGGTTCTTCCCTTTTTTATTCTGGTTTTCTATCAAAACTGAAACTAGAA

GCTGTATTCGCCAAAATCAAAAGACTCGTGTTAGATCACAATATCGGCCTCACTTATCAG

AGACTAAGAGAATTACATTGGTTGTTACATCTGATCTGATTACAATATTTGATCATATTA

ATAAATGTATATTTTATCTGACTTTTGAGATGCTGTTAATGTATTGCGATGTGATAGAAG

GTCGGTTAATGACTGAAACAGCTATGAGCTTGGACTGTCGGTTTACCAATCTATTGCCAA

GAGTGCAATATATGTGGGATTTACTAGATGGAATGTTTGAAAGTTTAGGCAATCAATTAT

ATTCAGTTATTGCATTATTAGAGCCTCTTTCTCTTGCTTATTTGCAATTGATAGATGCAG

ATCCACAGATTCGGGGAACATTCTTGCATCACTGCTTTTCCGAGTTAGAAGAAATTATAT

TTGACAAAACCCCTTTTGATCCTTTTGTGTATGAAAATTTAATTAATGGGCTTGATTACA

Figure 2-7

TTTATTTGACAGGTGATATTCATCTAACTGCAGAAGTTTTTCTTTTTTTAGAAGTTTTG
GTCATCCTTTTTTAGAGGCACAAAATGCTGCTAATAATGTAAGGAAGTATATGAATAAGC
CTAAGGTAATATCATATCAGACTTTAATGCAAGGACATGCGATTTTTTGCGGTATTATAA
TAAATGGATTTAGAGACCGCCACGGGGGAACATGGCCTCCTGTGGAGTTACCAAATCATG
CATCTGCTGTAATTAGAAATGCCCAGTTATCTGGAGAAGGGTTAACATCTGAACAATGTG
CTCAACACTGGAGATCCTTTTGTGGATTTAGATTTAAATGTTTTATGCCATTGAGTCTAG
ATAGTGACCTTACAATGTACCTTAGAGACAAGGCGCTGTCACCTGTCAGAAATGAGTGGG
ATTCAGTTTATGCTAAGGAGTATTTAAGGTATAATCCAGGATTACCCACAAGTTCCAGAA
GATTGGTAAATGTATTCTTAGAAGATGATAAGTTTGACCCATATGAAATGATCATGTACG
TGATAAATGGTGATTACTTAAGAGACAAAGAGTTTAACCTTTCATACAGCCTTAAAGAGA
AAGAAATTAAAGAGGTAGGTCGATTGTTTGCTAAAATGACCTATAAGATGAGGGCTTGTC
AAGTAATAGCTGAAAACCTGATTGCCAATGGAGTAGGGAAGTTTTTCAAAGATAATGGAA
TGGCAAAAGATGAACATAAATTAACTAAGACGTTACACAAATTAGCCATTTCAGGTGTAC
CTAAAGATAATTCTAAACTTTATTTAGATGAATGTTGGGAGCAAGTAATTCGACAATGTT
CAAGTAGTACACAGATAAGGGAACAGACTATGAATTCACAATCAAATAGGGAAATTGAAT
CAAAGTCTTCTAGGGCACGTCTTAATAATAGAGATATCTTAAAGGGCAAGAGAGATTCGA
ACAAACAAGTAAAGTATCCTTCAAACACCGAGTATTATGAGACTATCAGTAGTTTCATAA
CTACTGACCTTAAAAAGTATTGTCTTAACTGGCGATATGAATCAAGTAGTATGTTTGCAG
AGAGACTTAATGAAATTTATGGACTGCCTGGATTTTTCCAGTGGCTTCACAAGATTTTGG
AGAAATCTGTTCTATACGTTAGTGATCCATCTAGTCCACCTGACTTTGATCAACATGTCG
ATATAGAATCAGTCCCAAATGACCATATCTTTATCAAGTACCCGATGGGTGGAATAGAGG
GGTTCTGTCAAAAATTATGGACCATTAGTACAATTCCGTTCCTATATTTAGCAGCTTTTG
ATACAGGGGTTAGAATCTCATCATTGGTTCAAGGCGATAACCAGGCAATTGCAGTAACCA
AAAGAGTTCCGTCATCTTGGAGTTACTCAAAGAAAAGGAAGAATCAACTAAAATAACAA
CACAATATTTTCTTAATTTAAGACAACGCTTACACGATATAGGTCATGAATTGAAAGCAA
ATGAGACTATTATATCCTCTCATTTCTTTGTTTACTCTAAAGGTATTTATTATGATGGAA
TACTTCTCTCCCAGGCACTTAAAAGTATTGCAAGATGTGTCTTTTGGTCTGAAACGATTG
TTGATGAGACTAGGTCAGCTTGCAGTAATATATCTACGACACTCGCAAAGGCAATTGAAA

Figure 2-8

GGGGTTATGATAAATTTGTGGCGTACGCTATCAATATTTATAAAACAATACATCAGGTGT
TGATTGCATTGTCCTTTACGATTAATCCTACTATGACACCAGACATTACAGAACCTTTCT
ACAAGAGTTTAGATCTACTTAAGAATCTAGTTCTGATTCCTGCACCATTAGGGGGCATGA
ACTATATGAACATGAGCAGGTTATTTGTTAGGAATATAGGAGATCCCATTACTGCTTCAT
TTGCTGATATAAAGCGCATGATTGAATGTGGGTTGTTAGGATGTAGTATTCTGTCACAAA
TAATGTACCAAAAATGTGGTTCCTCCAAATACTTAGACTGGGCTAGTGATCCTTATTCAA
TAAACCTTCCTTATAGCCAAAGTATGACCAAGGTTTTAAAAAATGTAACGGCAAGATATG
TACTTATGCATAGTCCCAACCCTATGCTCAAAGATTTGTTCCATGAAAAGTCTCAGGAAG
AAGATGAAATCCTTGCTGAGTTTCTGTTAGACCGACACTTAATAATCCCTAGAGCAGCAC
ACGAGATTTTATCAAATTCAGTAACAGGTGCTAGAGAATCTATAGCAGGTATGCTTGACA
CTACTAAGGGTTTAATCCGTGCTAGTATGTCAAGAGGTGGGTTGACCTCATCACTTGTTT
TAAAATTATCAACATATGATTACCAACAGTTTAGAACATGTCTTGAATGGCTTTATGCTC
CTACTACGGGAATTGCTGTAAGCGTTGATTCTTGCTCTGTATTCTTAGCTAAGACCATCC
GGAAGAGAATGTGGGTTCACCTAACTAAAGGAAGGGAGATTTATGGGTTAGAAGTACCTG
ACATTTGGAATGTATGCAAAACAATATTATTGTTGATCACGAAGATTGTTACTCATGTA
TTCAAGGATCAAGATATTATACATGGTTTTTTGTACCTTCAAATTGTCAACTCGATCAAA
TAAATAAGTCAACAAATTCTCTCCGAGTACCTTATGTTGGATCAACAACTGAAGAAAGGA
GTGATATGAAGTTGTCATATGTGAGGTCACCTAGTCGGCCACTTAAAGCAGCAGTTCGAA
TTGCAGCAGTATATACATGGGCTTATGGTGATGATAATTTGTCTTGGCATGAAGCTTGGT
ATTTAGCAAGGACTAGAGCAAATATTACTTTTGACGAACTCAAATTAATAACACCTATAG
CTACATCTACAAATTTAGCACATAGATTGAGAGATAGAAGCACTCAAGTTAAATATTCAG
GAACTTCTTTAGTAAGAGTGGCACGCTATACAACAATATCTAATGATAATATGTCGTTCA
TTATTAATAACAAAAAAGTCGATACTAATTTTGTCTACCAGCAAGGAATGTTATTAGGTT
TGAGTATATTAGAATATATATTCAGATACTGTACAAGTACTGGACAGTCAAACACTGTAA
TTCACTTACATGCAGATGTTAATTGTTGTATAGTACAGATGACTGATCAGCCTTATACAC
CAAGCTTAACAAAAAAGCTACCTGATATTAGGCCCATTAATAATAAACTGATATATGATC
CGGCTCCTATAATCGATACCGATGCAGCTAGGCTATATTCCCAAAAATACCTGTCACATT
TAATAGATTTCCCAAGTTGGTCAACTACTCAGCTTAACACAGTGTTGGCGAAAGTGGTGG

Figure 2-9

CGGTATCCATTGTAGAATTAATTACAAAAGCTAGTAAAGACCATCTCAATGAGATAATAG

CAGTTGTTGGTGATGATGATATCAATAGCTTTATTACAGAATTTCTACTTGTTGATCCAC

GTCTGTTTACACTATATTTAGGCCAATACACATCATTACAATGGGCATATGAAGTCCATT

ATCATAGACCAGTGGGTAAATACCAGATGGCTGAAGTGTTGCATAATTTGCTGTCAAGAG

CTAGTAGAGGTATATTCAGCATATTGACCAATGCCTTTAGCCACCCCAGAGTCTACAAAA

GATTCTGGGAGTGTGGTTTATTGGAGCCTATTTATGGGCCCTATATAGGAAGTCAAAATC

TACATAATGCAATGATTGATTATATCTATAATGCATACATTACTTATTTGGATGCTTATT

TATCTGATCAAGTAGATGATACTGATATTATAATATGTGAAACAGAGGAGACATGTTTGG

CGAATCGAATTGACAATTATCAAAGCAGACACTTAGCTGTGCTTATAGATCTGTATTGTG

ATTCCACTAGATGTCCCAATATAAAAGGGGCAGATACAATTATGAGAAACTCAATTCTTA

GATCTTTCATTGATAATGAGAGGAGAACAAATCCACTCGGTTTGACATGGAACCTTGACC

CGTTACTCGTGGATCATTTTAGCTGTTCTATTACGTATCTGAGGAGAGGTATTATTAAAC

AGATGAGGTTAAGATTTGATCCAAGTGTATCGTTGGAACTATCTAGGATGATTAAGCCTG

ATGCGGTTTATCAAGCACCTAAAATTCCGTCTTCATGGGCTCTTATAGATATCAACCCTG

AAGTAAATGACCTTAATGTAATTTTTGGAGAGCTGAATAGCAAATGGAAAGACATTCCTA

TTGGACAGATTAGGATACAGAATTATGAAATACATGCATATAGGAGGATCGGAGTTAATT

CAACTGCATGTTATAAAGCTCTAGAGCTATTGTCTGTTCTAAATCGGTTTATGTCTAATC

CATCAGGTGCATTGTTTTAGGTGAAGGAGCAGGATCAATGCTGGTCACATACCGTGCTT

TTGTCCCATTTAAGACAATTTATTATAATAGTGGTATTTCAGTTCAAAATGTTCAGGGCC

AGAGAGAATTGAGTCTATATCCATCTGAAGTGGCACTAGTTGACAACAAAAATCGCTTGG

CTAATGACCCCAATATCAAAGTCTTGTTCAATGGTAAACCAGAGTCTACGTGGGTTGGAA

ACATCGACTGTTTTGCTTATATTCTTAGCCACATTGAGACCTCAAGCTTGACATTGATAC

ATAGTGATATTGAGTCCAGCTTAAGCAAGACGAAGAATAAAATTCTTGAGGAGCTGTGCC

ACATTCTGTCAATGGCACTCATTTTGGGGAAAATCGGATCTTTATTAGTTGTCAAGTTAT

TACCAAGGGTCGGTGACTATACGTATTCATTTTGCAGGTATGCATCGGAATTCTATCAAC

AAAGCCTCCTTGTTTTACCTAGGTTTAGTAACATGTCATCATCTGAGGTTTACTATATAG

GGATTCACCTCAATACAAATCGATTGATTGATCCTGATAGAATAGTACAATACATAGTTA

GAAATTTACAACCAACTCCAGTTACATTTTTGTCCTATATTTTTGAAACTAAGTATAGAA

Figure 2-10

ATAATATGGTTACAAATTATGGACTGTGCTTGTCAGACGGACACAAAAGTGATTACCTGT
CATCAATTACAAAAATAGAGAACGTTCTTCTGTCATGTGGGTTAGAATTGAATGGACCTA
AGATTATACAGCAATTATCAGGACATGACTATGCTAATGGGGAGACTAGTCTAGAATCAA
GTATAATGATATTAGTTAGAGAATATCTTAATGCAACTATACAAGGCCGGGAAACATTAG
GCTTGTTTTCACCTTACCCAGTCTTACATGAGAGTCAGTTAAGAGAAATTAATAAGTGTA
TTGCATTGAAATATGTTGTATATCTACTCTTTTATTCAAGCTCTACATTATCTAGTAAAC
AAATAATGAGTAATCTTAGAAAGGGAATATTGATGTATGATTTGAGAGATGAATTTTTCA
TATCAAGATTGTCAGCAAATTACAAGAAAAGGTGATGTCACAAGAAGTCAAAACTACCT
GGATCTTTAATCTTGATACTCCGACACGAAAAGCATTATATAAGTTAGTAGGTTATTCAT
TAATAATTAATCATGTATGATGATAGAGTATGATTATCCATCTTTAAAAGAGTAAGATAA
TATCAGATGTATGATAACCAATTAAGTATTACTTTTGAATTGAAAGGTTGCTCAATTACA
CGCTTTTTTAGTAATCGGGTTTTTATTCCAATTAGGGCAATTAGAAAAAACTTCAACGGT
TAGTCGAGCCCGAATTCATTCCATATAAGTTATATTTATAATCTTGGATAAGACTTTTGT
TTAGAATTATAACAGTAATACTAATTTATGAATGGAAGACAATTGATATCTAGTGTGAAT
TTTATGTTTATGTGTCTTAAACCTTATACTCACTATAATTGTTCTTTATTTGAGAATTTA
ATTATAGGTGTTTATGTGTTATGTGATGGGAACCATCAGTGCTGACATTATTAATAACCA
TAGGTATTGTATGGGATAGTGTTTATTTACTACCAATGTACAATCTCATATGTCGGACCC
CTCAACCTCCTCCTTATAGTTGAGTTTTCTGGAAAAACACAAAAGATGATCTTGAGTAAT
TGTACGGACCTATAGCTTTCTTTGTCTGGT

Figure 3-1

FmoPV 776U Cats/Hong Kong/2009 16050 bp

ACCAGACAAAGATGTCTGTGACCTATTCTAACGACAAGATTATTACTAAATATTTAGGAA
TAACGATTCCATTAGTGAGGTGAGGAGGAGGAATCAGGTATTCCACAATGTCTAGTCTAT
TGAGGTCACTTGCTGCATTTAAGAGACATAGGGAGCAACCAACAGCACCGTCAGGTTCAG
GTGGTACAATTAAAGGATTGAAAATACAATTATTGTTCCGGTTCCAGGGGATACAGTAA
TTACTACAAGGTCTAATTTGTTATTTAGATTAGTTTATATAATAGGCAATCCGGATACAC
CTTTAAGCACCTCGACGGGAGCAATAATATCATTGTTGACCCTATTTGTCGAATCTCCAG
GTCAATTAATTCAAAGAATTGCTGATGACCCTGATGCAGTTTTTAAATTGGTAGAGGTCA
TTCCTGAAGCTGGTAATCCTGGAGAATTAACTTTTGCATCTCGAGGGATTAATTTAGACA
AGCAAGCTCAACAATACTTTAAATTGGCTGAGAAAAATGATCAGGGGTATTATGTTAGCT
TAGGATTTGAGAACCCTCCAAATGATGACGATATAACATCTAGTCCTGAGATATTCAATT
ATATCCTGGCATCTGTACTTGCACAAGTTTGGATTCTTCTGGCAAAAGCTGTGACTGCTC
CAGATACGGCTGCTGAAGCCGAAAATCGTAGATGGATTAAATTAATGCAACAACGTAGGG
TGGATGGTGAACTGAGATTGAGCAAAGGATGGCTAGATTTAGTGAGAAACAAGATTGCGT
CAGATATTACAATAAGGCGATTCATGGTAGCATTAGTTCTTGACATCAAACGTTCTCCTG
GGACAAGACCCAGGATAGCTGAAATGATTTGTGATATTGATAATTATATTGTAGAAGCAG
GGCTTGCAAGTTTCTTATTAACCATTAAATTTGGCATAGAAACACGTTATCCAGCACTGG
CACTACATGAGTTTTCTGGAGAACTAGCCACTATTGAGGGGCTTATGAAATTGTACCAAT
CTATGGGGGAAATGGCACCATACATGGTAATTCTGGAAAACTCAATCCAAACCAGGTTTA
GTGCAGGGTCTTATCCTCTGCTATGGAGTTATGCAATGGGTGTCGGGGTGGAGCTTGAAA
GATCAATGGGTGGACTCAATTTCACTAGAAGCTTCTTTGACCCGACATATTTCAGACTTG
GTCAAGAGATGGTGAGGAGATCTTCAGGGATGGTTAATAGTTCATTTGCGAGAGAACTTG
GCCTATCTGAGCATGAAACACAACTGGTCAGCCAGATTGTCAATTCGGGAGGTGAATCCG
GGATACCTAAATTTGATGGATTCAGAGCAAATCCAACAACTTTTCTAGGAACCAAGGATA
ACATAGATGATAGAGGTGAAGATCAGTCAAATTCGATATCAGGGTTACCTGGTCCACTAT
TACCCAGCCGTGACCTAGATCTTTCCGGTGATTCATATGGAATTAATAGTGGTGTGAAAA
ATGTCAGTGACAAACTGAATGAAGGAGTAGGTCCAGACCATGATGTGTCCAGTTCTGCCA

Figure 3-2

TGGAAGAATTGAGAAGATTGGTTGAGTCTACCAACAGAATTGACACCAAACAGCCGGAAG
CTTCAGGTGTCACCAACCATTATAATGATACTGACCTTCTAAAATAATATGAGCATACCC
TAATTGATTATGATACAACTCAAATTAAGAAAAACTTAGGACCTCAAGGTTCACAACTGT
TGGCATATCACCAAAACACAGTCAGCTCTTCACCCACCCCATGTCCTCTCACCAAATCCA
ACAAGTCAAACATGGCCTCGAATCTTTACAAGAGATCAAAAGCAACCCTCCGCCTTCCCA
AGATGTCAATCTTGCCAGGGAGATTTACGAATCCATTAGACAAACAGGAACATCTTCAGT
GCAAGGAGGAGCCATTGCGGGAAATAATATTACGTCAGGGGGTAACAATGACTCAATGTA
TAGCCAAGGACCAAGTCCTCCTATTTCAAGTATTAACAAGAATATCGAAGGACCTACTGG
ATTCGATCATTCAGGACTATGGGATCCAGAGGGTAACCTCTGCATGCTATTCGAAAGCGA
TGATGATGAAAACCATTATTCAGAGATTAATGGCCGGTCTTCCACTATCGAAGGACTGGA
TGAACAGGATAATGAGAACTCAATTATTAAACAACCAGGAAATCAGTGTACTGAGGGAGT
GTCTAAGACTGATTCATCTCCTAGTTCCCAGGAAACTACACTATCTGTTGGGGGATCTGA
TATACCTGGGACAGGAATATCAACCTGTGCCTCTTTGGATATAACTGTAAATGAACTCGA
AGATGCAACTGTAAGAAATAGCAACAATATGAAAGGGAACTGGCCAATTCCTAAATTACT
AGTTAAGCCGCCACCTAGGGTAAAATCAAGTGTTGATCACAGTAATCCATTAAAAGGGGC
CACAGAAGGGAAATTAGCCTCACCTGGGATGGAGACTACATTATTCGAGAAGAGTGGTGC
AACCCCATCTGTACACCCATATACTCAACCTGCAAGCGACTTCAATGTAGGTGCAAGCAG
TGTCCATCAACCTGCCCTAAATGTGAATAATAATTGCAATGACGGTAGGGTAACAGCGCC
TAACTCACATAAAGATATCGAGGGTAAGTCTGAAATATCTATTCAAGATATATATAACTT
GATTCTTGGATTTAAGGATGATTACAGGAAATTATCAAACAAATTAGATATGGTATTAGA
GATGAAACAAGACATTGACAATCTTAAAAAGAATAGTGCTAAAGTGCAATTAGCTCTATC
AACTATTGAGGGACATCTATCCAGTGTTATGATTGCTATCCCTGGTTCAGGTATTGATTC
CACAGGGGATGAGGAAAAGGACCAGATAAATTCTGACTTAAAACCACTGCTAGGAAGGGA
TCATTGTAGAGCATTTCGAGAAGTTACCAATCCTCTAGATGAGTCTTCACTAGCCAATTC
TCCAACAAAACATGTTGCCAAGGTAAACAAGAACTGCACTCTTCAGAAGATCAACAAGAA
CGAAACATCTGCAATCAAATTTGTTCCTAGTGACAGTCATGCAAGCACATCAACCATCAG
GTCAATTATCAGGTCATCTAATCTCGATCAGGATTTGAAAACAAAATTGCTCACAATTTT
ATCCCAGATAAGAGGTGTAGACAATATTAGAGAATTCTATGAAAGGTTATGATATTAAT

Figure 3-3

AAAGAATAAGAATTAAATATTACAAATCTACATGCATTATAGGTTGTAATTGTCTTCAAT
AAGATTTGGTCAGTTTCATATATATGGTTATTGATTTGTGATAATTATAAAAAACTTAGG
AGCTAAAGATTACTCAGTCATATACAGCATGACTGAGATATTCAACCTTGATGAGAGCTC
ATGGTCAGTCAAAGGGACACTAGATCCGCTAACACCTGATACCTATCCTGATGGTCGACT
AGTGCCTAAAGTTCGAGTTATCGATCCGGGTCTAGGAGATCGCAAGAGTGGGGGGTATAT
GTATCTACTTCTTCATGGTGTCATAGAAGATAGTGAGACTATAATTAGTCCGAAAGGAAG
AGCATTTGGTGCATTCCCATTAGGAGTGGGTCAATCAACTGAAAACCCGGAAGACTTGTT
TAAGGAAATATTAACTCTCAACATCGTGACTCGTAGGACTGCTGGATTTAATGAGAAATT
GGTTTATTATAATACCACACCTCTACATTTACTGACCCCCTGGAAGAAAGTGTTGGCATA
TGGAGGCATTTTTAATGCTAATCAGGTCTGCAGTGATACAAGTTCCATACCAATAGACAT
TCCACAAAAATTTAGGCCAGTATATTTGACTGTTACAAAATTATCTGATGATGGCTATTA
TCAGATCCCAAAGATGATTCAAGATTTCAAATCGTCAAATTCTGTTGCATTTAACATCCT
TGTGCATCTGTCAATGGGCACAAATTTACTTGACCAATCCAAGGACCCTAGATTAAGAAG
TGCTGCAGAAACTGTGATCACATTTATGATTCATATTGGAAACTTTAAACGGAAGAGTAA
TAAGTCTTACTCACCTGAATATTGCAAGAGGAAAATAATGAGGCTTGGTTTAATATTCTC
ATTAGGTGCAATTGGTGGCACAAGCTTGCATATTAGATGTACAGGTAAGATGAGCAAACG
ACTACAGGCTTATTTGGGATTCAAAAGGACTTTATGTTACCCTTTGATGTATGTTAATGA
AGGGCTGAACAAGACCCTGTGGAGAAATGAATGCAGAATAGAGAAGGTTCAAGCAGTCCT
ACAGCCATCAGTCCCGAATGAGTTTAAGATATATGATGATGTTATTATTGATAATACCAA
TGGTCTCTTCAAGATTAAATAGACTATAACAATAATAAACCGCCACCAAATGGTACCATG
TATTCAAGTGTACACTGACAATTGCGAATAAAATATACCAGATTAACAACAGTATAGAGT
TAAGATCTAATTGATATGTGGGTTGGTACTCGATCATTTATTAGCTCTACTGATTATCTA
TATCCTAAATCACCAAATATAAGAGCATCAACAGGTAATAAGTTTGGGATTGCTAGATTA
ATACTTAATTCTCAGAACTAGAATACACAGATTGTCAAACCTATAATCTTGTTAGATTCA
TTAAAGTTAGATTCTTGTAATGTTGATCAATTATCACTCGAGCAATTATAAAAAACTAAG
GACCTAATGTAATAGGAGCCCAAATTCCATCCAGTGAGCTTTAAATCGCCATGCTTAAAC
ATTAATTTGTCCAGGGCCTATCTAACTCAGAACAAAGATCACAACTAGAGTCTGAAGGAG
TGGGTTAAGTCTGAATAATTATTAAGAGTTGAGATTTAAAACTGATTCCTTCTTAAATTT

Figure 3-4

AGAATTTTAATAATATATCATCCATTCAATATCATGAACAGGATTAAGGTTATAATAATT
AGTTCTTTATTACTATCAGATATTACGATTGCACAAATAGGTTGGGATAATTTGACTTCG
ATTGGAGTTATAAGTACTAAGCAATACGACTATAAAATAACTACTCTGAACACTGACCAG
TTAATGGTTATAAAGATGGTTCCTAATATATCATCAATCATTAATTGCACTAAACTCGAA
TTAACAAAATACAGAGAGTTAGTCTCAGGGATCATTAGACCAATAAATGAGTCATTAGAA
TTAATGAATTCATACATTAACATGAGAGCAGGTTCAGAGAGATTCATAGGGGCTGTAATA
GCTGGTGTAGCCTTAGGAGTGGCAACTGCAGCACAAATAACATCAGGGATTGCCCTACAT
AATTCAATTATGAACAAAAACAGATACAAGAATTGAGGAAGGCTCTTAGTACTACTAAC
AAAGCAATTGATGAAATAAGGATTGCAGGTGAAAGAACATTAATAGCAATTCAAGGTGTA
CAGGATTATATTAATAATATAATTATCCCTATGCAGGACAAACTCCAATGTGATATTTTA
TCATCACAACTTTCTGTTGCTTTACTCAGATATTATACAAATATATTAACAGTTTTTGGG
CCAAGTATACGGGATCCTATTACTAGTACAGTTTCAGTACAGGCACTCAGTCAAGCATTC
AATGGTAATCTTCAGGCATTGCTTGATGGATTGGGATATACTGGGAAAGACTTACGTGAT
CTTCTAGAGAGTAAATCTATCACTGGCCAGATAATTCATGCAGATATGACTGATTTGTTC
CTTGTTCTGAGAATAAATTATCCTTCTATAACTGAGATGCAGGGAGTAACAATATATGGG
CTCAATTCAATTACATATCATATTGGGCCTGAAGAGTGGTATACCATTATGCCTGATTTT
ATTGCTGTTCAGGGTTTTTTAATATCTAATTTTGATGAGAGAAAGTGTTCAATAACTAAA
TCAAGTATATTGTGCCAACAAAATTCAATTTACCCAATGTCAACAGAGATGCAAAGATGT
ATTAAGGGCGAAATAAGATTCTGTCCAAGATCCAAGGCAATTGGGACATTAGTCAATCGG
TTTATATTGACCAAAGGTAATTTGATGGCTAATTGTTTAGGGATTATATGCAGATGTTAT
ACTTCAGGCCAAGTTATAACACAAGACCCTAGTAAATTGATCACGATAATATCGCAAGAG
GAGTGCAAGGAAGTTGGTGTTGATGGTATCCGTATTATGGTAGGACCTAGAAAATTACCA
GATATTACCTTTAACGCTAGGTTGGAAATTGGTGTACCGATATCATTAAGCAAATTAGAT
GTCGGGACTGATTTAGCGATTGCTTCAGCTAAACTTAATAATTCTAAGGCATTGTTAGAG
CAATCAGATAAGATTTTGGATTCAATGTCTAAATTGGATTCTATGAACTCAAGAATAATA
GGGTTAATCTTAGCAATTATGATAATCTTTATAATCATTATTACTATTATCTGGATCATG
TATAAGAAATGTAAGAATAAAGATAATAAATTCAGTACTTCAATTGAACCGCTCTACATA
CCCCCTTCTTATAACTCACCTCATAGTGTGGTTAAATCTATTTGAGTACTGACTATATGA

Figure 3-5

TCCACTGTAATAAGTCCAATGAAAGTATCAATTAATAATATTGGTAGTGCAATAAGTATT
GATTGTATAATATACTCCTTTAAACTAGATAGTGATAAAGGGTTATAGATGATTTCAGTC
ACTTTAATATAATCATATATTGGTTTTATTATCTTGCATAACTATTATGTAATTGAATTA
TGTATCATCAATTAATAGCTTAATAATATGTTTTAATATACTTATATTGATAGATAAATG
TGTTATATTGTAATCAAGGAGTTGGTATTTAGAAGAGGAAAGAGTTAAATTTGTTGTTAA
TTAGTTATTGTGTATTCAATTAGAAAAAACTTAGGAATCCATGTTAATAGAAATTTATTA
TCATGGAGTCCAACAATATTAAGTACTACAAAGATTCTAGCCGGTACTTTGGTAAAATAT
TAGATGAACACAAAACAATTAATAGTCAATTATACAGTTTGAGTATCAAGGTAATTACCA
TTATTGCTATTATTGTAAGCCTGATTGCAACAATAATAACTATTATCAATGCCACTAGTG
GGAGAACTACCCTAAATAGTAATACAGACATACTACTCAGCCAACGAGATGAGATTCATA
ACATCCAAGAAATGATATTTGATCGTATTTATCCTTTGATAAATGCTATGAGTACAGAGC
TAGGACTTCATATTCCTACCTTATTGGATGAACTTACTAAAGCGATTGACCAGAAAATTA
AAATAATGCATCCTCCTGTGGACACTGTGACTTCTGACCTTAATTGGTGCATCAAACCCC
CTAATGGAATTATCATAGACCCAAAAAGTTATTGTGAGAGTATGGAATTGTCTAAAACTT
ATGAATTGTTACTTGACCAGTTAGATGTCTCAAGAAAGAAATCACTTATTATAAATAGAA
AGAATATTAACCAATGCCAATTAGTTGATAATTCAAAGATCATTTTTGCCACTGTCAACA
TACAATCTACACCGAGGTTTTTAAACTTTGGTCACACGGTCAGCAATCAACGTATAACAT
TTGGTCAAGGAACATATAGTAGTACTTATGTTATAACTATCCAAGAAGATGGAGTAACTG
ATGTTCAATATCGAGTGTTTGAGATCGGATATATTTGTGATCAGTTTGGTGTATTCCCCT
CCTTAATAGTATCGAGAGTGTTGCCGATACGCATGCTATTAGAAATGGAATCCTGTACCT
TGACAAGTGATAGACTAGGCGGGTATTTTTTATGTATGAATACACTGACACGATCTATAT
ACGATTATGTTAGCATAAGGGATTTGAAATCACTTTATATAACAATCCCTCATTATGGTA
AAGTTAATTATACTTACTTTAATTTTGGTAAGATCAGGAGCCCACATGAGATTGATAAAA
TTTGGTTAACATCTGATAGAGGCCAAATTATCTCTGGTTATTTTGCAGCATTTGTTACCA
TTACAATTCGGAACTATAATAATTATCCCTACAAATGCTTAAATAACCCATGTTTTGACA
ACTCTGAGAATTACTGTAGAGGATGGTATAAAAACATAACAGGAACTGATGATGTTCCGA
TATTAGCATACTTATTGGTTGAAATGTATGATGAAGAGGGACCTTTAATTACACTTGTGG
CAATACCACCTTACAATTATACAGCTCCATCTCATAATTCTCTTTACTATGATGACAAAG

Figure 3-6

```
TTAATAAATTAATAATGACTACATCTCACATAGGTTATATTCAAATCAATGAGGTGCATG
AGGTAATTGTTGGCGATAATTTGAAGGCTATCCTCTTAAACAGATTATCTGATGAACATC
CTAACCTGACTGCCTGTAGACTCAATCAGGGTATTAAGGAGCAATACAAGTCTGACGGAA
CAATAATTTCAAATTCTGTACTTATTGATATACAAGAACGAATGTACATTACAGTTAAAG
CTATTCCACCAGCAGGTAACTATAACTTTACAGTTGAGTTGCATTCTAGATCAAACACAT
CTTATGTATCGTTGCCAAGACAGTTTAATGCTAAGTATGACAAATTACATCTTGAGTGCT
TTAGCTGGGACAAATCCTGGTGGTGTGCTCTGATACCTCAGTTTTCATTAAGTTGGAATG
AATCCCTTTCTGTTGATACTGCCATTTTCAATTTAATAAGCTGTCAATGAACACATCAAT
CTATAGTTGATAGTTGTCAAAACATTAGCCAATTTGGGTTAAAGAAATAGGAAAATGAAA
TTATCAATATCTAATTAGATGTATGTTCAAGCTAAATTACAAAAAACTTAGGAGTCAGAG
ATTTCGTTGCAATGGAGCAGTCAGACTACCAAGATATTCTATACCCGGAAGTACATCTTA
ACAGTCCTATAGTAATTTCCAAATTAGTAGGTATTTAGAATATGCCCAAATTGGTCATA
ATCAACAATTATCAGACCGTACAATTATCAAGAATATTCAATTTAGATTAAGGAACGGAT
TTAATAGTTCAAGGGTACAGGTACTATCAACTATGGGTGAAATTATCAACAAAATTAGAA
ATAAATATCCTAATTATTTACACATACCTTACCCTGAATGCAACCAAAAACTATTTCGAA
TAGTAGATCCAGAACTAACATCAAAATTAGAATCTCTTCTAAACAAAGGTGACACACTGT
ATCTCAAGATTCGATCAGATATCATAAAGTGTTTTGATAGATTGAAAATGAAAATGAACA
TAAAGAATGATCTTCTCAATGACAATAGTCAATTGATTCTAGATCTTCCTTTAATTATCA
AAGGATCTCAGTGGTTCTTCCCTTTTTATTTTGGTTTTCTATCAAAACTGAAACTAGAA
GCTGTATTCGCCAAAATCAAAAGACTCGTGTTAGATCACAATATCGGCCTCACTTATCAG
AGACTAAGAGAATTACATTGGTTGTTACATCTGATCTGATTACAATATTTGATCATATTA
ATAAATGTATATTTTATTTGACTTTTGAGATGCTGTTAATGTATTGCGATGTGATAGAAG
GTCGGTTAATGACTGAAACAGCTATGAGCTTGGACTGTCGGTTTACCAATCTATTGCCAA
GAGTGCAATATATGTGGGATTTACTAGATGGAATGTTTGAAAGTTTAGGCAATCAATTAT
ATTCAGTTATTGCATTATTAGAGCCTCTTTCTCTTGCTTATTTGCAATTGATAGATGCAG
ATCCACAGATTCGGGGAACATTCCTGCATCACTGCTTTTCCGAGTTAGAAGAAATTATAT
TTGACAAAACCCCTTTTGATCCTTTCGTATATGAAAATTTAATTAATGGACTTGATTACA
TTTATTTGACAGATGATATTCATCTAACTGCAGAAGTTTTTTCTTTTTTTAGAAGTTTTG
```

Figure 3-7

```
GTCATCCTTTTTTAGAAGCACAAAATGCTGCCAATAATGTAAGGAAGTATATGAATAAAC
CTAAGGTAATCTCATATCAGACTTTAATGCAAGGACATGCGATTTTTTGCGGTATTATAA
TAAATGGATTTAGAGATCGCCACGGGGGAACATGGCCTCCTGTAGAGTTACCAAATCATG
CATCTGCTGTAATTAGAAATGCCCAGTTATCTGGAGAAGGGTTAACATCTGAACAATGTG
CTCAACACTGGAGATCCTTCTGTGGATTTAGATTTAAATGTTTATGCCATTGAGTCTAG
ACAGTGACCTTACAATGTACCTTAGAGACAAGGCGTTATCACCTGTCAGAAATGAGTGGG
ATTCAGTTTATGCTAAGGAGTATTTAAGATATAATCCAGGATTACCCACAAGTTCCAGAA
GATTGGTAAATGTATTCTTAGAAGATGATAAGTTTGATCCATATGAAATGATCATGTACG
TGATAAATGGTGATTACTTAAGAGACAAAGAGTTTAACCTTTCATACAGCCTTAAAGAGA
AAGAAATTAAAGAGGTAGGTCGATTGTTCGCTAAAATGACCTATAAAATGAGGGCTTGTC
AAGTAATAGCTGAAAACCTGATTGCCAATGGAGTAGGGAAGTTTTTCAAAGATAATGGAA
TGGCAAAAGATGAACATAAATTAACTAAAACGTTACACAAATTAGCCATTTCAGGTGTAC
CTAAAGATAATTCTCAACTTTATTTAGATGAATGTTGGGAGCAAGTAATTCGACAATGTT
CAAGTAGTACACAGATAAGGGAACAGGCTATGAATTCACAATCAAATAGGGAAATTGAAT
CAAAGTCTTCTAGGGCACGTCTTAATAATAGAGATATCTTAAAGGGCAAGAGAGATTCGA
ACAAACAAATAAAGTATCCTTCAAACACCGAGTATTATGAGACTATCAGTAGTTTCATAA
CTACTGACCTTAAAAAGTATTGTCTTAACTGGCGATATGAATCAAGTAGTGTATTTGCAG
AGAGACTTAATGAGATTTATGGACTGCCTGGATTTTTCCAGTGGCTTCACAAGATTTTGG
AGAAATCTGTTCTATACGTTAGTGATCCATATAGTCCACCTGACTTTGATCAACATATCG
ATATAGAATCAGTCCCAAACGACCATATCTTTATCAAGTACCCGATGGGTGGAATAGAGG
GGTTCTGTCAAAAATTATGGACCATTAGTACAATTCCGTTCCTATATTTAGCAGCTTTTG
ATACAGGGGTTAGAATCTCATCATTAGTTCAAGGCGATAACCAGGCAATTGCAGTGACCA
AAAGAGTTCCGTCATCTTGGAGTTATTCAAAGAAAAGGAAGAATCAACTAAAATAACAA
CACAGTATTTTCTTAATTTAAGACAACGCTTACACGACATAGGTCATGAATTGAAAGCAA
ATGAGACTATTATATCCTCTCATTTCTTTGTTTACTCTAAAGGTATTTATTATGATGGAA
TACTTCTCTCCCAGGCACTTAAAAGTATTGCAAGATGTGTCTTCTGGTCTGAAACGATTG
TTGATGAGACTAGGTCAGCTTGCAGTAACATATCTACGACACTCGCAAAGGCAATTGAAA
GGGGTTATGATAAATTTGTGGCGTACGCTATCAATATTTATAAAACAATACATCAGGTGT
```

Figure 3-8

TGATTGCATTGTCCTTTACGATTAATCCTACTATGACACCAGACATCACAGAACCTTTCT
ACAAGAGTTTAGATCTACTTAAGAATCTAGTCCTGATTCCTGCACCATTAGGGGGCATGA
ACTATATGAACATGAGCAGGTTATTTGTTAGGAATATAGGAGATCCCATTACTGCTTCAT
TTGCTGATATAAAGCGCATGATTGAATGTGGGTTGTTAGGATGTAGTATTCTGTCACAAA
TAATGTACCAAAAATGTGGTTCCTCTAAATACTTAGACTGGGCTAGTGATCCTTATTCAA
TAAACCTTCCTTATAGCCAAAGTATGACCAAGGTTTTAAAAAATGTAACGGCAAGATATG
TACTTATGCATAGTCCCAACCCTATGCTCAAAGATTTGTTCCATGAAAGTCTCAGGAAG
AAGATGAAATCCTTGCTGAGTTTCTGTTAGACCGACACTTAATAATCCCTAGAGCAGCAC
ACGAAATTTTATCAAATTCAGTAACAGGTGCTAGAGAATCTATAGCAGGTATGCTTGACA
CTACTAAGGGTTTAATCCGTGCTAGTATGTCAAGAGGTGGGTTGACCTCATCACTTGTTT
TAAAATTATCAACATATGATTACCAACAGTTTAGAACATGTCTTGAATGGCTTTATGCTC
CTACTACGGGAATTGCTGTAAGCGTTGATTCTTGCTCTGTATTCTTAGCTAAGACCATCC
GGAAGAGAATGTGGGTTCACCTAACTAAAGGAAGGGAGATTTATGGGTTAGAAGTACCTG
ACATTTTGGAATGTATGCAAAACAATATTATTGTTGATCACGAAGATTGTTACTCATGTA
TTCAAGGATCAAGATATTATACATGGTTTTTTGTACCTTCAAATTGTCAACTCGATCAAA
TAAATAAGTCAACAAATTCTCTCCGAGTACCTTATGTTGGATCAACAACTGAAGAAAGGA
GTGATATGAAGTTGTCATATGTAAGGTCACCTAGTCGGCCACTTAAAGCAGCAGTTAGGA
TTGCAGCAGTATATACATGGGCTTATGGTGATGATAATTTGTCTTGGCATGAAGCTTGGT
ATTTAGCAAGGACTAGAGCAAATATTACTTTTGACGAACTCAAATTAATAACACCTATAG
CTACATCTACAAACTTAGCACATAGATTGAGGGATAGAAGCACTCAAGTTAAATATTCAG
GAACTTCTTTAGTAAGAGTGGCACGCTATACAACAATATCTAATGATAATATGTCGTTCA
TTATTAATAACAAGAAAGTCGATACTAATTTTGTCTACCAGCAAGGAATGTTATTAGGTT
TGAGTATATTGGAATACATATTCAGATACTGTACAAGTACTGGACAGTCAAACACTGTAA
TTCACTTACATGCAGATGTTAATTGTTGTATAGTACAGATGACTGATCAGCCTTATACAC
CAAGTTTAACAAAAAGCTACCTGATATTAAGCCCATTAATAATAAACTGATATATGATC
CGGCTCCTATAATCGATACTGATGCAGCTAGGCTATATTCCCAAAAGTACCTGTCACATT
TAATAGATTTCCCAAGTTGGTCAACTACTCAGCTTAACACAGTATTGGCGAAAGTAGTGG
CGGTATCTATTGTGGAATTAATTACAAAAGCGAGTAAAGACCATCTCAATGAGATAATAG

Figure 3-9

CAGTTGTTGGTGATGATGATATCAATAGCTTTATTACAGAATTTCTACTTGTTGATCCAC

GTCTGTTTACACTATATTTAGGCCAATACACATCATTACAATGGGCATATGAAGTCCATT

ATCATAGACCAGTGGGTAAATACCAGATGGCTGAAGTGTTGCATAATTTGCTGTCAAGAG

CTAGTAGAGGTATATTCAGTATATTGACCAATGCCTTTAGCCACCCCAGAGTCTACAAAA

GATTCTGGGAGTGTGGTTTATTGGAGCCTATTTATGGGCCCTATATAGGAAGTCAAAATC

TACATAATGCAATGATTGATTATATCTATAATGCATACATTACTTATTTGGATGCTTATT

TATCTGATCAAGTAGATGATACTGATATTATAATATGTGAAACAGAGGAGACATGTTTGG

CGAATCGAATTGACAATTATCAAAGCAGACACTTAGCTGTGCTTATAGATCTGTATTGTG

ATTCCACTAGATGTCCCAATATAAAGGGGCAGATACAATTATGAGAAATTCAATTCTTA

GATCTTTCATTGATAATGAGAGGAGAACAAATCCACTTGGTTTGACATGGAACCTTGACC

CGTTACTTGTGGATCACTTTAGCTGTTCTATTACGTATCTGAGGAGAGGTATTATTAAAC

AGATGAGGTTAAGATTTGATCCAAGTGTATCGCTGGAACTATCTAGGATGATTAAACCTG

ATGCGGTTTATCAAGCACCTAAAATTCCGTCTTCATGGGCTCTTATAGATATCAACCCTG

AAGTAAATGACCTTAATGTAATTTTTGGAGAGCTGAATAGCAAGTGGAAAGATATCCCTA

TTGGACAGATTAGAATACAGAATTATGAAATACATGCATATAGGAGGATTGGAGTTAATT

CAACTGCCTGTTATAAAGCTCTAGAGCTATTATCTGTTCTAAATCGGTTTATGCCTAATC

CATCAGGTGCATTGTTTTAGGTGAAGGAGCAGGATCAATGCTGGTCACATACCGTGCTT

TTGTCCCATTTAAGACAATTTATTACAATAGTGGTATTTCAGTTCAAAATGTTCAGGGCC

AGAGAGAATTGAGTCTATATCCATCTGAAGTGGCACTAGTTGACAACAAAAATCGCTTGG

CTAATGACCCTAATATCAAAGTCTTGTTCAATGGTAAGCCAGAGTCTACGTGGGTTGGAA

ACATCGACTGTTTTGCTTATATTCTTAGCCACATTGAGACCTCAAGCTTGACATTGATAC

ATAGTGATATTGAGTCCAGCTTAAGCAAGACGAAGAATAAAATTCTTGAGGAGCTGTGCC

ACATTCTGTCAATGGCACTCATTTTGGGGAAAATCGGATCTTTATTAGTTGTTAAGTTAT

TACCAAGGGTCGGTGACTATACGTATTCATTTTGCAGGTATGCATCGGAATTCTATCAAC

AAAGCCTCCTTGTTTTACCTAGGTTTAGTAACATGTCATCATCTGAGGTTTACTATATAG

GAATTCACCTCAATACAAATCGATTGATTGATCCTGATAGAATAGTACAATACATAATTA

GAAATTTACAACCAACTCCAGTTACATTTTGTCCTATATTTTTGAAACTAAGTATAGGA

ATAATATGGTTACAAATTATGGACTGTGCTTGTCAGACGGACACAAAAGTGATTACCTGT

Figure 3-10

CATCAATTACAAAAATAGAGAATGTTCTCCTGTCATGTGGGTTAGAATTGAATGGACCTA
AGATTATACAGCAATTATCAGGACATGACTATGCTAATGGGGAGACTAGTCTAGAATCAA
GTATAATGATATTAGTTAGGGAATATCTTAATGCAACTATACAGGGCCGGGAAACATTAG
GCTTGTTTTCACCTTACCCAGTCTTACATGAGAGTCAGTTAAGAGAGATTAATAAGTGTA
TTGCATTGAAATATGTTGTATATCTACTCTTTTATTCAAACTCTACATTATCTAGTAAAC
AAATAATGAGTAATCTCAGAAAGGGAATATTGATGTATGATTTGAGAGATGAATTTTTCA
TATCAAGATTGTCAGCAAATTACAAGAAAAGGTGATGTCACAGGAAGTCAAGACTACCT
GGATCTTTAATATTGATACTCCGACACGAAAGCATTATATAAGTTAGTAGGTTATTCAT
TAATAATTAATCATGTATGATGATAGAGTGTGATTATCCATCTTTTAGAGAGTAAGATAA
TATCAGATGTATGATAACCAATTAAGTATTGCTTTTGAATTGAAAGGTTGCTCAATTACA
CGCTTCTTTAGTAATCGGGTTTTTATTCCAATTAAGGCAATTAGAAAAAACTTCAACAGT
TAGTCGAGCCCGAATTCATTTCATATAAGTTATATTTATAATCTTGGATAAGACTTTTGT
TTAGAATTATAACAGTAATACTAATTTATGAATGGAAGACAATTGATATCTAGTGTGAAT
TTCATGCTTATGTGTCCTTAACCTTATACTCACGATCATTATTCTTTATTTGAATTTA
ATTATAGGTGTTTATGTGTTATGTGATGGGAACCATCAATGCTGACATTATTAATAACCA
TAGGTATTGTATGAGATAATGTTTATTTACTACCAATGTACAATCTCATATGTCGGACCC
CTTAACCTCCTCCTTATAGTTGAGTTTTCTGGAAAAACACAAAAGATGATCTTGAGTAAT
TGTACGGACCTATAGCTTTCTTTGTCTGGT

Figure 4-1

FmoPV M252A Cats/China/2010 16050 bp

ACCAGACAAAGATGTCTGTGACCTATTCTAACGACAAGACTATTATTAAATATTTAGGAA

TAACGATTCCATTAGTGGGGTGAGGGGAAGGAATCAGGTATTCCAGAATGTCGAGTCTAC

TGAAGTCACTTGCCGCATTTAAAAGACATAGAGAGCAACCAACTACACCGTCAGGTTCAG

GTGGTACAATTAAAGGATTGAAAAACACAATTATTGTTCCAGTACCAGGGGATACAGTAA

TTACCACGAGGTCTAATTTGTTATTTAGATTAGTTTATATAATAGGCAATCCAGATACGC

CTCTAAGCACCTCGACGGGAGCAATAATATCATTATTGACCCTATTCGTCGAATCCCCAG

GTCAATTAATTCAAAGAATTGCCGATGACCCTGATGCAGTTTTTAAATTAGTAGAGGTCA

TTCCTGAAGCTGGTAATCCTGGAGAATTGACTTTTGCATCTCGAGGGATTAATTTAGATA

AGCAAGCCCAACAATACTTTAAACTGGCTGAGAGAAATGATCAGGGGTATTATGTTAGCT

TAGGATTTGAGAACCCACCAAACGATGATGATATAACATCTAGTCCTGAGATATTTAATT

ATATTTTGGCATCTGTACTTGCGCAAGTTTGGATTCTTCTGGCAAAAGCTGTGACTGCTC

CGGATACAGCTGCTGAAGCTGAAAACCGTAGATGGATTAAATTGATGCAACAACGTCGGG

TGGATGGTGAATTAAGATTGAGTAAAGGATGGCTAGATTTGGTGAGAAATAAAATTGCGT

CAGATATTACAATAAGACGATTTATGGTGGCATTAGTCCTTGACATCAAACGTTCTCCTG

GGACAAGACCCAGAATAGCTGAAATGATTTGTGATATTGATAATTATATTGTAGAGGCAG

GGCTTGCAAGTTTCTTGTTAACTATTAAATTTGGCATAGAGACACGTTATCCAGCATTGG

CATTGCATGAGTTCTCTGGAGAATTAGCTACTATTGAGGGACTTATGAAATTGTACCAAT

CTATGGGAGAAATGGCACCATATATGGTAATTCTGGAAAATTCAATTCAAACCAGGTTTA

GTGCCGGGTCTTATCCTTTGCTATGGAGTTATGCCATGGGCGTTGGTGTGGAGCTTGAAA

GATCGATGGGTGGACTTAATTTTACTAGGAGCTTCTTTGACCCTACGTACTTCAGACTTG

GTCAAGAGATGGTGAGAAGATCTTCAGGGATGGTTAATAGTTCATTTGCGCGAGAACTTG

GGCTATCTGAACATGAGACACAACTTGTCAGCCAAATTGTTAATTCGGGAGGTGAATCTG

GGATACCTAAATTTGATGGATTCAGAGCAAATCCAACAACCTTTCTAGGAACCAAAGATA

ATATTAATGATAAAGGTGAGGATCAGTCAAGTTCAGTATCAGGGTTACCTGGTCCATTAT

TACCCAGTCGTGACCTAACTCATCCAGGTGATTCATATGGAGCAGATGATGGTGTGAAAA

ATGTCAGTAATAAATTGAGTGAAGGAATAAGTCCAGATCATGATGTGTCTAGCTCTGCCA

Figure 4-2

```
TGGAAGAATTGAGGAGGTTAGTTGAGTCTACCAACAGAATTGACACCAAAAAGCCGGAAG
CTCCAGGTGTCACCAACCATTATAATGACACCGACCTTTTAAGATAATATGAGTATATCT
TATTTGATCATCATACAATTCAAATTAAGAAAAACTTAGGACCTCAAGGTTCACAACTGT
TGGCACATCACTGAGATATAGTCAATTCTTTACCCACCACATGTCCTCTCACCAGATTCA
ACAAGTCAAACATGGCCTCGAATCTTTACAAGAGATCAAAAACAACCCTCCGTCTTCCAA
AGATGTCGATCTTGGCAGGGAGATTTACGAATCCATTAGACAAACAGGAACATCTTCAGT
GCAAGGAGGAGCCATTGCGGGAGATAATATTACGTCAGGGGGTAACAATCACTCAATGCA
TAGCCAAGGACCAAGTTCTCCTATTTCAAGTGTTAACAAGAATATCGAAGGATCTACTGG
ATTCGATCATTCAGGACTATGGGATTCAGAGGGTAACCTCTGCATGTTATTCGAAAGCGA
TGATGATGAAAACCATTATTCAGAGATTAATGGCCGGTCTCCCGCTATCGAAGGATTGGA
TGAACAGGATACTGAGAACTCAATTATTAAACAACCAGGAAATCAGTGTACTGAGGGAGT
GTCTAAGACTAATTCACCTTCTAGTCCCCAGGAAACTACACTATCTGTTGGGGATCTAA
TATACCTGGGACAGGAATATCAACCTGTGCCTCTTTGGATATAACTGTAAATGAACTTGA
GGATGCAACTATAAGAAACAGCGACAATATGAAGGGAAACTGGCCAATTCCGAAATTACT
TGTTAAGCCGCCACCTAGGGCAAGATCAAGCATTGATCATAGCAATCCATTAAAAGGGGC
CACAGGAGGGAAATTAGTCTCACCTGGGATGGAGACTACATTATTCGAGAAGAGTGGTGC
AACCCTATCTGTACACCCATCTACTCAACCTGCAAGCGACTTCAATGTAAATGTAAGCAA
TGTCCATCAACCTGCCCCAAGTGTGAATAATGATTACAGAGACAGTGAGGTAACAGTGCT
TAACTTACATAAAGATATTGAGGATAAGTCTGAAATATCTATACAGGATATATATAACTT
GATTCTTGGATTTAAGGATGATTATAGGAAATTATTAAACAAATTAGATATGGTATTAGA
GATGAAACAAGACATTGACAATCTAAAAAGAGTAGTGCTAAGGTACAATTGGCATTGTC
AACTATTGAAGGACATCTATCTAGTGTTATGATTGCCATCCCTGGTTCAGGTATTGATTC
CACTGGGGAAGAGAAAAGGATCAGATGAATTCTGACTTAAAACCATTATTAGGGAGGGA
TCATTGTAGAGCATTTCGAGAAGTTACTAATCCTCTAGATGAGTCGTTACTGGCCAATTC
TCCAACAAAACATGTTGCCAAAATAGACAAGAATTGCACTCTTCAGAAAATCAACAAGAA
TGAAACATCTGCAATCAAGTTTGTTCCCAATGATAGTCATGCAAGCACATCGACCATCAA
ATCAATTATCAGGTCATCTAATCTCGATCAGGATTTGAAGACAAAATTGCTCACAATTCT
ATCCCAAATTAGAGGGACAGAGAATGTTAAAGAATTTTATGAGAAGGTCATGATATTGAT
```

Figure 4-3

AAAGAATAAGAACTAAATATCACCAATCTACATGCACTATGAGTTGTAATTGTCTTCAGT
AGAATTTAGTTGATTTAATACATACTGTTGTTGATTTGTAATAATTATAAAAAACTTAGG
AGCTAAAGGCTACTCAGTCATATACAACATGACTGAGATATTCACTCTTGATGAGAGCTC
ATGGTCAATCAAAGGAACACTTGATCCGCTAACACCTGATATCTATCCTGATGGGAGACT
CGTGCCCAAAGTTCGGGTTATCGATCCGGGCCTAGGAGATCGCAAGAGTGGGGGATATAT
GTATCTACTTCTCCATGGTGTCATAGAAGACAGCGAGAACATGATTAGTCCAAAGGGGAG
AGCATTTGGGGCATTCCCATTAGGAGTGGGTCAATCAACTGAAAACCCAGAAGATTTGTT
TAAGGAAATATTAACTCTCAATATCGTGACTCGTAGAACTGCTGGATTTAATGAGAAGTT
AGTTTATTATAATACCACACCTATACATTTACTGACCCCTGGAAAAAGGTGTTGGCATA
TGGAAGCATCTTTAATGCTAATCAGGTCTGCAGTGATACAAGCTCTATACCAATAGATAT
TCCACAAAAGTTTAGACCTGTATATTTGACTGTTACAAAATTATCTGATGATGGCTATTA
TCAGATACCAAAGATGATTCAAGATTTCAAATCGTCAAATTCTGTTGCATTCAACATCCT
TGTGCATCTATCAATGGGTACAAATTTACTTGACCAATCCAAAGACTCTCGATTAAGAAA
TGCTGGGGAAACTGTGATTACATTTATGATTCATATTGGGAACTTCAAACGGAAGAGTAA
TAAATCTTATTCAGCGGAATACTGCAAGAGGAAAATAATGAGGCTTGGTTTGATATTCTC
ATTAGGTGCAATTGGTGGCACAAGCTTACATATTAGATGCACAGGTAAGATGAGCAAACG
ACTACAGGCCTACTTAGGATTCAAAAGGACTTTATGTTACCCTCTGATGTATGTAAATGA
AGGGCTAAATAAAACACTGTGGAGAAATGAATGTAGAATAGAGAAGGTTCAAGCAGTCTT
ACAGCCATCTGTTCCAAATGAATTTAAGGTATATGATGATGTCATTATTGACAATACCAA
TGGTCTCTTCAAGATTAAATAGGTTATAACCGTAACAAACAGCTAATAAATGGTATTATG
TATTTAAGTGTACACTGATAATTGTGAATAAAATACATTGGGTTAATAACGGTATAGAGT
TAAAATCTAATTGATATGTGGGTTAATGCTTAAACACTTATTAGCTCTATTGATTATCTA
TATCTTGAGTTATCTAATATCAGAGTATCAACATGTAATCAGTTTAAACTTGTTGGATTA
ACGTTCAATTATTATAACCAGAATACACAAATTGTTAAACTTATAATTCTGTTAGATTCA
TTCAAGTTGAACTTATGTAGGGTTAACCAATTATCATTCGAGCAATTATAAAAAACTAAG
GATCTAATGTAGTAGGAACCTAAACTCCATCCAGTGAGCTCAAAATCACCACACTCAAAT
ATCAATTTGTCTAGGGCCTGTCTAACTCAAAACAAAGCTCATAACCAGGATCCAGACGAG
TGGGTTAAATCTGAATAACTATTAGGAATTGAGATTTTAAATTGATTCTCTCTTAACTCT

Figure 4-4

```
AAAGTTTTAGTAATATAGCATCAATTCAGCACCATGAACAGAATTAAAGTTATAATAATT
AGTTCTTTGTTATTATCAGATATTACGATTGCACAAATAGGCTGGGATAATTTAACTTCG
ATTGGGGTTATAAGTACTAAGCAGTACAACTATAAAATAACTACTCTAAATACTAATCAG
TTGATGGTTATAAAGATGGTTCCCAATATATCGTCAATCATTAATTGCACTAAACTTGAA
TTGATAAAATATAGAGAGTTAGTCTCAGGGATCATTAGACCAATAAATGAGTCATTAGAA
TTAATGAACTCATACATTAATATGAGAGTAGGTTCAGAGAGATTTATAGGGGCTGTAATA
GCTGGAGTAGCATTAGGAGTGGCAACTGCAGCACAAATAACATCAGGGATTGCCCTACAT
AATTCAATTATGAACAAAAAACAGATACAAGAGTTGAGGAAGGCTCTTAGTACTACCAAC
AAAGCAATTGATGAAATAAGGATTGCAGGTGAACGAACATTAATGGCAGTACAAGGTGTA
CAGGATTATATCAATAATATAATTGTCCCTATGCAGGACAAACTCCAATGTGATATTTTA
TCATCACAGCTTTCTGTTGCATTACTCAGATATTATACAAATATATTAACAGTCTTTGGA
CCAAGTATACGAGATCCTATCACTAGCACGATTTCGGTACAAGCACTTAGTCAAGCATTC
AATGGTAATCTTCAGGCACTACTTGACGGACTAGGATATACTGGGAGAGACTTACATGAC
CTTCTAGAGAGTAAATCTATCACTGGTCAGATAATTCATGCAGATATGACTGATTTGTTC
CTTGTTCTGAGAATTAATTACCCTTCCATAACTGAGATGCAGGGAGTAACAATATATGAA
CTGAATTCAATTACATATCATATTGGGCCTGAAGAGTGGTATACTATTATGCCTGATTTT
ATAGCTGTTCAGGGTTTTTTAATATCTAATTTTGATGAAAGAAAGTGTTCAATAACTAAA
TCGAGTGTAATATGCCAACAAAATTCAATTTACCCGATGTCAGCAGAGATGCAAAGATGT
ATTAAGGGCGAAATAAGATTCTGTCCAAGATCTAAGGCAATTGGGACGTTAGTTAATCGG
TTCATATTGACCAAAGGTAATTTAATGGCTAATTGTCTGGGAATTATATGCAGATGTTAT
ACCTCAGGCCAAGTTATAACACAGGACCCCAGTAAGTTAATTACAATAATATCACAAGAG
GAGTGCAAAGAAGTCGGTGTTGATGGTATCCGTATTATGGTAGGACCTAGAAAATTACCA
GATATTACCTTTAATGCTAGGTTAGAAATTGGTGTACCGATATCATTAAGCAAATTAGAT
GTCGGAAATGATTTAGCAATTGCTTCAGCTAAGCTTAATAATTCCAAAGCATTGTTAGAG
CAATCAGATAAGATTCTGGGTTCTATGTCTAAGTTGGATTCTATTAATTCAAGAATTATA
GGATTAATCTTAGCAATCATGATAATCTTTATAATTATTGTTACCATTATCTGGATCATA
TATAAAAATTGTAGAAATAAAGATACTAAATTCAGTACTTCAATTGAACCGCTCTACATA
CCCCCCTTCTTATAACTCACCTCATAGTGTGGTCAAGTCTATTTGAGTACTGACCATATGA
```

Figure 4-5

```
TTTACTGTAATAAGTCCAGTGGAAGTATCAATTGACAATACTGGTAGTATAATGAATATT
GAATATATAATATACTCTCTTAAATTGGATAGTGATAAAGAGTTATAGATGATTGCAATC
ATTTTAATATAATTATATATTGATTTGATTACCTGGTATAATTCTTATGCAATTGAATTA
TGTGTCATCAATTAATAGCTTAATAGCACTGTTTTATACACTTATGTTGATAGATAGATG
TGTTATATTGTAATCAAGGATTTAGTATCTAGAAGAGGAAAGAGTTCAATTGGTTGTTAA
TTGGTTATTGTGTATTCAATTAGAAAAAACTTAGGAATCCATGTTAATAAAAACTCATTA
TCATGGAGTCCAATAATGTTAAATATTACAAGGATTCTAACCGATACTTTGGTAAAATAT
TAGATGAACACAAAACAATTAATAGTCAATTGTACAGCTTAAGTATTAAAGTAATTACCA
TTATTGCCATAATTGTAAGCCTAATTGCAACAATAATGACTATTATTAATGCCACAAGTG
GGAGGACTGCCCTAAACAGTAATACAGACATACTGCTTAGCCAAAGAGATGAGATTCATA
ATATCCAAGAAATGATATTTGATCGTATTTATCCTTTGATAAATGCTATGAGTACAGAGT
TAGGACTTCATATTCCTACCTTATTGGATGAACTTACTAAAGCGATTGACCAAAAGATTA
AAATAATGAATCCCCCTATTGACACTGTGACGTCTGATCTTAATTGGTGCATCAAACCCC
CTAACGGAATTATTATAGACCCGAAGGGTTATTGTGAGAGTATGGAATTGTCCAAAACTT
ATAAATTACTACTTGACCAATTAGATGTCTTAAGAAAGAAATCACTCATTATAAATAGAA
AGAATATTAACCAGTGTCAATTAGTTGATGATTCAAAGATCATTTTTGCTACTGTCAACA
TACAATCTACACCGAGGTTTTTGAATTTTGGTCACACAGTCAGCAATCAACGTATAACAT
TTGGTCAAGGAACATATAGTAGTACTTATGTTATAACTATCCAAGAAGATGGGATAACTG
ATGTTCAATATCGAGTTTTTGAAATCGGGTATATCTCTGATCAGTTTGGTGTTTTCCCCT
CCTTAATAGTATCCAGAGTGTTGCCTATACGCATGCTATTAGGAATGGAATCCTGTACCT
TGACAAGTGACAGACTAGGTGGGTATTTCTTGTGTATGAATACACTGACACGATCTATAT
ATGATTATGTTAGCATAAGGGATTTGAAATCATTATATATAACACTCCCTCATTATGGTA
AGGTTAATTATACTTACTTTGATTTTGGTAAGATCAGAAGCCCACATGAAATAGATAAAA
TTTGGTTAACATCTGAGAGGGGCCAAATTATTTCTGGTTATTTTGCAGCATTTGTTACCA
TTACAATTCGGAATTATAATAATTATCCCTACAAATGTTTAAATAATCCATGCTTTGACA
ACTCTGAGAATTACTGTAGAGGGTGGTATAAAAACATAACAGGTACTGACGATGTTCCGA
TATTAGCATACCTATTAGTTGAAATGTATGATGAAGAAGGACCTTTAATTACACTTGTAG
CAATCCCGCCTTACAATTATACAGCTCCATCTCATAATTCTCTTTACTATGATGATAAAA
```

Figure 4-6

```
TCAATAAATTGATAATGACTACATCTCACATAGGTCATATTCAAGTTAATGAGGTGCATG
AGGTGATTGTTGGCGATAATTTAAAGGCTATCCTCCTAAACAGATTATCTGATGAACATC
CTAATCTTACTGCCTGTAGACTCAATCAGGGCATTAAGGAGCAGTACAGGTCTGACGGAA
CAATAATTTCAAATTCTGCACTTATTGATATACAAGAACGGATGTATATTACAATTAAAG
CTGTTCCACCAGTGGGTAACTATAACTTTACAGTTGAATTGCATTCTAGATCAAACACAT
CTTATCTATTGTTACCAAAACAGTTTAATGCTAAATACGACAAATTACATCTTGAGTGCT
TTAGCTGGGACAAATCTTGGTGGTGCGCCTTGATACCTCAGTTTTCATTAAGTTGGAATG
AATCCCTTTCTGTTGATACTGCTATTTTAATTTAATAAGTTGTAAATGAATATGTCAAC
TGATAGTTGATAGTTGTCAAAACATCAGCTAATTGAGATTAAAGAAATAAAAAAATGAAA
TTATCAAGATTTGACTAGATGTATACTCAAGCTAAATTACAAAAAACTTAGGAGTCAGAG
ACTTCGTTGCAATGGAGCAGTCAGACTACCAAGATATTCTATATCCTGAGGTACATCTTA
ACAGTCCTATAGTAATCTCTAAATTAGTAGGTATTTTAGAATATGCCCGAATTGCTCACA
ATCAACAACTATCAGACCATACAATTATCAAGAATATTCAATTTAGATTAAGAAATGGCT
TTAATAGTCCAAGGATACAGACACTATCAACTATGGGTGAAATCATCAACAAAATTAAAA
GCAAACACCCCAATTATTTACACATACCTTACCCCGAATGTAACCAAAAGCTATTTCGAA
TAGTAGATCCAGAACTGACATCAAAATTGGAATCTCTTCTGAACAAAGGTGATACACTGT
ATCTCAAAATTCGGTCAGATATCATAAAATGCTTTGATAGATTGAAAATGAAGATGAACA
TAAGGAATGATCTTCTTAATGACAATAGTCAATTAATTCTGGATCTTCCTTTAATTCTCA
AAGGATCTCAGTGGTTCTTCCCGTTTTTATTTTGGTTTTCGATTAAAACTGAGACTAGAA
GCTGTATCCGACAAAATCAAAAAGCTCGTGTTAGATCACAATATCGGCCTCACTTATCAG
AGACTAAGAGAATTACATTGGTTGTTACATCTGATCTAATTACGATATTTGATCATATTA
ATAAATGTATATTTTATCTGACTTTTGAGATGTTGTTAATGTATTGCGATGTGGTAGAAG
GTAGATTAATGACTGAAACAGCTATGAGCTTGGATTGTCGATTTATCAATCTATTGCCAA
GAGTGCAATATATGTGGGATTTGCTAGATGGAATGTTTGAAAGTTTAGGTAATCAATTAT
ATTCAGTTATTGCATTGTTAGAGCCTCTTTCTCTTGCTTATTTGCAATTAATAGATGCAG
ATCCACAGATTCGGGGAACATTCTTGCATCACTGTTTTTCAGAGTTAGAAGAAATTATAT
TTGACAAGTCTCCTTTTGATCCTTTTGTGTATGAAAATTTAATTAATGGACTAGATTATA
TTTATTTGACAGATGATATTCATCTAACTGCAGAAGTTTTTTCTTTTTTAGGAGCTTTG
```

Figure 4-7

GTCATCCTTTTTAGAAGCACAAAATGCTGCTAATAATGTGAGGAAGTATATGAATAAGC

CTAAAGTGATCTCATACCAGACTCTAATGCAAGGACATGCGATTTTCTGTGGTATTATAA

TAAATGGATTTAGAGATCGCCATGGGGGAACATGGCCTCCTGTAGAGTTACCAAATCATG

CATCTGCTGTAATTAGAAATGCCCAGCTATCTGGAGAAGGGTTAACATCTGAACAATGTG

CTCAACACTGGAGATCCTTTTGTGGATTTAAATTTAAATGTTTATGCCACTGAGTCTAG

ATAGTGACCTTACAATGTACCTTCGGGACAAGGCGTTGTCACCTGTCAAAAGTGAGTGGG

ATTCTGTTTATGCGAAAGAGTATTTAAGATACAATCCAGGATTACCTACAAGCTCTAGAA

GACTAGTGAATGTATTCTTAGAAGATGATAAGTTTGATCCATATGAAATGATCATGTACG

TGATAAATGGTGATTACTTAAGAGACAAAGAGTTTAATCTTTCATACAGTCTTAAAGAGA

AAGAGATCAAAGAGGTAGGTCGATTGTTCGCCAAAATGACTTATAAAATGAGGGCTTGCC

AAGTAATAGCTGAAAACCTGATTGCCAATGGAGTAGGGAAGTTCTTCAAAGATAATGGAA

TGGCAAAAGATGAACATAAACTAACTAAAACGTTACACAAATTAGCCATTTCAGGTGTAC

CTAAAGATAATTCTCAACTTTATTTAGATGAATGCTGGGAGCAAGTAGTTCGACAATGCT

CAAGTAGTACACAGATAGGAGAACAGACTATGAATTCACAATCGAAGAGGGCAATTGAAT

CAAAGTCTTCTAGATCACATCGAAATAATAGGGATATCTTAAGGGGCAGGAGAGATTTGA

ATAAACAGATAAAGTACCCTTCCAACACCGAGTATTATGAGACTATTAGTAGTTTCATAA

CTACTGACCTTAAAAAGTACTGTCTTAATTGGCGATATGAATCAAGTAGTGTGTTTGCAG

AGAGACTTAATGAAATTTATGGATTGCCTGGGTTTTTTCAGTGGCTTCACAAAATATTGG

AGAAATCTGTTTTATACGTTAGCGATCCGTCTAGTCCACCTGATTTTGATCGACATATCG

ATATAGAATCAGTTCCGAATGACCATATCTTTATTAAGTACCCGATGGGTGGAATAGAGG

GGTTCTGTCAAAAATTATGGACTATTAGTACGATTCCATTCCTATATTTAGCAGCTTTTG

ATACAGGAGTTAGAATCTCATCATTGGTTCAGGGCGATAATCAGGCAATTGCAGTGACCA

AAAGAGTTCCATCATCTTGGAGTTACTCAAAGAAAAGGAAGAATCAACTAAAATAACAA

CACAATATTTCCTTAATTTAAGACAACGCTTACACGACATAGGTCATGAATTAAAAGCAA

ATGAGACTATTATATCCTCTCATTTCTTTGTTTACTCTAAAGGTATTTATTACGATGGAA

TACTTCTCTCAAGCACTTAAAAGTATTGCAAGATGTGTTTTTTGGTCTGAAACAATTG

TTGATGAAACTAGATCAGCTTGCAGTAATATATCTACGACACTTGCAAAGGCAATTGAAA

GGGGTTATGATAAATTTGTGGCATATGCTATTAATATTTATAAAACAATACATCAAGTTT

Figure 4-8

TGATTGCATTATCTTTTACGATTAATCCTACTATGACACCAGACATTACAGAACCTTTCT
ACAAAAGTTTGGATCTACTTAAAAATCTAGTTCTAATCCCTGCACCATTGGGAGGCATGA
ATTATATGAACATGAGCAGGTTATTTGTTAGGAACATAGGTGACCCCATTACTGCTTCAT
TTGCTGATATAAAGCGCATGATCGAATGTGGGTTATTAGGATGTAGCATTCTGTCACAGA
TAATGTACCAAAAATGTGGTTCCTCTAAATACTTAGACTGGGCTAGTGATCCTTACTCAA
TAAACCTTCCTTATAGCCAAAGTATGACCAAGGTCTTAAAAAATGTAACAGCAAGATATG
TACTTATGCATAGCCCCAATCCTATGCTCAAAGATTTGTTCCATGAAAAGTCACAAGAAG
AAGATGAAATCCTTGCTGAATTTCTGTTAGACCGACACTTAATAATCCCTAGAGCAGCAC
ACGAAATTTTATCAAATTCAGTGACAGGTGCTAGGGAATCTATAGCAGGTATGCTTGACA
CTACTAAGGGTTTAATCCGTGCTAGTATGTCAAGAGGTGGGCTGACATCATCACTAGTTT
TAAAATTATCAACATATGACTACCAACAGTTTAGAACGTGTCTTGAATGGCTTTATGCTC
CTATCACGGGAATTGCTGTAAGCGTTGATTCTTGTTCTGTATTCTTAGCTAAGACCATCC
GAAAGAGAATGTGGGTTCATCTAACTAAGGGAAGGGAGATTTACGGGTTGGAGGTACCTG
ACATTTTGGAATGCATGCAAAACAATATAATTATTGATCATGAAGATTGTTACTCATGTA
TTCAAGGATCAAAATATTATACATGGTTTTTTGTACCTTCAAATTGTCAACTCGATCAGA
TAAATAAGTCAACAAATTCTCTCCGAGTACCTTATGTTGGATCAACAACTGAAGAAAGGA
GTGATATGAAGTTGTCATATGTGAGGTCACCAAGTAGACCACTTAAAGCAGCAGTCCGAA
TTGCAGCAGTATATACATGGGCTTATGGTGATGATGATTTATCCTGGCATGAGGCTTGGT
ATTTGGCAAGGACTAGGGCAAATATTACATTTGATGAACTCAAATTAATAACACCTATAG
CTACATCTACTAATTTGGCACATAGGTTGAGAGATAGAAGTACTCAAGTTAAATATTCAG
GGACTTCCTTAGTAAGAGTGGCACGCTATACAACAATATCTAATGATAACATGTCGTTCA
CTATTAACAACAGGAAAGTCGATACTAATTTTGTCTACCAGCAAGGGATGTTATTAGGCT
TGAGTATACTCGAATACATATTCAGATACTGTACAAGTACTGGACAATCAAACACTGTAA
TTCACTTACATGCAGATGTTAATTGTTGTATAGTACAGATGACTGATCAGCCTTATACGC
CAAGCTTAACTAAGAAGCTACCTGATATCAAACCCATCAATAATAAATTGATATATGATC
CGGCTCCTATAATTGATACTGATGCAGCTAGGTTGTATTCTCAAAAATATCTGTCACATC
TAATAGATTTTCCAAGTTGGTCAACTACTCAGCTTAACACAGTGTTGGCAAAAGTGGTAG
CAGTATCTATAGTAGAATTGATCACAAAAGCGAGTAAAGACCATCTCAATGAGATAATAG

Figure 4-9

CGGTTGTTGGTGATGATGATATCAATAGCTTTATTACAGAATTTCTACTTGTTGATCCAC
GTTTGTTTACACTATACTTAGGCCAATACATGTCTTTACAATGGGCATATGAAATCCATT
ATCATAGACCAGTGGGCAAGTACCAGATGGCCGAAGTATTACATAATTTGCTGTCAAGAG
CTAGTAGAGGCATATTTAGCATATTGACCAATGCCTTTAGCCATCCCCGGGTCTATAAAA
GATTCTGGGAATGTGGTTTATTGGAGCCTATTTATGGGCCTTATATAGGAAGTCAAAATC
TACATAGTGCAGTGATTGATTATATCTATAATGCATATCTTACTTATTTGGATGCTTATT
TATCTGATCAAGTAGATGATACTGATATTATAATCTGTGAAACAGAGGAGACATGTTTAG
CAAATAGAATTGACAATTACCAAAGTAGACACCTAGCTGTACTCATAGACTTGTACTGCG
ATTCCACTAGATGCCCCAATATAAAAGGGTCAGATACAATTATGAGAAATTCAATCCTTA
GATCCTTCATTGATAATGAGAGGAAAACAAACCCACTCGGTTTGACATGGAATCTTGATC
CATTACTTGTGGATCACTTTAGCTGTTCTATTACATATCTAAGGAGAGGTATTATTAAAC
AGATGAGATTAAGATTTGACCCAAGCGTATCTCTTGAATTATCTAGAATGATTAAACCTG
ATGTGATTTATCAAGCACCTAAAGTTCCGTCCTCATGGGCTCTTATAGATATCAACCCTG
AAGTAAATGACCTTAATACAATTTTTGGAGAGCTTAATAGCAAGTGGAAAGACATCCCTA
TAGGACAAATCAGAATCCAAAATTATGAAATACATGCATATAGGAGGATTGGAGTTAATT
CAACTGCATGTTATAAGGCTTTAGAGCTATTATCTGTTCTAAATCGGTTCATGTCTAACC
CATCAGGTGCATTGTTTTTAGGTGAAGGGGCAGGATCGATGCTGGTCACATATCGTGCCT
TTATTCCATTCAAGACAATTTATTATAATAGTGGTATTTCAGTTCAAAATGTTCAGGGTC
AGAGAGAATTAAGTCTATATCCATCTGAAGTGGCACTAGTTGATAACAAAAATCGCTTGG
CTAATGACCCTAATATCAAAGTCTTGTTTAATGGTAAGCCAGAGTCTACATGGGTTGGAA
ATATTGACTGTTTTGCTTATATTCTTAGCCATATTGAGACTTCAAGCTTGACATTGATAC
ATAGTGATATTGAGTCCAGCTTGAGCAAGACAAAGAATAAAATTCTTGAGGAGCTGTGCC
ATATTCTGTCAATGGCACTCATTTTGGGAAAGATCGGATCTTTATTAGTTGTTAAGTTGC
TACCAAGGGTCAGTGATTATACGTATTCATTTTGCAAATATGCATCAGAGTTCTATCAAC
AAAACTTTCTTGTTCTGCCTAGATTTAGTAACATGTCATCATCTGAGGTTTACTACATAG
GAATTCACCTTAATACAAATCGATTGATTGACCCTGATAGAATAGTACAATACATAATTA
GAAATTTACAACCTACTCCAGTTACATTTTTATCCTACATTTTTGAAACTAAGTATCGAA
ATAATATGGTTACAAATTATGGACTATGCTTGTCAGACGGACACAAAAGTGATTACTTGT

Figure 4-10

CATCAATTACAAAAATAGAGAGTGTTCTTCTGTCATGTGGGTTAGAATTGAACGGACCTA
AGATTATACAGCAATTATCAGGACATGACTATGCCAGTGGAGAGACTAGTCTGGAATCAA
GTATAATGATATTAGTTAGAGAATATCTTAATGCAACTATACAAGGCCGGGAAACATTAG
GCTTGTTTTCACCTTACCCGGTCCTTCATGAGAGTCAGTTAAGAGAAATCAATAAGTGTA
TTGTATTGAAGTATATTGTATATCTGCTCTTTTATTCAAACTCTACATTATCTAGTAAAC
AAATAATGAGTAATCTTAGAAAAGGAATATTGATGTATGATTTGAGAGATGAGTTTTTCA
TATCAAGATTGTCAGCAAATTACAAGAAAAAGTAATGTCACAGGAAGTTAAGACTACCT
GGATATTTAATATTGATACTCCGACACGAAAGGCGTTATATAAGTTAGTAGGTTACTCAT
TAATAATTAATCACATATGAAGGTTGGGCATGGTTATTCATTTTTTAAGGAGTAAGATAA
GACTTGATATATGATAACTGATTAAACATTACCTCTGAATTGAAGGATTGCTCAATTACA
TGGTTTTTGAGTAATTGAGATTTTATTCCAATTAGTACAATTAGAAAAAACTTCAACAGT
TGATTGAGCCTTAATTTACTCCATACTAGCTATATTTATAAGCTCGGATAAAACTTTGGT
TTGAAATTATAACAGTCATACCAATCTATCAAGGAAACACAATTGATGTCTAGTATGAAG
TTCATATTTATATGTTTTTAATCTTATACCCACTCTAATTAGTTCCTATTTAAGAATTAA
ATTATAGATGTTAACATGTTATATAATGGGAACCATCAATGCTGCTATTGTTGGTAACTA
TAGGCATTGTATTAGATAATGTTTATTTCTTAGAAATGTGCAATCTCATACGTCGGACCC
CTCAGCCTCCCCCTTATAGTTGCGTGATTTGAAAAAACACAAAAAATAATCATGAATGGG
TGTACGTACCTATAGCTTTCTTTGTCTGGT

Figure 5.

```
             MA(S,T)L
761U    MSSLLRSLAAFKRHREQPTAPSGSGGAIKGLKNTIIVPVPGDTVITTRSNLLFRLVYIIGNPDTPLSTSTGALIBLTLFVESPGQLIQRIADDPDAVFK  100
776U    ....L..................T.........................................................................  100
M252A   ....K.................T.........T................................................................  100
CdiPV   .A...K..TL...T.D..PLA......R.I.HV...LI...SS.V...R..D...RLV.D.KINGPKL............S........I....VSI.  100
DmoPV   .AT......L,..NKDRTPLIA......R.I.HV.V......SS.V...R..D...RLA.D.YISGPKL.M.IS......S......T....VSIR  100
MeaPV   .AT......L,..NKDK.PIT......R.I.HI...I...SS....R..D...RL....VSGPKL.L.GIS............T....VSIR  100
PprPV   .AT..K...L,..NKDKAPTA......R.I..V....I...SS.I...R..D...RLA.D..ING.KL.M.IS............T....VSIR  100
RinPV   .A...K...L,..AKDK.PLAA......R.I.HV.V..I...SS....R..D...KMV.D..ISGPKL.L.IS............T....ISI.  100
PdiPV   .A...K.,SL,.KT....PLA......R.I.HV...LI...SS.V...R..D...RMV.D.EVSGPKL.VI.IS............I....ISI.  100

QxW(I,V)xxxK(A,C)x
761U    LVEVIPEAGNPGELTFASRGINLDKQAQQYFKLAEKNDQGYYVSLGFENPPNDDDITSSPEIFNYILASVLA QVWILLAKAVT APDTAAEAENRRWIKLM  200
776U    ......................................................................... ........... ........................  200
M252A   ......................................................................R.. ........... ........................  200
CdiPV   ......SINSACG........AS..SE.DEF..IVDEGSKAQGQLGWL..KDIV.IEVDNA.Q..IL...I.. .I......... ......DS.M.....YT  200
DmoPV   ......QSEKSLSG........A.MEDE.DD...SIQAGEEGDTRGTHW...KEIVIEIEVQD..E..IL...I.. .I......... ......DS.T.....YT  200
MeaPV   .L....VQSDQSQSG.......T.MEDE.D...SHDDPSSSDQSR.GW...KEIS.IEVQD..G..M..GTI.. .I.V....... ......DS.L.....YT  200
PprPV   ......VQSTRSQSG.......AD..NE.DM..STEGPSSG.KKRINW...REII.IEVQD..E..ML...I.. .I......... ......DS.L...V.YT  200
RinPV   ....I.VQSDKTQSG.......TSM.DE.DR..TYE.P..GEERQ.YW...RDIQ.IEIQD..G..M...TI.. .I......... ......DS.L...V.YT  200
PdiPV   ......SINSTCG........AS..AE.DEF.GTMDEGSKDHNQMGWL..KDII.IEVNDA.Q..IL...I.. .I......... ......DS.M.....YT  200

FxxT(I,L)(R,K)Ø(G,A)(L,I,V)x
761U    QQRRVDGELRLSKGWLDLVRNKIASDITIRRFMVALVLDIKRSPGTRPRIAEMICDIDNYIVEAGLAS FLLTIKFGIET RYPALALHEFSGELATIEGLM  300
776U    .................................................................. ........... ........................  300
M252A   .................................................................. ........... ........................  300
CdiPV   .....V..F.MN.I...I...R..E.LSL.........NK.................I.. .I......... M...G......T..S..  300
DmoPV   .....V..F..D.....A...R..E.LSL.........I......T..NK.........T.... .I......... M...G......T.V.S..  300
MeaPV   .....V..F..ERK...V...R..E.LSL.........I......T..NK.........T.... .I......... M...G....A...S.L.S..  300
PprPV   .....I..F..D.....A...R..E.LSL.....S.I......T..NK................ .I......... M...G....A...S...S..  300
RinPV   ....I..F..D.....T...RV.E.LSL..........I......T..NK.........T.... .I......... M...G....A...S...S..  300
PdiPV   ....I..F.MN.I...I....R..E.LSL..........I.....NK.................. .I......... M...G........T...S..  300

FxxxxYPxxØSØAMG
761U    KLYQSMGEMAPYMVILENSIQTR FSAGSYPLLWSYAMG VGVELERSMGGLNFTRSFFDPTYFRLGQEMVRRSSGMVNSSFARELGLSDHETQLVSQIVNS  400
776U    ........................ ............... .......................................E..................  400
M252A   ........................ ............... .......................................E..................  400
CdiPV   M...Q...T..........V.NK ............... .........N......G..Y...A.......A.K.S.AL.A...ITKE.A....E.ASK  400
DmoPV   N...Q...T..........NK   ............... .........N......G..Y...A.......A.K.S..L.A...ITAEDAK...E.AAQ  400
MeaPV   N...Q...T..........NK   ............... .........N......G..Y...A.......A.K.S.TL.S...ITAEDAR...E.AMH  400
PprPV   N..QL..V...........NK   ....A.......... ....G..N......G..Y...A.......A.K.S.VI.A...ITAE.AK...E.ASQ  400
RinPV   N...Q...L..........NK   ....A.......... I........N......G..Y...A.......A.K.S.NL.S...ITEE.AR...E.AAY  400
PdiPV   V...Q...T..........V.NK ............... .........N......G..Y...A.......A.K.S.T..A.F.ITKE.A....E..SR  400

761U    GGESGIPKFDGFRANPTTFLGTKDNINDRGEDQSNSISGLPGPL-LPSRDLNLSGDSYGINSG--VKNVSDKLNEGVGPDHDVSSSAME--ELRRLVEST  495
776U    .........................D.....................-.......D.......-........................-.........  495
M252A   ........................K......S.V........THP.....ADD.--......N..S..IS...........--..........  495
CdiPV   TT.DRTIRAT.PKQSQI...HSERS--EVANQ.PPT.NKRSENQ-GGDKYPIHFS.E--RLP.YTPDVN.SEWS.SRYDTQIIQDDGND--DD.KSM.AI  493
DmoPV   ANDDRANRAI.PKQ.QIS...HPDRG---.ASTPG----NI.RANE-GDGSTRMKR.GNIATPK.TSIDQT.TT.SKDTLDIDEQ.CNTDDPISIQKSA.AL  493
MeaPV   TT.DR.SRAV.P.QAQVS...HGDQS--ENELPGLGGKEDRRVKQ-GRGEARESYRET-.SSRASDARAAHPPTSMPL-DIDTA.E.GQDPQDS..SADAL  495
PprPV   A.DERTARGT.P.QAQVS..QH.TG--EGESSAPATRE.VKAAIPNG.EERDRKQTRS.RPR.---ETP.QL.L.IMPE.EVSRE.GQNPR.AQ.SA.AL  495
RinPV   TSDDRNNRTS.PKQAQVS...R.DQG---SEAQHSASKKDEARA.Q-VKKETRTS.KSD-KHKE.TDKEP..SS-AMTLIDVDTTLEADTDPL.SKKSA.AL  495
PdiPV   TT.DRTTRAT.PKQSQI...HSER.--EAPNQRLPP.TMKSEFQ-GGDKYS.QLI.D--RL..YTSDVQ.SEWD.SRQITQLTQEGDHD--NDQQSMDGL  493

761U    NRIDT-----KQPEASGVTNH-YNDTDLLK                                                                        519
776U    .....-----................-............                                                              519
M252A   .......-----..K...P.....-.......R                                                                    519
CdiPV   AKMRMLTKMLS..GT.EDNSPV.S.KE..N                                                                        523
DmoPV   AKMRAMAKLLENQGPFRD..A.V...K...G                                                                       523
MeaPV   L.LQAMAGILEEQGSDTD.PRV...R...D                                                                        525
PprPV   F.LQAMAKILEDQ.EGEDNSQV...K...G                                                                        525
RinPV   L.LQAMAGILGDSTLGNDSLRA...K...N                                                                        525
PdiPV   AKMRQLTKILN.SDTN.EVSPAH..R...S                                                                        523
```

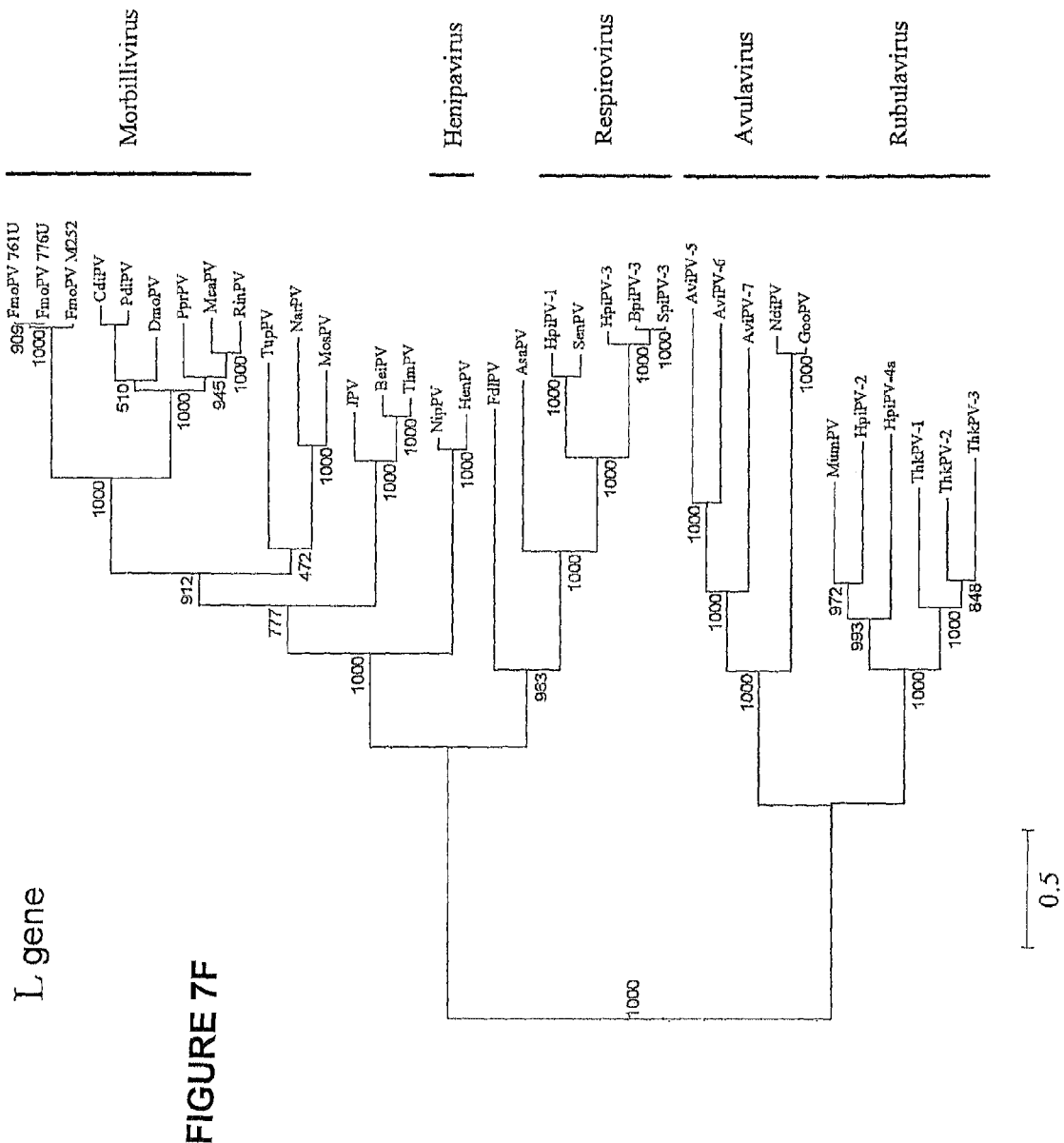

A: Mouse anti-Human Myeloid/Histocyte Antigen and Texas-red conjugated Goat anti-mouse IgG (JacksonImmunoResearch, West Grove, PA,USA)

B: Guinea Pig anti-NP and FITC conjugated Rabbit anti-Guinea pig IgG (Invitrogen, Camarillo, CA, USA)

C: Merged image

FIGURE 13

```
>FmoPV 776U Cats/Hong Kong/2009_L
AGAGACTTAATGAGATTTATGGACTGCCTGGATTTTTCCAGTGGCTTCACAAGATTTTGGAGAAATCTGTTCTATACGTTAGTG
ATCCATATAGTCCACCTGACTTTGATCAACATATCGATATAGAATCAGTCCCAAACGACCATATCTTTATCAAGTACCCGATGG
GTGG
>FmoPV M252A Cats/China/2010_L
AGAGACTTAATGAAATTTATGGATTGCCTGGGTTTTTTCAGTGGCTTCACAAAATATTGGAGAAATCTGTTTTATACGTTAGCG
ATCCGTCTAGTCCACCTGATTTTGATCGACATATCGATATAGAATCAGTTCCGAATGACCATATCTTTATTAAGTACCCGATGG
GTGG
>FmoPV 761U Cats/Hong Kong/2009_L
AGAGACTTAATGAAATTTATGGACTGCCTGGATTTTTCCAGTGGCTTCACAAGATTTTGGAGAAATCTGTTCTATACGTTAGTG
ATCCATCTAGTCCACCTGACTTTGATCAACATGTCGATATAGAATCAGTCCCAAATGACCATATCTTTATCAAGTACCCGATGG
GTGG >FmoPV 776U Cats/Hong Kong/2009 N protein
MSSLLRSLAAFKRHREQPTAPSGSGGTIKGLKNTIIVPVPGDTVITTRSNLLFRLVYIIGNPDTPLSTST
GAIISLLTLFVESPGQLIQRIADDPDAVFKLVEVIPEAGNPGELTFASRGINLDKQAQQYFKLAEKNDQG
YYVSLGFENPPNDDDITSSPEIFNYILASVLAQVWILLAKAVTAPDTAAEAENRRWIKLMQQRRVDGELR
LSKGWLDLVRNKIASDITIRRFMVALVLDIKRSPGTRPRIAEMICDIDNYIVEAGLASFLLTIKFGIETR
YPALALHEFSGELATIEGLMKLYQSMGEMAPYMVILENSIQTRFSAGSYPLLWSYAMGVGVELERSMGGL
NFTRSFFDPTYFRLGQEMVRRSSGMVNSSFARELGLSEHETQLVSQIVNSGGESGIPKFDGFRANPTTFL
GTKDNIDDRGEDQSNSISGLPGPLLPSRDLDLSGDSYGINSGVKNVSDKLNEGVGPDHDVSSSAMEELRR
LVESTNRIDTKQPEASGVTNHYNDTDLLK
>FmoPV M252A Cats/China/2010 N protein
MSSLLKSLAAFKRHREQPTTPSGSGGTIKGLKNTIIVPVPGDTVITTRSNLLFRLVYIIGNPDTPLSTST
GAIISLLTLFVESPGQLIQRIADDPDAVFKLVEVIPEAGNPGELTFASRGINLDKQAQQYFKLAERNDQG
YYVSLGFENPPNDDDITSSPEIFNYILASVLAQVWILLAKAVTAPDTAAEAENRRWIKLMQQRRVDGELR
LSKGWLDLVRNKIASDITIRRFMVALVLDIKRSPGTRPRIAEMICDIDNYIVEAGLASFLLTIKFGIETR
YPALALHEFSGELATIEGLMKLYQSMGEMAPYMVILENSIQTRFSAGSYPLLWSYAMGVGVELERSMGGL
NFTRSFFDPTYFRLGQEMVRRSSGMVNSSFARELGLSEHETQLVSQIVNSGGESGIPKFDGFRANPTTFL
GTKDNINDKGEDQSSSVSGLPGPLLPSRDLTHPGDSYGADDGVKNVSNKLSEGISPDHDVSSSAMEELRR
LVESTNRIDTKKPEAPGVTNHYNDTDLLR
>FmoPV 761U Cats/Hong Kong/2009 N protein
MSSLLRSLAAFKRHREQPTAPSGSGGAIKGLKNTIIVPVPGDTVITTRSNLLFRLVYIIGNPDTPLSTST
GAIISLLTLFVESPGQLIQRIADDPDAVFKLVEVIPEAGNPGELTFASRGINLDKQAQQYFKLAEKNDQG
YYVSLGFENPPNDDDITSSPEIFNYILASVLAQVWILLAKAVTAPDTAAEAENRRWIKLMQQRRVDGELR
LSKGWLDLVRNKIASDITIRRFMVALVLDIKRSPGTRPRIAEMICDIDNYIVEAGLASFLLTIKFGIETR
YPALALHEFSGELATIEGLMKLYQSMGEMAPYMVILENSIQTRFSAGSYPLLWSYAMGVGVELERSMGGL
NFTRSFFDPTYFRLGQEMVRRSSGMVNSSFARELGLSDHETQLVSQIVNSGGESGIPKFDGFRANPTTFL
GTKDNINDRGEDQSNSISGLPGPLLPSRDLNLSGDSYGINSGVKNVSDKLNEGVGPDHDVSSSAMEELRR
LVESTNRIDTKQPEASGVTNHYNDTDLLK
```

FELINE MORBILLIVIRUS AND USES THEREOF

CROSS-REFERENCE TO RELATED APPLICATIONS

The present application claims the benefit of U.S. patent application Ser. No. 61/588,778, filed Jan. 20, 2012, which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Apr. 30, 2013, is named Sequence_Listing_2748US1.txt and is 108,282 bytes in size.

INTRODUCTION

Described herein are isolated *paramyxovirus*, a *morbillivirus* (FmoPV), isolated nucleic acids encoding the genome of FmoPV, isolated amino acid sequences of FmoPV proteins, antibodies to FmoPV and its proteins, and uses thereof. In certain embodiments, the modified FmoPV is a feline *morbillivirus*. Also described herein is a recombinant FmoPV comprising a modified FmoPV gene or gene segments and the use of such a virus. The recombinant FmoPV may be used in the prevention and/or treatment of diseases related to FmoPV or as a delivery vector. Also described herein is a diagnostic assay for the FmoPV. In certain embodiments, the FmoPV causes kidney disease. In certain embodiments, the kidney disease is in felines. In certain embodiments, the kidney disease is tubulointerstitial nephritis ("TIN"). Also described herein is a quantitative assay for the detection of the FmoPV, natural or artificial variants, analogs, or derivatives thereof. In certain embodiments, the quantitative assay is reverse transcription and polymerase chain reaction (RT-PCR). Also described herein is a vaccine and a kit containing the vaccine for the prevention and treatment of FmoPV infection. Described herein is a diagnostic kit that comprises nucleic acid molecules for the detection of the FmoPV.

1. BACKGROUND OF THE INVENTION

*Paramyxoviruses* are enveloped, negative-sense single-stranded RNA viruses that are divided into two subfamilies, Paramyxovirinae and Pneumovirinae. Viruses in the subfamily Paramyxovirinae have been associated with a number of emerging diseases in humans and various animals in the past two decades (1-9). There are currently five genera within the subfamily Paramyxovirinae, namely *Respirovirus, Rubulavirus, Morbillivirus, Henipavirus* and *Avulavirus*, although some members of the subfamily remain unclassified. Among members of Paramyxovirinae, measles virus, mumps virus, and human parainfluenza viruses 1 to 4 are most well known human *paramyxoviruses* which cause outbreaks of respiratory to systemic infections (10-12). Three novel *rubulaviruses, Tuhoko* virus 1, 2 and 3, from fruit bats in mainland China and a novel unclassified *paramyxovirus, Tailam* virus, from Sikkim rats in Hong Kong were recently reported (13, 14). Despite the presence of *paramyxoviruses* in a variety of animals, no *paramyxoviruses* have been naturally observed in cats, although there is controversial evidence that cats may be infected with parainfluenza 5 virus (15,16).

Cats and dogs are the most common domestic animals and pets worldwide. As a result of their close relatedness, inter-species jumping of viruses among these two kinds of animals is not uncommon. For *coronaviruses*, feline *coronavirus* and canine *coronavirus* are classified under the same species *Alphacoronavirus* 1, and feline *coronavirus* type II strains were generated by double homologous recombination between feline *coronavirus* type I strains and canine *coronavirus* (17). For *parvoviruses*, the fatal canine *parvovirus* that emerged in the 1970s also originated from a feline *parvovirus*, feline panleukopaenia virus (18,19). As for herpesviruses, canid herpesvirus 1 and felid herpesvirus 1 are closely related and are classified under the genus *Varicellovirus* (20). Furthermore, for papillomaviruses, canine oral papillomavirus and feline papillomavirus are also closely related and are classified under the genus *Lambdapapillomavirus* (21). Dogs are well-known hosts of a *paramyxovirus*, canine distemper virus, in the genus *Morbillivirus* (22), but no *paramyxoviruses* have ever been discovered in domestic cats.

Many feline diseases have no known causes. For example, the cause of most cases of feline tubulointerstitial nephritis is hitherto unknown and therefore treatment is mainly supportive and prevention is difficult. Tubulointerstitial nephritis ("TIN") involves primary injury to renal tubules and interstitium and is the most common cause of renal failure and one of the leading causes of deaths in cats. However, the cause of most cases of feline TIN remains unknown and therefore treatment is mainly supportive and prevention is difficult. With millions of cats in households around the world, the disease burden from TIN is great. For example, in the United States of America, it is estimated that there are 75 million household cats, while there are an estimated 8 million household cats in United Kingdom (data from Chomel B B, Sun B., Zoo noses in the bedroom. Emerg Infect Dis. 2011 February: 17(2):167-72.). The capability to diagnose, treat or prevent feline kidney or other diseases would have a great benefit.

The citation of any reference herein should not be construed as an admission that such reference is available as "prior art" to the instant application.

2. SUMMARY OF THE INVENTION

In one aspect, provided herein are nucleic acid sequences comprising or consisting of a wild-type or a modified FmoPV gene segment (genomic RNA) or the complement thereof (antigenomic RNA). Also described herein are isolated nucleic acids encoding the genome of FmoPV, polypeptides encoded by portions of the isolated FmoPV, nucleic acids, primers, vectors, host cells, antibodies to FmoPV and to FmoPV polypeptides, immunogenic compositions, diagnostic methods, screening assays, methods of treatment and related uses.

In one aspect, described herein is a novel *paramyxovirus* in the genus *Morbillivirus*, a feline *morbillivirus* (hereinafter "FmoPV") from domestic cat (*Felis catus*). Also described herein is that this novel FmoPV virus is associated with tubulointerstitial nephritis (TIN) in cats.

In one aspect, the modified FmoPV gene segment comprises FmoPV nucleic acid sequence and also a heterologous nucleotide sequence. In some embodiments, the first and second heterologous nucleotide sequences encode different peptides or polypeptides. In other embodiments, the first and second heterologous nucleotide sequences encode the same peptide or polypeptides. In specific embodiments, a FmoPV comprising a modified FmoPV gene segment described herein achieves titers of approximately $3 \times 10^5$ pfu/ml, $3.5 \times 10^5$ pfu/ml, $4 \times 10^5$ pfu/ml, $5 \times 10^5$ pfu/ml, $1 \times 10^6$ pfu/ml, $5 \times 10^6$ pfu/ml, $1 \times 10^7$ pfu/ml, $5 \times 10^7$ pfu/ml, $1 \times 10^8$ pfu/ml, $5 \times 10^8$ pfu/ml, $1 \times 10^9$ pfu/ml or more after 1, 2, 3, 4, 5, 6, 7, 8, 9, 10 or more passages in cells (e.g., MDCK cells) or embryonated chick eggs. In certain embodiments, a FmoPV described herein comprises an attenuating mutation. In one aspect, provided herein are methods of using a FmoPV, wherein the FmoPV comprises a modified FmoPV gene segment.

In one embodiment, provided herein are methods for detecting the presence or expression of FmoPV, natural or artificial variants, analogs, or derivatives thereof, in a biological material, such as cells, blood, serum, plasma, saliva, urine, stool, sputum, nasopharyngeal aspirates, and so forth. The increased or decreased activity or expression of FmoPV in a sample relative to a control sample can be determined by contacting the biological material with an agent which can detect directly or indirectly the presence or expression of FmoPV. In a specific embodiment, the detecting agents are nucleic acid molecules of the present invention.

In a specific embodiment, provided herein is a diagnostic assay for FmoPV, natural or artificial variants, analogs, or derivatives thereof. In particular, provided herein is a quantitative assay for the detection of nucleic acid molecules of FmoPV using reverse transcription and polymerase chain reaction (RT-PCR). Also provided in the present invention are nucleic acid molecules that are suitable for hybridization to FmoPV nucleic acids such as, including, but not limited to, PCR primers, Reverse Transcriptase primers, probes for Southern analysis or other nucleic acid hybridization analysis for the detection of FmoPV nucleic acids. Said FmoPV nucleic acids consist of or comprise the nucleic acid sequence as described infra or a complement, analog, derivative, or fragment thereof, or a portion thereof.

In one aspect, the invention relates to the use of the isolated FmoPV for diagnostic methods. In a specific embodiment, the invention provides a method of detecting mRNA or genomic RNA of FmoPV of the invention in a biological material, such as cells, blood, serum, plasma, saliva, urine, stool, sputum, nasopharyngeal aspirates, and so forth. The increased or decreased level of mRNA or genomic RNA of FmoPV in a sample relative to a control sample can be determined by contacting the biological material with an agent which can detect directly or indirectly the mRNA or genomic RNA of FmoPV. In a specific embodiment, the detecting agents are the nucleic acid molecules of the present invention.

The present invention also relates to a method of identifying a subject infected with FmoPV, natural or artificial variants, analogs, or derivatives thereof. In a specific embodiment, the method comprises obtaining total RNA from a biological sample obtained from the subject; reverse transcribing the total RNA to obtain cDNA; and subjecting the cDNA to PCR assay using a set of primers derived from a nucleotide sequence of FmoPV.

The present invention further relates to a diagnostic kit comprising primers and a nucleic acid probe for the detection of mRNA or genomic RNA of FmoPV. In a specific embodiment, provided herein is a diagnostic kit comprising nucleic acid molecules which are suitable for use to detect FmoPV, natural or artificial variants, analogs, or derivatives thereof. In one embodiment, a kit provided herein comprises, in one or more containers, a nucleic acid sequence described herein. In another embodiment, a kit provided herein, comprises, in one or more containers, a FmoPV described herein.

In another aspect, provided herein are substrates (e.g., host cells and eggs) comprising a nucleic acid sequence described herein.

In one embodiment, provided herein is a method for eliciting an immune response against FmoPV in a subject, wherein the method comprises administering a FmoPV described herein or a composition thereof to the subject. In another embodiment, provided herein is a method of preventing and/or treating FmoPV infection in a subject, wherein the method comprises administering a FmoPV described herein or a composition thereof to the subject. In another embodiment, provided herein is a method for preventing and/or treating an FmoPV disease in a subject, wherein the method comprises administering a FmoPV described herein or a composition thereof to the subject.

In another embodiment, provided herein are methods for eliciting an immune response against an antigen in a subject, comprising administering a FmoPV described herein or a composition thereof to the subject. In another embodiment, provided herein are methods for generating or identifying antibodies that bind to a FmoPV utilizing a FmoPV described herein or a composition thereof.

In another aspect, the FmoPV described herein can be used to assess the antiviral activity of a compound or understand the life cycle of a FmoPV.

2.1 Terminology

As used herein, the term "variant" refers either to a naturally occurring genetic mutant of the FmoPV or a recombinantly prepared variation of the FmoPV, each of which contain one or more mutations in its genome compared to the FmoPV having a nucleic acid sequence disclosed in Genbank accession nos. JQ411014, JQ411015 and JQ411016. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "mutant" refers to the presence of mutations in the nucleotide sequence of an organism as compared to a wild-type organism.

As used herein, the terms "antibody" and "antibodies" refer to monoclonal antibodies, bispecific antibodies, multispecific antibodies, human antibodies, humanized antibodies, chimeric antibodies, camelised antibodies, single domain antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, IgG2, IgG3, IgG4, IgA1 and IgA2), or subclass.

As used herein, the term "antibody fragment" refers to a fragment of an antibody that immunospecifically binds to a FmoPV or any epitope of the FmoPV. Antibody fragments may be generated by any technique known to one of skill in the art. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain. Antibody fragments can be also produced by recombinant DNA technologies. Antibody fragments may be one or more complementarity determining regions (CDRs) of antibodies.

As used herein, the term "an antibody or an antibody fragment that immunospecifically binds a polypeptide of the invention" refers to an antibody or a fragment thereof that immunospecifically binds to the polypeptide encoded by the nucleic acid sequence of the FmoPV, or a complement, analog, derivative, or fragment thereof, or a portion thereof, or that immunospecifically binds to the polypeptide of the FmoPV, or a variant, analog, derivative, or fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention, can be identified by, for example, immunoassays or other techniques known to those skilled in the art.

As used herein, the term "epitope" refers to a fragment of FmoPV peptide, polypeptide or protein having antigenic or immunogenic activity in an animal, preferably a mammal, and most preferably in a feline. An epitope having immunogenic activity is a fragment of a polypeptide that elicits an antibody response in an animal. An epitope having antigenic activity is a fragment of a polypeptide or protein to which an antibody immunospecifically binds as determined by any method well known in the art, for example, by the immunoassays described herein. Antigenic epitopes need not necessarily be immunogenic.

As used herein, the term "antigenicity" refers to the ability of a substance (e.g., foreign objects, microorganisms, drugs, antigens, proteins, peptides, polypeptides, nucleic acids, DNA, RNA, etc.) to trigger an immune response in a particular organism, tissue, and/or cell. Sometimes, the term "antigenic" is synonymous with the term "immunogenic".

As used herein, the term "immunogenicity" refers to the property of a substance (e.g., foreign objects, microorganisms, drugs, antigens, proteins, peptides, polypeptides, nucleic acids, DNA, RNA, etc.) being able to evoke an immune response within an organism. Immunogenicity depends partly upon the size of the substance in question and partly upon how unlike the host molecules is the substance. Highly conserved proteins tend to have rather low immunogenicity.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, or 95% identity to each other typically remain hybridized to each other. Such hybridization conditions are described in, for example but not limited to, Current Protocols in Molecular Biology, John Wiley & Sons, N.Y. (1989), 6.3.1-6.3.6.; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at about 50° C. to 65° C.

An "isolated" or "purified" peptide or protein is substantially free of cellular material or other contaminating proteins from the cell or tissue source from which the protein is derived, or is substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than the polypeptide/protein fragment of interest. In a preferred embodiment, the polypeptides/proteins are isolated or purified.

As used herein, the term "isolated" virus is one which is separated from other organisms which are present in the natural source of the virus, e.g., biological material such as cells, blood, serum, plasma, saliva, urine, stool, sputum, nasopharyngeal aspirates, and so forth. The isolated virus can be used to infect a subject.

As used herein, the term "having a biological activity of the polypeptides of the invention" refers to the characteristics of the polypeptides or proteins having a common biological activity similar or identical structural domain and/or having sufficient amino acid identity to the polypeptide encoded by the nucleotide sequence of FmoPV or a complement, analog, derivative, or fragment thereof, or a portion thereof, or the polypeptide having the amino acid sequence of FmoPV, or a variant, analog, derivative, or fragment thereof. Such common biological activities of the polypeptides of the invention include antigenicity and immunogenicity.

As used herein, the term "portion" or "fragment" refers to a fragment of a nucleic acid molecule containing at least about 25, 30, 35, 40, 45, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 2,000, 3,000, 4,000, 5,000, 6,000, 7,000, 8,000, 9,000, 10,000, 11,000, 12,000, 13,000, 14,000, 15,000, 16,000, 17,000 or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360, 380, 400, 500, 600, 800, 1,000, 2,000, 3,000, 4,000, 5,000, 6,000, 7,000, 8,000, 9,000, 9,500 or more amino acid residues in length of the relevant protein or polypeptide and having at least one functional feature of the protein or polypeptide.

As used herein, the term "analogue" (e.g., proteins, polypeptides, peptides, and antibodies) refers to an agent that possesses a similar or identical function as a second agent but does not necessarily comprise a similar or identical amino acid sequence of the second agent, or possess a similar or identical structure of the second proteinaceous agent. In a specific embodiment, antibody analogues immunospecifically bind to the same epitope as the original antibodies from which the analogues were derived. In an alternative embodiment, antibody analogues immunospecifically bind to different epitopes than the original antibodies from which the analogues were derived. An agent that has a similar amino acid sequence refers to a second agent that satisfies at least one of the following: (a) an agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second agent; (b) an agent encoded by a nucleotide sequence that hybridizes under stringent conditions to a nucleotide sequence encoding a second agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) an agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second agent. An agent with similar structure to a second agent refers to an agent that has a similar secondary, tertiary or, quaternary structure to the second agent. The structure of an agent can be determined by methods known to those skilled in the art, including but not limited to, peptide sequencing, X ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "derivative" (e.g., proteins, polypeptides, peptides, and antibodies) refers to an agent that comprises an amino acid sequence which has been altered by the introduction of amino acid residue substitutions, deletions, and/or additions. The term "derivative" as used herein also refers to an agent which has been modified, i.e., by the covalent attachment of any type of molecule to the agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of an agent may be produced by chemical modifications using techniques known to those of skill in the art, including, but not limited to specific chemical cleavage, acetylation, formylation, metabolic synthesis of tunicamycin, etc. Further, a derivative of an agent may contain one or more non-classical amino acids. A derivative of an agent possesses a similar or identical function as the agent from which it was derived.

As used herein, the term "about" or "approximately" when used in conjunction with a number refers to any number within 1, 5 or 10% of the referenced number.

As used herein, the term "effective amount" in the context of administering a therapy to a subject refers to the amount of a therapy which has a prophylactic and/or therapeutic effect(s). In certain embodiments, in the context of administration of a therapy to a subject, "effective amount" refers to the amount of a therapy which is sufficient to achieve one, two, three, four, or more of the following effects: (i) reduction or amelioration in the severity of FmoPV infection, a FmoPV disease or symptom associated therewith; (ii) reduction in the duration of FmoPV infection, a FmoPV disease or symptom associated therewith; (iii) prevention of the progression of a FmoPV infection, a FmoPV disease or symptom associated therewith; (iv) regression of a FmoPV infection, a FmoPV disease or symptom associated therewith; (v) prevention of the development or onset of a FmoPV infection, a FmoPV disease or symptom associated therewith; (vi) prevention of the recurrence of a FmoPV infection, a FmoPV disease or symptom associated therewith; (vii) reduction or prevention of the spread of a FmoPV from one cell to another cell, one tissue to another tissue, or one organ to another organ; (viii) prevention or reduction of the spread/transmission of a FmoPV from one subject to another subject; (ix) reduction in organ failure associated with a FmoPV infection or FmoPV disease; (x) reduction in the hospitalization of a subject; (xi) reduction in the hospitalization length; (xii) an increase in the survival of a subject with a FmoPV infection or a disease associated therewith; (xiii) elimination of a FmoPV infection or a disease associated therewith; (xiv) inhibition or reduction in FmoPV replication; (xv) inhibition or reduction in the binding or fusion of FmoPV to a host cell(s); (xvi) inhibition or reduction in the entry of an FmoPV into a host cell(s); (xvii) inhibition or reduction of the replication of the FmoPV genome; (xviii) inhibition or reduction in the synthesis of FmoPV proteins; (xix) inhibition or reduction in the assembly of FmoPV particles; (xx) inhibition or reduction in the release of FmoPV particles from a host cell(s); (xxi) reduction in FmoPV titer; (xxii) reduction in the number of symptoms associated with a FmoPVB infection or a FmoPV disease; (xxiii) enhancement, improvement, supplementation, complementation, or augmentation of the prophylactic or therapeutic effect(s) of another therapy; (xxiv) prevention of the onset or progression of a secondary infection associated with a FmoPV infection; and/or (xxv) prevention of the onset or diminution of disease severity of occurring secondary to FmoPV infections. Exemplary doses of an effective amount are provided herein below.

In certain embodiments, the effective amount of a therapy does not result in complete protection from a FmoPV disease, but results in a lower titer or reduced number of FmoPV compared to an untreated subject. In certain embodiments, the effective amount of a therapy results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of FmoPV relative to an untreated subject. In certain embodiments, the effective amount of a therapy results in a reduction by 0.5 log, 1 log, 2 logs, 3 logs, 4 logs, 5, logs, 6, logs, 7 logs, or 10 logs or more in titer of FmoPV relative to an untreated subject. Benefits of a reduction in the titer, number or total burden of FmoPV include, but are not limited to, less severe symptoms of the infection, fewer symptoms of the infection, reduction in the length of the disease associated with the infection, and prevention of the onset or diminution of disease severity of infection occurring secondary to FmoPV infections.

As used herein, the term "fragment" in the context of a nucleic acid sequence refers to a nucleotide sequence comprising at least 2 or at least 3 consecutive nucleotides from a parent sequence. In a specific embodiment, the term refers to a nucleotide sequence of 2 to 30, 5 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

As used herein, the term "fragment" in the context of an amino acid sequence refers to an amino acid sequence comprising at least 2 consecutive amino acid residues from a parent sequence. In a specific embodiment, the term refers to an amino acid sequence of 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive amino acid residues of a parent sequence.

As used herein, the term "heterologous" refers to a unit that is not found naturally be associated with another unit. For example, a first nucleotide sequence is said be a heterologous to a second nucleotide sequence if the two nucleotide sequences are not found in nature to be associated with each other.

As used herein, the term "host cell" refers to any type of cell, e.g., a primary cell or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "in combination" in the context of the administration of a therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "FmoPV disease" and phrases referring to a disease associated with a FmoPV infection refer to the pathological state resulting from the presence of a FmoPV in a cell or subject or the invasion of a cell or subject by a FmoPV. In specific embodiments, the term refers to a kidney disease caused by a FmoPV.

As used herein, the term "isolated" in the context of nucleic acids refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized; however, "isolated" excludes members of a library of clones such as a cDNA library. In a specific embodiment, a nucleic acid described herein is isolated. In another specific embodiment, antibodies described herein are isolated. The language "substantially free of other cellular material" includes preparations of a nucleic acid molecule in which the nucleic acid molecule is separated from cellular components of the cells from which it is isolated or recombinantly produced. Thus, a nucleic acid molecule that is substantially free of cellular material includes preparations having less than about 30%, 20%, 10%, or 5% (by dry weight) of heterologous nucleic acid molecules or other cellular components. When the nucleic acid molecule is recombinantly produced, it is also preferably substantially free of culture medium, i.e., culture medium represents less than about 20%, 10%, or 5% of the volume of the nucleic acid molecule preparation. When the nucleic acid molecule is produced by chemical synthesis, it is preferably substantially free of chemical precursors or other chemicals, i.e., it is separated from chemical precursors or other chemicals which are involved in the synthesis of the nucleic acid molecule. Accordingly such preparations of the nucleic acid molecule have less than about 30%, 20%, 10%, 5% (by dry weight) of chemical precursors or compounds other than the nucleic acid molecule of interest.

As used herein, the phrase "multiplicity of infection" or "MOI" is the average number of virus per infected cell. The MOI is determined by dividing the number of virus added (ml added×plaque forming units (pfu)) by the number of cells added (ml added×cells/ml).

As used herein, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acids (e.g., mRNA or RNA).

As used herein, the terms "prevent," "preventing" and "prevention" in the context of the administration of a therapy(ies) to a subject refer to a prophylactic effect that results from the administration of a therapy or a combination of therapies. In a specific embodiment, the terms "prevent," "preventing" and "prevention" in the context of the administration of a therapy(ies) to a subject to prevent a disease refer to one or more of the following effects resulting from the administration of a therapy or a combination of therapies: (i) the inhibition or reduction in the development or onset of a disease or a symptom thereof; (ii) the inhibition or reduction in the recurrence of a disease or a symptom associated therewith; and (iii) the reduction or inhibition in a pathogen infection and/or replication. In other specific embodiment, the terms "prevent," "preventing" and "prevention" in the context of the administration of a therapy(ies) to a subject to prevent a FmoPV disease refer to one or more of the following effects resulting from the administration of a therapy or a combination of therapies: (i) the inhibition or reduction in the development or onset of a FmoPV disease or a symptom thereof; (ii) the inhibition or reduction in the recurrence of a FmoPV disease or a symptom associated therewith; and (iii) the reduction or inhibition in FmoPV infection and/or replication.

In another specific embodiment, the terms "prevent", "preventing" and "prevention" in the context of the administration of a therapy(ies) to a subject to prevent a FmoPV infection refer to one or more of the following effects resulting from the administration of a therapy or a combination of therapies: (i) the reduction or inhibition of the spread of FmoPV from one cell to another cell; (ii) the reduction or inhibition of the spread of FmoPV from one organ or tissue to another organ or tissue; and/or (iii) the reduction or inhibition of the spread of FmoPV from one region of an organ or tissue to another region of the organ or tissue (e.g., the reduction in the spread of FmoPV from the upper to the lower respiratory tract).

As used herein, the terms "subject" and "patient" are used interchangeably to refer to an animal (e.g., cats, dogs, birds, reptiles, and mammals). In a specific embodiment, a subject is a cat. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a non-human mammal. In another embodiment, a subject is a human.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an immunogenic composition (e.g., a FmoPV vaccine).

As used herein, the terms "treat," "treatment," and "treating" in the context of the administration of a therapy(ies) to a subject refer a beneficial or therapeutic effect resulting from the administration of a therapy or a combination of therapies. In specific embodiments, such terms refer to one, two, three, four, five or more of the following effects resulting from the administration of a therapy or a combination of therapies: (i) reduction or amelioration in the severity of a disease or a symptom associated therewith; (ii) reduction in the duration of a disease or a symptom associated therewith; (iii) prevention of the progression of a disease or symptom associated therewith; (iv) regression of a disease or a symptom associated therewith; (v) prevention of the development or onset of a disease or a symptom associated therewith; (vi) prevention of the recurrence of a disease or a symptom associated therewith; (vii) reduction or prevention of the spread of a pathogen from one cell to another cell, one tissue to another tissue, or one organ to another organ; (viii) prevention or reduction of the spread/transmission of a pathogen from one subject to another subject; (ix) reduction in organ failure associated with a disease; (x) reduction in the hospitalization of a subject; (xi) reduction in the hospitalization length; (xii) an increase in the survival of a subject with a disease associated therewith; (xiii) elimination of a disease; (xiv) inhibition or reduction in pathogen replication; (xv) reduction in pathogen numbers; (xv) the reduction in the number of symptoms associated with a disease; and (xvi) enhancement, improvement, supplementation, complementation, or augmentation of the prophylactic or therapeutic effect(s) of another therapy.

As used herein, in some embodiments, the term "wild-type" in the context of a virus refers to the types of viruses that are prevalent, circulating and naturally producing typical outbreaks of disease.

4. BRIEF DESCRIPTION OF THE DRAWINGS

FIG. 1 shows the genome organization of FmoPV and other *morbilliviruses*. The genes are shown as boxes that are drawn to scale. For the P gene, the first line above the box labeled "P" with the letter V at the end of the line represents the region of V CDS and the second line with the letter C at the end of the line represents the C CDS.

FIGS. 2-1 to 2-10 indicate the 16050 bp nucleotide sequence of FmoPV 761U Cats/Hong Kong/2009 (SEQ ID NO: 1).

FIGS. 3-1 to 3-10 indicate the 16050 bp nucleotide sequence of FmoPV 776U Cats/Hong Kong/2009 (SEQ ID NO: 2).

FIGS. 4-1 to 4-10 indicate the 16050 bp nucleotide sequence of FmoPV M252A Cats/Hong Kong/2009 (SEQ ID NO: 3).

FIG. 5 Multiple alignments of N proteins of FmoPV and other *morbilliviruses* (SEQ ID NOS 9, 7-8 and 21-26, respectively, in order of appearance). The conserved MA(S,T)L motif in *morbilliviruses* and the three conserved motifs in *paramyxoviruses* are marked in open boxes with solid line border and reported consensus sequences (SEQ ID NOS 27-28, respectively, in order of appearance) are indicated above the alignment (where x represents any amino acid residue and Ø represents an aromatic amino acid residue). Amino acid residue numbers for each protein are shown to the right of each sequence. Dots indicate identical residues and dashes indicate gaps. The NES are in open boxes with dotted line border and the NLS in open box with dashed line border.

FIGS. 6A-D indicate four panels. Panel A shows the cytopathic effects of FmoPV on CRFK cells. The open squares show the formation of giant cells. Panels B and C, show indirect immunofluorescent antigen detection in uninfected and infected CRFK cells using serum from guinea pig immunized with recombinant N protein of FmoPV, showing specific apple green cytoplasmic fluorescence in FmoPV infected CRFK cells. Panel D is an electron microscopic examination of infected CRFK cell culture supernatant showing enveloped virus with burst envelope and typical "herring bone" appearance of helical N in *paramyxoviruses*.

FIGS. 7A-F are phylogenetic analyses of the N, P, M, F, A and L amino acid sequences of FmoPV. The trees were constructed by maximum likelihood method with bootstrap values calculated from 1000 trees and rooted on midpoint. The scale bars indicate the branch length that corresponds to 0.5 substitutions per site. Three strains from FmoPV were named as 761U, 776U, M252A. Names and accession numbers of the other viruses are listed in Table 3.

Figure 8:
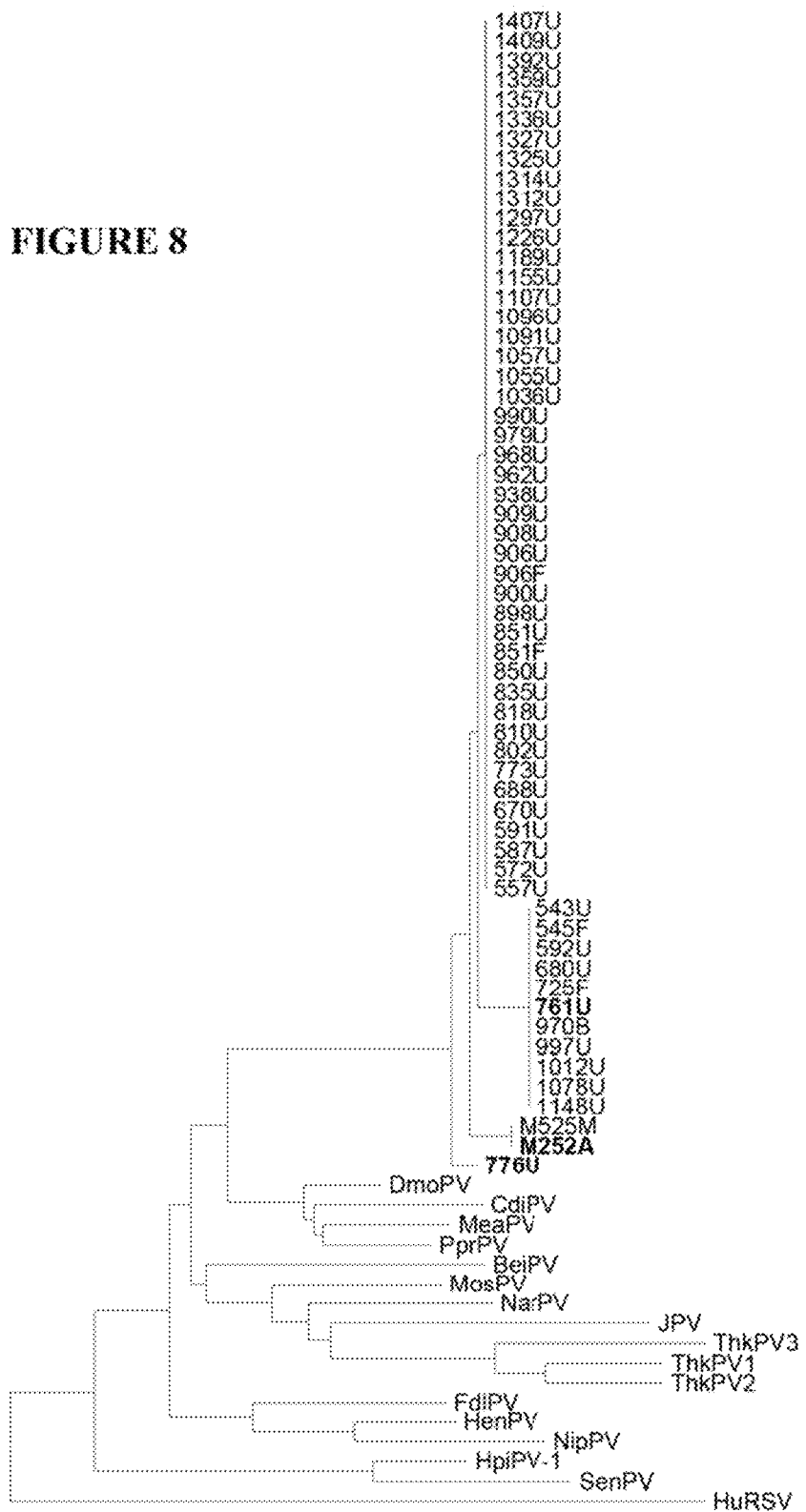

FIG. 8 is a phylogenetic analysis of amino acid sequences of 72-bp fragment of L gene of *paramyxoviruses* identified from cats in the present study. The tree was constructed by neighbor-joining method. The scale bar indicates the branch length that corresponds to 2 amino acid differences per sequence. The three strains from stray cats numbered 761U, 776U and M252A with genome sequences determined are shown in bold. RSV, respiratory syncitial virus (U39661); DmoPV, Dolphin *morbillivirus* (NC_005283); PprPV, Pestedes-petits ruminants virus (NC_006383); MeaPV, Measles virus (NC_001498); CdiPV, Canine distemper virus (NC_001921); MosPV, Mossman virus (NC_005339); NarPV, Nariva virus (FJ362497); ThkPV3, *Tuhoko* virus 3 (GU128082); ThkPV2, *Tuhoko* virus 2 (GU128081); ThkPV, *Tuhoko* virus 1 (GU128080); JPV, J-virus (NC_007454); BeiPV, Beilong virus (NC_007803); NipPV, Nipah virus (NC_002728); HenPV, Hendra virus (NC_001906); Fd1PV, Fer-de-lance virus (NC_005084); SenPV, Sendai virus (NC_001552); HpiPV-1, Human parainfluenza virus 1 (NC_003461).

Figure 9:
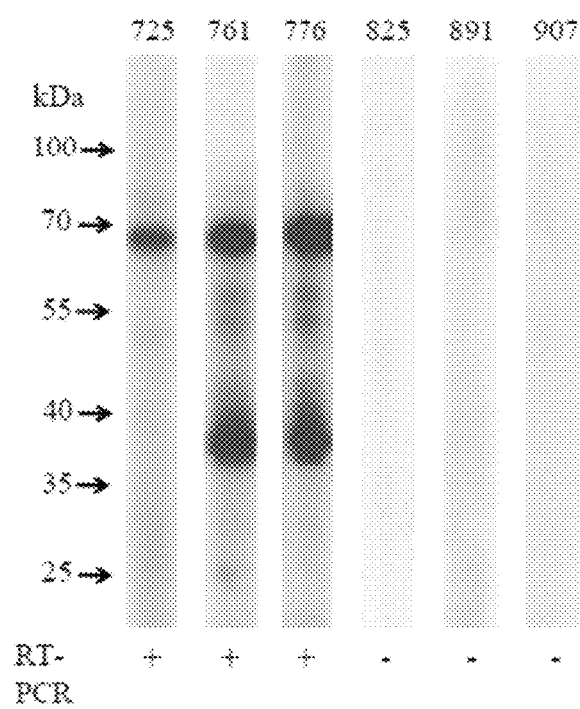

FIG. 9 shows a Western blot analysis with stray cat sera against the purified (His)$_6$-tagged ("(His)6" disclosed as SEQ ID NO: 10) recombinant FmoPV N protein antigen. Results of RT-PCR of the corresponding urine samples for FmoPV are also shown.

FIGS. 10A-F indicate six panels. Panels A and B show histological section of kidneys stained by H & E from a stray cat with FmoPV detected in urine and a normal cat, showing aggregates of inflammatory cells in the interstitium and renal tubular degeneration in the infected cat. Panels C and D show immunohistochemical staining of kidney sections of a stray cat with FmoPV detected in urine using guinea pig serum positive for anti-FmoPV N protein antibody and preimmune guinea pig serum, showing positive renal tubular cells. Panels E and F show immunohistochemical staining of lymph node sections of a stray cat positive for FmoPV using guinea pig serum positive for anti-FmoPV N protein antibody and preimmune guinea pig serum, showing positive mononuclear cells.

Figure 11:
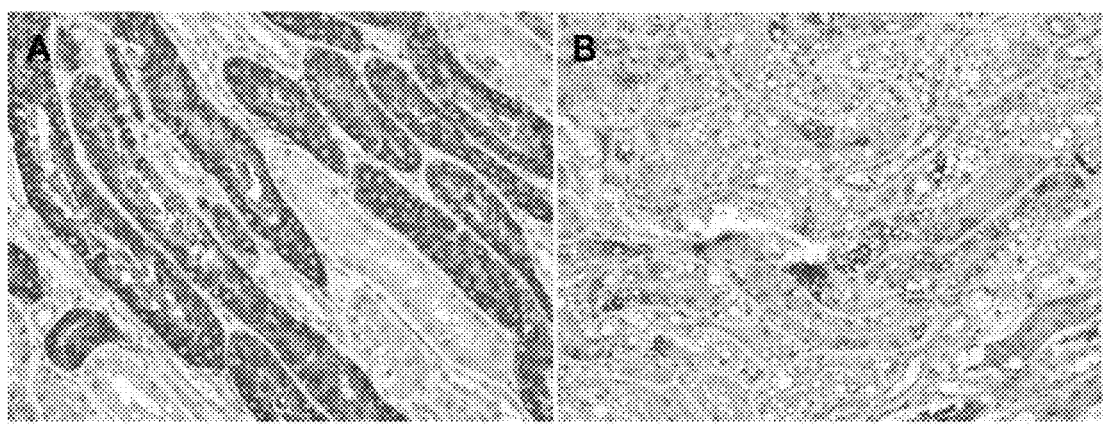

FIGS. 11A-B present representative images of cauxin-immunohistochemical stained paraffin-embedded renal sections of cats without and with histological evidence of TIN in Panels A and B, respectively.

FIGS. 12A-C show double staining of the lymph node of an FmoPV infected stray cat for (A) mouse anti-human myeloid/histocyte antigen and then labeled with Texas-red conjugated goat anti-mouse IgG; (B) guinea pig antiserum against the N protein of FmoPV, followed by FITC conjugated rabbit anti-guinea pig IgG; (C) the merged photo showed that both antigens co-localized in cytoplasm of the cells.

FIG. 13 shows the N protein polypeptide comprising the sequence of 776U, M252A, and 761U. which is used as an antigenic peptide.

5. DETAILED DESCRIPTION OF THE INVENTION

5.1 Nucleic Acids

In one aspect, provided herein are nucleic acid sequences comprising or consisting of a wild-type or a modified feline *morbillivirus* ("FmoPV"). Also provided are modified FmoPV gene segment (genomic RNA) or the complement thereof (antigenomic RNA).

In one aspect, described herein is the entire nucleotide sequence of the FmoPV. In certain embodiments, the nucleotide sequences are Genbank accession numbers: JQ411014, JQ411015 and JQ411016. The JQ411014 nucleotide sequence is shown in FIG. 2, labeled as FmoPV 761U Cats/Hong Kong/2009. The JQ411015 nucleotide sequence is shown in FIG. 3, labeled as FmoPV 776U Cats/Hong Kong/2009. The JQ411016 nucleotide sequence is shown in FIG. 4, labeled as FmoPV M252A Cats/Hong Kong/2009.

In other aspects, described herein are a complement, analog, derivative, or fragment thereof, or a portion of the FmoPV nucleotide sequence. In certain embodiments, described herein are nucleic acid molecules that hybridizes to any portion of the genome of the FmoPV, under stringent conditions. In specific embodiment, described herein are nucleic acid molecules which are suitable for use as primers consisting of or comprising the nucleic acid sequence of the FmoPV. In another embodiment, described herein are nucleic acid molecules that are suitable for use as hybridization probes for the detection of FmoPV. The primers and probes are contained in a kit for the detection of nucleic acid molecules or proteins from wild-type, natural or artificial variants, analogs, or derivatives of FmoPV.

Described herein is a natural variant of FmoPV having a sequence that is different from the genomic sequence of Genbank accession numbers: JQ411014, JQ411015 and JQ411016 due to one or more naturally occurred mutations, including, but not limited to, point mutations, rearrangements, insertions, deletions, etc., to the genomic sequence that may or may not result in a phenotypic change. Preferably, the variants include 1-5, 6-10, 11-10, 20-40, 40-60, 60-100, 100-500, 500-1000, 1000-2000 nucleic acid changes in the genome. In certain embodiments, the mutation of the genomic sequence of the FmoPV resulted in rearrangements, insertions, and/or deletions relative to the wild-type genomic sequence of FmoPV.

In certain embodiments, a nucleic acid sequence described herein is part of or incorporated into a vector. In a specific embodiment, a nucleic acid sequence described herein is part of or incorporated into a vector that facilitates the production of a modified FmoPV gene segment or the complement thereof. In one embodiment, a nucleic acid sequence described herein is part of or incorporated into the pDZ vector (see, e.g., Quinlivan et al., 2005, J. of Virology 79: 8431-8439 for information relating to the pDZ vector). In another embodiment, a nucleic acid sequence described herein is part of or incorporated into the pHW2000 vector (see, e.g., Hoffmann et al., 2000, Proc Natl Acad Sci USA. 97(11):6108-13 for information relating to the pHW2000 vector). In another embodiment, a nucleic acid sequence described herein is part of or incorporated into the pAD3000 vector (see, e.g., Hoffmann et al., 2000, Proc Natl Acad Sci USA. 97(11):6108-13 for information relating to the pAD3000 vector). In another embodiment, a nucleic acid sequence described herein is part of or incorporated into the pAD4000 vector (see, e.g., Wang et al., 2007, J. of Virology 4: 102 for information relating to the pAD4000 vector). In one embodiment, a nucleic acid sequence described herein is part of or incorporated into the vector in Section 6 infra.

Techniques for the production or use of the nucleic acids will employ, unless otherwise indicated, routine conventional techniques of molecular biology and recombinant DNA manipulation and production. Any cloning technique known to the skilled artisan can be used to assemble the nucleic acids described herein and to mutate nucleotides where necessary. Such techniques are well-known and are available to the skilled artisan in laboratory manuals such as Sambrook and Russell, Molecular Cloning: A Laboratory Manual, $3^{rd}$ edition, Cold Spring Harbor Laboratory Press, Cold Spring Harbor, N.Y. (2001). In particular, polymerase chain reaction, restriction enzymes, ligase enzyme, mutagenic primers, and amplification of nucleic acid fragments in vectors can be used to generate the individual elements of the nucleic acids described herein and then to assemble them.

In some embodiments, a nucleic acid sequence described herein is introduced (e.g., transfected) into a substrate, such as a host cell or an embryonated egg. Thus, in some embodiments, provided herein is a substrate (e.g., host cells or eggs) comprising a nucleic acid sequence described herein. In other embodiments, a nucleic acid sequence described herein that is part of or incorporated into a vector is introduced (e.g., transfected) into a substrate, such as a host cell or an embryonated egg. Thus, in some embodiments, provided herein is a substrate (e.g., host cells or eggs) comprising a nucleic acid sequence described herein that is part of or incorporated into a vector. In certain embodiments, provided herein is a cell line that is transformed with the vector containing FmoPV nucleic acid sequences. In certain embodiments, provided herein is a transgenic animal containing a vector comprising FmoPV nucleic acid sequences.

In certain embodiments, the FmoPV nucleic acid is used in a diagnostic assay for the FmoPV infection. In particular, the diagnostic assay is a quantitative assay for the detection of the FmoPV, natural or artificial variants, analogs, or derivatives thereof. In certain embodiments, the quantitative assay is PCR or RT-PCR. In certain embodiments, the FmoPV nucleic acid is in separate containers in a diagnostic kit. In specific embodiments, the nucleic acid that encodes a portion or fragment of any gene of FmoPV, natural or artificial variants, analogs, or derivatives thereof, can be used as a target for diagnostic purpose. In a specific embodiment, the nucleic acid that encodes the L gene of FmoPV is used as target for diagnosis. In one specific embodiment, diagnosis is made by amplifying a 172 bp L gene fragment from a cDNA template using quantitative PCR system. In a specific embodiment, the primers (LPW124905'-CAGAGACTTAATGAAATT-TATGG-3'; LPW124915'-CCACCCATCGGGTACTT-3' (SEQ ID NO: 12)) are used. Sequences of target fragments are shown in FIG. 13.

5.2 Proteins

The open reading frames of FmoPV gene segments can be determined using standard molecular biology and virology techniques. Provided herein are FmoPV polypeptides expressed by the FmoPV nucleic acid molecule comprising the FmoPV nucleic acid sequences. In certain embodiments, the FmoPV proteins are. In certain embodiments, FmoPV antigens are fragments or full length N, P/V/C(P), P/V/C/(V), P/VC(C), M, F, H and L proteins. Also described herein are recombinant or chimeric viruses encoded by viral vectors derived from the genome of FmoPV or natural variants thereof.

In another specific embodiment, described herein is a chimeric FmoPV virus which further comprises a heterologous nucleotide sequence. In certain embodiments, a chimeric virus may be encoded by a nucleotide sequence in which heterologous nucleotide sequences have been added to the genome or in which endogenous or native nucleotide sequences have been replaced with heterologous nucleotide sequences.

In certain embodiments, the chimeric viruses are encoded by the vectors which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains or variants of FmoPV. In particular, the chimeric virus is encoded by nucleotide sequences that encode antigenic polypeptides derived from different strains or variants of FmoPV.

A chimeric virus may be of particular use for the generation of recombinant vaccines protecting against two or more viruses (Tao et al., J. Virol. 72:2955-2961; Durbin et al., 2000, J. Virol. 74:6821-6831; Skiadopoulos et al., 1998, J. Virol. 72:1762-1768; Teng et al., 2000, J. Virol. 74:9317-9321). For example, it can be envisaged that a vector expressing one or more proteins of FmoPV and FmoPV variants, will protect a subject vaccinated with such vector against infections by both the FmoPV and FmoPV variant. Attenuated and replication-defective viruses may be of use for vaccination purposes with live vaccines.

In accordance with the present invention the heterologous sequence to be incorporated into the viral vectors encoding the recombinant or chimeric viruses of the invention include sequences obtained or derived from different strains or variants of the FmoPV.

In certain embodiments, the chimeric or recombinant viruses of the invention are encoded by viral vectors derived from viral genomes wherein one or more sequences, intergenic regions, termini sequences, or portions or entire ORF have been substituted with a heterologous or non-native sequence. In certain embodiments of the invention, the chimeric viruses of the invention are encoded by viral vectors derived from viral genomes wherein one or more heterologous sequences have been inserted or added to the vector.

Any nucleotide sequence heterologous to FmoPV may be included in a modified FmoPV gene segment described herein. In certain embodiments, the heterologous nucleotide sequence is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous nucleotide sequence is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length. In some embodiments, the heterologous nucleotide encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length; 250 to 300 amino acids in length, 300 to 400 amino acids in length, or 500 or more amino acids in length. In some embodiments, the heterologous nucleotide encodes a polypeptide that does not exceed 500 amino acids in length. In specific embodiments the heterologous nucleotide sequence does not contain a stop codon. In certain embodiments, the heterologous nucleotide sequence is codon-optimized. Techniques for codon optimization are known in the art and can be applied to codon optimize a heterologous nucleotide sequence.

In one embodiment, a heterologous nucleotide sequence encodes an antigen of any infectious pathogen or an antigen associated with any disease that is capable of eliciting an immune response. In a specific embodiment, the antigen is a glycoprotein. In certain embodiments, a heterologous nucleotide sequence encodes a viral antigen. In other embodiments, the viral antigen is an antigen from a virus other than a FmoPV.

In specific embodiments, a FmoPV described herein is attenuated. In a particular embodiment, the FmoPV is attenuated such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response.

In some embodiments, a FmoPV described herein comprises one or more attenuating mutations in a modified FmoPV gene segment. In some embodiments, a FmoPV described herein comprises one or more attenuating mutations in a complementing FmoPV gene segment. In certain embodiments, a FmoPV described herein comprises one or more attenuating mutations in two, three or more complementing FmoPV gene segments. In some embodiments, a FmoPV described herein comprises one or more attenuating mutations in a modified FmoPV gene segment and one or more attenuating mutations in a complementing FmoPV gene segment.

The selection of the viral vector may depend on the species of the subject that is to be treated or protected from a viral infection. If the subject is a feline, then an attenuated FmoPV can be used to provide the antigenic sequences.

In accordance with the present invention, the viral vectors can be engineered to provide antigenic sequences which confer protection against infection by the FmoPV, natural or artificial variants, analogs, or derivatives thereof. The viral vectors may be engineered to provide one, two, three or more antigenic sequences. In accordance with the present invention the antigenic sequences may be derived from the same virus, from different strains or variants of the same type of virus, or from different viruses.

The expression products and/or recombinant or chimeric virions obtained in accordance with the invention may advantageously be utilized in vaccine formulations. The expression products and chimeric virions of may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with the FmoPV, natural or artificial variants, analogs, or derivatives thereof.

In another aspect, the mutation of the genomic sequence of the FmoPV resulted in changes in the FmoPV proteins. In certain embodiments, the mutation of the genomic sequence of the FmoPV resulted in less than 25, 20, 15, 10, 5, 4, 3, or 2 amino acid substitutions in the FmoPV proteins.

Either conservative or non-conservative amino acid substitutions can be made at one or more amino acid residues. In preferred embodiments, the variants have conservative amino acid substitutions that are made at one or more predicted non-essential amino acid residues (i.e., amino acid residues which are not critical for the expression of the biological activities of the virus, e.g., infectivity, replicability, protein synthesis ability, assembling ability, and cytotoxic effect). In other embodiments, the variants have non-conservative amino acid substitutions that are made at one or more predicted non-essential amino acid residues (i.e., amino acid residues which are not critical for the biological activities of the virus, e.g., infectivity, replication ability, protein synthesis ability, assembling ability, and cytotoxic effect). In other embodiments, the amino acid substitutions are made at essential amino acid residues (i.e., amino acid residues which are critical for the biological activities of the virus, e.g., infectivity, replicability, protein synthesis ability, assembling ability, and cytotoxic effect).

A "conservative amino acid substitution" is one in which the amino acid residue is replaced with an amino acid residue having a side chain with a similar charge. A "non-conservative amino acid substitution" is one in which the amino acid residue is replaced with an amino acid residue having a side chain with an opposite charge. Families of amino acid residues having side chains with similar charges have been defined in the art. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (See, for example, Biochemistry, 4th ed., Ed. by L. Stryer, WH Freeman and Co.: 1995).

The invention further relates to mutant FmoPV peptides. In one embodiment, mutations can be introduced randomly along all or part of the coding sequence of the FmoPV or variants thereof, such as by saturation mutagenesis, and the resultant mutants can be screened for biological activity to identify mutants that retain activity. Techniques for mutagenesis known in the art can also be used, including but not limited to, point-directed mutagenesis, chemical mutagenesis, in vitro site-directed mutagenesis, using, for example, the QuikChange Site-Directed Mutagenesis Kit (Stratagene), etc. Non-limiting examples of such modifications include substitutions of amino acids to cysteines toward the formation of disulfide bonds; substitution of amino acids to tyrosine and subsequent chemical treatment of the polypeptide toward the formation of dityrosine bonds, as disclosed in detail herein; one or more amino acid substitutions and/or biological or chemical modification toward generating a binding pocket for a small molecule (substrate or inhibitor), and/or the introduction of side-chain specific tags (e.g., to characterize molecular interactions or to capture protein-protein interaction partners). In a specific embodiment, the biological modification comprises alkylation, phosphorylation, sulfation, oxidation or reduction, ADP-ribosylation, hydroxylation, glycosylation, glucosylphosphatidylinositol addition, ubiquitination. In another specific embodiment, the chemical modification comprises altering the charge of the recombinant virus. In yet another embodiment, a positive or negative charge is chemically added to an amino acid residue where a charged amino acid residue is modified to an uncharged residue.

5.3 Construction of Recombinant FmoPV

Techniques known to one skilled in the art may be used to produce a recombinant FmoPV containing a modified FmoPV gene segment described herein. For example, reverse genetics techniques may be used to generate such a FmoPV. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles.

Alternatively, helper-free plasmid technology may be used to produce a recombinant FmoPV containing a modified FmoPV gene segment. Briefly, full length cDNAs of viral segments are amplified using PCR with primers that include unique restriction sites, which allow the insertion of the PCR product into the plasmid vector. The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used.

5.4. Propagation of FmoPV

The FmoPV described herein can be propagated in any substrate that allows the virus to grow to titers that permit the uses of the viruses described herein. In one embodiment, the substrate allows the FmoPV described herein to grow to titers comparable to those determined for the corresponding wild-type viruses.

The FmoPV described herein may be grown in host cells (e.g., cat, avian cells, chicken cells, etc.) that are susceptible to infection by the viruses, embryonated eggs or animals (e.g., birds). Specific examples of host cells include Vero cells, MDCK cells, MBCK cells, COS cells, 293 cells, 293T cells, A549 cells, MDBK cells, etc. Such methods are well-known to those skilled in the art. In a specific embodiment, the FmoPV described herein may be propagated in cell lines. In another embodiment, the FmoPV described herein described herein are propagated in chicken cells or embryonated eggs. Representative chicken cells include, but are not limited to, chicken embryo fibroblasts and chicken embryo kidney cells.

For virus isolation, the FmoPV described herein can be removed from cell culture and separated from cellular components, typically by well known clarification procedures, e.g., such as gradient centrifugation and column chromatography, and may be further purified as desired using procedures well known to those skilled in the art, e.g., plaque assays.

5.5 Compositions & Routes of Administration

The FmoPV described herein may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing and/or treating an FmoPV infection. The compositions may also be used in methods or preventing and/or treating FmoPV disease. The composition may be used in methods of eliciting an immune response to a particular antigen(s) or in methods of delivering a certain protein to a subject.

In one embodiment, a pharmaceutical composition comprises a FmoPV in an admixture with a pharmaceutically acceptable carrier. In some embodiments, a pharmaceutical composition may comprise one or more other therapies in addition to a FmoPV. In specific embodiments, a FmoPV described herein that is incorporated into a pharmaceutical composition (e.g., an immunogenic composition such as a vaccine) is a live virus. An immunogenic composition comprising a live FmoPV for administration to a subject may be preferred because multiplication of the virus in the subject may lead to a prolonged stimulus of similar kind and magnitude to that occurring in natural infections, and therefore, confer substantial, long lasting immunity.

In some embodiments, a FmoPV described herein that is incorporated into a pharmaceutical composition (e.g., an immunogenic composition such as a vaccine) is inactivated. Techniques known to one of skill in the art may be used to inactivate FmoPV described herein.

In specific embodiments, immunogenic compositions described herein are monovalent formulations. In other embodiments, immunogenic compositions described herein are multivalent formulations.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. Liposomes or micelles can also be used as pharmaceutically acceptable carriers. These can be prepared according to methods known to those skilled in the art, for example, as described in U.S. Pat. No. 4,522,811.

In a specific embodiment, pharmaceutical compositions are formulated to be suitable for the intended route of administration to a subject. For example, the pharmaceutical composition may be formulated to be suitable for parenteral, oral, intradermal, intranasal, transdermal, pulmonary, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein comprise, or are administered in combination with, an adjuvant. The adjuvant for administration in combination with a composition described herein may be administered before, concomitantly with, or after administration of the composition. In specific embodiments, an inactivated virus immunogenic composition described herein comprises one or more adjuvants. In some embodiments, the term "adjuvant" refers to a compound that when administered in conjunction with or as part of a composition described herein augments, enhances and/or boosts the immune response to a FmoPV virus, but when the compound is administered alone does not generate an immune response to the virus. In some embodiments, the adjuvant generates an immune response to a FmoPV and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211) and QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine.

The pharmaceutical compositions described herein can be included in a container, pack, or dispenser together with instructions for administration.

In a particular embodiment, the recombinant N proteins of the present invention have antigenicity, making them suitable for use in immunogenic compositions. The antigenicity of these recombinant N proteins is demonstrated in Example 7. Among tested sera from the 56 cats that were RT-PCR positive and 401 cats that were RT-PCR negative for FmoPV, 49 (76.7%) and 78 (19.4%), respectively, were positive for IgG against N protein of FmoPV by Western blot analysis ($P<0.0001$). See FIG. 9 and see Table 6 below. Among tested sera from the 56 cats that were RT-PCR positive for FmoPV, only 5 (8.9%) were positive for IgM against N protein of FmoPV.

In one embodiment, a sequence for use as an antigenic peptide is the N protein polypeptide comprising the sequence of 776U, M252A, and 761U as shown in FIG. 13. The antigenic polypeptide is used to detect the presence of FmoPV in a sample.

In FIG. 9, a Western blot analysis with stray cat sera against the purified $(His)_6$-tagged ("(His)6" disclosed as SEQ ID NO: 10) recombinant FmoPV N protein antigen, prominent immunoreactive protein bands of about 69 kDa, consistent with the expected size of 68.7 kDa of the recombinant protein, were detected in three of the six cat serum samples shown, indicating antigen-antibody interactions between the recombinant FmoPV N protein and serum antibodies. Results of RT-PCR of the corresponding urine samples for FmoPV are also shown. Table 6 shows the FmoPV viral load and antibody level of RT-PCR positive stray cats in this study.

TABLE 6

| Cat no. | Date of sample collection | Type of positive sample(s) | FmoPV Viral load (copies/ml) | Western blot |
|---|---|---|---|---|
| 543 | 14 May 2009 | Urine | $1.4 \times 10^4$ | + |
| 545 | 14 May 2009 | Faecal swab | $3.8 \times 10^5$ | − |
| 557 | 12 Jun. 2009 | Urine | $9.5 \times 10^2$ | + |
| 572 | 24 Jun. 2009 | Urine | $1.2 \times 10$ | + |
| 587 | 02 Jul. 2009 | Urine | 4.88 | ++ |
| 591 | 08 Jul. 2009 | Urine | $2.7 \times 10^4$ | +++ |
| 592 | 08 Jul. 2009 | Urine | $3.0 \times 10^3$ | +++ |
| 670 | 27 Aug. 2009 | Urine | $2.7 \times 10^3$ | + |
| 680 | 31 Aug. 2009 | Urine | $8.8 \times 10^3$ | +++ |
| 688 | 03 Sep. 2009 | Urine | $7.1 \times 10^3$ | +++ |
| 725 | 03 Nov. 2009 | Faecal swab | $2.7 \times 10^3$ | ++ |
| 761 | 24 Nov. 2009 | Urine | $5.9 \times 10^5$ | +++ |
| 773 | 01 Dec. 2009 | Urine | $6.4 \times 10^4$ | + |
| 776 | 04 Dec. 2009 | Urine | $2.3 \times 10^3$ | +++ |
| 802 | 24 Dec. 2009 | Urine | 2.76 | − |
| 810 | 29 Dec. 2009 | Urine | $1.6 \times 10^2$ | − |
| 818 | 12 Jan. 2010 | Urine | 1.06 | − |
| 835 | 22 Jan. 2010 | Urine | $2.4 \times 10^4$ | + |
| 850 | 29 Jan. 2010 | Urine | $2.1 \times 10^4$ | ++ |
| 851 | 29 Jan. 2010 | Urine | 2.6 | ++ |
|  |  | Faecal swab | $5.0 \times 10^2$ |  |
| 858 | 26 Feb. 2010 | Urine | $6.9 \times 10^4$ | + |
| 898 | 23 Mar. 2010 | Urine | $2.4 \times 10^4$ | + |
| 900 | 23 Mar. 2010 | Urine | $1.6 \times 10^4$ | + |
| 906 | 23 Mar. 2010 | Urine | $9.8 \times 10^3$ | ++ |
|  |  | Faecal swab | $2.0 \times 10^4$ |  |
| 908 | 25 Mar. 2010 | Urine | $8.8 \times 10^2$ | + |
| 909 | 25 Mar. 2010 | Urine | $2.6 \times 10^3$ | − |
| 938 | 29 Apr. 2010 | Urine | $2.1 \times 10^2$ | ++ |
| 962 | 06 May 2010 | Urine | $8.0 \times 10^3$ | +++ |
| 968 | 10 May 2010 | Urine | $4.7 \times 10^2$ | +++ |
| 970 | 10 May 2010 | Blood | $3.1 \times 10^4$ | +++ |
| 979 | 17 May 2010 | Urine | $5.3 \times 10^3$ | +++ |
| 990 | 24 May 2010 | Urine | $1.4 \times 10^3$ | ++ |
| 997 | 31 May 2010 | Urine | $5.0 \times 10^3$ | ++ |
| 1012 | 10 Jun. 2010 | Urine | $9.5 \times 10^3$ | + |
| 1036 | 28 Jun. 2010 | Urine | $1.6 \times 10^4$ | ++ |
| 1055 | 02 Aug. 2010 | Urine | $1.0 \times 10^3$ | + |
| 1057 | 02 Aug. 2010 | Urine | $9.7 \times 10^3$ | ++ |
| 1078 | 09 Sep. 2010 | Urine | $2.0 \times 10^5$ | + |
| 1091 | 24 Sep. 2010 | Urine | $7.0 \times 10^3$ | + |
| 1096 | 27 Sep. 2010 | Urine | $2.0 \times 10^1$ | +++ |
| 1107 | 07 Oct. 2010 | Urine | $4.6 \times 10^3$ | ++ |
| 1148 | 25 Oct. 2010 | Urine | $1.4 \times 10^5$ | ++ |
| 1155 | 28 Oct. 2010 | Urine | $3.2 \times 10^{-1}$ | + |
| 1189 | 25 Nov. 2010 | Urine | $6.9 \times 10^3$ | + |
| 1226 | 06 Jan. 2011 | Urine | $3.7 \times 10^{-2}$ | +++ |
| 1297 | 28 Feb. 2011 | Urine | $2.7 \times 10^2$ | + |
| 1312 | 09 Mar. 2011 | Urine | 3.8 | ++ |

TABLE 6-continued

| Cat no. | Date of sample collection | Type of positive sample(s) | FmoPV Viral load (copies/ml) | Western blot |
|---|---|---|---|---|
| 1314 | 09 Mar. 2011 | Urine | $1.6 \times 10^3$ | – |
| 1325 | 14 Mar. 2011 | Urine | $2.3 \times 10^3$ | ++ |
| 1327 | 24 Mar. 2011 | Urine | $3.7 \times 10^4$ | + |
| 1336 | 31 Mar. 2011 | Urine | $5.4 \times 10^5$ | ++ |
| 1357 | 28 Apr. 2011 | Urine | $1.0 \times 10^2$ | ++ |
| 1359 | 28 Apr. 2011 | Urine | $2.0 \times 10^5$ | + |
| 1392 | 30 May 2011 | Urine | $5.2 \times 10^4$ | – |
| 1407 | 13 Jun. 2011 | Urine | $3.5 \times 10$ | ++ |
| 1409 | 16 Jun. 2011 | Urine | $1.4 \times 10^6$ | + |

Figure 6:
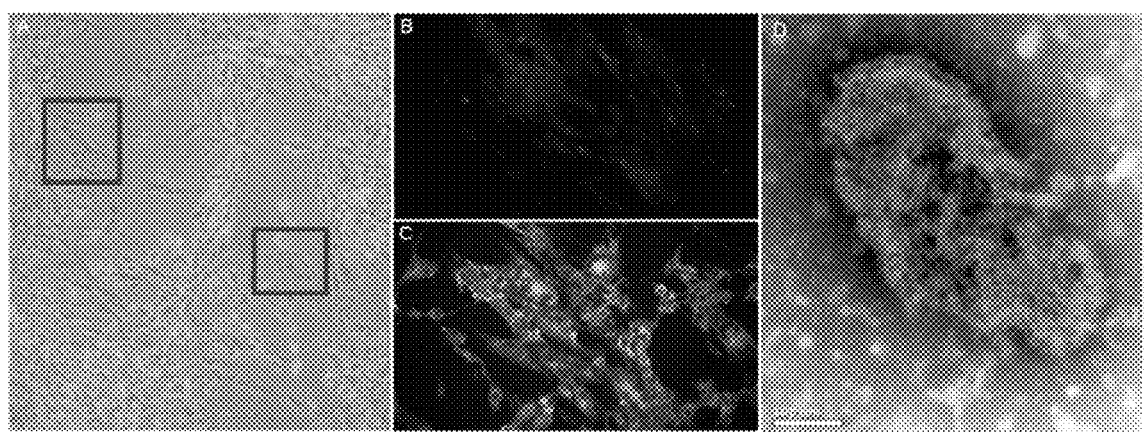
Figure 7A:
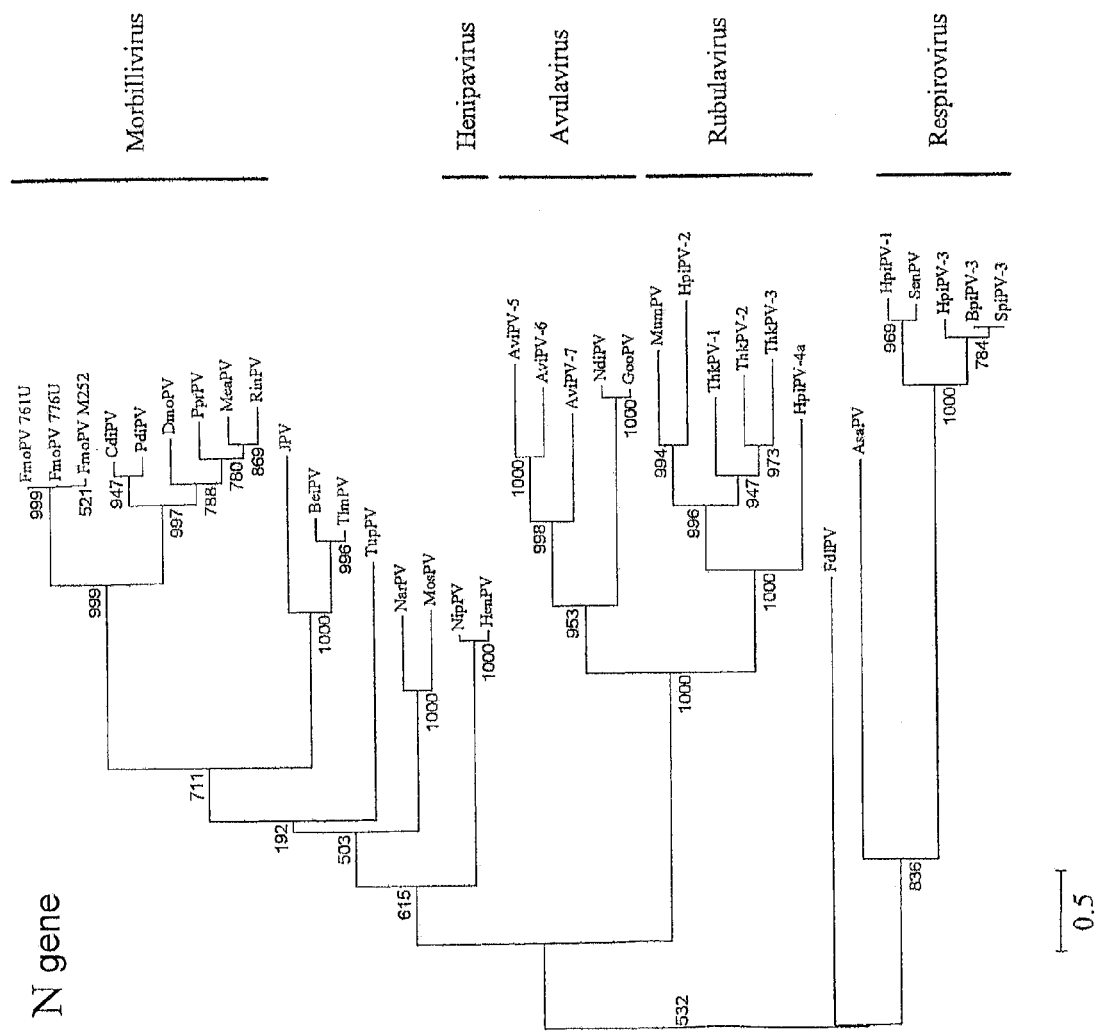
Figure 7B:
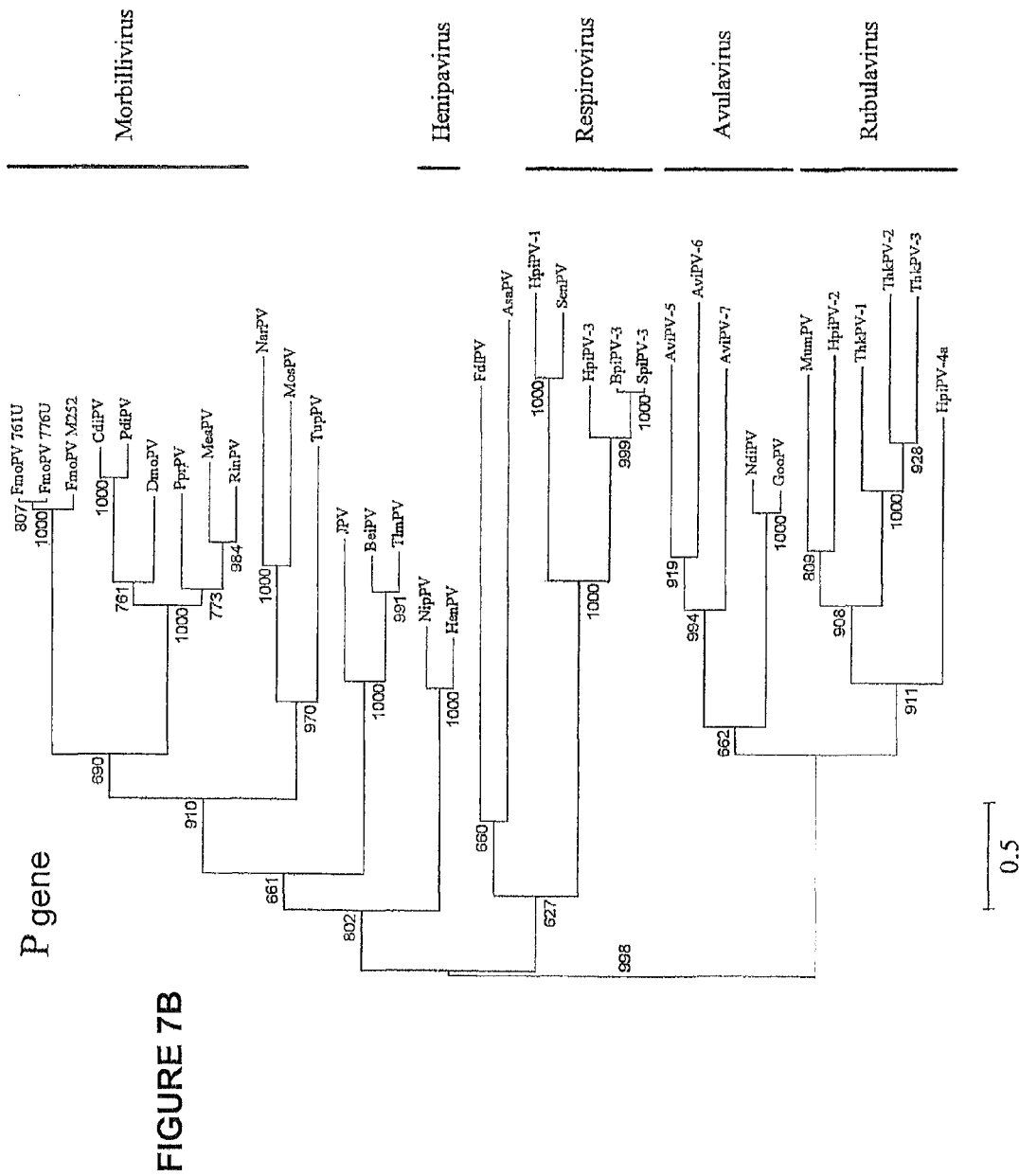
Figure 7C:
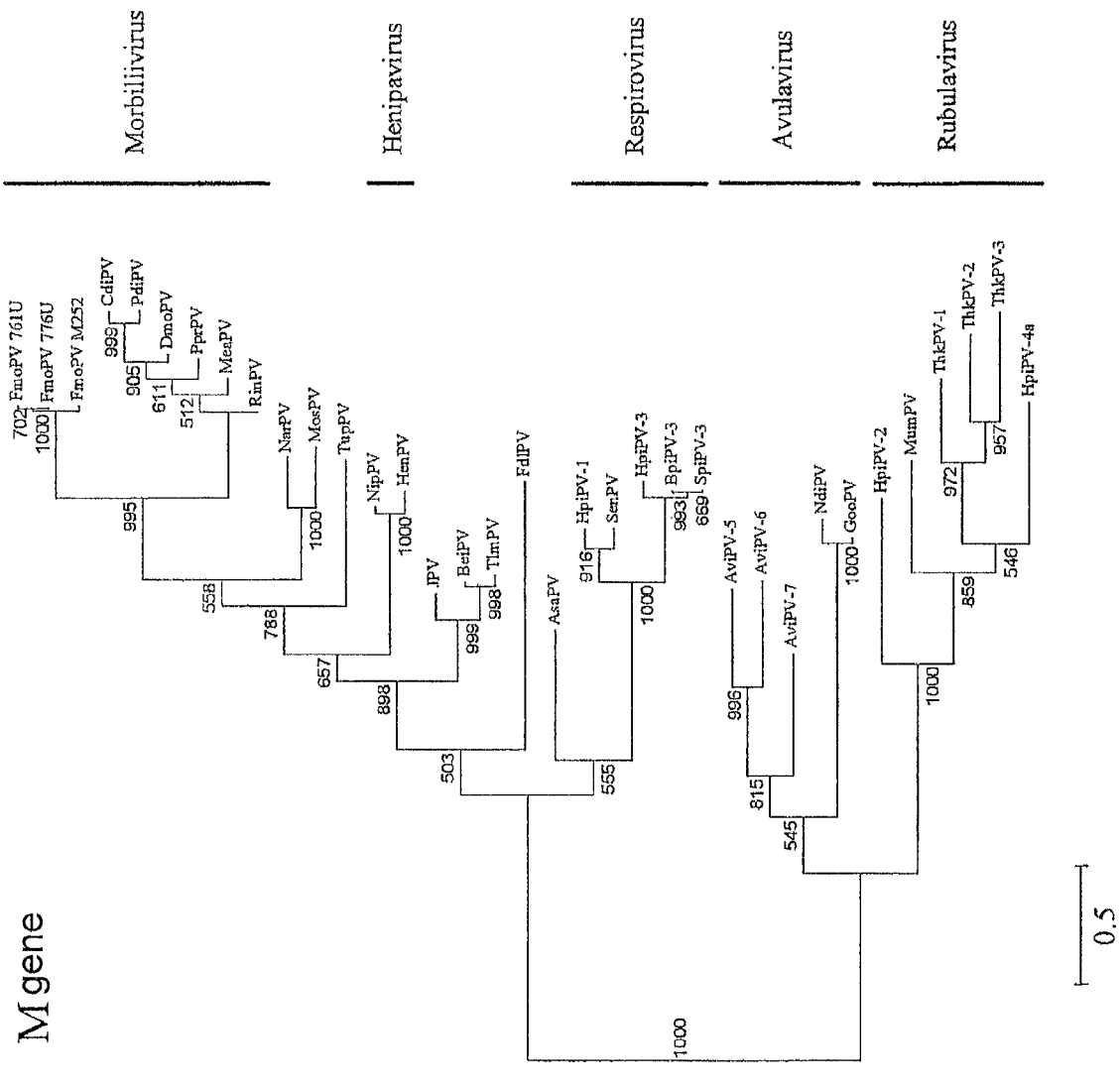
Figure 7D:
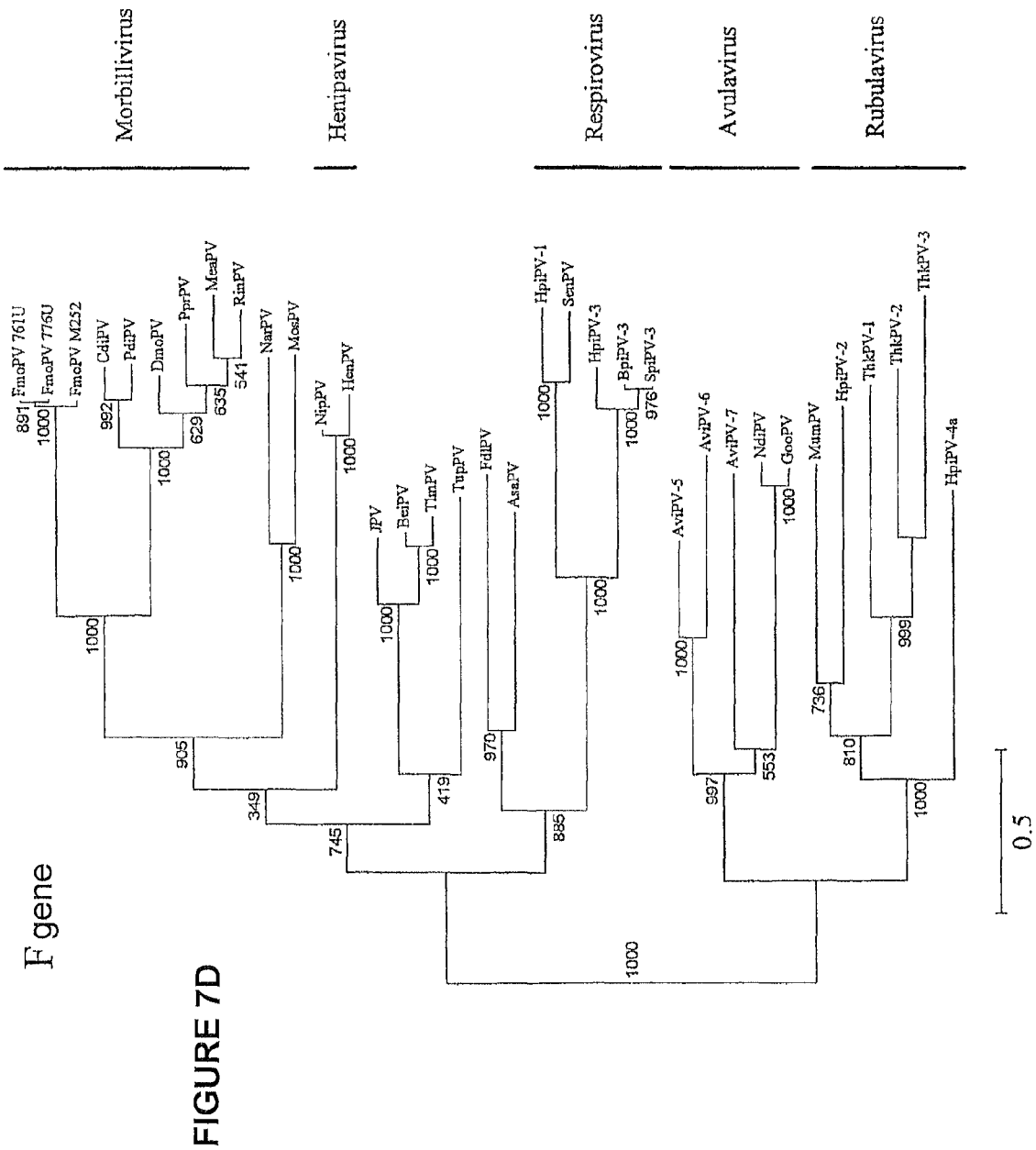
Figure 7E:
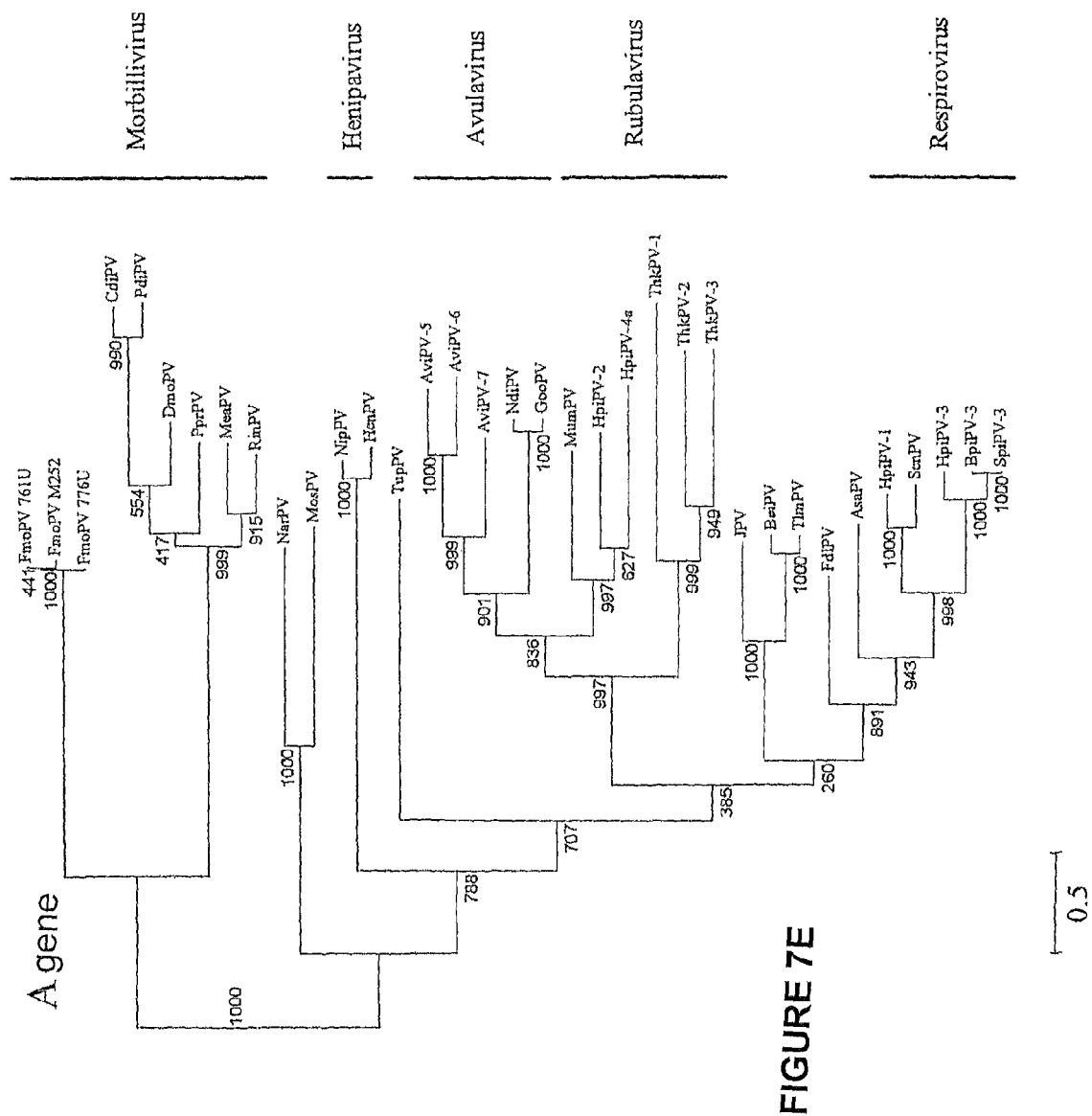

Specific apple green finely granular and diffuse cytoplasmic fluorescence was also observed using serum from guinea pig immunized with recombinant N protein of FmoPV or corresponding serum of the infected cat (FIG. 6).

5.6 Immunogenic Compositions Comprising Live Viruses

In one embodiment, provided herein are immunogenic compositions (e.g., vaccines) comprising one or more live FmoPV described herein. In some embodiments, the live virus is attenuated. In some embodiments, an immunogenic composition comprises two, three, four or more live viruses.

In certain embodiments, provided herein are immunogenic compositions (e.g., vaccines) comprising about $10^5$ to about $10^{10}$ fluorescent focus units (FFU) of live attenuated FmoPV described herein, about 0.1 to about 0.5 mg monosodium glutamate, about 1.0 to about 5.0 mg hydrolyzed porcine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 μg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated FmoPV described herein, 0.188 mg monosodium glutamate, 2.0 mg hydrolyzed porcine gelatin, 2.42 mg arginine, 13.68 mg sucrose, 2.26 mg dibasic potassium phosphate, 0.96 mg monobasic potassium phosphate, and <0.015 μg/ml gentamicin sulfate per dose. In some embodiments, the immunogenic compositions (e.g., vaccines) are packaged as pre-filled sprayers containing single 0.2 ml doses.

In a specific embodiment, the live virus is propagated in embryonated chicken eggs before its use in an immunogenic composition described herein. In another specific embodiment, the live virus is not propagated in embryonated chicken eggs before its use in an immunogenic composition described herein. In another specific embodiment, the live virus is propagated in mammalian cells before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and, therefore, confer substantial, long lasting immunity.

5.7 Generation of Antibodies

The FmoPV described herein may be used to elicit antibodies against FmoPV or a heterologous nucleotide sequence. In a specific embodiment, a FmoPV described herein or a composition thereof may be administered to a non-human subject (e.g., mouse, rabbit, rat, guinea pig, cat, etc.) to induce an immune response that includes the production of antibodies which may be isolated using techniques known to one of skill in the art (e.g., immunoaffinity chromatography, centrifugation, precipitation, etc.).

Alternatively, a virus described herein may be used to screen for antibodies from antibody libraries. For example, a FmoPV may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to a FmoPV described herein. Any screening assay, such as a panning assay, ELISA, surface plasmon resonance, or other antibody screening assay known in the art may be used to screen for antibodies that bind to a FmoPV. The antibody library screened may be a commercially available antibody library, an in vitro generated library, or a library obtained by identifying and cloning or isolating antibodies from a subject infected with FmoPV. In particular embodiments, the antibody library is generated from a survivor of an FmoPV outbreak. Antibody libraries may be generated in accordance with methods known in the art. In a particular embodiment, the antibody library is generated by cloning the antibodies and using them in phage display libraries or a phagemid display library.

Antibodies elicited or identified in accordance with the methods described herein may be tested for specificity for FmoPV antigens and the ability to neutralize FmoPV using the biological assays known in the art or described herein. In one embodiment, an antibody identified or isolated from a non-human animal antibody specifically binds to a FmoPV antigen.

Antibodies elicited or identified in accordance with the methods described herein may be tested for specificity to, and the ability to neutralize, a peptide or polypeptide antigen encoded by a heterologous nucleotide sequence described herein using the biological assays known in the art or described herein. In one embodiment, an antibody identified or isolated from a non-human animal antibody specifically binds to a peptide or polypeptide antigen encoded by a heterologous nucleotide sequence described herein. In one embodiment, the neutralizing antibody neutralizes the viral, bacterial, fungal or other pathogen, or a tumor that expresses the peptide or polypeptide antigen encoded by a heterologous nucleotide sequence described herein.

Antibodies elicited or identified using a FmoPV described herein include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., IgG1, IgG2, IgG3, IgG4, IgA1 and IgA2) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a FmoPV described herein may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716, 111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize FmoPV and the specificity of the antibodies for FmoPV antigens may be tested prior to using the antibodies in passive immunotherapy. Antibodies against FmoPV antigens are used to detect the presence of FmoPV in a subject. In specific embodiments, FmoPV antibodies are used to diagnose FmoPV infections in feline. In specific embodiments, FmoPV antibodies are used to diagnose TIN in feline.

The antibodies elicited or identified using a FmoPV described herein may be incorporated into compositions. In a specific embodiment, the compositions are pharmaceutical compositions. In some embodiments, a pharmaceutical composition may comprise one or more other therapies in addition to an antibody. The pharmaceutical compositions provided herein can be in any form that allows for the composition to be administered to a subject. In a specific embodiment, the pharmaceutical compositions are suitable for veterinary and/or human administration. In another specific embodiment, the antibody compositions are formulated for the intended route of administration (e.g., parenteral, intranasal, or pulmonary administration). The antibody compositions may be used in methods of preventing and/or treating a FmoPV infection. The antibody compositions may also be used in methods or preventing and/or treating FmoPV disease.

Antibodies elicited or identified using a FmoPV described herein may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

5.8 Prophylactic & Therapeutic Uses

In one aspect, provided herein are methods for inducing an immune response in a subject utilizing a FmoPV described herein or an immunogenic composition thereof. In a specific embodiment, a method for inducing an immune response to a FmoPV in a subject comprises administering to a subject in need thereof an effective amount of a FmoPV or an immunogenic composition thereof. In certain embodiments, the FmoPV or immunogenic composition thereof expresses FmoPV proteins from two or more types, subtypes or strains of FmoPV, and thus, may be used to induce an immune response to two or more types, subtypes or strains of FmoPV. In a specific embodiment, a method for inducing an immune response to a FmoPV in a subject comprises administering to a subject in need thereof a FmoPV described herein as a live virus vaccine. In particular embodiments, the live virus vaccine comprises an attenuated virus. In another embodiment, a method for inducing an immune response to FmoPV in a subject comprises administering to a subject in need thereof a FmoPV described herein as an inactivated virus vaccine.

In another aspect, provided herein are methods for preventing and/or treating a FmoPV infection in a subject utilizing a FmoPV described herein or a pharmaceutical composition thereof. In one embodiment, a method for preventing or treating a FmoPV infection in a subject comprises administering to a subject in need thereof an effective amount of a FmoPV or a composition thereof. In another embodiment, a method for preventing or treating an FmoPV infection in a subject comprises administering to a subject in need thereof an effective amount of a FmoPV or a pharmaceutical composition thereof and one or more other therapies. In another embodiment, a method for preventing or treating a FmoPV infection in a subject comprises administering to a subject in need thereof a FmoPV described herein as a live virus vaccine. In particular embodiments, the live virus vaccine comprises an attenuated virus. In another embodiment, a method for preventing or treating a FmoPV infection in a subject comprises administering to a subject in need thereof a FmoPV described herein as an inactivated virus vaccine.

In another aspect, provided herein are methods for preventing and/or treating a FmoPV in a subject utilizing a FmoPV described herein or a pharmaceutical composition thereof. In a specific embodiment, a method for preventing or treating a FmoPV disease in a subject comprises administering to a subject in need thereof an effective amount of a FmoPV or a pharmaceutical composition thereof. In another embodiment, a method for preventing or treating a FmoPV in a subject comprises administering to a subject in need thereof an effective amount of a FmoPV or a pharmaceutical composition thereof and one or more other therapies. In another embodiment, a method for preventing or treating a FmoPV disease in a subject comprises administering to a subject in need thereof a FmoPV described herein as a live virus vaccine. In particular embodiments, the live virus vaccine comprises an attenuated virus. In another embodiment, a method for preventing or treating a FmoPV disease in a subject comprises administering to a subject in need thereof a FmoPV described herein as an inactivated virus vaccine.

5.9 Dosage and Frequency of Administration

A FmoPV, an antibody or a composition described herein may be delivered to a subject by a variety of routes. These include, but are not limited to, intranasal, intratracheal, oral, intradermal, intramuscular, topical intraperitoneal, transdermal, intravenous, pulmonary, conjunctival and subcutaneous routes. In some embodiments, a composition is formulated for topical administration, for example, for application to the skin. In specific embodiments, the composition is formulated for nasal administration, e.g., as part of a nasal spray. In certain embodiments, a composition is formulated for intramuscular administration. In some embodiments, a composition is formulated for subcutaneous administration. In specific embodiments for live virus vaccines, the vaccine is formulated for administration by a route other than injection. In some embodiments it may be desirable to introduce the pharmaceutical compositions into the lungs by any suitable route. Pulmonary administration can also be employed, e.g., by use of an inhaler or nebulizer, and formulation with an aerosolizing agent for use as a spray.

In some embodiments, when a FmoPV or a composition thereof is administered to a non-human subject (e.g., a cat), the virus or composition is administered orally to the subject in the subject's food. In other embodiments, when a FmoPV or a composition thereof is administered to a subject (e.g., cat), the virus or composition is administered orally to the subject in the subject's water. In other embodiments, when a FmoPV or a composition thereof is administered to a non-human subject, the virus or composition is administered by spraying the subject with the virus or composition.

The amount of a FmoPV, an antibody or composition described herein which will be effective in the treatment and/or prevention of a FmoPV infection or a FmoPV disease will depend on the nature of the disease, and can be determined by standard techniques. The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the subject (including age, body weight, health), whether the subject is human or an animal, whether other medications are administered, and whether treatment is prophylactic or therapeutic. Similarly, the amount of a FmoPV or a composition thereof that will be effective as a delivery vector will vary and can be determined by standard techniques. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for live FmoPV may vary from 10-100, or more, virions per dose. In some embodiments, suitable dosages of a live FmoPV virus are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed. In another embodiment, a live FmoPV is formulated such that a 0.2-mL dose contains $10^{6.5}$-$10^{7.5}$ fluorescent focal units of live FmoPV. In another embodiment, an inactivated vaccine is formulated such that it contains about 15 μg to about 100 μg, about 15 μg to about 75 μg, about 15 μg to about 50 μg, or about 15 μg to about 30 μg of a FmoPV protein.

In certain embodiments, a FmoPV described herein or a composition thereof is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different FmoPV strain or a composition thereof. In some embodiments, the administration of the same FmoPV strain or a composition thereof may be repeated and the administrations may be separated by at least 1 day, 2 days, 3 days, 5 days, 10 days, 15 days, 30 days, 45 days, 2 months, 75 days, 3 months, or at least 6 months.

For passive immunization with an antibody, the dosage ranges from about 0.0001 to 100 mg/kg, and more usually 0.01 to 50 mg/kg or 0.1 to 15 mg/kg, of the subject body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the FmoPV in the patient.

5.10 Screening Assays

In one aspect, a FmoPV described herein may be used to study the life cycle of a FmoPV. For example, a FmoPV described herein that expresses a detectable heterologous sequence (e.g., a detectable substance such as described above) is introduced into a host cell and the life cycle of the virus is monitored by the assessing the expression of the detectable heterologous sequence. A FmoPV described herein that expresses a detectable heterologous sequence may also be administered to a non-human animal and the infection monitored by assessing the expression of the detectable heterologous sequence.

In another aspect, provided herein are high throughput screening assays for the identification or validation of compounds that modulate the replication of negative-sense, single-stranded RNA viruses, in particular FmoPV. In a specific embodiment, the high throughput screening assay to identify a compound that modulates the replication of a negative-sense, single-stranded RNA virus (in particular FmoPV) comprises: (a) contacting a compound or a member of a library of compounds with a host cell infected with a FmoPV described herein that expresses a detectable heterologous nucleotide sequence; and (b) measuring the expression or activity of a product encoded by the detectable heterologous nucleotide sequence. In another embodiment, the high throughput screening assay to identify a compound that modulates the replication of a negative-sense, single-stranded RNA virus (in particular FmoPV) comprises: (a) infecting a host cell with a FmoPV described herein that expresses a detectable heterologous nucleotide sequence in the presence of a compound or a member of a library of compounds; and (b) measuring the expression or activity a product encoded by the detectable heterologous nucleotide sequence. In another embodiment, the high throughput screening assay to identify a compound that modulates the replication of a negative-sense, single-stranded RNA virus (in particular FmoPV) comprises: (a) contacting a host cell with a compound or a member of a library of compounds: (b) infecting the host cell with a FmoPV described herein that expresses a detectable heterologous nucleotide sequence; and (c) measuring the expression or activity a product encoded by the detectable heterologous nucleotide sequence.

Any method known to one of skill in the art can be used measure the expression or activity of a product encoded by the detectable heterologous nucleotide sequence. In one embodiment, the product encoded by the detectable heterologous nucleotide sequence is RNA and a technique known to one of skill in the art, such as RT-PCR or Northern blot analysis, is used to measure the expression of the RNA product. In another embodiment, the product encoded by the detectable heterologous nucleotide sequence is protein and a technique known to one of skill in the art, such as western blot analysis or an ELISA, is used to measure the expression of the protein product. In another embodiment, the product encoded by the detectable heterologous nucleotide sequence is protein and the activity of the protein is measured using a technique known to one of skill in the art.

Any screening assay described herein can be performed individually, e.g., just with the test compound, or with appropriate controls. For example, a parallel assay without the test compound, or other parallel assays without other reaction components (e.g., virus) can be performed. In one embodiment, a parallel screening assay as described above is performed except that a negative control and/or a positive control are used in place of a test compound. In another embodiment, to eliminate cytotoxic compounds that appear as false positives, a counter screen is performed in which uninfected cells are transfected with a nucleic acid construct (e.g., a plasmid) comprising a detectable heterologous nucleotide sequence and the expression or activity of a product encoded by the detectable heterologous nucleotide sequence is measured. Alternatively, it is possible to compare assay results to a reference, e.g., a reference value, e.g., obtained from the literature, a prior assay, and so forth. Appropriate correlations and art known statistical methods can be used to evaluate an assay result.

In another aspect, the antiviral effect of a compound on FmoPV can be assessed in a non-human animal using a FmoPV described herein. In one embodiment, the antiviral effect of a compound on FmoPV can be assessed by a method comprising: (a) administering (for example, parenterally, subcutaneously, intranasally, or intraperitoneally) to a non-human subject, concurrently, subsequently or prior to administration of a compound, an effective amount of a FmoPV described herein; b) waiting for a time interval following the administration of the FmoPV; and d) detecting the FmoPV in the subject or in a biological specimen from the subject.

5.11 Kits

In one aspect, provided herein is a kit comprising, in one or more containers, one or more nucleic acid sequences described herein. In a specific embodiment, a kit comprises, in a container, a FmoPV gene segment or a complement thereof. In another embodiment, a kit comprises, in one, two or more containers, a nucleic acid sequence encoding a FmoPV gene segments or a complement thereof. The kit may further comprise one or more of the following: host cells suitable for rescue of the virus, reagents suitable for transfecting plasmid DNA into a host cell, helper virus, plasmids encoding one or more types of FmoPV gene segments, one or more expression plasmids encoding viral proteins, and/or one or more primers specific for a FmoPV gene segment or a complement thereof, or nucleic acid sequences encoding the same.

In another aspect, provided herein is a kit comprising one or more containers filled with one or more of the one or more FmoPV described herein or a composition thereof. In a specific embodiment, provided herein is a pharmaceutical pack or kit comprising, in one or more containers, a composition comprising one or more FmoPV described herein. In another aspect, provided herein is a kit comprising, in one or more containers, primers specific for a particular FmoPV gene segment.

In another aspect, provided herein is a kit comprising one or more containers filled with one or more antibodies generated or identified using a FmoPV described herein. In one embodiment, a kit comprises an antibody described herein, preferably an isolated antibody, in one or more containers. In a specific embodiment, a kit encompassed herein contains an isolated FmoPV antigen that the antibodies encompassed herein react with as a control. In a specific, a kit provided herein further comprise a control antibody which does not react with a FmoPV antigen that an antibody encompassed herein reacts with. In another specific embodiment, a kit provided herein contains a means for detecting the binding of an antibody to a FmoPV antigen that an antibody encompassed herein reacts with (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, a kit may include a recombinantly produced or chemically synthesized FmoPV antigen. The FmoPV antigen provided in the kit may also be attached to a solid support. In a more specific embodiment the detecting means of the above described kit includes a solid support to which a FmoPV antigen is attached. Such a kit may also include a non-attached reporter-labeled anti-human antibody. In this embodiment, binding of the antibody to the FmoPV antigen can be detected by binding of the said reporter-labeled antibody.

Optionally associated with such a kit can be a notice in the form prescribed by a governmental agency regulating the manufacture, use or sale of pharmaceuticals or biological products, which notice reflects approval by the agency of manufacture, use or sale for human administration.

Example 2 demonstrates a diagnostic test done by RT-PCR. Another diagnostic test. demonstrated in Example 3, is a viral load test using real-time quantitative RT-PCR using the above genomic information obtained from sequencing.

5.12 Complete Genome Sequencing and Analysis

Three complete genomes of FmoPV, from two urine (761U, 776U) and one rectal swab (M252A) samples, were amplified and sequenced using RNA extracted directly from the specimens as templates with a strategy described in our previous publications (13, 14). Genome analysis was performed as described in our previous publications (13, 14, 23, 24, 25). Phylogenetic trees were constructed by maximum likelihood method using PhyML 3.0 (26).

The complete genome sequences of three strains of FmoPV designated 761U, 776U and M252A were determined. The genome sequence for FmoPV strain 761U was deposited at GenBank and given accession number JQ411014. The FmoPV 761U nucleotide sequence is shown in FIG. 2. The genome sequence for FmoPV strain 776U was deposited at GenBank and given accession number JQ411015. The FmoPV 776U nucleotide sequence is shown in FIG. 3. The genome sequence for FmoPV strain M252A was deposited at GenBank and given accession number JQ411016. The FmoPV M252A nucleotide sequence is shown in FIG. 4.

The genome size of these FmoPV nucleotide sequences are 16050 bases and G+C contents 35.1% to 35.3%, with FmoPV having the largest genome among all *morbilliviruses* with genome sequences available (see FIG. 1). The genome of FmoPV conforms to the rule of six as in other *paramyxovirus* genomes. It contains a 12-nt complementary 3' leader and 5' trailer sequence. The 3' leader sequence is 55 nt. In contrast to other *morbilliviruses* which only have 5' trailer sequences of 40 or 41 nt, the genome of FmoPV has a trailer sequence of 400 nt, accounting for its bigger genome size. Such long trailer sequences of >400 nt have only been observed in avian *paramyxoviruses* 3 (681-707 nt) and 5 (552 nt) and tupaia *paramyxovirus* (590 nt).

Similar to other *morbilliviruses*, the genome of FmoPV contains six genes (3'-N-P/V/C-M-F-H-L-5') (see FIG. 1). Pairwise alignment of the predicted gene products among FmoPV and other *paramyxoviruses* showed the highest amino acid identities with members of the genus *Morbillivirus*, with the N, P/V/C(P), P/V/C(V), P/V/C(C), M, F, H and L of FmoPV having 54.3-56.8%, 25.6-31.7%, 20.7-25.7%, 18.3-25.4%, 57.6-60.0%, 35.8-45.1%, 20.4-24.1% and 55.2-57.3% amino acid identities to those of other *morbilliviruses* (see Table 1). The lengths and characteristics of the major structural genes and intergenic regions (IGRs) are summarized in Table 2.

TABLE 1

Pairwise amino acid identities of predicted gene products of FmoPV compared to other paramyxoviruses

| | Percentage of amino acid sequence identity | | | | | | | | |
|---|---|---|---|---|---|---|---|---|---|
| | N | | | P | | | M | | |
| Paramyxoviruses | 761U | 776U | M252A | 761U | 776U | M252A | 761U | 776U | M252A |
| Morbillivirus | | | | | | | | | |
| FmoPV 761U | — | 99.2 | 96.0 | — | 97.4 | 89.2 | — | 98.8 | 95.8 |
| FmoPV 776U | 99.2 | — | 96.1 | 97.4 | — | 88.6 | 98.8 | — | 96.4 |
| FmoPV M252A | 96.0 | 96.1 | — | 89.2 | 88.6 | — | 95.8 | 96.4 | — |
| CdiPV | 56.8 | 56.5 | 56.2 | 29.7 | 29.3 | 27.5 | 58.8 | 58.5 | 58.8 |
| DmoPV | 54.5 | 54.3 | 55.0 | 26.4 | 25.8 | 25.6 | 59.3 | 59.6 | 59.5 |
| MeaPV | 55.4 | 55.2 | 54.6 | 29.0 | 28.8 | 27.8 | 60.0 | 59.7 | 59.0 |
| PprPV | 55.6 | 55.8 | 55.8 | 31.6 | 31.7 | 31.6 | 58.2 | 58.5 | 58.8 |
| RinPV | 55.5 | 55.5 | 55.6 | 28.4 | 28.4 | 26.8 | 59.5 | 59.2 | 58.2 |
| PdiPV | 56.6 | 56.2 | 56.2 | 30.6 | 30.4 | 28.8 | 57.9 | 57.9 | 57.6 |
| Avulavirus | | | | | | | | | |
| AviPV-6 | 29.1 | 29.3 | 28.1 | 18.3 | 17.9 | 18.6 | 23.5 | 23.5 | 22.9 |
| NdiPV | 27.1 | 27.1 | 28.0 | 19.8 | 18.8 | 18.1 | 19.5 | 20.0 | 20.9 |
| Henipavirus | | | | | | | | | |
| HenPV | 33.6 | 33.2 | 32.8 | 21.1 | 22.2 | 23.3 | 43.9 | 44.2 | 44.2 |
| NipPV | 33.8 | 33.4 | 33.0 | 22.4 | 21.8 | 22.8 | 43.1 | 43.3 | 43.4 |
| Respirovirus | | | | | | | | | |
| BpiPV-3 | 25.7 | 25.9 | 25.4 | 18.0 | 18.7 | 19.2 | 33.9 | 33.6 | 34.2 |
| SenPV | 24.2 | 25.2 | 25.0 | 19.0 | 18.5 | 20.5 | 34.7 | 34.7 | 34.4 |
| Rubulavirus | | | | | | | | | |
| HpiPV-2 | 27.5 | 27.7 | 27.9 | 19.4 | 19.6 | 16.8 | 22.8 | 23.1 | 21.8 |
| MumPV | 27.6 | 27.8 | 27.7 | 19.6 | 19.9 | 17.2 | 20.4 | 20.0 | 20.7 |
| Unclassified Paramyxovirinae | | | | | | | | | |
| AsaPV | 29.8 | 29.8 | 28.4 | 16.4 | 17.2 | 17.1 | 34.7 | 34.7 | 34.7 |
| TlmPV | 35.7 | 36.4 | 36.0 | 22.7 | 22.7 | 23.0 | 48.0 | 48.3 | 48.8 |
| BeiPV | 36.6 | 36.2 | 36.3 | 23.5 | 23.3 | 23.9 | 47.4 | 47.7 | 48.5 |
| FdlPV | 28.4 | 28.4 | 28.5 | 19.9 | 21.1 | 20.8 | 34.9 | 34.5 | 33.9 |
| JPV | 34.0 | 34.0 | 34.0 | 23.1 | 23.3 | 22.3 | 47.8 | 48.1 | 48.4 |
| MosPV | 38.6 | 38.6 | 37.6 | 22.9 | 22.9 | 22.0 | 47.5 | 48.2 | 46.9 |
| TupPV | 33.4 | 32.7 | 32.1 | 23.2 | 23.2 | 23.9 | 43.9 | 43.2 | 42.5 |
| NarPV | 37.2 | 36.9 | 38.1 | 22.7 | 23.8 | 22.6 | 51.5 | 51.5 | 50.6 |

| | Percentage of amino acid sequence identity | | | | | | | | |
|---|---|---|---|---|---|---|---|---|---|
| | F | | | A | | | L | | |
| Paramyxoviruses | 761U | 776U | M252A | 761U | 776U | M252A | 761U | 776U | M252A |
| Morbillivirus | | | | | | | | | |
| FmoPV 761U | — | 98.9 | 96.3 | — | 99.0 | 96.3 | — | 99.4 | 97.0 |
| FmoPV 776U | 98.9 | — | 95.9 | 99.0 | — | 95.3 | 99.4 | — | 97.3 |
| FmoPV M252A | 96.3 | 95.9 | — | 96.3 | 95.3 | — | 97.0 | 97.3 | — |
| CdiPV | 36.0 | 35.8 | 36.1 | 20.4 | 20.6 | 20.6 | 55.5 | 55.4 | 55.4 |
| DmoPV | 43.0 | 42.2 | 42.4 | 24.1 | 24.1 | 23.9 | 56.4 | 56.4 | 56.5 |
| MeaPV | 44.0 | 44.0 | 43.9 | 20.7 | 20.9 | 20.7 | 56.0 | 55.9 | 55.8 |
| PprPV | 42.8 | 42.8 | 43.2 | 21.6 | 21.8 | 21.6 | 57.3 | 57.3 | 57.2 |
| RinPV | 44.6 | 44.3 | 45.1 | 21 | 21.1 | 22.4 | 55.4 | 55.3 | 55.2 |
| PdiPV | 42.7 | 42.9 | 42.9 | 20.6 | 20.8 | 20.9 | 55.4 | 55.4 | 55.7 |
| Avulavirus | | | | | | | | | |
| AviPV-6 | 26.8 | 27.0 | 26.6 | 17.7 | 17.6 | 17.3 | 28.5 | 28.6 | 29.1 |
| NdiPV | 25.8 | 25.8 | 25.4 | 17.5 | 17.2 | 16.2 | 27.7 | 27.5 | 27.6 |
| Henipavirus | | | | | | | | | |
| HenPV | 32.4 | 32.6 | 33.0 | 17.8 | 17.8 | 18.9 | 43.4 | 43.4 | 43.4 |
| NipPV | 33.0 | 33.2 | 33.3 | 18.2 | 18.2 | 18.9 | 44.9 | 44.8 | 45.2 |
| Respirovirus | | | | | | | | | |
| BpiPV-3 | 28.5 | 28.2 | 28.5 | 18.9 | 18.9 | 18.2 | 38.4 | 38.6 | 38.9 |
| SenPV | 27.1 | 26.5 | 26.5 | 20.5 | 20.3 | 21.1 | 39.1 | 39.3 | 39.4 |

TABLE 1-continued

Pairwise amino acid identities of predicted gene products of FmoPV compared to other paramyxoviruses

| Rubulavirus | | | | | | | | | |
|---|---|---|---|---|---|---|---|---|---|
| HpiPV-2 | 25.0 | 24.4 | 25.0 | 18.0 | 18.0 | 18.3 | 30.4 | 30.2 | 30.2 |
| MumPV | 26.4 | 26.2 | 25.7 | 18.1 | 17.8 | 18.7 | 30.0 | 30.1 | 29.9 |
| Unclassified Paramyxovirinae | | | | | | | | | |
| AsaPV | 30.9 | 30.6 | 30.8 | 20.1 | 20.1 | 19.0 | 40.0 | 40.1 | 40.4 |
| TlmPV | 32.7 | 32.9 | 33.0 | 16.1 | 15.8 | 16.6 | 46.4 | 46.4 | 46.4 |
| BeiPV | 32.9 | 32.7 | 32.7 | 16.1 | 15.8 | 15.8 | 46.3 | 46.3 | 46.6 |
| FdlPV | 29.0 | 29.2 | 29.7 | 19.9 | 19.9 | 19.2 | 40.0 | 40.0 | 39.7 |
| JPV | 31.8 | 31.8 | 32.9 | 14.8 | 15.0 | 14.4 | 46.9 | 46.9 | 47.2 |
| MosPV | 36.3 | 36.3 | 35.8 | 19.0 | 19.2 | 19.9 | 48.6 | 48.8 | 48.8 |
| TupPV | 35.0 | 35.4 | 35.0 | 14.7 | 14.4 | 15.6 | 47.3 | 47.2 | 47.1 |
| NarPV | 33.0 | 32.5 | 32.6 | 18.6 | 18.4 | 18.7 | 47.7 | 48.0 | 47.9 |

TABLE 2

Molecular features and predicted gene products of FmoPV and other morbilliviruses

| | | mRNA features (nt) | | | | | | Deduced protein | | | |
|---|---|---|---|---|---|---|---|---|---|---|---|
| Virus | Gene | Total length | 5' UTR | ORF | 3' UTR | hexamer phase | Intergenic regions (nt) | Size (aa) | MW (kDa) | pI | Coding frame |
| FmoPV 761U | Leader | 55 | | | | | (TTT) | | | | |
| | N | 1659 | 52 | 1560 | 47 | 2 | CTT | 519 | 57.01 | 5.27 | 3 |
| | P/V/C(P) | 1637 | 63 | 1476 | 98 | 2 | CTT | 491 | 53.12 | 5.20 | 2 |
| | P/V/C(V) | 1638 | 63 | 831 | 744 | 2 | CTT | 276 | 29.97 | 4.85 | 2 |
| | P/V/C(C) | 1637 | 94 | 513 | 1030 | 2 | CTT | 170 | 19.90 | 9.69 | 3 |
| | M | 1378 | 31 | 1014 | 333 | 4 | CTA | 337 | 38.05 | 9.29 | 2 |
| | F | 2191 | 215 | 1632 | 344 | 5 | CTT | 543 | 60.26 | 8.80 | 1 |
| | H | 1934 | 30 | 1788 | 116 | 3 | CTT | 595 | 68.11 | 6.25 | 3 |
| | L | 6781 | 22 | 6609 | 150 | 2 | (CTT) | 2202 | 252.87 | 8.32 | 3 |
| | Trailer | 400 | | | | | | | | | |
| FmoPV 776U | Leader | 55 | | | | | (TTT) | | | | |
| | N | 1659 | 52 | 1560 | 47 | 2 | CTT | 519 | 57.06 | 5.15 | 3 |
| | P/V/C(P) | 1637 | 63 | 1476 | 98 | 2 | CTT | 491 | 53.19 | 5.33 | 2 |
| | P/V/C(V) | 1638 | 63 | 831 | 744 | 2 | CTT | 276 | 29.99 | 4.91 | 2 |
| | P/V/C(C) | 1637 | 94 | 513 | 1030 | 2 | CTT | 170 | 19.87 | 9.69 | 3 |
| | M | 1378 | 31 | 1014 | 333 | 4 | CTA | 337 | 38.02 | 9.29 | 2 |
| | F | 2191 | 215 | 1632 | 344 | 5 | CTT | 543 | 60.21 | 8.79 | 1 |
| | H | 1934 | 30 | 1788 | 116 | 3 | CTT | 595 | 68.24 | 6.03 | 3 |
| | L | 6781 | 22 | 6609 | 150 | 2 | (CTT) | 2202 | 253.01 | 8.23 | 3 |
| | Trailer | 400 | | | | | | | | | |
| FmoPV M252A | Leader | 55 | | | | | (TTT) | | | | |
| | N | 1659 | 52 | 1560 | 47 | 2 | CTT | 519 | 57.08 | 5.34 | 3 |
| | P/V/C(P) | 1637 | 63 | 1476 | 98 | 2 | CTT | 491 | 53.41 | 5.44 | 2 |
| | P/V/C(V) | 1638 | 63 | 831 | 744 | 2 | CTT | 276 | 29.94 | 5.13 | 2 |
| | P/V/C(C) | 1637 | 94 | 513 | 1030 | 2 | CTT | 170 | 19.86 | 9.69 | 3 |
| | M | 1378 | 31 | 1014 | 333 | 4 | CTA | 337 | 38.06 | 9.29 | 2 |
| | F | 2191 | 215 | 1632 | 344 | 5 | CTT | 543 | 60.19 | 8.80 | 1 |
| | H | 1934 | 30 | 1788 | 116 | 3 | CTT | 595 | 68.18 | 6.25 | 3 |
| | L | 6781 | 22 | 6609 | 150 | 2 | (CTT) | 2202 | 252.91 | 8.28 | 3 |
| | Trailer | 400 | | | | | | | | | |
| MeaPV | Leader | 55 | | | | | (CTT) | | | | |
| | N | 1689 | 52 | 1578 | 59 | 2 | CTT | 525 | 58.02 | 5.11 | 3 |
| | P/V/C(P) | 1655 | 59 | 1524 | 72 | 2 | CTT | 507 | 53.90 | 4.99 | 1 |
| | P/V/C(V) | 1656 | 59 | 900 | 697 | 2 | CTT | 299 | 31.85 | 4.66 | 1 |
| | P/V/C(C) | 1655 | 81 | 561 | 1013 | 2 | CTT | 186 | 21.11 | 10.36 | 2 |
| | M | 1466 | 32 | 1008 | 426 | 4 | CTT | 335 | 37.71 | 9.07 | 3 |
| | F | 2373 | 583 | 1653 | 137 | 3 | CTT | 550 | 59.53 | 8.78 | 1 |
| | H | 1958 | 20 | 1854 | 84 | 3 | CGT | 617 | 69.17 | 7.88 | 2 |
| | L | 6643 | 22 | 6552 | 69 | 2 | (CTT) | 2183 | 247.74 | 8.43 | 3 |
| | Trailer | 40 | | | | | | | | | |
| CdiPV | Leader | 55 | | | | | (CTT) | | | | |
| | N | 1683 | 52 | 1572 | 59 | 2 | CTT | 523 | 58.14 | 5.20 | 3 |
| | P/V/C(P) | 1655 | 59 | 1524 | 72 | 2 | CTT | 507 | 54.75 | 5.03 | 1 |
| | P/V/C(V) | 1656 | 59 | 900 | 697 | 2 | CTT | 299 | 33.11 | 4.66 | 1 |
| | P/V/C(C) | 1655 | 81 | 525 | 1049 | 2 | CTT | 174 | 20.26 | 10.30 | 2 |
| | M | 1447 | 32 | 1008 | 407 | 4 | CTT | 335 | 37.77 | 8.87 | 3 |
| | F | 2206 | 85 | 1989 | 132 | 2 | CTT | 662 | 72.95 | 9.18 | 3 |
| | H | 1946 | 20 | 1815 | 111 | 3 | CTA | 604 | 67.99 | 6.74 | 2 |

TABLE 2-continued

Molecular features and predicted gene products of FmoPV and other morbilliviruses

| Virus | Gene | mRNA features (nt) | | | | | | Deduced protein | | | |
|---|---|---|---|---|---|---|---|---|---|---|---|
| | | Total length | 5' UTR | ORF | 3' UTR | hexamer phase | Intergenic regions (nt) | Size (aa) | MW (kDa) | pI | Coding frame |
| | L | 6642 | 22 | 6555 | 65 | 2 | (CAA) | 2184 | 248.19 | 8.39 | 3 |
| | Trailer | 41 | | | | | | | | | |
| DmoPV | Leader | 55 | | | | | (CTT) | | | | |
| | N | 1683 | 52 | 1572 | 59 | 2 | CTT | 523 | 57.49 | 5.14 | 3 |
| | P/V/C(P) | 1655 | 59 | 1521 | 75 | 2 | CTT | 506 | 55.26 | 5.09 | 1 |
| | P/V/C(V) | 1656 | 59 | 912 | 685 | 2 | CTT | 303 | 33.69 | 4.75 | 1 |
| | P/V/C(C) | 1655 | 81 | 534 | 1040 | 2 | CTT | 177 | 20.41 | 10.19 | 2 |
| | M | 1453 | 32 | 1008 | 413 | 4 | CTT | 335 | 37.97 | 8.97 | 3 |
| | F | 2212 | 421 | 1659 | 132 | 2 | CTT | 552 | 59.87 | 8.81 | 3 |
| | H | 1946 | 20 | 1815 | 111 | 3 | CTT | 604 | 68.04 | 6.18 | 2 |
| | L | 6643 | 22 | 6552 | 69 | 2 | (CAA) | 2183 | 248.07 | 8.52 | 3 |
| | Trailer | 40 | | | | | | | | | |
| PprPV | Leader | 55 | | | | | (CTT) | | | | |
| | N | 1689 | 52 | 1578 | 59 | 2 | CTT | 525 | 57.78 | 5.21 | 3 |
| | P/V/C(P) | 1655 | 59 | 1530 | 66 | 2 | CTT | 509 | 54.79 | 5.14 | 1 |
| | P/V/C(V) | 1656 | 59 | 897 | 700 | 2 | CTT | 298 | 31.34 | 4.58 | 1 |
| | P/V/C(C) | 1655 | 81 | 534 | 1040 | 2 | CTT | 177 | 19.93 | 9.92 | 2 |
| | M | 1483 | 32 | 1008 | 443 | 4 | CTT | 335 | 37.95 | 8.97 | 3 |
| | F | 2411 | 634 | 1641 | 136 | 2 | CTT | 546 | 59.12 | 8.71 | 3 |
| | H | 1957 | 20 | 1830 | 107 | 4 | CTT | 609 | 68.76 | 6.64 | 3 |
| | L | 6643 | 22 | 6552 | 69 | 2 | (CTA) | 2183 | 247.27 | 7.73 | 3 |
| | Trailer | 40 | | | | | | | | | |
| RinPV | Leader | 55 | | | | | (CTT) | | | | |
| | N | 1689 | 52 | 1578 | 59 | 2 | CTT | 525 | 58.04 | 5.08 | 3 |
| | P/V/C(P) | 1655 | 59 | 1524 | 72 | 2 | CTT | 507 | 54.36 | 4.82 | 1 |
| | P/V/C(V) | 1656 | 59 | 900 | 697 | 2 | CTT | 299 | 32.57 | 4.56 | 1 |
| | P/V/C(C) | 1655 | 81 | 534 | 1040 | 2 | CTT | 177 | 19.93 | 10.29 | 2 |
| | M | 1460 | 32 | 1008 | 420 | 4 | CTT | 335 | 37.54 | 9.15 | 3 |
| | F | 2367 | 589 | 1641 | 137 | 3 | CTT | 546 | 58.73 | 8.43 | 1 |
| | H | 1958 | 20 | 1830 | 108 | 3 | CGT | 609 | 67.90 | 6.61 | 2 |
| | L | 6643 | 22 | 6552 | 69 | 2 | (CTT) | 2183 | 248.21 | 8.48 | 3 |
| | Trailer | 40 | | | | | | | | | |

The conserved N-terminal motif MA(T/S)L in *morbilliviruses* was absent in the N protein of FmoPV, which contained the sequence MSSL (SEQ ID NO: 13) as a result of A→S (G→U at first codon position) substitution at the second amino acid (FIG. 5). Similar to the nuclear localization signal (NLS) of the N proteins in CdiPV, MeaPV and RinPV but different from the classical NLS sequence (PMID: 16716375), a leucine/isoleucine-rich motif at amino acid positions 70-77 is identified in the N protein of FmoPV (see SI FIG. 5). Similar to the nuclear export signal (NES) of the N proteins in CdiPV and RinPV, a leucine-rich motif at amino acid positions 4-11 is also identified in the N protein of FmoPV (see FIG. 5).

As in other *morbilliviruses*, the P/V/C gene of FmoPV contains two initiation codons, the first one for translation of P and V and the second for translation of C. Similar to most members of Paramyxoviridae, the P/V/C gene of FmoPV contains a UC-rich editing site that allows the addition of non-templated G residues to mRNA products during P/V/C gene transcription, resulting in the production of different proteins with a common N-terminal region. In all three strains of FmoPV, this common N-terminal region consists of 226 amino acids.

To determine the exact location of P gene editing site and the number and frequency of G-residue insertions, a small cDNA fragment including the UC-rich region was amplified, cloned and sequenced using mRNA extracted from FmoPV infected CRFK cells. Among 23 independent clones sequenced, 13 contained the sequence TTAAAAGGGG (without G insertion, encoding P protein) and 10 contained the sequence TTAAAAGGGGG (one G inserted, encoding V protein). The sequence TTA$_n$G$_n$ is conserved as in other *paramyxovirus* editing sites except for those of *rubulaviruses*. In contrast to other *morbilliviruses* in which the sequence is TTA$_5$G$_3$ (SEQ ID NO: 16) (33), the TTA$_n$G$_n$ sequence in FmoPV is TTA$_4$G$_4$ (SEQ ID NO: 14).

Different from all other known *morbilliviruses*, the F protein of FmoPV has a single-basic protein cleavage site, whereas the cleavage sites in other *morbilliviruses* are multi-basic (34). Cellular trypsin-like protease cleaves the F protein into F1 and F2 before cell fusion occurs, which facilitates the isolation of these viruses in cell lines. Two heptad repeat sequences similar to those in F proteins of other *paramyxoviruses* were also identified in the F$_1$ of FmoPV. The F protein of FmoPV also contains the 10 Cys residues that are highly conserved in other *morbilliviruses* and 5 potential N-glycosylation sites, most of which located in the F$_2$ peptide.

Phylogenetic trees constructed using the predicted amino acid sequences of N, P, M, F, H and L genes of FmoPV and other members of Paramyxoviridae are shown in FIG. 7. In all six trees, the three viruses were clustered with *morbilliviruses*, with high bootstrap supports, forming a distinct subgroup (see FIG. 7). The trees were constructed by maximum likelihood method with bootstrap values calculated from 1000 trees and rooted on midpoint. The scale bars in FIG. 7 indicate the branch length that corresponds to 0.5 substitutions per site. Three strains from FmoPV were named as 761U, 776U, M252A. Names and accession numbers of the other viruses in FIG. 7 are listed in Table 3 below.

TABLE 3

Viruses and GenBank accession numbers

| Abbreviation | Virus name | GenBank accession no. |
|---|---|---|
| AsaPV | Atlantic Salmon paramyxovirus | EU156171 |
| AviPV-5 | Avian paramyxovirus 5 | GU206351 |
| AviPV-6 | Avian paramyxovirus 6 | NC_003043 |
| AviPV-7 | Avian paramyxovirus 7 | FJ231524 |
| BeiPV | Beilong virus | NC_007803 |
| BpiPV-3 | Bovine parainfluenza virus 3 | NC_002161 |
| CdiPV | Canine distemper virus | NC_001921 |
| DmoPV | Dolphin morbillivirus | NC_005283 |
| FdlPV | Fer-de-lance virus | NC_005084 |
| GooPV | Goose paramyxovirus SF02 | NC_005036 |
| HenPV | Hendra virus | NC_001906 |
| HpiPV-1 | Human parainfluenza virus 1 | NC_003461 |
| HpiPV-2 | Human parainfluenza virus 2 | NC_003443 |
| HpiPV-3 | Human parainfluenza virus 3 | NC_001796 |
| HpiPV-4a | Human parainfluenza virus 4a | BAJ11741 |
| HuRSV | Human respiratory syncytial virus | NC_001781 |
| JPV | J-virus | NC_007454 |
| MeaPV | Measles virus | NC_001498 |
| MosPV | Mossman virus | NC_005339 |
| MumPV | Mumps virus | NC_002200 |
| NarPV | Nariva virus | FJ362497 |
| NdiPV | Newcastle disease virus | NC_002617 |
| NipPV | Nipah virus | NC_002728 |
| PdiPV | Phocine distemper virus | P35944, P35939, BAA01205, BAA01206, CAA12080, CAA70843 |
| PprPV | Peste-des-petits-ruminants virus | NC_006383 |
| RinPV | Rinderpest virus | NC_006396 |
| SenPV | Sendai virus | NC_001552 |
| SpiPV-3 | Swine parainfluenza virus 3 | EU439429 |
| ThkPV-1 | Tuhoko virus 1 | GU128080 |
| ThkPV-2 | Tuhoko virus 2 | GU128081 |
| ThkPV-3 | Tuhoko virus 3 | GU128082 |
| TlmPV | Tailam virus | JN689227 |
| TupPV | Tupaia paramyxovirus | NC_002199 |

5.13 Detection of FmoPV Infection in Felines

Infection of a feline by FmoPV can be detected in sera by the use of immunofluorescent antibodies as demonstrated in Example 9, or by the detection of neutralizing antibodies as demonstrated in Example 10. Of the 27 cat sera samples tested in Example 9, immunofluorescent antibody was detected from 7 cats with titer from 1:40 to 1:640. Table 4 below shows the association between TIN and evidence of FmoPV infection.

TABLE 4

Association between TIN and evidence of FmoPV infection

| Sample No. | Urine TIN | RT-PCR | Western Blot | IF (IgG) with serum dilution | | | | | |
|---|---|---|---|---|---|---|---|---|---|
| | | | | 1:10 | 1:40 | 1:160 | 1:640 | 1:2560 | 1:10240 |
| 1357 | + | + | ++ | + | + | + | + | − | − |
| 1359 | + | + | + | + | + | + | − | − | − |
| 1363 | − | − | + | − | − | − | − | − | − |
| 1364 | − | − | − | − | − | − | − | − | − |
| 1365 | − | − | + | − | − | − | − | − | − |
| 1366 | + | − | − | − | − | − | − | − | − |
| 1367 | − | − | − | − | − | − | − | − | − |
| 1368 | − | − | − | − | − | − | − | − | − |
| 1391 | − | − | − | − | − | − | − | − | − |
| 1392 | + | + | − | + | + | − | − | − | − |
| 1393 | + | − | + | + | + | − | − | − | − |
| 1394 | − | − | − | − | − | − | − | − | − |
| 1395 | − | − | − | − | − | − | − | − | − |
| 1396 | − | − | − | − | − | − | − | − | − |
| 1397 | − | − | ++ | + | + | − | − | − | − |
| 1402 | − | − | + | − | − | − | − | − | − |
| 1403 | − | − | + | − | − | − | − | − | − |
| 1404 | − | − | − | − | − | − | − | − | − |
| 1405 | − | − | − | − | − | − | − | − | − |
| 1406 | − | − | − | − | − | − | − | − | − |
| 1407 | + | + | ++ | + | + | + | − | − | − |
| 1408 | + | − | − | − | − | − | − | − | − |
| 1409 | + | + | + | + | + | + | − | − | − |
| 1417 | + | − | + | − | − | − | − | − | − |
| 1418 | − | − | − | − | − | − | − | − | − |
| 1419 | − | − | − | − | − | − | − | − | − |
| 1420 | − | − | − | − | − | − | − | − | − |

The same 27 cat sera samples used in Example 9 were tested for the presence of neutralization antibody in Example 10. Neutralization antibody was detected from 6 cats with titer from 1:20 to 1:40, shown below in Table 5, of which all are positive for immunofluorescent antibody (Table 4).

TABLE 5

Neutralizing antibody detected from cats' sera

| Sample No. | Neutralizing IF (IgG) with serum dilution | | | | | | | | |
|---|---|---|---|---|---|---|---|---|---|
| | 1:10 | 1:20 | 1:40 | 1:80 | 1:160 | 1:320 | 1:640 | 1:1280 | 1:2560 |
| 1357 | + | + | − | − | − | − | − | − | − |
| 1359 | + | + | − | − | − | − | − | − | − |
| 1363 | − | − | − | − | − | − | − | − | − |
| 1364 | − | − | − | − | − | − | − | − | − |
| 1365 | − | − | − | − | − | − | − | − | − |
| 1366 | − | − | − | − | − | − | − | − | − |
| 1367 | − | − | − | − | − | − | − | − | − |
| 1368 | − | − | − | − | − | − | − | − | − |
| 1391 | − | − | − | − | − | − | − | − | − |
| 1392 | + | + | − | − | − | − | − | − | − |
| 1393 | + | + | − | − | − | − | − | − | − |
| 1394 | − | − | − | − | − | − | − | − | − |
| 1395 | − | − | − | − | − | − | − | − | − |
| 1396 | − | − | − | − | − | − | − | − | − |
| 1397 | − | − | − | − | − | − | − | − | − |
| 1402 | − | − | − | − | − | − | − | − | − |
| 1403 | − | − | − | − | − | − | − | − | − |
| 1404 | − | − | − | − | − | − | − | − | − |
| 1405 | − | − | − | − | − | − | − | − | − |
| 1406 | − | − | − | − | − | − | − | − | − |
| 1407 | + | + | − | − | − | − | − | − | − |
| 1408 | − | − | − | − | − | − | − | − | − |
| 1409 | + | + | + | − | − | − | − | − | − |
| 1417 | − | − | − | − | − | − | − | − | − |
| 1418 | − | − | − | − | − | − | − | − | − |
| 1419 | − | − | − | − | − | − | − | − | − |
| 1420 | − | − | − | − | − | − | − | − | − |

6. EXAMPLES

Described herein is a novel feline *paramyxovirus*, FmoPV, from stray cats in Hong Kong, which represents the first documentation of *paramyxoviruses* found in the domestic cat (*Felis catus*). Woo et al. (2012) "Feline *morbillivirus*, a novel *paramyxovirus* associated with tubulointerstitial nephritis in domestic cats," PNAS (in press), which is incorporated herein by reference in its entirety.

A molecular epidemiology study was carried out in stray cats in Hong Kong and on diseased cats from mainland China from which the novel feline *paramyxovirus*, FmoPV, was isolated and characterized as shown in the following examples.

Figure 10:
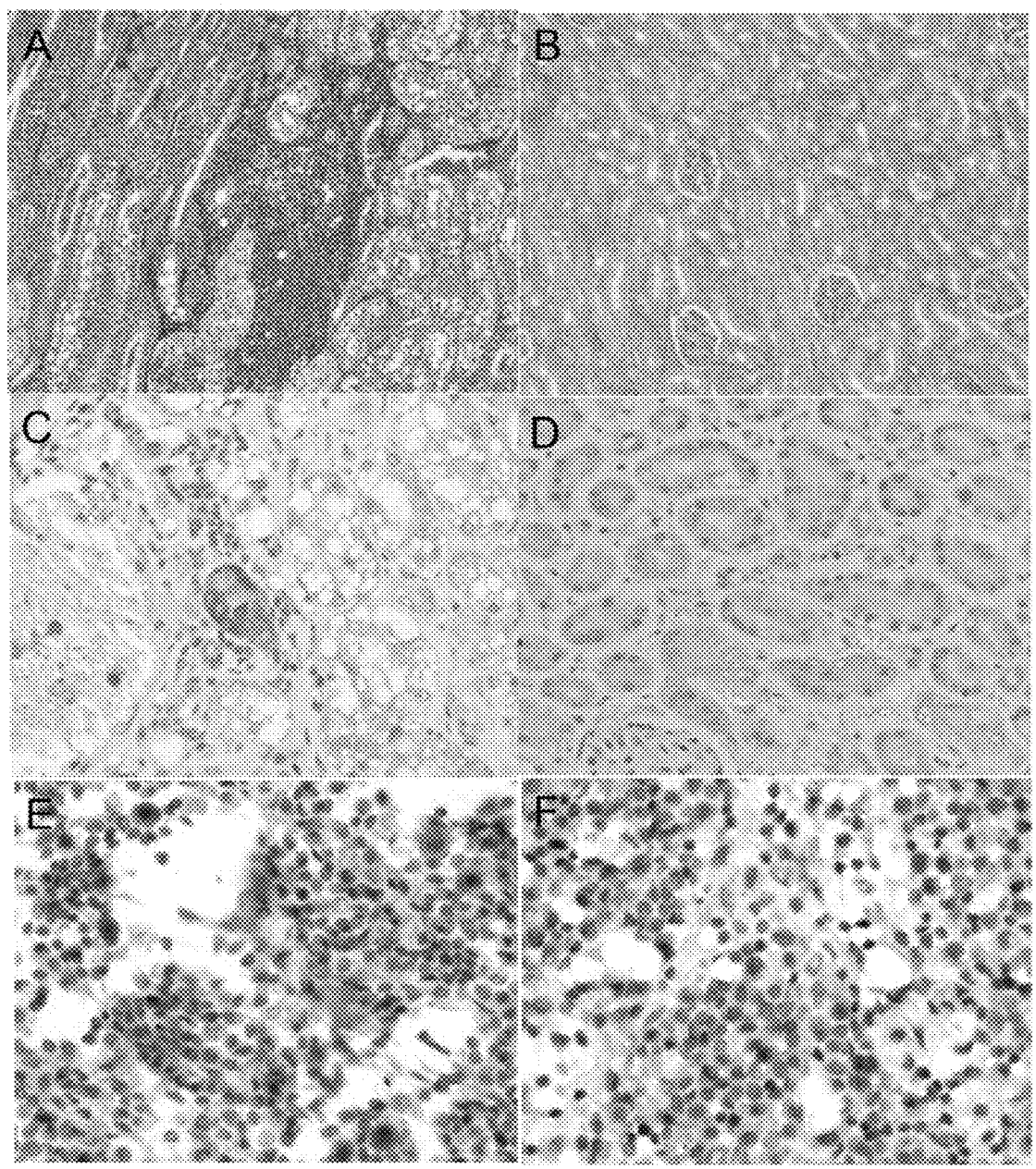

To summarize, FmoPV was detected in the urine samples of 53 of 457 stray cats and in the rectal swab and blood samples of four and one of these cats, respectively. Western blot analysis revealed a seroprevalence of 27.8% among tested cats for IgG against recombinant N protein and the presence of antibody is highly associated with the presence of virus. Analysis of the complete genomes of three FmoPV strains, described earlier in Section 5.12, showed that they formed a distinct cluster among the *morbilliviruses* in all six phylogenetic trees constructed using the N, P, M, F, H and L genes (FIG. 7). Immunohistochemistry also showed that, similar to other *morbilliviruses* such as measles virus, FmoPV infects both mononuclear cells and parenchymal cells (FIG. 10). The three strains of FmoPV exhibited high sequence similarity and identical genome organization, suggesting a single species of FmoPV and a high degree of species specificity in FmoPV. Although no recombination was identified in the present FmoPV strains (data not shown), other viruses from cats, such as feline *coronaviruses* and feline papillomavirus, have been shown to be closely related to or recombine with their canine counterparts in dogs, suggesting that feline viruses may have the potential to cross species barrier in animals of similar living habitat (17, 35).

Some recent studies suggested that feline TIN is mediated by an autoimmune mechanism because cats vaccinated with CRFK cell lysates developed antibodies to both CRFK and kidney cell lysates (36-38). Half of these cats sensitized to CRFK lysates on multiple occasions developed tubulointerstitial nephritis at 2 weeks post-sensitization. Sera from CRFK inoculated cats were confirmed to recognize annexin A2 and alpha-enolase by Western blot. In humans, alpha-enolase antibodies are nephritogenic and alpha-enolase and annexin A2 antibodies have been associated with autoimmune diseases. It is therefore possible that a feline nephrotropic virus, such as FmoPV, may trigger off a self-sustained immunopathological process after this acute insult. Notably, some *morbilliviruses*, such as Peste des Petits Ruminants virus, Rinderpest virus and canine distemper virus, have also been found in kidney and/or urine (39-41). Further studies would delineate if these viruses are also associated with renal pathologies in these animals.

Although domestic cats have been associated with humans for almost 10,000 years, they usually pose little physical hazards to humans. However, as a result of cat bites or via other routes, cats can transmit a range of bacteria (e.g. *Bartonella henselae*), protozoa (e.g. *Toxoplasma gondii*), and uncommonly viruses (e.g. rabies virus), causing diseases in humans. Apart from the present novel *paramyxovirus*, viruses of at least 15 families have been found in cats, including the recent discovery of the first picornavirus in cats (23). Moreover, the domestic cats have also been shown to be susceptible to infection by highly pathogenic avian influenza viruses H5N1 and H7N7 and SARS *coronavirus*, suggesting that they can be susceptible to viruses associated with serious infections (42-44). A previous survey in Hong Kong showed that one in every eight households was keeping pets with 22.3% keeping cats. The number of locally licensed pet shops selling cats and dogs in Hong Kong has increased from 77 in 2000 to 155 in 2009. In many households, owners having pets share their beds with their pets, and the pet owners often kiss or are being licked by their pets. Such behavior may allow significant exposure to zoonotic agents carried by the pet or parasitizing arthropods (45). Continuous surveillance of viruses in these animals is important to understand their potential for causing emerging infectious diseases in other mammals, including humans.

6.1 Example 1

Sample Collection

The Agriculture Fisheries and Conservation Department (AFCD), Hong Kong provided samples collected from 457 stray cats captured from various locations in Hong Kong over a 2-year period (March 2009 to February 2011) as part of a surveillance program. Tracheal and rectal swabs, urine and blood were collected using procedures described previously (23). In addition, oral and rectal swabs from 16 diseased cats from mainland China were also collected. The study was approved by the Committee on the Use of Live Animals in Teaching and Research, The University of Hong Kong. Samples were collected immediately after euthanasia as routine policies for disposal of locally captured stray cats.

Necropsies of FmoPV-Infected Stray Cats

To identify possible diseases associated with FmoPV, necropsies were performed on two euthanized stray cats positive for FmoPV by RT-PCR. Tissue samples were collected from the lungs; brain; heart; prescaspular, retropharyngeal, submandibular and thoracic lymph nodes; spleen; liver; kidneys; urinary bladder; gall bladder; thymus; salivary gland; eyeball; nasal turbinate; intestine; pancreas; foot pads; testicles or ovary; tonsil and adrenal gland. Half of each tissue sample was fixed in 10% neutral buffered formalin for histological processing and the other half was submerged in viral transport medium for RNA extraction and virus isolation.

Since the kidneys of the two stray cats showed histopathological features compatible with TIN, the kidneys, urine and plasma were obtained from a total of 27 strayed cats, including the two cats with necropsies performed, and were subject to RT-PCR, histopathology and antibody detection by western blot and immunofluorescence to examine for possible association between FmoPV infection (RT-PCR and/or antibody positive) and TIN.

6.2 Example 2

RT-PCR of L Gene of *Morbilliviruses* and DNA Sequencing

Viral RNA was extracted from tracheal and rectal swabs, urine and blood using EZ1 Virus Mini Kit (QIAgen) and from tissue samples using QIAamp Viral RNA Mini Kit (QIAgen). *Morbillivirus* detection was performed by amplifying a 155-bp fragment of L gene of *morbilliviruses* using conserved primers (LPW12490 5'-CAGAGACTTAATGAAATT-TATGG-3' (SEQ ID NO: 11) and LPW12491 5'-CCAC-CCATCGGGTACTT-3' (SEQ ID NO: 12)) designed by multiple alignments of available L gene sequences of *morbilliviruses*. Reverse transcription, PCR and sequencing were performed according to our previous publications (13, 14).

6.3 Example 3

Real-Time Quantitative RT-PCR

Real-time quantitative RT-PCR to detect L gene of FmoPV was performed on the 56 positive samples using LightCyler FastStart DNA Master SYBR Green I Mix reagent kit (Roche), with primers LPW12490 and LPW12491. Complementary DNA (cDNA) was amplified by LightCycler 2.0 (Roche) with 20-μl reaction mixtures containing FastStart DNA Master SYBR Green I Mix reagent kit (Roche), 2 μl of cDNA, 4 mmol/L $MgCl_2$, and 0.5 mmol/l primers at 95° C. for 10 min, followed by 50 cycles of 95° C. for 10 s, 60° C. for 5 s and 72° C. for 8 s. A plasmid containing the target sequence was used for generating the standard curves.

RT-PCR for a 155-bp fragment in the L gene of *morbilliviruses* was positive in samples from 56 (12.3%) cats from Hong Kong, including 53 urine, 4 rectal swabs and 1 blood specimens. For the 16 diseased cats from mainland China, one (6.25%) cat was RT-PCR positive in both its oral and rectal swabs. Real-time quantitative RT-PCR showed a median viral load of $3.9\times10^3$ (range 0.037 to $1.4\times10^6$) copies/ml. Sequencing results suggested the presence of a novel *paramyxovirus* of the genus *Morbillivirus*, with <80% nt identities to known *paramyxoviruses* (FIG. 8). This novel *paramyxovirus* was named FmoPV.

6.4 Example 4

Analysis of P mRNA Editing

To examine the number of G insertions at the P mRNA editing site, mRNA from original specimens was extracted using the Oligotex mRNA Mini kit (QIAgen). First strand cDNA synthesis was performed using SuperScript III kit (Invitrogen) with random hexamer primers. Primers (5'-TTCATCTCTTAGTTCCCAGGAA-3' (SEQ ID NO: 17) and 5'-TTTCAGACTCACCCTCGATATCT-3' (SEQ ID NO: 18)) were used to amplify a 442-bp product of FmoPV covering the putative editing site. PCR, cloning and sequencing were performed as described in our previous publication (13).

6.5 Example 5

Cloning and Purification of $(His)_6$-Tagged ("(His)6" Disclosed as SEQ ID NO: 10) Recombinant Nucleoprotein (N) from *Escherichia coli*

Primers (5'-ACGCGGATCCGATGTCTAGTCTA-3' (SEQ ID NO: 19) and 5'-CGGAATTCGGTTTTAGAAGGT-CAGTA-3' (SEQ ID NO: 20)) were used to amplify the N gene (519 amino acids) of FmoPV strain 761U by RT-PCR. Cloning, expression and purification of $(His)_6$-tagged ("(His) 6" disclosed as SEQ ID NO: 10) recombinant N protein was performed as described in (1) Lau S K, et al. (2010) Virology 404:106-116; (2) Woo P C, et al. (2005) J Virol 79:884-895; and (3) Woo P C, et al. (2004) Lancet 363:841-845.

6.6 Example 6

Guinea Pig Sera

Guinea pig antiserum against the N protein of FmoPV was produced by injecting 100 μg purified N protein of FmoPV, with an equal volume of complete Freund's adjuvant (Sigma), subcutaneously to three guinea pigs. Incomplete Freund's adjuvant (Sigma) was used in subsequent immunizations. Three inoculations at once every two weeks per guinea pig were administered. Two weeks after the last immunization, 1 ml of blood was taken via the lateral saphenous vein of the guinea pigs to obtain the sera.

Such hyperimmune guinea pig antibody can be used for diagnostic purposes or as a vaccine in the following ways:
1. The recombinant nucleoprotein, N protein, can be used as the target antigen for detecting specific antibody against this virus from cats' sera.
2. The hyperimmune antibody can be used for immunohistochemical detection of viral protein in tissues or infected cell culture to confirm the specific presence of this virus.
3. The recombinant nucleoprotein can be used as a vaccine to induce antibody production.

6.7 Example 7

Western Blot Analysis

Antibodies against the N protein of FmoPV were detected in plasma samples of the 56 cats that were RT-PCR positive and 401 cats that were RT-PCR negative for FmoPV by Western blot. Western blot analysis was performed as described in our previous publications (24, 25, 27), using 1000 ng purified $(His)_6$-tagged ("(His)6" disclosed as SEQ ID NO: 10) recombinant N protein, 1:1000 dilutions of cat plasma samples, 1:4000 dilution of horse radish peroxidase conjugated goat anti-cat IgG antibody and 1:10000 dilution of goat anti-cat IgM antibody (Bethyl laboratories).

Among tested sera from the 56 cats that were RT-PCR positive and 401 cats that were RT-PCR negative for FmoPV, 49 (76.7%) and 78 (19.4%) were positive for IgG against N protein of FmoPV by western blot analysis respectively ($P<0.0001$) (FIG. 9, Table 6). Among tested sera from the 56 cats that were RT-PCR positive for FmoPV, only 5 (8.9%) were positive for IgM against N protein of FmoPV.

Prominent immunoreactive protein bands of about 69 kDa, consistent with the expected size of 68.7 kDa of the recombinant protein, were detected in three of the six cat serum samples shown in FIG. 9, indicating antigen-antibody interactions between the recombinant FmoPV N protein and serum antibodies. Results of RT-PCR of the corresponding urine samples for FmoPV are also shown.

6.8 Example 8

Viral Culture

Viral culture and electron microscopy were performed according to our previous publications (28, 29). Two hundred microliters of the three samples used for complete genome sequencing were subject to virus culture. After centrifugation, they were diluted five folds with viral transport medium and filtered. 200 μl of the filtrate was inoculated to 200 μl of MEM with polybrene. 400 μl of the mixture was added to 24-well tissue culture plates, with CRFK (feline kidney), B95 (marmoset B-cell), CEF (chicken embryo fibroblast), NIH/3T3 (mouse embryo fibroblast) or Vero E6 (African green monkey kidney) cells, by adsorption inoculation. After 1 h of adsorption, excess inoculum was discarded, the wells were washed twice with phosphate buffered saline and replaced by 1 ml of serum free MEM supplemented by 0.1 μg/ml of L-1-tosylamide-2-phenylethyl chloromethyl ketone-treated trypsin (Sigma). Cultures were incubated at 37° C. with 5% $CO_2$ and inspected daily by inverted microscopy for cytopathic effects (CPE). After two to three weeks of incubation, subculturing to fresh cell line was performed even if there were no CPE and culture lysates were collected for RT-PCR for FmoPV. Immunostaining and electron microscopy were performed on samples that were RT-PCR positive for FmoPV.

CRFK and Vero E6 cells that were positive for FmoPV by RT-PCR were fixed in chilled acetone at −20° C. for 10 min. The fixed cells were incubated with 1:200 dilution of guinea pig antiserum against the N protein of FmoPV, followed by 1:50 diluted FITC-rabbit anti-guinea pig IgG (Invitrogen). Cells were then examined under fluorescence microscope. Uninoculated cells were used as negative control.

At the $8^{th}$ passage, CRFK cells inoculated with a urine sample (761U) positive for FmoPV showed CPE at day 14, in the form of cell rounding, followed by cell detachment from the monolayer and cell lysis. At the $16^{th}$ passage, CPE were evident at day 10 with syncytia formation (FIG. 6). RT-PCR for FmoPV using the culture supernatants and cell lysates showed positive results in CRFK cells inoculated with urine sample 761U and VeroE6 cells inoculated with supernatant of CRFK cells positive for FmoPV. Specific apple green finely granular and diffuse cytoplasmic fluorescence was also observed using serum from guinea pig immunized with recombinant N protein of FmoPV or corresponding serum of the infected cat (FIG. 6). Electron microscopy showed an enveloped virus with the typical "herring bone" appearance of the helical N in *paramyxoviruses* (FIG. 6). Virions are highly variable in size, ranging approximately from 130 to 380 nm in diameter. No CPE and no viruses were detected by RT-PCR in 3T3, B95 and CEF cells inoculated with the samples.

6.9 Example 9

Immunofluorescence Antibody Test

CRFK cells infected with FmoPV were fixed in chilled acetone at −20° C. for 10 min. The fixed cells were incubated with 4-fold dilutions of plasma from 1:10 to 1:10240 from the 27 cats with necropsies, followed by 1:20 diluted FITC-goat anti-cat IgG (Sigma). Cells were then examined under fluorescence microscope. Uninfected cells were used as negative control. Out of the 27 cats, immunofluorescent antibody was detected from 7 cats with titer from 1:40 to 1:640 (see Table 4, supra).

6.10 Example 10

Neutralizing Antibody Detection

100 TCID50 FmoPV were incubated with 2-fold dilutions of plasma from 1:10 to 1:2560 from the 27 cats with necropsies at 37° C. for 1 h. The mixtures were inoculated to 96-well plates of confluent CRFK cells. After 1 h of adsorption, the inoculums were removed and the plates were washed once with phosphate buffered saline and replaced by serum free MEM supplemented by 0.1 μg/ml of L-1-tosylamide-2-phenylethyl chlormethyl ketone-treated trypsin (Sigma). The plates were incubated at 37° C. with 5% $CO_2$ for 7 days. The supernatants were removed and the cell monolayers were washed once with phosphate buffered saline and fixed in chilled methanol at −20° C. for 10 min. The fixed cells were incubated with 1:200 dilution of guinea pig antiserum against the N protein of FmoPV, followed by 1:50 diluted FITC-rabbit anti-guinea pig IgG (Invitrogen). Cells were then examined under fluorescence microscope. Cells infected with neutralized FMoPV showed no fluorescence. FmoPV infected cells were used as negative control. Out of the 27 cats, neutralization antibody was detected from 6 cats with titer from 1:20 to 1:40 (see Table 5, supra), of which all were positive for immunofluorescent antibody (see Table 4, supra).

6.11 Example 11

Histopathological Examination and Immunohistochemical Staining of FmoPV N Protein in Tissues and Cauxin Protein in Kidneys To determine if FmoPV is associated with renal pathologies, such as TIN, histopathology and immunohistochemistry were performed on necropsy kidney tissues of two stray cats with positive FmoPV RT-PCR in their urine samples as described below, showing histopathological features compatible with TIN as well as detection of N protein of FmoPV in the renal tubules by immunohistochemistry.

Fixed necropsy organs of the two stray cats were embedded in paraffin. Tissue sections of 5 μm were stained with hematoxylin and eosin (H&E). Histopathological changes were observed using Nikon 80i microscope and imaging system. Expression of FmoPV N protein was examined by immunohistochemical staining. Tissue sections were deparaffinized and rehydrated, followed by blocking endogenous peroxidase with 3% $H_2O_2$ for 20 min, and then with 10% normal rabbit serum/PBS at room temperature for 1 h to minimize non-specific staining. The sections were incubated at 4° C. overnight with 1:250 dilution of guinea pig anti-N protein antiserum, followed by incubation of 30 min at room temperature with 1:500 dilution of biotin-conjugated rabbit anti-guinea pig IgG, H & L chain (Abeam) (30). Streptavidin/peroxidase complex reagent (Vector Laboratories) was then added and incubated at room temperature for 30 min. Color development was performed using 3,3'-diaminobenzidine and images captured with Nikon 80i imaging system and Spot-advance computer software. Double staining of lymph node was performed using mouse anti-human myeloid/histocyte antigen antiserum MAC387 (DakoCyomation) and labeled with Texas-red conjugated goat anti-mouse IgG (Jackson ImmunoResearch) (31). Cauxin protein expression was detected according to a published protocol (32).

Figure 12:
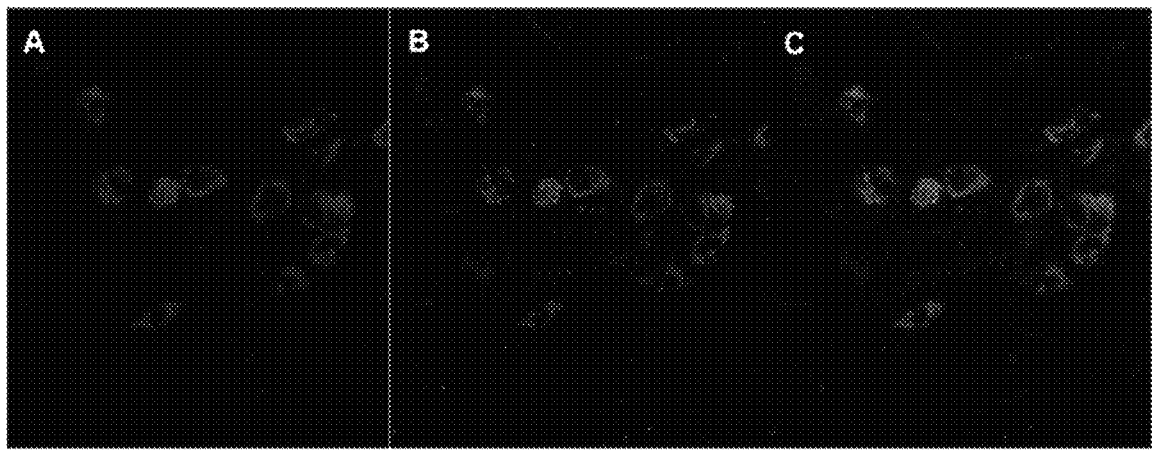

Histological examination of various organs of two stray cats with FmoPV detected in urine revealed interstitial inflammatory infiltrate and renal tubular degeneration or necrosis in their kidneys (FIG. 10). In addition, there was also marked decrease in cauxin expression in the degenerated tubular epithelial cells, compatible with tubulointerstitial nephritis in cats with histological evidence of TIN (FIG. 11A), compared to cats without histological evidence of TIN where cauxin-positive proximal straight renal tubules were observed between the inner cortex and outer medulla (FIG. 11B). Immunohistochemical staining of their organs using guinea pig serum positive for anti-FmoPV N protein antibody revealed positive renal tubular cells in kidney sections and positive mononuclear cells in lymph node sections (FIG. 10). Using mouse anti-human myeloid/histocyte antigen antiserum MAC387, the targets of FmoPV in lymph node sections were shown to be macrophages (FIG. 12).

6.12 Example 12

Case Control Study

Among 27 stray cats, TIN was observed in 7 of 12 cats with evidence of FmoPV infection, but only in 2 of 15 cats without evidence of FmoPV infection (P<0.05 by Fisher's exact test) (Table 4). These results support a positive association between FmoPV infection (RT-PCR and/or antibody positivity) and TIN in cats.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

REFERENCES CITED IN APPLICATION

1. Barrett T (1999) *Morbillivirus* infections, with special emphasis on *morbilliviruses* of carnivores. *Vet Microbiol* 69:3-13.
2. Chua K B, et al. (2000) Nipah virus: a recently emergent deadly *paramyxovirus*. *Science* 288:1432-1435.
3. Halpin K, Young P L, Field H E, Mackenzie J S (2000) Isolation of Hendra virus from pteropid bats: a natural reservoir of Hendra virus. *J Gen Virol* 81:1927-1932.
4. Moreno-Lopez J, Correa-Giron P, Martinez A, Ericsson A (1986) Characterization of a *paramyxovirus* isolated from the brain of a piglet in Mexico. *Arch Virol* 91:221-231.
5. Osterhaus A D, et al. (1995) *Morbillivirus* infections of aquatic mammals: newly identified members of the genus. *Vet Microbiol* 44:219-227.
6. Philbey A W, et al. (1998) An apparently new virus (family Paramyxoviridae) infectious for pigs, humans, and fruit bats. *Emerg Infect Dis* 4(2):269-271.
7. Tidona C A, Kurz H W, Gelderblom H R, Darai G (1999) Isolation and molecular characterization of a novel cytopathogenic *paramyxovirus* from tree shrews. *Virology* 258:425-434.
8. Stone B, et al. (2011) Fatal cetacean *morbillivirus* infection in an Australian offshore bottlenose dolphin (*Tursiops truncatus*). *Aust Vet J* 89:452-457.
9. Young P L, et al. (1996) Serologic evidence for the presence in *Pteropus* bats of a *paramyxovirus* related to equine *morbillivirus*. *Emerg Infect Dis* 2:239-240.
10. Lau S K, et al. (2005) Human parainfluenza virus 4 outbreak and the role of diagnostic tests. *J Clin Microbiol* 43:4515-4521.
11. Lau S K, et al. (2009) Clinical and molecular epidemiology of human parainfluenza virus 4 infections in hong long: subtype 4B as common as subtype 4A. *J Clin Microbiol* 47:1549-1552.
12. Virtue E R, Marsh G A, Wang L F (2009) *Paramyxoviruses* infecting humans: the old, the new and the unknown. *Future Microbiol* 4:537-554
13. Lau S K, et al. (2010) Identification and complete genome analysis of three novel *paramyxoviruses, Tuhoko* virus 1, 2 and 3, in fruit bats from China. *Virology* 404:106-116.
14. Woo P C, et al. (2011) Complete genome sequence of a novel *paramyxovirus, Tailam* virus, discovered in Sikkim rats. *J Virol* 85:13473-13474.
15. Bart M, Guscetti F, Zurbriggen A, Pospischil A, Schiller I (2000) Feline infectious pneumonia: a short literature review and a retrospective immunohistological study on the involvement of *Chlamydia* spp. and distemper virus. *Vet J* 159:220-230.

16. Chatziandreou N, et al. (2004) Relationships and host range of human, canine, simian and porcine isolates of simian virus 5 (parainfluenza virus 5). *J Gen Virol* 85:3007-3016.
17. Herrewegh A A, Smeenk I, Horzinek M C, Rottier P J, de Groot R J (1998) Feline *coronavirus* type II strains 79-1683 and 79-1146 originate from a double recombination between feline *coronavirus* type I and canine *coronavirus*. *J Virol* 72:4508-4514.
18. Siegl G, et al. (1985) Characteristics and taxonomy of Parvoviridae. *Intervirology* 23:61-73.
19. Truyen U (2006) Evolution of canine *parvovirus*—a need for new vaccines? *Vet Microbiol* 117:9-13.
20. King A M Q, Adams M J, Carsten E B, Lefkowitz E J (2012) *Virus Taxonomy: Ninth report of the International Committee on Taxonomy of Viruses* (Elsevier, San Diego) pp 111-122.
21. King A M Q, Adams M J, Carsten E B, Lefkowitz E J (2012) *Virus Taxonomy: Ninth report of the International Committee on Taxonomy of Viruses* (Elsevier, San Diego) pp 235-248.
22. Knipe D M, et al. (2007) *Fields Virology* (Lippincott Williams and Wilkins, Philadelphia), pp 1551-1586.
23. Lau S K, et al. (2011) Identification of a novel feline picornavirus from the domestic cat. *J Virol* (In press).
24. Lau S K, et al. (2005) Severe acute respiratory syndrome *coronavirus*-like virus in Chinese horseshoe bats. *Proc Natl Acad Sci USA* 102:14040-14045.
25. Woo P C, et al. (2005) Characterization and complete genome sequence of a novel *coronavirus, coronavirus* HKU1, from patients with pneumonia. *J Virol* 79:884-895.
26. Guindon S, et al. (2010) New algorithms and methods to estimate maximum-likelihood phylogenies: assessing the performance of PhyML 3.0. *Syst Biol* 59:307-321.
27. Woo P C, et al. (2004) Relative rates of non-pneumonic SARS *coronavirus* infection and SARS *coronavirus* pneumonia. *Lancet* 363:841-845.
28. Li I W, et al. (2009) Differential susceptibility of different cell lines to swine-origin influenza A H1N1, seasonal human influenza A H1N1, and avian influenza A H5N1 viruses. *J Clin Virol* 46:325-330.
29. Peiris J S, et al. (2003) Clinical progression and viral load in a community outbreak of *coronavirus*-associated SARS pneumonia: a prospective study. *Lancet* 361:1767-1772.
30. Chan K H, et al. (2010) Wild type and mutant 2009 pandemic influenza A (H1N1) viruses cause more severe disease and higher mortality in pregnant BALB/c mice. *PLoS One* 5:e13757.
31. Susta L, Torres-Velez F, Zhang J, Brown C (2009) An in situ hybridization and immunohistochemical study of cytauxzoonosis in domestic cats. *Vet Pathol* 46:1197-1204.
32. Miyazaki. M, et al. (2007) Tubulointerstitial nephritis causes decreased renal expression and urinary excretion of cauxin, a major urinary protein of the domestic cat. *Res Vet Sci* 82:76-79.
33. Chard L S, Bailey D S, Dash P, Banyard A C, Barrett T (2008) Full genome sequences of two virulent strains of peste-des-petits ruminants virus, the Cote d'Ivoire 1989 and Nigeria 1976 strains. *Virus Res* 136:192-197.
34. Visser I K, et al. (1993) Fusion protein gene nucleotide sequence similarities, shared antigenic sites and phylogenetic analysis suggest that phocid distemper virus type 2 and canine distemper virus belong to the same virus entity. *J Gen Virol* 74:1989-1994.
35. Terai M, Burk R D (2002) *Felis domesticus* papillomavirus, isolated from a skin lesion, is related to canine oral papillomavirus and contains a 1.3 kb non-coding region between the E2 and L2 open reading frames. *J Gen Virol* 83:2303-2307.
36. Whittemore J C, Hawley J R, Jensen W A, Lappin M R (2010) Antibodies against Crandell Rees feline kidney (CRFK) cell line antigens, alpha-enolase, and annexin A2 in vaccinated and CRFK hyperinoculated cats. *J Vet Intern Med* 24:306-313.
37. Lappin M R, et al. (2005) Investigation of the induction of antibodies against Crandell-Rees feline kidney cell lysates and feline renal cell lysates after parenteral administration of vaccines against feline viral rhinotracheitis, calicivirus, and panleukopenia in cats. *Am J Vet Res* 66:506-511.
38. Lappin M R, Basaraba R J, Jensen W A (2006) Interstitial nephritis in cats inoculated with Crandell Rees feline kidney cell lysates. *J Feline Med Surg* 8(5):353-356.
39. Kul O, Kabakci N, Atmaca H T, Ozkul A (2007) Natural peste des petits ruminants virus infection: novel pathologic findings resembling other *morbillivirus* infections. *Vet Pathol* 44:479-486.
40. Liess B, Plowright W (1964) Studies on the Pathogenesis of Rinderpest in Experimental Cattle. I. Correlation of Clinical Signs, Viraemia and Virus Excretion by Various Routes. *J Hyg* (Lond) 62:81-100.
41. Saito T B, et al. (2006) Detection of canine distemper virus by reverse transcriptase-polymerase chain reaction in the urine of dogs with clinical signs of distemper encephalitis. *Res Vet Sci* 80:116-119.
42. Marschall J, Hartmann K (2008) Avian influenza A H5N1 infections in cats. *J Feline Med Surg* 10:359-365.
43. Martina B E, et al. (2003) Virology: SARS virus infection of cats and ferrets. *Nature* 425:915.
44. van Riel D, Rimmelzwaan G F, van Amerongen G, Osterhaus A D, Kuiken T (2010) Highly pathogenic avian influenza virus H7N7 isolated from a fatal human case causes respiratory disease in cats but does not spread systemically. *Am J Pathol* 177:2185-2190.
45. Chomel B B, Sun B (2011) Zoonoses in the bedroom. *Emerg Infect Dis* 17:167-172.

What is claimed is:

1. A method of detecting kidney disease in a feline comprising the steps of: (i) obtaining a sample from the feline; (ii) amplifying a DNA molecule derived from the sample using a set of primers that binds to the DNA molecule, wherein the primers are at least 95% identical to the nucleotide sequence of SEQ ID NO: 11, 12, 19, or 20; and (iii) detecting the amplified DNA molecule, which is at least 20 base pair in length, and wherein the feline is infected with a *morbillivirus* and has kidney disease if the DNA molecule is at least 95% identical to the nucleotide sequence of FmoPV 776U, FmoPV M252A, or FmoPV 761U, and encodes the amino acid sequence of SEQ ID NO:7, 8 or 9, respectively.

2. The method of claim 1 wherein the sample is a cell, blood, serum, plasma, saliva, urine, stool or sputum.

3. The method of claim 1 wherein the kidney disease is tubulointerstitial

4. The method of claim 1 wherein the set of primers comprises a primer having the sequence of SEQ ID NO:11 or SEQ ID NO:12.

5. The method of claim 1 wherein the set of primers comprises primers having the sequences of SEQ ID NO:11 and SEQ ID NO:12.

6. The method of claim 1 wherein the set of primers comprises a primer having the sequence of SEQ ID NO:19 or SEQ ID NO:20.

7. The method of claim 1 wherein the set of primers comprises primers having the sequences of SEQ ID NO:19 and SEQ ID NO:20.

8. The method of claim 1 wherein the amplified DNA molecule is less than 200 base pair in length.

9. A method of diagnosing kidney disease in a feline comprising the steps of: (i) obtaining a sample from the feline; (ii) amplifying a DNA molecule derived from the sample using a set of primers that binds to the DNA molecule, wherein the primers are at least 95% identical to the nucleotide sequence of SEQ ID NO: 11, 12, 19, or 20; and (iii) detecting the amplified DNA molecule, which is at least 20 base pair in length, and wherein the feline is infected with a *morbillivirus* and has kidney disease if the DNA molecule is at least 95% identical to the nucleotide sequence of FmoPV 761U, FmoPV 776U or FmoPV M252A, and encodes the nucleotide sequence of SEQ ID NO: 1, 2 or 3, respectively.

\* \* \* \* \*

SEQUENCE LISTING

```
<160> NUMBER OF SEQ ID NOS: 28

<210> SEQ ID NO 1
<211> LENGTH: 16050
<212> TYPE: DNA
<213> ORGANISM: Feline morbillivirus
<400> SEQUENCE: 1
accagacaaa gatgtttgtg acctattcta acgacaagac tattattaaa tatttaggaa     60
```

```
taacgattcc attagtgagg tgaggggggag gaatcaggta ttccacaatg tctagtctat    120
tgaggtcact tgctgcattt aagagacata gggagcaacc aacagcaccg tcaggttcgg    180
gtggtgcaat taaaggattg aaaaatacaa ttattgttcc agttccaggg gatacagtaa    240
ttactacaag gtctaatttg ttatttagat tagtttatat aataggcaat ccggatacac    300
ctttaagcac ctcgacggga gcaataatat cattgttgac cttatttgtc gaatctccag    360
gtcaattaat tcaaagaatt gctgatgacc ctgatgcagt ttttaaattg gtagaggtca    420
ttcctgaagc tggtaatcct ggagaattaa cttttgcatc tcgagggatt aatttagaca    480
agcaagctca acaatacttt aaattggctg agaaaaatga tcagggtat tatgttagct    540
taggatttga gaacccacca aatgatgacg atataacatc tagtcctgag atattcaatt    600
atatcctggc atctgtactt gcacaagttt ggattcttct ggcaaaagct gtgactgctc    660
cagatacggc tgctgaagcc gaaaatcgta gatggattaa attaatgcaa caacgtaggg    720
tggatggtga actgagattg agcaagggat ggctagattt ggtgagaaac aagattgcgt    780
cagatattac aataaggcga ttcatggtag cattagttct tgacatcaaa cgttctcctg    840
ggacaagacc caggatagct gaaatgattt gtgatattga taattatatt gtagaggcag    900
ggcttgcaag tttcttgtta actattaaat ttggcataga gacacgttat ccagcactgg    960
cactacatga gttttctgga gaactagcca ctattgaggg gcttatgaaa ttgtaccaat   1020
ctatggggga aatggcacca tacatggtaa ttctggaaaa ttcaatccaa accaggttta   1080
gtgcagggtc ttatcctctg ctatggagtt atgccatggg tgtcggggtg gagcttgaaa   1140
gatcaatggg tggactcaat ttcactagaa gcttctttga ccctacatat ttcagacttg   1200
gtcaagagat ggtgaggaga tcttcaggga tggttaatag ttcatttgcg agagaacttg   1260
gcctatctga tcatgaaaca caactggtca gccagattgt caattcggga ggtgaatctg   1320
ggatacctaa atttgatgga ttcagagcaa atccaacaac ttttctagga accaaagata   1380
acataaatga tagaggtgaa gatcagtcaa attcgatatc agggttacct ggtccactat   1440
tacccagccg tgacctaaat cttcaggtg attcatatgg aattaatagt ggtgtgaaaa   1500
atgtcagtga caaactgaat gaaggagtag gtccagacca tgatgtgtcc agttctgcca   1560
tggaagaatt gagaagattg gttgagtcca ccaacagaat agacaccaaa cagccagaag   1620
cttcaggtgt caccaaccat tataatgata ctgaccttct aaaataatat gagcataccc   1680
taattgctta ttatgcaact caaattaaga aaaacttagg acctcaaggt tcacaactgt   1740
tggcatatca ctaaaataca gtcagctctt cacccaccac atgtcctctc accaaatcca   1800
gcaagtcaaa catggcctcg aatctttaca agagatcaaa aacaaccctc cgtcttccca   1860
agatgtcaat cttgccaggg agatttacga atccattaga caaacaggaa catcttcagt   1920
gcaaggagga gccattgcgg gagataatat tacgtcaggg ggtaacaatg actcaatgta   1980
tagccaagga ccaagtcctc ctatttcaag tgttaacaag aatatcgaag gacctactgg   2040
attcgatcat tcaggactat gggatccaga gggtaacctc tgcatgctat tcgaaagcga   2100
tgatgatgaa aaccattatt cagagattaa tggccggtct tccgctatcg aaggactgga   2160
tgaacaggat aatgagaact caattattaa acaaccagga atcagtgta ctgagggagt   2220
gtctaagact gattcatctc ttagttccca ggaaactaca ctatctgttg ggggatctga   2280
tatacctggg gcaggaatat caacctgtgc ctctttggat ataactgtaa atgaactcga   2340
agatgcaact gtaagaaata gcaacaatat gaaagggaac tggccaattc ctaaattact   2400
tgttaagccg ccacctaggg taaaaacaag cgttgatcac agtaatccat taaaagggc   2460
```

```
cacaggaggg aaattagcct cacctgggat ggagactaca ttattcgaga ggagtggtgc    2520
aaccccatct gtacacccat atactcaacc tgcaagcgac ttcaatgtag gtgcaagcaa    2580
tgtccatcaa cctgccctaa atgtgaataa taattgcaat gatggtaggg taacagcgcc    2640
taactcacat aaagatatcg agggtgagtc tgaaatatct attcaagata tatataactt    2700
gattcttgga tttaaggatg attacaggaa attatcaaac aaattagata tggtattaga    2760
gatgaaacaa gacattgaca atctaaaaaa gaatagtgct aaagtgcaat tggctctatc    2820
aactattgag ggacatctat ccagtgttat gattgccatc cctggttcag gtattgattc    2880
cacaggggat gaggaaaagg atcagataaa ttctgactta aaaccactgc taggaaggga    2940
tcattgtaga gcatttcgag aagttaccaa tcctctagat gagtcttcac tagccaattc    3000
tccaacaaaa catgttgcca aggtaaacaa aaactgcact cttcagaaga tcaacaagaa    3060
cgaaacatct gcaatcaaat ttgttcctag tgacagtcat gcaagcacat caaccatcag    3120
atcaattatc aggtcatcta atctcgatca ggatttgaaa acaaaattgc tcacaattct    3180
atcccagatt agaggggcag acaatattag agaattctat gaaaaggtta tgatattaat    3240
aaagaataag aattaaatat tacaaatcta cattcattat aggttgtaat tgtcttcaat    3300
aagatttggt cagtttcata tatatggtta ttgatttgtg ataattataa aaaacttagg    3360
agctaaaggt tactcagtca tatacagcat gactgagata ttcaaccttg atgagagctc    3420
atggtcagtc aaagggatac tagatccgtt aacacctgat acctatcctg atggtcgact    3480
agtgcctaaa gttcgagtta tcgatccggg tctaggagat cgcaagagtg gggggtatat    3540
gtacctactt cttcatggtg tcatagaaga tagtgagact ataattagcc cgaaaggaag    3600
agcatttggt gcattcccat taggagtggg tcaatcaact gaaaacccgg aagacttgtt    3660
taaggaaata ttaactctca acatcgtgac tcgtaggact gctggattta atgagaaatt    3720
ggtttattat aataccacac ctctacattt actgaccccc tggaaaaaag tgttggcata    3780
tggaggcatt tttaatgcta atcaggtctg cagtgataca agttccatac caatagacat    3840
tccacaaaaa tttaggccag tatatttgac tgttacaaaa ttatctgatg atggctatta    3900
tcagatccca aagatgattc aagatttcaa atcgtcaaat tctgttgcat tcaacatcct    3960
tgtgcatctg tcaatgggca taaatttact tgaccaatcc aaggacccta gattaagaaa    4020
tgctgcagaa actgtgatca catttatgat tcatattgga aactttaaac ggaagagtaa    4080
taagtcttac tcacctgaat attgcaagag gaaaataatg aggctgggtt taatattctc    4140
attaggtgca attggtggca caagcttgca tattagatgt acaggtaaga tgagcaaacg    4200
actacaggct tatttaggat tcaaaaggac tttatgttac cctttgatgt atgttaatga    4260
agggctgaac aagaccctgt ggagaagtga atgcagaata gagaaggttc aagcagtctt    4320
acagccatca gtcccgaatg aatttaagat atatgatgat gttattattg ataataccaa    4380
tggtctcttc aagattaaat agactataac aataataaac agctactaaa tagtattatg    4440
tatttaagtg tacactgata attgcgaata aaatacacca gattaataac agtatagagt    4500
taagatctaa ttgatatgtg ggttggtact cgatcattta ttagctctac tgattatcta    4560
tatcttgaat caccaaatgt aagagcatca acaggtaata agttttggat tgctagattg    4620
acacttaatt ctcagaacta gaatacccag attgtcaaac ctataacctt gttagattca    4680
ttaaagttag attcttgtaa tgttgatcaa ttatcacttg agcaattata aaaaactaag    4740
gacctaatgt aataggaacc caaactccat ccagtgagct ctaaatcgcc atgcttgaat    4800
```

```
attaatttat ctagggcctg tctaactcag aacaaagatc acaactagag tctaaaggag    4860
tgggtcaagt ctgaacaatt atcaagagcc gagattcaaa actgattcct ccttaaactc    4920
agaaccctaa caatatatca tccactcaac atcatgaaca gaattaaggt tatgataatt    4980
agttctttat tattatcaga tattacgatt gcacaaatag gttgggataa tttgacttcg    5040
attggagtta taagtactaa gcaatacgac tataaaataa ctactctgaa cactgaccag    5100
ttaatggtta taaagatggt tcctaatata tcatcaatca ttaattgcac taaactcgaa    5160
ttaacaaaat atagagagtt agtctcaggg atcattagac aataaatga gtcattagaa     5220 ttaatgaatt catacattaa catgagagca ggttcagaga gatttatagg ggctgtaata    5280
gctggtgtag ccttaggagt ggcaactgca gcacaaataa catcagggat tgccctacat    5340
aattcaatta tgaacaaaaa acaaatacaa gaattgagga aggctcttag tactaccaac    5400
aaagcaattg atgaaataag gattgcaggt gaaagaacat taatagcaat tcaaggtgta    5460
caggattata ttaataatat aattatccct atgcaggaca aactccaatg tgatatttta    5520
tcatcacaac tttctgttgc tttactcaga tattatacaa atatactaac agttttgggg    5580
ccaagtatac gggatcctat tactagtaca atttcagtac aagcactcag tcaagcattc    5640
aatggtaatc ttcaggcatt gcttgatgga ctggggtata ctgggagaga cttacgtgat    5700
cttctagaga gtaaatctat cactggccag ataattcatg cagatatgac tgatttgttc    5760
cttgttttga gaataaatta tccttccata actgagatgc agggagtaac aatatatggg    5820
ctcaattcaa ttacatatca tattgggcct gaagagtggt ataccattat gcctgatttt    5880
attgctgttc agggttttt aatatctaat tttgatgaga gaaagtgttc agtaactaaa    5940
tcaagtatat tgtgccaaca aaattcaatt tacccaatgt caacagagat gcaaagatgt    6000
attaagggcg agataagatt ctgtccaaga tccaaggcaa ttgggacatt agttaatcgg    6060
tttatattga ccaaaggtaa tttaatggct aattgtttag ggattatatg cagatgttat    6120
acttcaggac aagttataac acaagaccca agtaaattga ttacgataat atcgcaagag    6180
gagtgcaagg aagttggtgt tgatggtatt cgtattatgg taggacctag aaaattacca    6240
gatattacct ttaatgctag gttggaaatt ggtgtaccaa tatcattgag caaattggat    6300
gtcgggactg atttagcgat tgcttcagct aaacttaata attctaaggc attgttagag    6360
caatcagata agatttttaga ttcaatgtct aaattggatt ctatgaattc aagaataata    6420
ggattaatct tagcaattat gataatcttt ataatcatta ttactattat ctggatcata    6480 tataaaaat gtaggaataa agataataaa ttcagtactt caattgaacc gctctacata    6540
cccccttctt ataactcacc tcatagtgtg gttaagtcta tttgagcact gaccatatga    6600
tccactgtaa taagtccaat gaaagtatca attaataata ttggtagtgc aatgagtatt    6660
gattgtataa tatactcctt taaactagat agtgataaag ggttatagat gatttcagtt    6720
attttaatat aatcatatat tgattttatt atcttacatg actattatgt aattgaatta    6780
tgtgtcatca attaatagct taataatatc gtttaatgta cttatattga tggatagatg    6840
tgttatattg taatcaagga tttagtattt agaaaaggaa agagtttaat ttgttgttaa    6900
ttagttattg tgtattcaat tagaaaaaac ttaggaatcc atgttaataa aaatttatta    6960
tcatggagtc caacaatatt aagtattaca aagattctag ccggtacttt ggtaaaatat    7020
tagatgaaca caaaacaatt aatagtcaat tgtacagttt gagtatcaag gtaattacca    7080
ttattgctat tattgtaagc ctgattgcaa caataataac tattatcaat gccactagtg    7140
ggagaactac cctaaatagt aatacagaca tactactcag ccaacgagat gagattcata    7200
```

-continued

```
acatccaaga aatgatattt gatcgtattt atcctttgat aaatgctatg agtacagagc    7260
taggacttca tattcctacc ttattggatg aacttactaa agcgattgac cagaaaatta    7320
aaataatgca tcctcctgtg gacactgtga cttctgacct taattggtgc atcaaacccc    7380
ctaatggaat tatcatagac ccaaaaagtt attgtgagag tatggaattg tctaaaactt    7440
atgaactgtt acttgaccag ttagatgtct caagaaagaa atcacttatt ataaatagaa    7500
agaatatcaa ccagtgccaa ttagttgata attcaaagat cattttttgct actgtcaaca   7560 tacaatctac accgaggttt ttaaactttg gtcacacggt cagcaatcaa cgtataacat    7620
ttggtcaagg aacatatagt agtacttatg ttataactat ccaagaagat ggagtaactg    7680
atgttcaata tcgagtgttt gagatcggat atatttctga tcagtttggt gtattcccct    7740
ccttaatagt atcgagagtg ttgccgatac gtatgctatt aggaatggaa tcctgtacct    7800
tgacaagtga tagactaggc gggtatttt tatgtatgaa tacactgaca cgatctatat     7860
atgattatgt tagcataagg gatttgaaat cactttatat aacaatccct cattatggta    7920
aagttaatta tacttacttt aattttggta agatcaggag cccacatgag attgataaaa    7980
tttggttaac atctgataga ggccaaatta tctctggtta ttttgcagca tttgttacca    8040
ttacaattcg gaactataat aattatccct acaaatgctt aaataaccca tgttttgaca    8100
actctgagaa ttactgtaga ggatggtata aaaacataac aggaactgat gatgttccga    8160
tattagcata cttattggtt gaaatgtatg atgaggaggg acctttaatt acacttgtgg    8220
caataccacc ttacaattat acagctccat ctcataattc tctttactat gatgacaaaa    8280
ttaataaatt aataatgact acatctcaca taggttatat tcaaatcaac gaggtgcatg    8340
aggtaattgt tggcgataat ttgaaggcta tcctcttaaa cagattgtct gatgaacatc    8400
ctaacctgac tgcctgtaga ctcaatcagg gtattaagga gcaatacaag tctgacggaa    8460
caataatttc aaattctgca cttattgata tacaagaacg aatgtacatt acagttaaag    8520
ctattccacc agcaggtaac tataaactta cagttgagtt gcattctaga tcaaacacat    8580
cctatgtatc gttaccaaaa cagtttaatg ctaagtatga caaattacat cttgagtgct    8640
ttagctggga caaatcctgg tggtgtgctc tgataccca gttttcatta agttggaatg    8700
aatccctttc tgttgatact gccatttttca atttaataag ctgtaaatga acacatcaat    8760
ctatagttga tagttgtcaa acattagct aatttgggtt taagaaatag gaaaatgaaa     8820
ttaccaatat ctaattagat gtatgttcaa gctaaattac aaaaaactta ggagtcagag    8880
acttcgttgc aatggagcag tcagactacc aagatattct ataccccggaa gtacatctta   8940 acagtcctat agtaatttcc aaattagtag gtattttaga atacgcccaa attgctcata   9000
atcaacaatt atcagaccgt acaattatca agaatattca atttagatta aggaacggat   9060
ttaatagttc aagggtacag gtactatcag ctatgggtga aattatcaac aaaattagaa    9120
ataaatatcc taattatta cacataccttt accctgaatg caaccaaaaa ctatttcgaa    9180
tagtagatcc agaactaaca tcaaaattag aatctcttct aaacaaaggt gacacactgt    9240
atctcaagat tcgatcagat atcataaaat gttttgatag attgaaaatg aaaatgaata    9300
taaagaatga tcttcttaat gacaaatagtc aattgattct agatcttcct ttaattatca    9360
aaggatctca gtggttcttc cctttttat tctggttttc tatcaaaact gaaactagaa     9420
gctgtattcg ccaaaatcaa aagactcgtg ttagatcaca atatcggcct cacttatcag    9480
agactaagag aattacattg gttgttacat ctgatctgat tacaatattt gatcatatta    9540
```

-continued

```
ataaatgtat attttatctg acttttgaga tgctgttaat gtattgcgat gtgatagaag    9600
gtcggttaat gactgaaaca gctatgagct tggactgtcg gtttaccaat ctattgccaa    9660
gagtgcaata tatgtgggat ttactagatg gaatgtttga aagtttaggc aatcaattat    9720
attcagttat tgcattatta gagcctcttt ctcttgctta tttgcaattg atagatgcag    9780
atccacagat tcggggaaca ttcttgcatc actgcttttc cgagttagaa gaaattatat    9840
ttgacaaaac ccttttttgat cctttttgtgt atgaaaattt aattaatggg cttgattaca   9900
tttatttgac aggtgatatt catctaactg cagaagtttt ttcttttttt agaagttttg    9960
gtcatccttt tttagaggca caaaatgctg ctaataatgt aaggaagtat atgaataagc   10020
ctaaggtaat atcatatcag actttaatgc aaggacatgc gattttttgc ggtattataa   10080
taaatggatt tagagaccgc cacgggggaa catggcctcc tgtggagtta ccaaatcatg   10140
catctgctgt aattagaaat gcccagttat ctggagaagg gttaacatct gaacaatgtg   10200
ctcaacactg gagatccttt tgtggattta gatttaaatg ttttatgcca ttgagtctag   10260
atagtgacct tacaatgtac cttagagaca aggcgctgtc acctgtcaga aatgagtggg   10320
attcagttta tgctaaggag tatttaaggt ataatccagg attacccaca agttccagaa   10380
gattggtaaa tgtattctta gaagatgata agtttgaccc atatgaaatg atcatgtacg   10440
tgataaatgg tgattactta agagacaaag agtttaacct ttcatacagc cttaaagaga   10500
aagaaattaa agaggtaggt cgattgtttg ctaaaatgac ctataagatg agggcttgtc   10560
aagtaatagc tgaaaacctg attgccaatg gagtagggaa gttttcaaa gataatggaa    10620
tggcaaaaga tgaacataaa ttaactaaga cgttacacaa attagccatt tcaggtgtac   10680
ctaaagataa ttctaaactt tatttagatg aatgttggga gcaagtaatt cgacaatgtt   10740
caagtagtac acagataagg gaacagacta tgaattcaca atcaaatagg gaaattgaat   10800
caaagtcttc tagggcacgt cttaataata gagatatctt aaagggcaag agagattcga   10860
acaaacaagt aaagtatcct tcaaacaccg agtattatga gactatcagt agtttcataa   10920
ctactgacct taaaaagtat tgtcttaact ggcgatatga atcaagtagt atgtttgcag   10980
agagacttaa tgaaatttat ggactgcctg gattttttcca gtggcttcac aagatttggg  11040
agaaatctgt tctatacgtt agtgatccat ctagtccacc tgactttgat caacatgtcg   11100
atatagaatc agtcccaaat gaccatatct ttatcaagta cccgatgggt ggaatagagg   11160
ggttctgtca aaaattatgg accattagta caattccgtt cctatattta gcagcttttg   11220
atacaggggt tagaatctca tcattggttc aaggcgataa ccaggcaatt gcagtaacca   11280
aaagagttcc gtcatcttgg agttactcaa agaaaaagga agaatcaact aaaataacaa   11340
cacaatattt tcttaattta agacaacgct tacacgatat aggtcatgaa ttgaaagcaa   11400
atgagactat tatatcctct catttctttg tttactctaa aggtatttat tatgatggaa   11460
tacttctctc ccaggcactt aaaagtattg caagatgtgt cttttggtct gaaacgattg   11520
ttgatgagac taggtcagct tgcagtaata tatctacgac actcgcaaag gcaattgaaa   11580
ggggttatga taaatttgtg gcgtacgcta tcaatatta aaaacaata catcaggtgt     11640
tgattgcatt gtccttacg attaatccta ctatgacacc agacattaca gaaccttctct   11700
acaagagttt agatctactt aagaatctag ttctgattcc tgcaccatta gggggcatga   11760
actatatgaa catgagcagg ttatttgtta ggaatatagg agatcccatt actgcttcat   11820
ttgctgatat aaagcgcatg attgaatgtg gttgttagg atgtagtatt ctgtcacaaa    11880
taatgtacca aaaatgtggt tcctccaaat acttagactg ggctagtgat ccttattcaa   11940
```

```
taaaccttcc ttatagccaa agtatgacca aggttttaaa aaatgtaacg gcaagatatg   12000
tacttatgca tagtcccaac cctatgctca aagatttgtt ccatgaaaag tctcaggaag   12060
aagatgaaat ccttgctgag tttctgttag accgacactt aataatccct agagcagcac   12120
acgagatttt atcaaattca gtaacaggtg ctagagaatc tatagcaggt atgcttgaca   12180
ctactaaggg tttaatccgt gctagtatgt caagaggtgg gttgacctca tcacttgttt   12240
taaaattatc aacatatgat taccaacagt ttagaacatg tcttgaatgg ctttatgctc   12300
ctactacggg aattgctgta agcgttgatt cttgctctgt attcttagct aagaccatcc   12360
ggaagagaat gtgggttcac ctaactaaag gaagggagtt ttatgggtta gaagtacctg   12420
acattttgga atgtatgcaa acaatatta ttgttgatca cgaagattgt tactcatgta   12480
ttcaaggatc aagatattat acatggtttt ttgtaccttc aaattgtcaa ctcgatcaaa   12540
taaataagtc aacaaattct ctccgagtac cttatgttgg atcaacaact gaagaaagga   12600
gtgatatgaa gttgtcatat gtgaggtcac ctagtcggcc acttaaagca gcagttcgaa   12660
ttgcagcagt atatacatgg gcttatggtg atgataattt gtcttggcat gaagcttggt   12720
atttagcaag gactagagca aatattactt ttgacgaact caaattaata cacctatag   12780 ctacatctac aaatttagca catagattga gagatagaag cactcaagtt aaatattcag   12840
gaacttcttt agtaagagtg gcacgctata aacaatatc taatgataat atgtcgttca   12900
ttattaataa caaaaagtc gatactaatt ttgtctacca gcaaggaatg ttattaggtt   12960
tgagtatatt agaatatata ttcagatact gtacaagtac tggacagtca aacactgtaa   13020
ttcacttaca tgcagatgtt aattgttgta tagtacagat gactgatcag ccttatacac   13080
caagcttaac aaaaaagcta cctgatatta ggcccattaa taataaactg atatatgatc   13140
cggctcctat aatcgatacc gatgcagcta ggctatattc ccaaaaatac ctgtcacatt   13200
taatagattt cccaagttgg tcaactactc agcttaacac agtgttggcg aaagtggtgg   13260
cggtatccat tgtagaatta attacaaaag ctagtaaaga ccatctcaat gagataatag   13320
cagttgttgg tgatgatgat atcaatagct ttattacaga atttctactt gttgatccac   13380
gtctgtttac actatattta ggccaataca catcattaca atgggcatat gaagtccatt   13440
atcatagacc agtgggtaaa taccagatgg ctgaagtgtt gcataatttg ctgtcaagag   13500
ctagtagagg tatattcagc atattgacca atgccttag ccaccccaga gtctacaaaa   13560
gattctggga gtgtggttta ttggagccta tttatgggcc ctatataga agtcaaaatc   13620 tacataatgc aatgattgat tatatctata atgcatacat tacttatttg gatgcttatt   13680
tatctgatca agtagatgat actgatatta aatatgtga acagaggag acatgtttgg   13740 cgaatcgaat tgacaattat caaagcagac acttagctgt gcttatagat ctgtattgtg   13800
attccactag atgtcccaat ataaaagggg cagatacaat tatgagaaac tcaattctta   13860
gatctttcat tgataatgag aggagaacaa atccactcgg tttgacatgg aaccttgacc   13920
cgttactcgt ggatcatttt agctgttcta ttacgtatct gaggagaggt attattaaac   13980
agatgaggtt aagatttgat ccaagtgtat cgttggaact atctaggatg attaagcctg   14040
atgcggttta tcaagcacct aaaattccgt cttcatgggc tcttatagat atcaaccctg   14100
aagtaaatga ccttaatgta atttttggag agctgaatag caaatggaaa gacattccta   14160
ttggacagat taggatacag aattatgaaa tacatgcata taggaggatc ggagttaatt   14220
caactgcatg ttataaagct ctagagctat tgtctgttct aaatcggttt atgtctaatc   14280
```

-continued

```
catcaggtgc attgttttta ggtgaaggag caggatcaat gctggtcaca taccgtgctt  14340
ttgtcccatt taagacaatt tattataata gtggtatttc agttcaaaat gttcagggcc  14400
agagagaatt gagtctatat ccatctgaag tggcactagt tgacaacaaa aatcgcttgg  14460
ctaatgaccc caatatcaaa gtcttgttca atggtaaacc agagtctacg tgggttggaa  14520
acatcgactg ttttgcttat attcttagcc acattgagac ctcaagcttg acattgatac  14580
atagtgatat tgagtccagc ttaagcaaga cgaagaataa aattcttgag gagctgtgcc  14640
acattctgtc aatggcactc attttgggga aaatcggatc tttattagtt gtcaagttat  14700
taccaagggt cggtgactat acgtattcat tttgcaggta tgcatcggaa ttctatcaac  14760
aaagcctcct tgttttacct aggtttagta acatgtcatc atctgaggtt tactatatag  14820
ggattcacct caatacaaat cgattgattg atcctgatag aatagtacaa tacatagtta  14880
gaaatttaca accaactcca gttacatttt tgtcctatat ttttgaaact aagtatagaa  14940
ataatatggt tacaaattat ggactgtgct tgtcagacgg acacaaaagt gattacctgt  15000
catcaattac aaaaatagag aacgttcttc tgtcatgtgg gttagaattg aatggaccta  15060
agattataca gcaattatca ggacatgact atgctaatgg ggagactagt ctagaatcaa  15120
gtataatgat attagttaga gaatatctta atgcaactat acaaggccgg gaaacattag  15180
gcttgttttc accttaccca gtcttacatg agagtcagtt aagagaaatt aataagtgta  15240
ttgcattgaa atatgttgta tatctactct tttattcaag ctctacatta tctagtaaac  15300
aaataatgag taatcttaga aagggaatat tgatgtatga tttgagagat gaatttttca  15360
tatcaagatt gtcagcaaat tacaagaaaa aggtgatgtc acaagaagtc aaaactacct  15420
ggatctttaa tcttgatact ccgacacgaa aagcattata taagttagta ggttattcat  15480
taataattaa tcatgtatga tgatagagta tgattatcca tctttaaaag agtaagataa  15540
tatcagatgt atgataacca attaagtatt acttttgaat tgaaaggttg ctcaattaca  15600
cgctttttta gtaatcgggt ttttattcca attagggcaa ttagaaaaaa cttcaacggt  15660
tagtcgagcc cgaattcatt ccatataagt tatatttata atcttggata agacttttgt  15720
ttagaattat aacagtaata ctaatttatg aatggaagac aattgatatc tagtgtgaat  15780
tttatgttta tgtgtcttaa accttatact cactataatt gttctttatt tgagaattta  15840
attataggtg tttatgtgtt atgtgatggg aaccatcagt gctgacatta ttaataacca  15900
taggtattgt atgggatagt gtttatttac taccaatgta caatctcata tgtcggaccc  15960
ctcaacctcc tccttatagt tgagttttct ggaaaaacac aaaagatgat cttgagtaat  16020
tgtacggacc tatagctttc tttgtctggt                                  16050
```

<210> SEQ ID NO 2
<211> LENGTH: 16050
<212> TYPE: DNA
<213> ORGANISM: Feline morbillivirus

<400> SEQUENCE: 2

```
accagacaaa gatgtctgtg acctattcta acgacaagat tattactaaa tatttaggaa     60
taacgattcc attagtgagg tgaggaggag gaatcaggta ttccacaatg tctagtctat    120
tgaggtcact tgctgcattt aagagacata gggagcaacc aacagcaccg tcaggttcag    180
gtggtacaat taaaggattg aaaaatacaa ttattgttcc ggttccaggg gatacagtaa    240
ttactacaag gtctaatttg ttatttagat tagtttatat aataggcaat ccggatacac    300
ctttaagcac ctcgacggga gcaataatat cattgttgac cctatttgtc gaatctccag    360
```

```
gtcaattaat tcaaagaatt gctgatgacc ctgatgcagt ttttaaattg gtagaggtca      420
ttcctgaagc tggtaatcct ggagaattaa cttttgcatc tcgagggatt aatttagaca      480
agcaagctca acaatacttt aaattggctg agaaaaatga tcaggggtat tatgttagct      540
taggatttga gaaccctcca aatgatgacg atataacatc tagtcctgag atattcaatt      600
atatcctggc atctgtactt gcacaagttt ggattcttct ggcaaaagct gtgactgctc      660
cagatacggc tgctgaagcc gaaaatcgta gatggattaa attaatgcaa caacgtaggg      720
tggatggtga actgagattg agcaaaggat ggctagattt agtgagaaac aagattgcgt      780
cagatattac aataaggcga ttcatggtag cattagttct tgacatcaaa cgttctcctg      840
ggacaagacc caggatagct gaaatgattt gtgatattga taattatatt gtagaagcag      900
ggcttgcaag tttcttatta accattaaat ttggcataga aacacgttat ccagcactgg      960
cactacatga gttttctgga gaactagcca ctattgaggg gcttatgaaa ttgtaccaat     1020
ctatggggga aatggcacca tacatggtaa ttctggaaaa ctcaatccaa accaggttta     1080
gtgcagggtc ttatcctctg ctatggagtt atgcaatggg tgtcggggtg gagcttgaaa     1140
gatcaatggg tggactcaat ttcactagaa gcttctttga cccgacatat ttcagacttg     1200
gtcaagagat ggtgaggaga tcttcaggga tggttaatag ttcatttgcg agagaacttg     1260
gcctatctga gcatgaaaca caactggtca gccagattgt caattcggga ggtgaatccg     1320
ggatacctaa atttgatgga ttcagagcaa atccaacaac ttttctagga accaaggata     1380
acatagatga tagaggtgaa gatcagtcaa attcgatatc agggttacct ggtccactat     1440
tacccagccg tgacctagat cttttccggtg attcatatgg aattaatagt ggtgtgaaaa     1500
atgtcagtga caaactgaat gaaggagtag gtccagacca tgatgtgtcc agttctgcca     1560
tggaagaatt gagaagattg gttgagtcta ccaacagaat tgacaccaaa cagccggaag     1620
cttcaggtgt caccaaccat tataatgata ctgaccttct aaaataatat gagcataccc     1680
taattgatta tgatacaact caaattaaga aaaacttagg acctcaaggt tcacaactgt     1740
tggcatatca ccaaaacaca gtcagctctt cacccacccc atgtcctctc accaaatcca     1800
acaagtcaaa catggcctcg aatctttaca agagatcaaa agcaaccctc cgccttccca     1860
agatgtcaat cttgccaggg agatttacga atccattaga caaacaggaa catcttcagt     1920
gcaaggagga gccattgcgg gaaataatat tacgtcaggg ggtaacaatg actcaatgta     1980
tagccaagga ccaagtcctc ctatttcaag tattaacaag aatatcgaag gacctactgg     2040
attcgatcat tcaggactat gggatccaga gggtaacctc tgcatgctat tcgaaagcga     2100
tgatgatgaa aaccattatt cagagattaa tggccggtct tccactatcg aaggactgga     2160
tgaacaggat aatgagaact caattattaa acaaccagga aatcagtgta ctgagggagt     2220
gtctaagact gattcatctc ctagttccca ggaaactaca ctatctgttg ggggatctga     2280
tatacctggg acaggaatat caacctgtgc ctctttggat ataactgtaa atgaactcga     2340
agatgcaact gtaagaaata gcaacaatat gaaagggaac tggccaattc ctaaattact     2400
agttaagccg ccacctaggg taaaatcaag tgttgatcac agtaatccat taaaaggggc     2460
cacagaaggg aaattagcct cacctgggat ggagactaca ttattcgaga agagtggtgc     2520
aaccccatct gtacacccat atactcaacc tgcaagcgac ttcaatgtag gtgcaagcag     2580
tgtccatcaa cctgccctaa atgtgaataa taattgcaat gacggtaggg taacagcgcc     2640
taactcacat aaagatatcg agggtaagtc tgaaatatct attcaagata tatataactt     2700
```

```
gattcttgga tttaaggatg attacaggaa attatcaaac aaattagata tggtattaga    2760
gatgaaacaa gacattgaca atcttaaaaa gaatagtgct aaagtgcaat tagctctatc    2820
aactattgag ggacatctat ccagtgttat gattgctatc cctggttcag gtattgattc    2880
cacaggggat gaggaaaagg accagataaa ttctgactta aaaccactgc taggaaggga    2940
tcattgtaga gcatttcgag aagttaccaa tcctctagat gagtcttcac tagccaattc    3000
tccaacaaaa catgttgcca aggtaaacaa gaactgcact cttcagaaga tcaacaagaa    3060
cgaaacatct gcaatcaaat ttgttcctag tgacagtcat gcaagcacat caaccatcag    3120
gtcaattatc aggtcatcta atctcgatca ggatttgaaa acaaaattgc tcacaatttt    3180
atcccagata agaggtgtag acaatattag agaattctat gaaaaggtta tgatattaat    3240
aaagaataag aattaaatat tacaaatcta catgccattat aggttgtaat tgtcttcaat    3300
aagatttggt cagtttcata tatatggtta ttgatttgtg ataattataa aaaacttagg    3360
agctaaagat tactcagtca tatacagcat gactgagata ttcaaccttg atgagagctc    3420
atggtcagtc aaagggacac tagatccgct aacacctgat acctatcctg atggtcgact    3480
agtgcctaaa gttcgagtta tcgatccggg tctaggagat cgcaagagtg gggggtatat    3540
gtatctactt cttcatggtg tcatagaaga tagtgagact ataattagtc cgaaaggaag    3600
agcatttggt gcattcccat taggagtggg tcaatcaact gaaaacccgg aagacttgtt    3660
taaggaaata ttaactctca acatcgtgac tcgtaggact gctggattta atgagaaatt    3720
ggtttattat aataccacac ctctacattt actgaccccc tggaagaaag tgttggcata    3780
tggaggcatt tttaatgcta atcaggtctg cagtgataca agttccatac caatagacat    3840
tccacaaaaa tttaggccag tatatttgac tgttacaaaa ttatctgatg atggctatta    3900
tcagatccca aagatgattc aagatttcaa atcgtcaaat tctgttgcat ttaacatcct    3960
tgtgcatctg tcaatgggca caaatttact tgaccaatcc aaggaccta gattaagaag    4020 tgctgcagaa actgtgatca catttatgat tcatattgga aactttaaac ggaagagtaa    4080
taagtcttac tcacctgaat attgcaagag gaaaataatg aggcttggtt taatattctc    4140
attaggtgca attggtggca caagcttgca tattagatgt acaggtaaga tgagcaaacg    4200
actacaggct tatttgggat tcaaaaggac tttatgttac cctttgatgt atgttaatga    4260
agggctgaac aagaccctgt ggagaaatga atgcagaata gagaaggttc aagcagtcct    4320
acagccatca gtcccgaatg agtttaagat atatgatgat gttattattg ataataccaa    4380
tggtctcttc aagattaaat agactataac aataataaac cgccaccaaa tggtaccatg    4440
tattcaagtg tacactgaca attgcgaata aaatatacca gattaacaac agtatagagt    4500
taagatctaa ttgatatgtg ggttggtact cgatcattta ttagctctac tgattatcta    4560
tatcctaaat caccaaatat aagagcatca acaggtaata agtttgggat tgctagatta    4620
atacttaatt ctcagaacta gaatacacag attgtcaaac ctataatctt gttagattca    4680
ttaaagttag attcttgtaa tgttgatcaa ttatcactcg agcaattata aaaaactaag    4740
gacctaatgt aataggagcc caaattccat ccagtgagct ttaaatcgcc atgcttaaac    4800
attaatttgt ccagggccta tctaactcag aacaaagatc acaactagag tctgaaggag    4860
tgggttaagt ctgaataatt attaagagtt gagatttaaa actgattcct tcttaaattt    4920
agaattttaa taatatatca tccattcaat atcatgaaca ggattaaggt tataataatt    4980
agttctttat tactatcaga tattcgatt gcacaaatag gttgggataa tttgacttcg    5040
attggagtta taagtactaa gcaatacgac tataaaataa ctactctgaa cactgaccag    5100
```

```
ttaatggtta taaagatggt tcctaatata tcatcaatca ttaattgcac taaactcgaa   5160
ttaacaaaat acagagagtt agtctcaggg atcattagac caataaatga gtcattagaa   5220
ttaatgaatt catacattaa catgagagca ggttcagaga gattcatagg ggctgtaata   5280
gctggtgtag ccttaggagt ggcaactgca gcacaaataa catcagggat tgccctacat   5340
aattcaatta tgaacaaaaa acagatacaa gaattgagga aggctcttag tactactaac   5400
aaagcaattg atgaaataag gattgcaggt gaaagaacat taatagcaat tcaaggtgta   5460
caggattata ttaataatat aattatccct atgcaggaca aactccaatg tgatatttta   5520
tcatcacaac tttctgttgc tttactcaga tattatacaa atatattaac agttttcggg   5580
ccaagtatac gggatcctat tactagtaca gtttcagtac aggcactcag tcaagcattc   5640
aatggtaatc ttcaggcatt gcttgatgga ttgggatata ctgggaaaga cttacgtgat   5700
cttctagaga gtaaatctat cactggccag ataattcatg cagatatgac tgatttgttc   5760
cttgttctga gaataaatta tccttctata actgagatgc agggagtaac aatatatggg   5820
ctcaattcaa ttacatatca tattgggcct gaagagtggt ataccattat gcctgatttt   5880
attgctgttc agggtttttt aatatctaat tttgatgaga gaaagtgttc aataactaaa   5940
tcaagtatat tgtgccaaca aaattcaatt tacccaatgt caacagagat gcaaagatgt   6000
attaagggcg aaataagatt ctgtccaaga tccaaggcaa ttgggacatt agtcaatcgg   6060
tttatattga ccaaaggtaa tttgatggct aattgtttag ggattatatg cagatgttat   6120
acttcaggcc aagttataac acaagaccct agtaaattga tcacgataat atcgcaagag   6180
gagtgcaagg aagttggtgt tgatggtatc cgtattatgg taggacctag aaaattacca   6240
gatattacct ttaacgctag gttggaaatt ggtgtaccga tatcattaag caaattagat   6300
gtcgggactg atttagcgat tgcttcagct aaacttaata attctaaggc attgttagag   6360
caatcagata agattttgga ttcaatgtct aaattggatt ctatgaactc aagaataata   6420
gggttaatct tagcaattat gataatcttt ataatcatta ttactattat ctggatcatg   6480
tataagaaat gtaagaataa agataataaa ttcagtactt caattgaacc gctctacata   6540
ccccttctt ataactcacc tcatagtgtg gttaaatcta tttgagtact gactatatga   6600
tccactgtaa taagtccaat gaaagtatca attaataata ttggtagtgc aataagtatt   6660
gattgtataa tatactcctt taaactagat agtgataaag ggttatagat gatttcagtc   6720
actttaatat aatcatatat tggttttatt atcttgcata actattatgt aattgaatta   6780
tgtatcatca attaatagct taataatatg ttttaatata cttatattga tagataaatg   6840
tgttatattg taatcaagga gttggtattt agaagaggaa agagttaaat ttgttgttaa   6900
ttagttattg tgtattcaat tagaaaaaac ttaggaatcc atgttaatag aaatttatta   6960
tcatggagtc caacaatatt aagtactaca aagattctag ccggtacttt ggtaaaatat   7020
tagatgaaca caaacaatt aatagtcaat tatacagttt gagtatcaag gtaattacca   7080
ttattgctat tattgtaagc ctgattgcaa caataataac tattatcaat gccactagtg   7140
ggagaactac cctaaatagt aatacagaca tactactcag ccaacgagat gagattcata   7200
acatccaaga aatgatattt gatcgtattt atcctttgat aaatgctatg agtacagagc   7260
taggacttca tattcctacc ttattggatg aacttactaa agcgattgac cagaaaatta   7320
aaataatgca tcctcctgtg gacactgtga cttctgacct taattggtgc atcaaaccccc  7380
ctaatggaat tatcatagac ccaaaaagtt attgtgagag tatggaattg tctaaaactt   7440
```

```
atgaattgtt acttgaccag ttagatgtct caagaaagaa atcacttatt ataaatagaa    7500
agaatattaa ccaatgccaa ttagttgata attcaaagat cattttttgcc actgtcaaca    7560 tacaatctac accgaggttt taaactttg gtcacacggt cagcaatcaa cgtataacat    7620
ttggtcaagg aacatatagt agtacttatg ttataactat ccaagaagat ggagtaactg    7680
atgttcaata tcgagtgttt gagatcggat atatttgtga tcagtttggt gtattcccct    7740
ccttaatagt atcgagagtg ttgccgatac gcatgctatt agaaatggaa tcctgtacct    7800
tgacaagtga tagactaggc gggtattttt tatgtatgaa tacactgaca cgatctatat    7860
acgattatgt tagcataagg gatttgaaat cactttatat aacaatccct cattatggta    7920
aagttaatta tacttacttt aattttggta agatcaggag cccacatgag attgataaaa    7980
tttggttaac atctgataga ggccaaatta tctctggtta ttttgcagca tttgttacca    8040
ttacaattcg gaactataat aattatccct acaaatgctt aataaccca tgttttgaca    8100 actctgagaa ttactgtaga ggatggtata aaaacataac aggaactgat gatgttccga    8160
tattagcata cttattggtt gaaatgtatg atgaagaggg acctttaatt acacttgtgg    8220
caataccacc ttacaattat acagctccat ctcataattc tctttactat gatgacaaag    8280
ttaataaatt aataatgact acatctcaca taggttatat tcaaatcaat gaggtgcatg    8340
aggtaattgt tggcgataat ttgaaggcta tcctcttaaa cagattatct gatgaacatc    8400
ctaacctgac tgcctgtaga ctcaatcagg gtattaagga gcaatacaag tctgacggaa    8460
caataatttc aaattctgta cttattgata tacaagaacg aatgtacatt acagttaaag    8520
ctattccacc agcaggtaac tataacttta cagttgagtt gcattctaga tcaaacacat    8580
cttatgtatc gttgccaaga cagtttaatg ctaagtatga caaattacat cttgagtgct    8640
ttagctggga caaatcctgg tggtgtgctc tgatacctca gttttcatta agttggaatg    8700
aatcccttcc tgttgatact gccattttca atttaataag ctgtcaatga acacatcaat    8760
ctatagttga tagttgtcaa aacattagcc aatttgggtt aaagaaatag gaaaatgaaa    8820
ttatcaatat ctaattagat gtatgttcaa gctaaattac aaaaaactta ggagtcagag    8880
atttcgttgc aatggagcag tcagactacc aagatattct atacccggaa gtacatctta    8940
acagtcctat agtaatttcc aaattagtag gtattttaga atatgcccaa attggtcata    9000
atcaacaatt atcagaccgt acaattatca agaatattca atttagatta aggaacggat    9060
ttaatagttc aagggtacag gtactatcaa ctatgggtga aattatcaac aaaattagaa    9120
ataaatatcc taattattta cacataccctt accctgaatg caaccaaaaa ctatttcgaa    9180
tagtagatcc agaactaaca tcaaaattag aatctcttct aaacaaaggt gacacactgt    9240
atctcaagat tcgatcagat atcataaagt gttttgatag attgaaaatg aaaatgaaca    9300 taagaatga tcttctcaat gacaatagtc aattgattct agatcttcct ttaattatca    9360
aaggatctca gtggttcttc cctttttat tttggttttc tatcaaaact gaaactagaa    9420
gctgtattcg ccaaaatcaa aagactcgtg ttagatcaca atatcggcct cacttatcag    9480
agactaagag aattacattg gttgttacat ctgatctgat tacaatattt gatcatatta    9540
ataaatgtat attttatttg acttttgaga tgctgttaat gtattgcgat gtgatagaag    9600
gtcggttaat gactgaaaca gctatgagct tggactgtcg gtttaccaat ctattgccaa    9660
gagtgcaata tatgtgggat ttactagatg gaatgtttga agtttaggc aatcaattat    9720 attcagttat tgcattatta gagcctcttt ctcttgctta tttgcaattg atagatgcag    9780
atccacagat tcggggaaca ttcctgcatc actgcttttc cgagttagaa gaaattatat    9840
```

```
ttgacaaaac cccttttgat cctttcgtat atgaaaattt aattaatgga cttgattaca    9900
tttatttgac agatgatatt catctaactg cagaagtttt ttctttttt agaagttttg     9960
gtcatccttt tttagaagca caaaatgctg ccaataatgt aaggaagtat atgaataaac   10020
ctaaggtaat ctcatatcag actttaatgc aaggacatgc gatttttgc ggtattataa   10080
taaatggatt tagagatcgc cacggggaa catggcctcc tgtagagtta ccaaatcatg    10140
catctgctgt aattagaaat gcccagttat ctggagaagg gttaacatct gaacaatgtg   10200
ctcaacactg gagatccttc tgtggattta gatttaaatg ttttatgcca ttgagtctag   10260
acagtgacct tacaatgtac cttagagaca aggcgttatc acctgtcaga atgagtggg    10320
attcagttta tgctaaggag tatttaagat ataatccagg attacccaca agttccagaa   10380
gattggtaaa tgtattctta gaagatgata agtttgatcc atatgaaatg atcatgtacg   10440
tgataaatgg tgattactta agagacaaag agtttaacct ttcatacagc cttaaagaga   10500
aagaaattaa agaggtaggt cgattgttcg ctaaaatgac ctataaaatg agggcttgtc   10560
aagtaatagc tgaaaacctg attgccaatg gagtagggaa gttttcaaa gataatggaa    10620
tggcaaaaga tgaacataaa ttaactaaaa cgttacacaa attagccatt tcaggtgtac   10680
ctaaagataa ttctcaactt tatttagatg aatgttggga gcaagtaatt cgacaatgtt   10740
caagtagtac acagataagg gaacaggcta tgaattcaca atcaaatagg gaaattgaat   10800
caaagtcttc tagggcacgt cttaataata gagatatctt aaagggcaag agagattcga   10860
acaaacaaat aaagtatcct tcaaacaccg agtattatga gactatcagt agtttcataa   10920
ctactgacct taaaaagtat tgtcttaact ggcgatatga atcaagtagt gtatttgcag   10980
agagacttaa tgagatttat ggactgcctg gattttcca gtggcttcac aagattttgg    11040
agaaatctgt tctatacgtt agtgatccat atagtccacc tgactttgat caacatatcg   11100
atatagaatc agtcccaaac gaccatatct ttatcaagta cccgatgggg ggaatagagg    11160
ggttctgtca aaaattatgg accattagta caattccgtt cctatatta gcagcttttg    11220
atacagggt tagaatctca tcattagttc aaggcgataa ccaggcaatt gcagtgacca   11280
aaagagttcc gtcatcttgg agttattcaa agaaaaagga agaatcaact aaaataacaa   11340
cacagtattt tcttaattta agacaacgct tacacgacat aggtcatgaa ttgaaagcaa   11400
atgagactat tatatcctct catttctttg tttactctaa aggtatttat tatgatgaa    11460
tacttctctc ccaggcactt aaaagtattg caagatgtgt cttctggtct gaaacgattg   11520
ttgatgagac taggtcagct tgcagtaaca tatctacgac actcgcaaag gcaattgaaa   11580
ggggttatga taaatttgtg gcgtacgcta tcaatattta taaaacaata catcaggtgt   11640
tgattgcatt gtccttacg attaatccta ctatgacacc agacatcaca gaaccttct    11700
acaagagttt agatctactt aagaatctag tcctgattcc tgcaccatta ggggcatga    11760
actatatgaa catgagcagg ttatttgtta ggaatatagg agatcccatt actgcttcat   11820
ttgctgatat aaagcgcatg attgaatgtg ggttgttagg atgtagtatt ctgtcacaaa   11880
taatgtacca aaaatgtggt tcctctaaat acttagactg ggctagtgat ccttattcaa   11940
taaaccttcc ttatagccaa agtatgacca aggttttaaa aaatgtaacg gcaagatatg   12000
tacttatgca tagtcccaac cctatgctca aagatttgtt ccatgaaaag tctcaggaag   12060
aagatgaaat ccttgctgag tttctgttag accgacactt aataatccct agagcagcac   12120
acgaaatttt atcaaattca gtaacaggtg ctagagaatc tatagcaggt atgcttgaca   12180
```

```
ctactaaggg tttaatccgt gctagtatgt caagaggtgg gttgacctca tcacttgttt    12240
taaaattatc aacatatgat taccaacagt ttagaacatg tcttgaatgg ctttatgctc    12300
ctactacggg aattgctgta agcgttgatt cttgctctgt attcttagct aagaccatcc    12360
ggaagagaat gtgggttcac ctaactaaag gaagggagat ttatgggtta gaagtacctg    12420
acattttgga atgtatgcaa aacaatatta ttgttgatca cgaagattgt tactcatgta    12480
ttcaaggatc aagatattat acatggtttt ttgtaccttc aaattgtcaa ctcgatcaaa    12540
taaataagtc aacaaattct ctccgagtac cttatgttgg atcaacaact gaagaaagga    12600
gtgatatgaa gttgtcatat gtaaggtcac ctagtcggcc acttaaagca gcagttagga    12660
ttgcagcagt atatacatgg gcttatggtg atgataattt gtcttggcat gaagcttggt    12720
atttagcaag gactagagca aatattactt ttgacgaact caaattaata acacctatag    12780
ctacatctac aaacttagca catagattga gggatagaag cactcaagtt aaatattcag    12840
gaacttcttt agtaagagtg gcacgctata caacaatatc taatgataat atgtcgttca    12900
ttattaataa caagaaagtc gatactaatt ttgtctacca gcaaggaatg ttattaggtt    12960
tgagtatatt ggaatacata ttcagatact gtacaagtac tggacagtca aacactgtaa    13020
ttcacttaca tgcagatgtt aattgttgta tagtacagat gactgatcag ccttatacac    13080
caagtttaac aaaaaagcta cctgatatta agcccattaa taataaactg atatatgatc    13140
cggctcctat aatcgatact gatgcagcta ggctatattc ccaaaagtac ctgtcacatt    13200
taatagattt cccaagttgg tcaactactc agcttaacac agtattggcg aaagtagtgg    13260
cggtatctat tgtggaatta attacaaaag cgagtaaaga ccatctcaat gagataatag    13320
cagttgttgg tgatgatgat atcaatagct ttattacaga atttctactt gttgatccac    13380
gtctgtttac actatattta ggccaataca catcattaca atgggcatat gaagtccatt    13440
atcatagacc agtgggtaaa taccagatgg ctgaagtgtt gcataatttg ctgtcaagag    13500
ctagtagagg tatattcagt atattgacca atgcctttag ccaccccaga gtctacaaaa    13560
gattctggga gtgtggttta ttggagccta tttatgggcc ctatataggaa agtcaaaatc    13620 tacataatgc aatgattgat tatatctata atgcatacat tacttatttg gatgcttatt    13680
tatctgatca agtagatgat actgatatta aatatgtga aacagaggag acatgtttgg    13740
cgaatcgaat tgacaattat caaagcagac acttagctgt gcttatagat ctgtattgtg    13800
attccactag atgtcccaat ataaaagggg cagatacaat tatgagaaat tcaattctta    13860 gatcttcat tgataatgag aggagaacaa atccacttgg tttgacatgg aaccttgacc    13920
cgttacttgt ggatcacttt agctgttcta ttacgtatct gaggagaggt attattaaac    13980
agatgaggtt aagatttgat ccaagtgtat cgctggaact atctaggatg attaaacctg    14040
atgcggttta tcaagcacct aaaattccgt cttcatgggc tcttatagat atcaaccctg    14100
aagtaaatga ccttaatgta atttttggag agctgaatag caagtggaaa gatatcccta    14160
ttggacagat tagaatacag aattatgaaa tacatgcata taggaggatt ggagttaatt    14220
caactgcctg ttataaagct ctagagctat tatctgttct aaatcggttt atgcctaatc    14280
catcaggtgc attgttttta ggtgaaggag caggatcaat gctggtcaca taccgtgctt    14340
ttgtcccatt taagacaatt tattacaata gtggtatttc agttcaaaat gttcagggcc    14400
agagagaatt gagtctatat ccatctgaag tggcactagt tgacaacaaa aatcgcttgg    14460
ctaatgaccc taatatcaaa gtcttgttca atggtaagcc agagtctacg tgggttggaa    14520
acatcgactg ttttgcttat attcttagcc acattgagac ctcaagcttg acattgatac    14580
```

```
atagtgatat tgagtccagc ttaagcaaga cgaagaataa aattcttgag gagctgtgcc  14640
acattctgtc aatggcactc attttgggga aaatcggatc tttattagtt gttaagttat  14700
taccaagggt cggtgactat acgtattcat tttgcaggta tgcatcggaa ttctatcaac  14760
aaagcctcct tgttttacct aggtttagta acatgtcatc atctgaggtt tactatatag  14820
gaattcacct caatacaaat cgattgattg atcctgatag aatagtacaa tacataatta  14880
gaaatttaca accaactcca gttacatttt tgtcctatat ttttgaaact aagtatagga  14940
ataatatggt tacaaattat ggactgtgct tgtcagacgg acacaaaagt gattacctgt  15000
catcaattac aaaaatagag aatgttctcc tgtcatgtgg gttagaattg aatggaccta  15060
agattataca gcaattatca ggacatgact atgctaatgg ggagactagt ctagaatcaa  15120
gtataatgat attagttagg gaatatctta atgcaactat acagggccgg gaaacattag  15180
gcttgttttc accttaccca gtcttacatg agagtcagtt aagagagatt aataagtgta  15240
ttgcattgaa atatgttgta tatctactct tttattcaaa ctctacatta tctagtaaac  15300
aaataatgag taatctcaga aagggaatat tgatgtatga tttgagagat gaatttttca  15360
tatcaagatt gtcagcaaat tacaagaaaa aggtgatgtc acaggaagtc aagactacct  15420
ggatctttaa tattgatact ccgacacgaa aagcattata taagttagta ggttattcat  15480
taataattaa tcatgtatga tgatagagtg tgattatcca tcttttagag agtaagataa  15540
tatcagatgt atgataacca attaagtatt gcttttgaat tgaaaggttg ctcaattaca  15600
cgcttcttta gtaatcgggt tttattccca attaaggcaa ttagaaaaaa cttcaacagt  15660
tagtcgagcc cgaattcatt tcatataagt tatatttata atcttggata agacttttgt  15720
ttagaattat aacagtaata ctaatttatg aatggaagac aattgatatc tagtgtgaat  15780
ttcatgctta tgtgtcctta accttatact cacgatcatt attctttatt tgagaattta  15840
attataggtg tttatgtgtt atgtgatggg aaccatcaat gctgacatta ttaataacca  15900
taggtattgt atgagataat gtttatttac taccaatgta caatctcata tgtcggaccc  15960
cttaacctcc tccttatagt tgagttttct ggaaaaacac aaaagatgat cttgagtaat  16020
tgtacggacc tatagctttc tttgtctggt                                  16050
```

<210> SEQ ID NO 3
<211> LENGTH: 16050
<212> TYPE: DNA
<213> ORGANISM: Feline morbillivirus

<400> SEQUENCE: 3

```
accagacaaa gatgtctgtg acctattcta acgacaagac tattattaaa tatttaggaa     60
taacgattcc attagtgggg tgaggggaag gaatcaggta ttccagaatg tcgagtctac    120
tgaagtcact tgccgcattt aaaagacata gagagcaacc aactacaccg tcaggttcag    180
gtggtacaat taaaggattg aaaaacacaa ttattgttcc agtaccaggg gatacagtaa    240
ttaccacgag gtctaatttg ttatttagat tagtttatat aataggcaat ccagatacgc    300
ctctaagcac ctcgacggga gcaataatat cattattgac cctattcgtc gaatccccag    360
gtcaattaat tcaaagaatt gccgatgacc ctgatgcagt ttttaaatta gtagaggtca    420
ttcctgaagc tggtaatcct ggagaattga cttttgcatc tcgagggatt aatttagata    480
agcaagccca acaatacttt aaactggctg agagaaatga tcaggggtat tatgttagct    540
taggatttga gaacccacca aacgatgatg atataacatc tagtcctgag atatttaatt    600
```

```
atattttggc atctgtactt gcgcaagttt ggattcttct ggcaaaagct gtgactgctc    660
cggatacagc tgctgaagct gaaaaccgta gatggattaa attgatgcaa caacgtcggg    720
tggatggtga attaagattg agtaaaggat ggctagattt ggtgagaaat aaaattgcgt    780
cagatattac aataagacga tttatggtgg cattagtcct tgacatcaaa cgttctcctg    840
ggacaagacc cagaatagct gaaatgattt gtgatattga taattatatt gtagaggcag    900
ggcttgcaag tttcttgtta actattaaat ttggcataga gacacgttat ccagcattgg    960
cattgcatga gttctctgga gaattagcta ctattgaggg acttatgaaa ttgtaccaat   1020
ctatgggaga aatggcacca tatatggtaa ttctggaaaa ttcaattcaa accaggttta   1080
gtgccgggtc ttatcctttg ctatggagtt atgccatggg cgttggtgtg gagcttgaaa   1140
gatcgatggg tggacttaat tttactagga gcttctttga ccctacgtac ttcagacttg   1200
gtcaagagat ggtgagaaga tcttcaggga tggttaatag ttcatttgcg cgagaacttg   1260
ggctatctga acatgagaca caacttgtca gccaaattgt taattcggga ggtgaatctg   1320
ggatacctaa atttgatgga ttcagagcaa atccaacaac ctttctagga accaaagata   1380
atattaatga taaaggtgag gatcagtcaa gttcagtatc agggttacct ggtccattat   1440
tacccagtcg tgacctaact catccaggtg attcatatgg agcagatgat ggtgtgaaaa   1500
atgtcagtaa taaattgagt gaaggaataa gtccagatca tgatgtgtct agctctgcca   1560
tggaagaatt gaggaggtta gttgagtcta ccaacagaat tgacaccaaa aagccggaag   1620
ctccaggtgt caccaaccat tataatgaca ccgacctttt aagataatat gagtatatct   1680
tatttgatca tcatacaatt caaattaaga aaaacttagg acctcaaggt tcacaactgt   1740
tggcacatca ctgagatata gtcaattctt tacccaccac atgtcctctc accagattca   1800
acaagtcaaa catggcctcg aatctttaca agagatcaaa acaaccctc cgtcttccaa    1860 agatgtcgat cttgccaggg agatttacga atccattaga caaacaggaa catcttcagt   1920
gcaaggagga gccattgcgg gagataatat tacgtcaggg ggtaacaatc actcaatgca   1980
tagccaagga ccaagttctc ctatttcaag tgttaacaag aatatcgaag gatctactgg   2040
attcgatcat tcaggactat gggattcaga gggtaacctc tgcatgttat tcgaaagcga   2100
tgatgatgaa aaccattatt cagagattaa tggccggtct cccgctatcg aaggattgga   2160
tgaacaggat actgagaact caattattaa acaaccagga aatcagtgta ctgagggagt   2220
gtctaagact aattcacctt ctagtcccca ggaaactaca ctatctgttg ggggatctaa   2280
tatacctggg acaggaatat caacctgtgc ctctttggat ataactgtaa atgaacttga   2340
ggatgcaact ataagaaaca gcgacaatat gaagggaaac tggccaattc cgaaattact   2400
tgttaagccg ccacctaggg caagatcaag cattgatcat agcaatccat aaaagggggc   2460
cacaggaggg aaattagtct cacctgggat ggagactaca ttattcgaga agagtggtgc   2520
aaccctatct gtacacccat ctactcaacc tgcaagcgac ttcaatgtaa atgtaagcaa   2580
tgtccatcaa cctgccccaa gtgtgaataa tgattacaga gacagtgagg taacagtgct   2640
taacttacat aaagatattg aggataagtc tgaaatatct atacaggata tatataactt   2700
gattcttgga tttaaggatg attataggaa attattaaac aaattagata tggtattaga   2760
gatgaaacaa gacattgaca atctaaaaaa gagtagtgct aaggtacaat ggcattgtc    2820 aactattgaa ggcatctat ctagtgttat gattgccatc cctggttcag gtattgattc    2880 cactgggaa gagaaaaagg atcagatgaa ttctgactta aaaccattat tagggaggga   2940
tcattgtaga gcatttcgag aagttactaa tcctctagat gagtcgttac tggccaattc   3000
```

```
tccaacaaaa catgttgcca aaatagacaa gaattgcact cttcagaaaa tcaacaagaa    3060
tgaaacatct gcaatcaagt ttgttcccaa tgatagtcat gcaagcacat cgaccatcaa    3120
atcaattatc aggtcatcta atctcgatca ggatttgaag acaaaattgc tcacaattct    3180
atcccaaatt agagggacag agaatgttaa agaattttat gagaaggtca tgatattgat    3240
aaagaataag aactaaatat caccaatcta catgcactat gagttgtaat tgtcttcagt    3300
agaatttagt tgatttaata catactgttg ttgatttgta ataattataa aaacttagg     3360 agctaaaggc tactcagtca tatacaacat gactgagata ttcactcttg atgagagctc    3420
atggtcaatc aaaggaacac ttgatccgct aacacctgat atctatcctg atgggagact    3480
cgtgcccaaa gttcgggtta tcgatccggg cctaggagat cgcaagagtg ggggatatat    3540
gtatctactt ctccatggtg tcatagaaga cagcgagaac atgattagtc aaaggggag     3600 agcatttggg gcattcccat taggagtggg tcaatcaact gaaaacccag aagatttgtt    3660
taaggaaata ttaactctca atatcgtgac tcgtagaact gctggattta atgagaagtt    3720
agtttattat aataccacac ctatacattt actgaccccc tggaaaaagg tgttggcata    3780
tggaagcatc tttaatgcta atcaggtctg cagtgataca agctctatac aatagatat    3840 tccacaaaag tttagacctg tatatttgac tgttacaaaa ttatctgatg atggctatta    3900
tcagatacca aagatgattc aagatttcaa atcgtcaaat tctgttgcat tcaacatcct    3960
tgtgcatcta tcaatgggta caaatttact tgaccaatcc aaagactctc gattaagaaa    4020
tgctggggaa actgtgatta catttatgat tcatattggg aacttcaaac ggaagagtaa    4080
taaatcttat tcagcggaat actgcaagag gaaaataatg aggcttggtt tgatattctc    4140
attaggtgca attggtggca caagcttaca tattagatgc acaggtaaga tgagcaaacg    4200
actacaggcc tacttaggat tcaaaaggac tttatgttac cctctgatgt atgtaaatga    4260
agggctaaat aaaacactgt ggagaaatga atgtagaata gagaaggttc aagcagtctt    4320
acagccatct gttccaaatg aatttaaggt atatgatgat gtcattattg acaataccaa    4380
tggtctcttc aagattaaat aggttataac cgtaacaaac agctaataaa tggtattatg    4440
tatttaagtg tacactgata attgtgaata aaatacattg ggttaataac ggtatagagt    4500
taaaatctaa ttgatatgtg ggttaatgct taaacactta ttagctctat tgattatcta    4560
tatcttgagt tatctaatat cagagtatca acatgtaatc agtttaaact tgttggatta    4620
acgttcaatt attataacca gaatacacaa attgttaaac ttataattct gttagattca    4680
ttcaagttga acttatgtag ggttaaccaa ttatcattcg agcaattata aaaaactaag    4740
gatctaatgt agtaggaacc taaactccat ccagtgagct caaaatcacc acactcaaat    4800
atcaatttgt ctagggcctg tctaactcaa aacaaagctc ataaccagga tccagacgag    4860
tgggttaaat ctgaataact attaggaatt gagattttaa attgattctc tcttaactct    4920
aaagttttag taatatagca tcaattcagc accatgaaca gaattaaagt tataataatt    4980
agttctttgt tattatcaga tattacgatt gcacaaatag gctgggataa tttaacttcg    5040
attggggtta taagtactaa gcagtacaac tataaaataa ctactctaaa tactaatcag    5100
ttgatggtta taaagatggt tcccaatata tcgtcaatca ttaattgcac taaacttgaa    5160
ttgataaaat atagagagtt agtctcaggg atcattagac caataaatga gtcattagaa    5220
ttaatgaact catacattaa tatgagagta ggttcagaga gatttatagg ggctgtaata    5280
gctggagtag cattaggagt ggcaactgca gcacaaataa catcagggat tgccctacat    5340
```

```
aattcaatta tgaacaaaaa acagatacaa gagttgagga aggctcttag tactaccaac    5400
aaagcaattg atgaaataag gattgcaggt gaacgaacat taatggcagt acaaggtgta    5460
caggattata tcaataatat aattgtccct atgcaggaca aactccaatg tgatatttta    5520
tcatcacagc tttctgttgc attactcaga tattatacaa atatattaac agtctttgga    5580
ccaagtatac gagatcctat cactagcacg atttcggtac aagcacttag tcaagcattc    5640
aatggtaatc ttcaggcact acttgacgga ctaggatata ctgggagaga cttacatgac    5700
cttctagaga gtaaatctat cactggtcag ataattcatg cagatatgac tgatttgttc    5760
cttgttctga gaattaatta cccttccata actgagatgc agggagtaac aatatatgaa    5820
ctgaattcaa ttacatatca tattgggcct gaagagtggt atactattat gcctgatttt    5880
atagctgttc agggtttttt aatatctaat tttgatgaaa gaaagtgttc ataactaaa     5940 tcgagtgtaa tatgccaaca aaattcaatt tacccgatgt cagcagagat gcaaagatgt    6000
attaagggcg aaataagatt ctgtccaaga tctaaggcaa ttgggacgtt agttaatcgg    6060
ttcatattga ccaaaggtaa tttaatggct aattgtctgg gaattatatg cagatgttat    6120
acctcaggcc aagttataac acaggacccc agtaagttaa ttacaataat atcacaagag    6180
gagtgcaaag aagtcggtgt tgatggtatc cgtattatgg taggacctag aaaattacca    6240
gatattacct ttaatgctag gttagaaatt ggtgtaccga tatcattaag caaattagat    6300
gtcggaaatg atttagcaat tgcttcagct aagcttaata attccaaagc attgttagag    6360
caatcagata agattctggg ttctatgtct aagttggatt ctattaattc aagaattata    6420
ggattaatct tagcaatcat gataatcttt ataattattg ttaccattat ctggatcata    6480
tataaaaatt gtagaaataa agatactaaa ttcagtactt caattgaacc gctctacata    6540
cccccttctt ataactcacc tcatagtgtg gtcaagtcta tttgagtact gaccatatga    6600
tttactgtaa taagtccagt ggaagtatca attgacaata ctggtagtat aatgaatatt    6660
gaatatataa tatactctct taaattggat agtgataaag agttatagat gattgcaatc    6720 atttaatat aattatatat tgatttgatt acctggtata attcttatgc aattgaatta     6780
tgtgtcatca attaatagct taatagcact gttttataca cttatgttga tagatagatg    6840
tgttatattg taatcaagga tttagtatct agaagaggaa agagttcaat tggttgttaa    6900
ttggttattg tgtattcaat tagaaaaaac ttaggaatcc atgttaataa aaactcatta    6960
tcatggagtc caataatgtt aaatattaca aggattctaa ccgatacttt ggtaaaatat    7020
tagatgaaca caaacaatt aatagtcaat tgtacagctt aagtattaaa gtaattacca     7080
ttattgccat aattgtaagc ctaattgcaa caataatgac tattattaat gccacaagtg    7140
ggaggactgc cctaaacagt aatacagaca tactgcttag ccaaagagat gagattcata    7200
atatccaaga aatgatattt gatcgtattt atcctttgat aaatgctatg agtacagagt    7260
taggacttca tattcctacc ttattggatg aacttactaa agcgattgac caaaagatta    7320
aaataatgaa tcccctatt gacactgtga cgtctgatct taattggtgc atcaaacccc     7380
ctaacggaat tattatagac ccgaagggtt attgtgagag tatggaattg tccaaaactt    7440
ataaattact acttgaccaa ttagatgtct taagaaagaa atcactcatt ataaatagaa    7500
agaatattaa ccagtgtcaa ttagttgatg attcaaagat catttttgct actgtcaaca    7560
tacaatctac accgaggttt ttgaattttg gtcacacagt cagcaatcaa cgtataacat    7620
ttggtcaagg aacatatagt agtacttatg ttataactat ccaagaagat gggataactg    7680
atgttcaata tcgagttttt gaaatcgggt atatctctga tcagtttggt gttttcccct    7740
```

```
ccttaatagt atccagagtg ttgcctatac gcatgctatt aggaatggaa tcctgtacct   7800
tgacaagtga cagactaggt gggtatttct tgtgtatgaa tacactgaca cgatctatat   7860
atgattatgt tagcataagg gatttgaaat cattatatat aacactccct cattatggta   7920
aggttaatta tacttacttt gattttggta agatcagaag cccacatgaa atagataaaa   7980
tttggttaac atctgagagg ggccaaatta tttctggtta ttttgcagca tttgttacca   8040
ttacaattcg gaattataat aattatccct acaaatgttt aaataatcca tgctttgaca   8100
actctgagaa ttactgtaga gggtggtata aaaacataac aggtactgac gatgttccga   8160
tattagcata cctattagtt gaaatgtatg atgaagaagg acctttaatt acacttgtag   8220
caatcccgcc ttacaattat acagctccat ctcataattc tctttactat gatgataaaa   8280
tcaataaatt gataatgact acatctcaca taggtcatat tcaagttaat gaggtgcatg   8340
aggtgattgt tggcgataat ttaaaggcta tcctcctaaa cagattatct gatgaacatc   8400
ctaatcttac tgcctgtaga ctcaatcagg gcattaagga gcagtacagg tctgacggaa   8460
caataatttc aaattctgca cttattgata tacaagaacg gatgtatatt acaattaaag   8520
ctgttccacc agtgggtaac tataaacttta cagttgaatt gcattctaga tcaaacacat   8580
cttatctatt gttaccaaaa cagtttaatg ctaaatacga caaattacat cttgagtgct   8640
ttagctggga caaatcttgg tggtgcgcct tgatacctca gttttcatta agttggaatg   8700
aatcccttc tgttgatact gctatttta atttaataag ttgtaaatga atatgtcaac   8760
tgatagttga tagttgtcaa aacatcagct aattgagatt aaagaaataa aaaaatgaaa   8820
ttatcaagat ttgactagat gtatactcaa gctaaattac aaaaaactta ggagtcagag   8880
acttcgttgc aatggagcag tcagactacc aagatattct atatcctgag gtacatctta   8940
acagtcctat agtaatctct aaattagtag gtattttaga atatgcccga attgctcaca   9000
atcaacaact atcagaccat acaattatca agaatattca atttagatta agaaatggct   9060
ttaatagtcc aaggatacag acactatcaa ctatgggtga atcatcaac aaaattaaaa   9120
gcaaacaccc caattatttta cacataccctt accccgaatg taaccaaaag ctatttcgaa   9180
tagtagatcc agaactgaca tcaaaattgg aatctcttct gaacaaaggt gatacactgt   9240
atctcaaaat tcggtcagat atcataaaat gctttgatag attgaaaatg aagatgaaca   9300
taaggaatga tcttcttaat gacaaatagtc aattaattct ggatcttcct ttaattctca   9360
aaggatctca gtggttcttc ccgtttttat tttggttttc gattaaaact gagactagaa   9420
gctgtatccg acaaaatcaa aaagctcgtg ttagatcaca atatcggcct cacttatcag   9480
agactaagag aattacattg gttgttacat ctgatctaat tacgatattt gatcatatta   9540
ataaatgtat attttatctg acttttgaga tgttgttaat gtattgcgat gtggtagaag   9600
gtagattaat gactgaaaca gctatgagct tggattgtcg atttatcaat ctattgccaa   9660
gagtgcaata tatgtgggat ttgctagatg gaatgtttga agtttaggt aatcaattat   9720
attcagttat tgcattgtta gagcctcttt ctcttgctta tttgcaatta atagatgcag   9780
atccacagat tcggggaaca ttcttgcatc actgttttc agagttagaa gaaattatat   9840
ttgacaagtc tccttttgat ccttttgtgt atgaaaattt aattaatgga ctagattata   9900
tttatttgac agatgatatt catctaactg cagaagtttt ttcttttttt aggagctttg   9960
gtcatccttt tttagaagca caaaatgctg ctaataatgt gaggaagtat atgaataagc  10020
ctaaagtgat ctcataccag actctaatgc aaggacatgc gattttctgt ggtattataa  10080
```

```
taaatggatt tagagatcgc catgggggaa catggcctcc tgtagagtta ccaaatcatg   10140
catctgctgt aattagaaat gcccagctat ctggagaagg gttaacatct gaacaatgtg   10200
ctcaacactg gagatccttt tgtggattta aatttaaatg ttttatgcca ctgagtctag   10260
atagtgacct tacaatgtac cttcgggaca aggcgttgtc acctgtcaaa agtgagtggg   10320
attctgttta tgcgaaagag tatttaagat acaatccagg attacctaca agctctagaa   10380
gactagtgaa tgtattctta gaagatgata agtttgatcc atatgaaatg atcatgtacg   10440
tgataaatgg tgattactta agagacaaag agtttaatct ttcatacagt cttaaagaga   10500
aagagatcaa agaggtaggt cgattgttcg ccaaaatgac ttataaaatg agggcttgcc   10560
aagtaatagc tgaaaacctg attgccaatg gagtagggaa gttcttcaaa gataatggaa   10620
tggcaaaaga tgaacataaa ctaactaaaa cgttacacaa attagccatt tcaggtgtac   10680
ctaaagataa ttctcaactt tatttagatg aatgctggga gcaagtagtt cgacaatgct   10740
caagtagtac acagatagga gaacagacta tgaattcaca atcgaagagg gcaattgaat   10800
caaagtcttc tagatcacat cgaaataata gggatatctt aagggggcagg agagatttga   10860 ataaacagat aaagtaccct tccaacaccg agtattatga gactattagt agtttcataa   10920
ctactgacct taaaaagtac tgtcttaatt ggcgatatga atcaagtagt gtgtttgcag   10980
agagacttaa tgaaatttat ggattgcctg ggttttttca gtggcttcac aaaatattgg   11040
agaaatctgt tttatacgtt agcgatccgt ctagtccacc tgattttgat cgacatatcg   11100
atatagaatc agttccgaat gaccatatct ttattaagta cccgatgggt ggaatagagg   11160
ggttctgtca aaaattatgg actattagta cgattccatt cctatattta gcagcttttg   11220
atacaggagt tagaatctca tcattggttc agggcgataa tcaggcaatt gcagtgacca   11280
aaagagttcc atcatcttgg agttactcaa agaaaaagga agaatcaact aaaataacaa   11340
cacaatattt ccttaattta agacaacgct tacacgacat aggtcatgaa ttaaaagcaa   11400
atgagactat tatatcctct catttctttg tttactctaa aggtatttat tacgatggaa   11460
tacttctctc tcaagcactt aaaagtattg caagatgtgt tttttggtct gaaacaattg   11520
ttgatgaaac tagatcagct tgcagtaata tatctacgac acttgcaaag gcaattgaaa   11580
ggggttatga taaatttgtg gcatatgcta ttaatattta taaacaata catcaagttt   11640 tgattgcatt atcttttacg attaatccta ctatgacacc agacattaca gaacctttct   11700
acaaaagttt ggatctactt aaaaatctag ttctaatccc tgcaccattg ggaggcatga   11760
attatatgaa catgagcagg ttatttgtta ggaacatagg tgaccccatt actgcttcat   11820
ttgctgatat aaagcgcatg atcgaatgtg ggttattagg atgtagcatt ctgtcacaga   11880
taatgtacca aaaatgtggt tcctctaaat acttagactg ggctagtgat ccttactcaa   11940
taaaccttcc ttatagccaa agtatgacca aggtcttaaa aatgtaaca gcaagatatg   12000 tacttatgca tagccccaat cctatgctca aagatttgtt ccatgaaaag tcacaagaag   12060
aagatgaaat ccttgctgaa tttctgttag accgacactt aataatccct agagcagcac   12120
acgaaatttt atcaaattca gtgacaggtg ctagggaatc tatagcaggt atgcttgaca   12180
ctactaaggg tttaatccgt gctagtatgt caagaggtgg gctgacatca tcactagttt   12240
taaaattatc aacatatgac taccaacagt ttagaacgtg tcttgaatgg ctttatgctc   12300
ctatcacggg aattgctgta agcgttgatt cttgttctgt attcttagct aagaccatcc   12360
gaaagagaat gtgggttcat ctaactaagg gaagggagat ttacgggttg gaggtacctg   12420
acattttgga atgcatgcaa aacaatataa ttattgatca tgaagattgt tactcatgta   12480
```

```
ttcaaggatc aaaatattat acatggtttt ttgtaccttc aaattgtcaa ctcgatcaga    12540
taaataagtc aacaaattct ctccgagtac cttatgttgg atcaacaact gaagaaagga    12600
gtgatatgaa gttgtcatat gtgaggtcac caagtagacc acttaaagca gcagtccgaa    12660
ttgcagcagt atatacatgg gcttatggtg atgatgattt atcctggcat gaggcttggt    12720
atttggcaag gactagggca aatattacat ttgatgaact caaattaata acacctatag    12780
ctacatctac taatttggca cataggttga gagatagaag tactcaagtt aaatattcag    12840
ggacttcctt agtaagagtg gcacgctata caacaatatc taatgataac atgtcgttca    12900
ctattaacaa caggaaagtc gatactaatt ttgtctacca gcaagggatg ttattaggct    12960
tgagtatact cgaatacata ttcagatact gtacaagtac tggacaatca aacactgtaa    13020
ttcacttaca tgcagatgtt aattgttgta tagtacagat gactgatcag ccttatacgc    13080
caagcttaac taagaagcta cctgatatca aacccatcaa taataaattg atatatgatc    13140
cggctcctat aattgatact gatgcagcta ggttgtattc tcaaaaatat ctgtcacatc    13200
taatagattt tccaagttgg tcaactactc agcttaacac agtgttggca aaagtggtag    13260
cagtatctat agtagaattg atcacaaaag cgagtaaaga ccatctcaat gagataatag    13320
cggttgttgg tgatgatgat atcaatagct ttattacaga atttctactt gttgatccac    13380
gtttgtttac actatactta ggccaataca tgtctttaca atgggcatat gaaatccatt    13440
atcatagacc agtgggcaag taccagatgg ccgaagtatt acataatttg ctgtcaagag    13500
ctagtagagg catatttagc atattgacca atgcctttag ccatccccgg gtctataaaa    13560
gattctggga atgtggttta ttggagccta tttatgggcc ttatatagga agtcaaaatc    13620
tacatagtgc agtgattgat tatatctata atgcatatct tacttatttg gatgcttatt    13680
tatctgatca agtagatgat actgatatta aatctgtga acagaggag acatgtttag    13740 caaatagaat tgacaattac caaagtagac acctagctgt actcatagac ttgtactgcg    13800
attccactag atgccccaat ataaaagggt cagatacaat tatgagaaat tcaatccta    13860 gatccttcat tgataatgag aggaaaacaa acccactcgg tttgacatgg aatcttgatc    13920
cattacttgt ggatcacttt agctgttcta ttacatatct aaggagaggt attattaaac    13980
agatgagatt aagatttgac ccaagcgtat ctcttgaatt atctagaatg attaaacctg    14040 atgtgatttta tcaagcacct aaagttccgt cctcatgggc tcttatagat atcaaccctg    14100
aagtaaatga ccttaataca atttttggag agcttaatag caagtggaaa gacatcccta    14160
taggacaaat cagaatccaa aattatgaaa tacatgcata taggaggatt ggagttaatt    14220
caactgcatg ttataaggct ttagagctat tatctgttct aaatcggttc atgtctaacc    14280
catcaggtgc attgttttta ggtgaagggg caggatcgat gctggtcaca tatcgtgcct    14340
ttattccatt caagacaatt tattataata gtggtatttc agttcaaaat gttcagggtc    14400
agagagaatt aagtctatat ccatctgaag tggcactagt tgataacaaa aatcgcttgg    14460
ctaatgaccc taatatcaaa gtcttgttta atggtaagcc agagtctaca tgggttggaa    14520
atattgactg ttttgcttat attcttagcc atattgagac ttcaagcttg acattgatac    14580
atagtgatat tgagtccagc ttgagcaaga caaagaataa aattcttgag gagctgtgcc    14640
atattctgtc aatggcactc attttgggaa agatcggatc tttattagtt gttaagtttc    14700
taccaagggt cagtgattat acgtattcat tttgcaaata tgcatcagag ttctatcaac    14760 aaaacttct tgttctgcct agatttagta acatgtcatc atctgaggtt tactacatag    14820
```

```
gaattcacct taatacaaat cgattgattg accctgatag aatagtacaa tacataatta  14880
gaaatttaca acctactcca gttacatttt tatcctacat ttttgaaact aagtatcgaa  14940
ataatatggt tacaaattat ggactatgct tgtcagacgg acacaaaagt gattacttgt  15000
catcaattac aaaaatagag agtgttcttc tgtcatgtgg gttagaattg aacggaccta  15060
agattataca gcaattatca ggacatgact atgccagtgg agagactagt ctggaatcaa  15120
gtataatgat attagttaga gaatatctta atgcaactat acaaggccgg gaaacattag  15180
gcttgttttc accttacccg gtccttcatg agagtcagtt aagagaaatc aataagtgta  15240
ttgtattgaa gtatattgta tatctgctct tttattcaaa ctctacatta tctagtaaac  15300
aaataatgag taatcttaga aaaggaatat tgatgtatga tttgagagat gagtttttca  15360
tatcaagatt gtcagcaaat tacaagaaaa aagtaatgtc acaggaagtt aagactacct  15420
ggatatttaa tattgatact ccgacacgaa aggcgttata taagttagta ggttactcat  15480
taataattaa tcacatatga aggttgggca tggttattca ttttttaagg agtaagataa  15540
gacttgatat atgataactg attaaacatt acctctgaat tgaaggattg ctcaattaca  15600
tggtttttga gtaattgaga ttttattcca attagtacaa ttagaaaaaa cttcaacagt  15660
tgattgagcc ttaatttact ccatactagc tatatttata agctcggata aaactttggt  15720
ttgaaattat aacagtcata ccaatctatc aaggaaacac aattgatgtc tagtatgaag  15780
ttcatattta tatgttttta atcttatacc cactctaatt agttcctatt taagaattaa  15840
attatagatg ttaacatgtt atataatggg aaccatcaat gctgctattg ttggtaacta  15900
taggcattgt attagataat gtttatttct tagaaatgtg caatctcata cgtcggaccc  15960
ctcagcctcc cccttatagt tgcgtgattt gaaaaaacac aaaaaataat catgaatggg  16020
tgtacgtacc tatagctttc tttgtctggt                                  16050
```

<210> SEQ ID NO 4
<211> LENGTH: 172
<212> TYPE: DNA
<213> ORGANISM: Feline morbillivirus

<400> SEQUENCE: 4

```
agagacttaa tgagatttat ggactgcctg gatttttcca gtggcttcac aagattttgg     60
agaaatctgt tctatacgtt agtgatccat atagtccacc tgactttgat caacatatcg    120
atatagaatc agtcccaaac gaccatatct ttatcaagta cccgatgggt gg            172
```

<210> SEQ ID NO 5
<211> LENGTH: 172
<212> TYPE: DNA
<213> ORGANISM: Feline morbillivirus

<400> SEQUENCE: 5

```
agagacttaa tgaaatttat ggattgcctg ggtttttca gtggcttcac aaaatattgg     60
agaaatctgt tttatacgtt agcgatccgt ctagtccacc tgattttgat cgacatatcg    120
atatagaatc agttccgaat gaccatatct ttattaagta cccgatgggt gg            172
```

<210> SEQ ID NO 6
<211> LENGTH: 172
<212> TYPE: DNA
<213> ORGANISM: Feline morbillivirus

<400> SEQUENCE: 6

```
agagacttaa tgaaatttat ggactgcctg gatttttcca gtggcttcac aagattttgg     60
```

```
agaaatctgt tctatacgtt agtgatccat ctagtccacc tgactttgat caacatgtcg    120
atatagaatc agtcccaaat gaccatatct ttatcaagta cccgatgggt gg             172
```

<210> SEQ ID NO 7
<211> LENGTH: 519
<212> TYPE: PRT
<213> ORGANISM: Feline morbillivirus

<400> SEQUENCE: 7

```
Met Ser Ser Leu Leu Arg Ser Leu Ala Ala Phe Lys Arg His Arg Glu
1               5                   10                  15

Gln Pro Thr Ala Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Ile Pro Glu Ala Gly Asn Pro Gly
            100                 105                 110

Glu Leu Thr Phe Ala Ser Arg Gly Ile Asn Leu Asp Lys Gln Ala Gln
        115                 120                 125

Gln Tyr Phe Lys Leu Ala Glu Lys Asn Asp Gln Gly Tyr Tyr Val Ser
    130                 135                 140

Leu Gly Phe Glu Asn Pro Pro Asn Asp Asp Asp Ile Thr Ser Ser Pro
145                 150                 155                 160

Glu Ile Phe Asn Tyr Ile Leu Ala Ser Val Leu Ala Gln Val Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu
        195                 200                 205

Leu Arg Leu Ser Lys Gly Trp Leu Asp Leu Val Arg Asn Lys Ile Ala
    210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
        275                 280                 285

Phe Ser Gly Glu Leu Ala Thr Ile Glu Gly Leu Met Lys Leu Tyr Gln
    290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Gly Leu Asn Phe
            340                 345                 350
```

Thr Arg Ser Phe Phe Asp Pro Thr Tyr Phe Arg Leu Gly Gln Glu Met
            355                 360                 365

Val Arg Arg Ser Ser Gly Met Val Asn Ser Ser Phe Ala Arg Glu Leu
    370                 375                 380

Gly Leu Ser Glu His Glu Thr Gln Leu Val Ser Gln Ile Val Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Thr Lys Asp Asn Ile Asp Asp Arg Gly Glu Asp
                420                 425                 430

Gln Ser Asn Ser Ile Ser Gly Leu Pro Gly Pro Leu Leu Pro Ser Arg
            435                 440                 445

Asp Leu Asp Leu Ser Gly Asp Ser Tyr Gly Ile Asn Ser Gly Val Lys
    450                 455                 460

Asn Val Ser Asp Lys Leu Asn Glu Gly Val Gly Pro Asp His Asp Val
465                 470                 475                 480

Ser Ser Ser Ala Met Glu Glu Leu Arg Arg Leu Val Glu Ser Thr Asn
                485                 490                 495

Arg Ile Asp Thr Lys Gln Pro Glu Ala Ser Gly Val Thr Asn His Tyr
                500                 505                 510

Asn Asp Thr Asp Leu Leu Lys
            515

<210> SEQ ID NO 8
<211> LENGTH: 519
<212> TYPE: PRT
<213> ORGANISM: Feline morbillivirus

<400> SEQUENCE: 8

Met Ser Ser Leu Leu Lys Ser Leu Ala Ala Phe Lys Arg His Arg Glu
1               5                   10                  15

Gln Pro Thr Thr Pro Ser Gly Ser Gly Gly Thr Ile Lys Gly Leu Lys
            20                  25                  30

Asn Thr Ile Ile Val Pro Val Pro Gly Asp Thr Val Ile Thr Thr Arg
        35                  40                  45

Ser Asn Leu Leu Phe Arg Leu Val Tyr Ile Ile Gly Asn Pro Asp Thr
    50                  55                  60

Pro Leu Ser Thr Ser Thr Gly Ala Ile Ile Ser Leu Leu Thr Leu Phe
65                  70                  75                  80

Val Glu Ser Pro Gly Gln Leu Ile Gln Arg Ile Ala Asp Asp Pro Asp
                85                  90                  95

Ala Val Phe Lys Leu Val Glu Val Ile Pro Glu Ala Gly Asn Pro Gly
                100                 105                 110

Glu Leu Thr Phe Ala Ser Arg Gly Ile Asn Leu Asp Lys Gln Ala Gln
            115                 120                 125

Gln Tyr Phe Lys Leu Ala Glu Arg Asn Asp Gln Gly Tyr Tyr Val Ser
        130                 135                 140

Leu Gly Phe Glu Asn Pro Pro Asn Asp Asp Ile Thr Ser Ser Pro
145                 150                 155                 160

Glu Ile Phe Asn Tyr Ile Leu Ala Ser Val Leu Ala Gln Val Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu
        195                 200                 205

```
Leu Arg Leu Ser Lys Gly Trp Leu Asp Leu Val Arg Asn Lys Ile Ala
        210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
        275                 280                 285

Phe Ser Gly Glu Leu Ala Thr Ile Glu Gly Leu Met Lys Leu Tyr Gln
290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Gly Gly Leu Asn Phe
            340                 345                 350

Thr Arg Ser Phe Phe Asp Pro Thr Tyr Phe Arg Leu Gly Gln Glu Met
        355                 360                 365

Val Arg Arg Ser Ser Gly Met Val Asn Ser Ser Phe Ala Arg Glu Leu
370                 375                 380

Gly Leu Ser Glu His Glu Thr Gln Leu Val Ser Gln Ile Val Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Thr Lys Asp Asn Ile Asn Asp Lys Gly Glu Asp
            420                 425                 430

Gln Ser Ser Ser Val Ser Gly Leu Pro Gly Pro Leu Leu Pro Ser Arg
        435                 440                 445

Asp Leu Thr His Pro Gly Asp Ser Tyr Gly Ala Asp Asp Gly Val Lys
450                 455                 460

Asn Val Ser Asn Lys Leu Ser Glu Gly Ile Ser Pro Asp His Asp Val
465                 470                 475                 480

Ser Ser Ser Ala Met Glu Glu Leu Arg Arg Leu Val Glu Ser Thr Asn
                485                 490                 495

Arg Ile Asp Thr Lys Lys Pro Glu Ala Pro Gly Val Thr Asn His Tyr
            500                 505                 510

Asn Asp Thr Asp Leu Leu Arg
        515

<210> SEQ ID NO 9
<211> LENGTH: 519
<212> TYPE: PRT
<213> ORGANISM: Feline morbillivirus

<400> SEQUENCE: 9

Met Ser Ser Leu Leu Arg Ser Leu Ala Ala Phe Lys Arg His Arg Glu
1               5                   10                  15

Gln Pro Thr Ala Pro Ser Gly Ser Gly Ala Ile Lys Gly Leu Lys
                20                  25                  30

Asn Thr Ile Ile Val Pro Val Pro Gly Asp Thr Val Ile Thr Thr Arg
            35                  40                  45

Ser Asn Leu Leu Phe Arg Leu Val Tyr Ile Ile Gly Asn Pro Asp Thr
```

-continued

```
            50                  55                  60
Pro Leu Ser Thr Ser Thr Gly Ala Ile Ile Ser Leu Leu Thr Leu Phe
 65                  70                  75                  80

Val Glu Ser Pro Gly Gln Leu Ile Gln Arg Ile Ala Asp Asp Pro Asp
                 85                  90                  95

Ala Val Phe Lys Leu Val Glu Val Ile Pro Glu Ala Gly Asn Pro Gly
            100                 105                 110

Glu Leu Thr Phe Ala Ser Arg Gly Ile Asn Leu Asp Lys Gln Ala Gln
            115                 120                 125

Gln Tyr Phe Lys Leu Ala Glu Lys Asn Asp Gln Gly Tyr Tyr Val Ser
130                 135                 140

Leu Gly Phe Glu Asn Pro Pro Asn Asp Asp Ile Thr Ser Ser Pro
145                 150                 155                 160

Glu Ile Phe Asn Tyr Ile Leu Ala Ser Val Leu Ala Gln Val Trp Ile
                165                 170                 175

Leu Leu Ala Lys Ala Val Thr Ala Pro Asp Thr Ala Ala Glu Ala Glu
            180                 185                 190

Asn Arg Arg Trp Ile Lys Leu Met Gln Gln Arg Arg Val Asp Gly Glu
            195                 200                 205

Leu Arg Leu Ser Lys Gly Trp Leu Asp Leu Val Arg Asn Lys Ile Ala
210                 215                 220

Ser Asp Ile Thr Ile Arg Arg Phe Met Val Ala Leu Val Leu Asp Ile
225                 230                 235                 240

Lys Arg Ser Pro Gly Thr Arg Pro Arg Ile Ala Glu Met Ile Cys Asp
                245                 250                 255

Ile Asp Asn Tyr Ile Val Glu Ala Gly Leu Ala Ser Phe Leu Leu Thr
            260                 265                 270

Ile Lys Phe Gly Ile Glu Thr Arg Tyr Pro Ala Leu Ala Leu His Glu
            275                 280                 285

Phe Ser Gly Glu Leu Ala Thr Ile Glu Gly Leu Met Lys Leu Tyr Gln
290                 295                 300

Ser Met Gly Glu Met Ala Pro Tyr Met Val Ile Leu Glu Asn Ser Ile
305                 310                 315                 320

Gln Thr Arg Phe Ser Ala Gly Ser Tyr Pro Leu Leu Trp Ser Tyr Ala
                325                 330                 335

Met Gly Val Gly Val Glu Leu Glu Arg Ser Met Gly Gly Leu Asn Phe
            340                 345                 350

Thr Arg Ser Phe Phe Asp Pro Thr Tyr Phe Arg Leu Gly Gln Glu Met
            355                 360                 365

Val Arg Arg Ser Ser Gly Met Val Asn Ser Ser Phe Ala Arg Glu Leu
370                 375                 380

Gly Leu Ser Asp His Glu Thr Gln Leu Val Ser Gln Ile Val Asn Ser
385                 390                 395                 400

Gly Gly Glu Ser Gly Ile Pro Lys Phe Asp Gly Phe Arg Ala Asn Pro
                405                 410                 415

Thr Thr Phe Leu Gly Thr Lys Asp Asn Ile Asn Asp Arg Gly Glu Asp
            420                 425                 430

Gln Ser Asn Ser Ile Ser Gly Leu Pro Gly Pro Leu Leu Pro Ser Arg
            435                 440                 445

Asp Leu Asn Leu Ser Gly Asp Ser Tyr Gly Ile Asn Ser Gly Val Lys
450                 455                 460

Asn Val Ser Asp Lys Leu Asn Glu Gly Val Gly Pro Asp His Asp Val
465                 470                 475                 480
```

Ser Ser Ser Ala Met Glu Glu Leu Arg Arg Leu Val Glu Ser Thr Asn
                485                 490                 495

Arg Ile Asp Thr Lys Gln Pro Glu Ala Ser Gly Val Thr Asn His Tyr
            500                 505                 510

Asn Asp Thr Asp Leu Leu Lys
        515

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagagactta atgaaattta tgg                                            23

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccacccatcg ggtactt                                                   17

<210> SEQ ID NO 13
<211> LENGTH: 4
<212> TYPE: PRT
<213> ORGANISM: Feline morbillivirus

<400> SEQUENCE: 13

Met Ser Ser Leu
1

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ttaaaagggg                                                           10

<210> SEQ ID NO 15
<211> LENGTH: 11
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 15
ttaaaagggg g                                                               11

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttaaaagggg                                                                 10

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcatctctt agttcccagg aa                                                   22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttcagactc accctcgata tct                                                  23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acgcggatcc gatgtctagt cta                                                  23

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggaattcgg ttttagaagg tcagta                                               26

<210> SEQ ID NO 21
<211> LENGTH: 523
<212> TYPE: PRT
<213> ORGANISM: Canine distemper virus
```

```
<400> SEQUENCE: 21

Met Ala Ser Leu Leu Lys Ser Leu Thr Leu Phe Lys Arg Thr Arg Asp
1               5                   10                  15

Gln Pro Pro Leu Ala Ser Gly Ser Gly Gly Ala Ile Arg Gly Ile Lys
            20                  25                  30

His Val Ile Ile Val Leu Ile Pro Gly Asp Ser Ser Ile Val Thr Arg
        35                  40                  45

Ser Arg Leu Leu Asp Arg Leu Val Arg Leu Val Gly Asp Pro Lys Ile
    50                  55                  60

Asn Gly Pro Lys Leu Thr Gly Ile Leu Ile Ser Ile Leu Ser Leu Phe
65                  70                  75                  80

Val Glu Ser Pro Gly Gln Leu Ile Gln Arg Ile Ile Asp Asp Pro Asp
                85                  90                  95

Val Ser Ile Lys Leu Val Glu Val Ile Pro Ser Ile Asn Ser Ala Cys
            100                 105                 110

Gly Leu Thr Phe Ala Ser Arg Gly Ala Ser Leu Asp Ser Glu Ala Asp
        115                 120                 125

Glu Phe Phe Lys Ile Val Asp Glu Gly Ser Lys Ala Gln Gly Gln Leu
    130                 135                 140

Gly Trp Leu Glu Asn Lys Asp Ile Val Asp Ile Glu Val Asp Asn Ala
145                 150                 155                 160

Glu Gln Phe Asn Ile Leu Leu Ala Ser Ile Leu Ala Gln Ile Trp Ile
                165                 170                 175

Leu Leu Ala Lys Ala Val Thr Ala Pro Asp Thr Ala Ala Asp Ser Glu
            180                 185                 190

Met Arg Arg Trp Ile Lys Tyr Thr Gln Gln Arg Arg Val Val Gly Glu
        195                 200                 205

Phe Arg Met Asn Lys Ile Trp Leu Asp Ile Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Ser Pro Gly Asn Lys Pro Arg Ile Ala Glu Met Ile Cys Asp
                245                 250                 255

Ile Asp Asn Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ser Gly Glu Leu Thr Thr Ile Glu Ser Leu Met Met Leu Tyr Gln
    290                 295                 300

Gln Met Gly Glu Thr Ala Pro Tyr Met Val Ile Leu Glu Asn Ser Val
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Ala Leu Ala Ala Glu Leu
    370                 375                 380

Gly Ile Thr Lys Glu Glu Ala Gln Leu Val Ser Glu Ile Ala Ser Lys
385                 390                 395                 400

Thr Thr Glu Asp Arg Thr Ile Arg Ala Thr Gly Pro Lys Gln Ser Gln
                405                 410                 415
```

```
Ile Thr Phe Leu His Ser Glu Arg Ser Glu Val Ala Asn Gln Gln Pro
                420                 425                 430

Pro Thr Ile Asn Lys Arg Ser Glu Asn Gln Gly Gly Asp Lys Tyr Pro
                435                 440                 445

Ile His Phe Ser Asp Glu Arg Leu Pro Gly Tyr Thr Pro Asp Val Asn
            450                 455                 460

Ser Ser Glu Trp Ser Glu Ser Arg Tyr Asp Thr Gln Ile Ile Gln Asp
465                 470                 475                 480

Asp Gly Asn Asp Asp Arg Lys Ser Met Glu Ala Ile Ala Lys Met
                485                 490                 495

Arg Met Leu Thr Lys Met Leu Ser Gln Pro Gly Thr Ser Glu Asp Asn
                500                 505                 510

Ser Pro Val Tyr Ser Asp Lys Glu Leu Leu Asn
            515                 520

<210> SEQ ID NO 22
<211> LENGTH: 523
<212> TYPE: PRT
<213> ORGANISM: Dolphin morbillivirus

<400> SEQUENCE: 22

Met Ala Thr Leu Leu Arg Ser Leu Ala Leu Phe Lys Arg Asn Lys Asp
1               5                   10                  15

Arg Thr Pro Leu Ile Ala Gly Ser Gly Ala Ile Arg Gly Ile Lys
                20                  25                  30

His Val Ile Val Pro Val Pro Gly Asp Ser Ser Ile Val Thr Arg
            35                  40                  45

Ser Arg Leu Leu Asp Arg Leu Val Arg Leu Ala Gly Asp Pro Tyr Ile
    50                  55                  60

Ser Gly Pro Lys Leu Thr Gly Val Met Ile Ser Ile Leu Ser Leu Phe
65                  70                  75                  80

Val Glu Ser Pro Ser Gln Leu Ile Gln Arg Ile Thr Asp Asp Pro Asp
                85                  90                  95

Val Ser Ile Arg Leu Val Glu Val Ile Gln Ser Glu Lys Ser Leu Ser
                100                 105                 110

Gly Leu Thr Phe Ala Ser Arg Gly Ala Asn Met Glu Asp Glu Ala Asp
            115                 120                 125

Asp Tyr Phe Ser Ile Gln Ala Gly Glu Glu Gly Asp Thr Arg Gly Thr
    130                 135                 140

His Trp Phe Glu Asn Lys Glu Ile Val Glu Ile Glu Val Gln Asp Pro
145                 150                 155                 160

Glu Glu Phe Asn Ile Leu Leu Ala Ser Ile Leu Ala Gln Ile Trp Ile
                165                 170                 175

Leu Leu Ala Lys Ala Val Thr Ala Pro Asp Thr Ala Ala Asp Ser Glu
                180                 185                 190

Thr Arg Arg Trp Ile Lys Tyr Thr Gln Gln Arg Val Val Gly Glu
            195                 200                 205

Phe Arg Leu Asp Lys Gly Trp Leu Asp Ala Val Arg Asn Arg Ile Ala
    210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
```

```
                260                 265                 270
Ile Lys Phe Gly Ile Glu Thr Met Tyr Pro Ala Leu Gly Leu His Glu
        275                 280                 285

Phe Ser Gly Glu Leu Thr Thr Val Glu Ser Leu Met Asn Leu Tyr Gln
        290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Leu Ala Ala Glu Leu
        370                 375                 380

Gly Ile Thr Ala Glu Asp Ala Lys Leu Val Ser Glu Ile Ala Ala Gln
385                 390                 395                 400

Ala Asn Asp Asp Arg Ala Asn Arg Ala Ile Gly Pro Lys Gln Asn Gln
                405                 410                 415

Ile Ser Phe Leu His Pro Asp Arg Gly Asp Ala Ser Thr Pro Gly Asn
                420                 425                 430

Ile Leu Arg Ala Asn Glu Gly Asp Gly Ser Thr Arg Met Lys Arg Gly
            435                 440                 445

Gly Asn Ile Ala Thr Pro Lys Gly Thr Ser Ile Asp Gln Thr Ser Thr
        450                 455                 460

Thr Leu Ser Lys Asp Thr Leu Asp Ile Asp Glu Gln Ser Asp Asn Thr
465                 470                 475                 480

Asp Asp Pro Ile Ser Ile Gln Lys Ser Ala Glu Ala Leu Ala Lys Met
                485                 490                 495

Arg Ala Met Ala Lys Leu Leu Glu Asn Gln Gly Pro Arg Asp Val Thr
            500                 505                 510

Ala His Val Tyr Asn Asp Lys Asp Leu Leu Gly
        515                 520

<210> SEQ ID NO 23
<211> LENGTH: 525
<212> TYPE: PRT
<213> ORGANISM: Measles virus

<400> SEQUENCE: 23

Met Ala Thr Leu Leu Arg Ser Leu Ala Leu Phe Lys Ar

-continued

Gly Leu Thr Phe Ala Ser Arg Gly Thr Asn Met Glu Asp Glu Ala Asp
            115                 120                 125

Gln Tyr Phe Ser His Asp Asp Pro Ser Ser Asp Gln Ser Arg Ser
130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190

Leu Arg Arg Trp Ile Lys Tyr Thr Gln Gln Arg Arg Val Val Gly Glu
            195                 200                 205

Phe Arg Leu Glu Arg Lys Trp Leu Asp Val Val Arg Asn Arg Ile Ala
210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
                245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
        275                 280                 285

Phe Ala Gly Glu Leu Ser Thr Leu Glu Ser Leu Met Asn Leu Tyr Gln
        290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
        355                 360                 365

Val Arg Arg Ser Ala Gly Lys Val Ser Ser Thr Leu Ala Ser Glu Leu
        370                 375                 380

Gly Ile Thr Ala Glu Asp Ala Arg Leu Val Ser Glu Ile Ala Met His
385                 390                 395                 400

Thr Thr Glu Asp Arg Ile Ser Arg Ala Val Gly Pro Arg Gln Ala Gln
                405                 410                 415

Val Ser Phe Leu His Gly Asp Gln Ser Glu Asn Glu Leu Pro Gly Leu
            420                 425                 430

Gly Gly Lys Glu Asp Arg Arg Val Lys Gln Gly Arg Gly Glu Ala Arg
        435                 440                 445

Glu Ser Tyr Arg Glu Thr Gly Ser Ser Arg Ala Ser Asp Ala Arg Ala
        450                 455                 460

Ala His Pro Pro Thr Ser Met Pro Leu Asp Ile Asp Thr Ala Ser Glu
465                 470                 475                 480

Ser Gly Gln Asp Pro Gln Asp Ser Arg Arg Ser Ala Asp Ala Leu Leu
                485                 490                 495

Arg Leu Gln Ala Met Ala Gly Ile Leu Glu Glu Gln Gly Ser Asp Thr
            500                 505                 510

Asp Thr Pro Arg Val Tyr Asn Asp Arg Asp Leu Leu Asp
        515                 520                 525

<210> SEQ ID NO 24
<211> LENGTH: 525
<212> TYPE: PRT
<213> ORGANISM: Peste-des-petits ruminants virus

<400> SEQUENCE: 24

| | | | | | | | | | | | | | | |
|---|---|---|---|---|---|---|---|---|---|---|---|---|---|---|
| Met | Ala | Thr | Leu | Leu | Lys | Ser | Leu | Ala | Leu | Phe | Lys | Arg | Asn | Lys | Asp |
| 1 | | | | 5 | | | | | 10 | | | | | 15 | |
| Lys | Ala | Pro | Thr | Ala | Ser | Gly | Ser | Gly | Gly | Ala | Ile | Arg | Gly | Ile | Lys |
| | | | 20 | | | | | 25 | | | | | 30 | | |
| Asn | Val | Ile | Ile | Val | Pro | Ile | Pro | Gly | Asp | Ser | Ser | Ile | Ile | Thr | Arg |
| | | | 35 | | | | | 40 | | | | | 45 | | |
| Ser | Arg | Leu | Leu | Asp | Arg | Leu | Val | Arg | Leu | Ala | Gly | Asp | Pro | Asp | Ile |
| | 50 | | | | | 55 | | | | | 60 | | | | |
| Asn | Gly | Ser | Lys | Leu | Thr | Gly | Val | Met | Ile | Ser | Met | Leu | Ser | Leu | Phe |
| 65 | | | | | 70 | | | | | 75 | | | | | 80 |
| Val | Glu | Ser | Pro | Gly | Gln | Leu | Ile | Gln | Arg | Ile | Thr | Asp | Asp | Pro | Asp |
| | | | | 85 | | | | | 90 | | | | | 95 | |
| Val | Ser | Ile | Arg | Leu | Val | Glu | Val | Val | Gln | Ser | Thr | Arg | Ser | Gln | Ser |
| | | | 100 | | | | | 105 | | | | | 110 | | |
| Gly | Leu | Thr | Phe | Ala | Ser | Arg | Gly | Ala | Asp | Leu | Asp | Asn | Glu | Ala | Asp |
| | | | 115 | | | | | 120 | | | | | 125 | | |
| Met | Tyr | Phe | Ser | Thr | Glu | Gly | Pro | Ser | Ser | Gly | Gly | Lys | Lys | Arg | Ile |
| | 130 | | | | | 135 | | | | | 140 | | | | |
| Asn | Trp | Phe | Glu | Asn | Arg | Glu | Ile | Ile | Asp | Ile | Glu | Val | Gln | Asp | Pro |
| 145 | | | | | 150 | | | | | 155 | | | | | 160 |
| Glu | Glu | Phe | Asn | Met | Leu | Leu | Ala | Ser | Ile | Leu | Ala | Gln | Val | Trp | Ile |
| | | | | 165 | | | | | 170 | | | | | 175 | |
| Leu | Leu | Ala | Lys | Ala | Val | Thr | Ala | Pro | Asp | Thr | Ala | Ala | Asp | Ser | Glu |
| | | | 180 | | | | | 185 | | | | | 190 | | |
| Leu | Arg | Arg | Trp | Val | Lys | Tyr | Thr | Gln | Gln | Arg | Arg | Val | Ile | Gly | Glu |
| | | | 195 | | | | | 200 | | | | | 205 | | |
| Phe | Arg | Leu | Asp | Lys | Gly | Trp | Leu | Asp | Ala | Val | Arg | Asn | Arg | Ile | Ala |
| | 210 | | | | | 215 | | | | | 220 | | | | |
| Glu | Asp | Leu | Ser | Leu | Arg | Arg | Phe | Met | Val | Ser | Leu | Ile | Leu | Asp | Ile |
| 225 | | | | | 230 | | | | | 235 | | | | | 240 |
| Lys | Arg | Thr | Pro | Gly | Asn | Lys | Pro | Arg | Ile | Ala | Glu | Met | Ile | Cys | Asp |
| | | | | 245 | | | | | 250 | | | | | 255 | |
| Ile | Asp | Asn | Tyr | Ile | Val | Glu | Ala | Gly | Leu | Ala | Ser | Phe | Ile | Leu | Thr |
| | | | 260 | | | | | 265 | | | | | 270 | | |
| Ile | Lys | Phe | Gly | Ile | Glu | Thr | Met | Tyr | Pro | Ala | Leu | Gly | Leu | His | Glu |
| | | | 275 | | | | | 280 | | | | | 285 | | |
| Phe | Ala | Gly | Glu | Leu | Ser | Thr | Ile | Glu | Ser | Leu | Met | Asn | Leu | Tyr | Gln |
| | 290 | | | | | 295 | | | | | 300 | | | | |
| Gln | Leu | Gly | Glu | Val | Ala | Pro | Tyr | Met | Val | Ile | Leu | Glu | Asn | Ser | Ile |
| 305 | | | | | 310 | | | | | 315 | | | | | 320 |
| Gln | Asn | Lys | Phe | Ser | Ala | Gly | Ala | Tyr | Pro | Leu | Leu | Trp | Ser | Tyr | Ala |
| | | | | 325 | | | | | 330 | | | | | 335 | |
| Met | Gly | Val | Gly | Val | Gly | Leu | Glu | Asn | Ser | Met | Gly | Gly | Leu | Asn | Phe |
| | | | 340 | | | | | 345 | | | | | 350 | | |
| Gly | Arg | Ser | Tyr | Phe | Asp | Pro | Ala | Tyr | Phe | Arg | Leu | Gly | Gln | Glu | Met |
| | | | 355 | | | | | 360 | | | | | 365 | | |
| Val | Arg | Arg | Ser | Ala | Gly | Lys | Val | Ser | Ser | Val | Ile | Ala | Ala | Glu | Leu |
| | 370 | | | | | 375 | | | | | 380 | | | | |

-continued

```
Gly Ile Thr Ala Glu Glu Ala Lys Leu Val Ser Glu Ile Ala Ser Gln
            385                 390                 395                 400

Ala Gly Asp Glu Arg Thr Ala Arg Gly Thr Gly Pro Arg Gln Ala Gln
                    405                 410                 415

Val Ser Phe Leu Gln His Lys Thr Gly Glu Gly Glu Ser Ser Ala Pro
                420                 425                 430

Ala Thr Arg Glu Gly Val Lys Ala Ala Ile Pro Asn Gly Ser Glu Glu
                435                 440                 445

Arg Asp Arg Lys Gln Thr Arg Ser Gly Arg Pro Arg Gly Glu Thr Pro
            450                 455                 460

Ser Gln Leu Leu Glu Ile Met Pro Glu Asp Glu Val Ser Arg Glu
465                 470                 475                 480

Ser Gly Gln Asn Pro Arg Glu Ala Gln Arg Ser Ala Glu Ala Leu Phe
                485                 490                 495

Arg Leu Gln Ala Met Ala Lys Ile Leu Glu Asp Gln Glu Gly Glu
                500                 505                 510

Asp Asn Ser Gln Val Tyr Asn Asp Lys Asp Leu Leu Gly
                515                 520                 525

<210> SEQ ID NO 25
<211> LENGTH: 525
<212> TYPE: PRT
<213> ORGANISM: Rinderpest virus

<400> SEQUENCE: 25

Met Ala Ser Leu Leu Lys Ser Leu Ala Leu Phe Lys Arg Ala Lys Asp
1               5                   10                  15

Lys Pro Pro Leu Ala Ala Gly Ser Gly Ala Ile Arg Gly Ile Lys
                20                  25                  30

His Val Ile Val Pro Ile Pro Gly Asp Ser Ser Ile Thr Thr Arg
            35                  40                  45

Ser Arg Leu Leu Asp Arg Leu Val Lys Met Val Gly Asp Pro Asp Ile
50                  55                  60

Ser Gly Pro Lys Leu Thr Gly Ala Leu Ile Ser Ile Leu Ser Leu Phe
65                  70                  75                  80

Val Glu Ser Pro Gly Gln Leu Ile Gln Arg Ile Thr Asp Asp Pro Asp
                85                  90                  95

Ile Ser Ile Lys Leu Val Glu Val Gln Ser Asp Lys Thr Gln Ser
            100                 105                 110

Gly Leu Thr Phe Ala Ser Arg Gly Thr Ser Met Asp Asp Glu Ala Asp
            115                 120                 125

Arg Tyr Phe Thr Tyr Glu Glu Pro Asn Asp Gly Glu Glu Arg Gln Ser
            130                 135                 140

Tyr Trp Phe Glu Asn Arg Asp Ile Gln Asp Ile Glu Ile Gln Asp Pro
145                 150                 155                 160

Glu Gly Phe Asn Met Ile Leu Ala Thr Ile Leu Ala Gln Ile Trp Ile
                165                 170                 175

Leu Leu Ala Lys Ala Val Thr Ala Pro Asp Thr Ala Ala Asp Ser Glu
            180                 185                 190

Leu Arg Arg Trp Val Lys Tyr Thr Gln Gln Arg Val Ile Gly Glu
            195                 200                 205

Phe Arg Leu Asp Lys Gly Trp Leu Asp Thr Val Arg Asn Arg Val Ala
            210                 215                 220

Glu Asp Leu Ser Leu Arg Arg Phe Met Val Ala Leu Ile Leu Asp Ile
225                 230                 235                 240
```

```
Lys Arg Thr Pro Gly Asn Lys Pro Arg Ile Ala Glu Met Ile Cys Asp
            245                 250                 255

Ile Asp Thr Tyr Ile Val Glu Ala Gly Leu Ala Ser Phe Ile Leu Thr
        260                 265                 270

Ile Lys Phe Gly Ile Glu Thr Met Tyr Pro Ala Leu Gly Leu His Glu
    275                 280                 285

Phe Ala Gly Glu Leu Ser Thr Ile Glu Ser Leu Met Asn Leu Tyr Gln
    290                 295                 300

Gln Met Gly Glu Leu Ala Pro Tyr Met Val Ile Leu Glu Asn Ser Ile
305                 310                 315                 320

Gln Asn Lys Phe Ser Ala Gly Ala Tyr Pro Leu Leu Trp Ser Tyr Ala
            325                 330                 335

Met Gly Ile Gly Val Glu Leu Glu Asn Ser Met Gly Gly Leu Asn Phe
        340                 345                 350

Gly Arg Ser Tyr Phe Asp Pro Ala Tyr Phe Arg Leu Gly Gln Glu Met
    355                 360                 365

Val Arg Arg Ser Ala Gly Lys Val Ser Ser Asn Leu Ala Ser Glu Leu
    370                 375                 380

Gly Ile Thr Glu Glu Glu Ala Arg Leu Val Ser Glu Ile Ala Ala Tyr
385                 390                 395                 400

Thr Ser Asp Asp Arg Asn Asn Arg Thr Ser Gly Pro Lys Gln Ala Gln
            405                 410                 415

Val Ser Phe Leu Arg Thr Asp Gln Gly Ser Glu Ala Gln His Ser Ala
        420                 425                 430

Ser Lys Lys Asp Glu Ala Arg Ala Pro Gln Val Lys Lys Glu Thr Arg
    435                 440                 445

Thr Ser Ser Lys Ser Asp Lys His Lys Glu Gly Thr Asp Lys Glu Pro
    450                 455                 460

Val Ser Ser Ser Ala Met Thr Leu Ile Asp Val Asp Thr Thr Leu Glu
465                 470                 475                 480

Ala Asp Thr Asp Pro Leu Glu Ser Lys Lys Ser Ala Glu Ala Leu Leu
            485                 490                 495

Arg Leu Gln Ala Met Ala Gly Ile Leu Gly Asp Ser Thr Leu Gly Asn
        500                 505                 510

Asp Ser Leu Arg Ala Tyr Asn Asp Lys Asp Leu Leu Asn
    515                 520                 525
```

<210> SEQ ID NO 26
<211> LENGTH: 523
<212> TYPE: PRT
<213> ORGANISM: Phocine distemper virus

<400> SEQUENCE: 26

```
Met Ala Ser Leu Leu Lys Ser Leu Ser Leu Phe Lys Lys Thr Arg Glu
1               5                   10                  15

Gln Pro Pro Leu Ala Ser Gly Ser Gly Gly Ala Ile Arg Gly Ile Lys
            20                  25                  30

His Val Ile Ile Val Leu Ile Pro Gly Asp Ser Ser Ile Val Thr Arg
        35                  40                  45

Ser Arg Leu Leu Asp Arg Leu Val Arg Met Val Gly Asp Pro Glu Val
    50                  55                  60

Ser Gly Pro Lys Leu Thr Gly Val Leu Ile Ser Ile Leu Ser Leu Phe
65                  70                  75                  80

Val Glu Ser Pro Gly Gln Leu Ile Gln Arg Ile Ile Asp Asp Pro Asp

85                  90                  95
Ile Ser Ile Lys Leu Val Glu Val Ile Pro Ser Ile Asn Ser Thr Cys
            100                 105                 110

Gly Leu Thr Phe Ala Ser Arg Gly Ala Ser Leu Asp Ala Glu Ala Asp
            115                 120                 125

Glu Phe Phe Gly Thr Met Asp Glu Gly Ser Lys Asp His Asn Gln Met
            130                 135                 140

Gly Trp Leu Glu Asn Lys Asp Ile Ile Asp Ile Glu Val Asn Asp Ala
145                 150                 155                 160

Glu Gln Phe Asn Ile Leu Leu Ala Ser Ile Leu Ala Gln Ile Trp Ile
                            165                 170                 175

Leu Leu Ala Lys Ala Val Thr Ala Pro Asp Thr Ala Ala Asp Ser Glu
                180                 185                 190

Met Arg Arg Trp Ile Lys Tyr Thr Gln Gln Arg Val Ile Gly Glu
                195                 200                 205

Phe Arg Met Asn Lys Ile Trp Leu Asp Ile Val Arg Asn Arg Ile Ala
            210                 215                 220

Glu Asp Leu Ser Leu Arg Arg Phe Met Val Ala Leu Ile Leu Asp Ile
225                 230                 235                 240

Lys Arg Ser Pro Gly Asn Lys Pro Arg Ile Ala Glu Met Ile Cys Asp
                    245                 250                 255

Ile Asp Asn Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
            275                 280                 285

Phe Ser Gly Glu Leu Thr Thr Ile Glu Ser Leu Met Val Leu Tyr Gln
290                 295                 300

Gln Met Gly Glu Thr Ala Pro Tyr Met Val Ile Leu Glu Asn Ser Val
305                 310                 315                 320

Gln Asn Lys Phe Ser Ala Gly Ser Tyr Pro Leu Leu Trp Ser Tyr Ala
                325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
            355                 360                 365

Val Arg Arg Ser Ala Gly Lys Val Ser Ser Thr Phe Ala Ala Glu Phe
            370                 375                 380

Gly Ile Thr Lys Glu Glu Ala Gln Leu Val Ser Glu Ile Val Ser Arg
385                 390                 395                 400

Thr Thr Glu Asp Arg Thr Thr Arg Ala Thr Gly Pro Lys Gln Ser Gln
                405                 410                 415

Ile Thr Phe Leu His Ser Glu Arg Asn Glu Ala Pro Asn Gln Arg Leu
                420                 425                 430

Pro Pro Ile Thr Met Lys Ser Glu Phe Gln Gly Gly Asp Lys Tyr Ser
            435                 440                 445

Asn Gln Leu Ile Asp Asp Arg Leu Ser Gly Tyr Thr Ser Asp Val Gln
            450                 455                 460

Ser Ser Glu Trp Asp Glu Ser Arg Gln Ile Thr Gln Leu Thr Gln Glu
465                 470                 475                 480

Gly Asp His Asp Asn Asp Gln Gln Ser Met Asp Gly Leu Ala Lys Met
                            485                 490                 495

Arg Gln Leu Thr Lys Ile Leu Asn Gln Ser Asp Thr Asn Gly Glu Val
                500                 505                 510

```
Ser Pro Ala His Asn Asp Arg Asp Leu Leu Ser
        515                 520

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Ile or Val
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(9)
<223> OTHER INFORMATION: Ala or Cys
<220> FEATURE:
<221> NAME/KEY: MOD_RES
<222> LOCATION: (10)..(10)
<223> OTHER INFORMATION: Any amino acid

<400> SEQUENCE: 27

Gln Xaa Trp Xaa Xaa Xaa Xaa Lys Xaa Xaa Thr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (8)..(9)
<223> OTHER INFORMATION: Any amino acid
<220> FEATURE:
<221> NAME/KEY: MOD_RES
<222> LOCATION: (10)..(10)
<223> OTHER INFORMATION: Any aromatic amino acid
<220> FEATURE:
<221> NAME/KEY: MOD_RES
<222> LOCATION: (12)..(12)
<223> OTHER INFORMATION: Any aromatic amino acid

<400> SEQUENCE: 28

Phe Xaa Xaa Xaa Xaa Tyr Pro Xaa Xaa Xaa Ser Xaa Ala Met Gly
1               5                   10                  15
```